US010030320B2

(12) United States Patent
Rhodius et al.

(10) Patent No.: US 10,030,320 B2
(45) Date of Patent: Jul. 24, 2018

(54) ANTI-SIGMAS FOR PROGRAMMABLE TRANSCRIPTIONAL REGULATION

(71) Applicants: Massachusetts Institute of Technology, Cambridge, MA (US); The Regents of the University of California, Oakland, CA (US)

(72) Inventors: Virgil A. Rhodius, El Sobrante, CA (US); Christopher Voigt, Belmont, MA (US); Carol A. Gross, Berkeley, CA (US)

(73) Assignees: Massachusetts Institute of Technology, Cambridge, MA (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 14/388,030

(22) PCT Filed: Mar. 15, 2013

(86) PCT No.: PCT/US2013/032145
§ 371 (c)(1),
(2) Date: Sep. 25, 2014

(87) PCT Pub. No.: WO2013/148321
PCT Pub. Date: Oct. 3, 2013

(65) Prior Publication Data
US 2015/0051112 A1    Feb. 19, 2015

Related U.S. Application Data

(60) Provisional application No. 61/616,176, filed on Mar. 27, 2012.

(51) Int. Cl.
| | |
|---|---|
| *C12N 15/79* | (2006.01) |
| *C40B 30/02* | (2006.01) |
| *C07K 14/195* | (2006.01) |
| *C12N 15/63* | (2006.01) |
| *G06N 3/12* | (2006.01) |
| *B82Y 10/00* | (2011.01) |

(52) U.S. Cl.
CPC ............. *C40B 30/02* (2013.01); *B82Y 10/00* (2013.01); *C07K 14/195* (2013.01); *C12N 15/63* (2013.01); *C12N 15/635* (2013.01); *G06N 3/123* (2013.01)

(58) Field of Classification Search
None
See application file for complete search history.

(56) References Cited

U.S. PATENT DOCUMENTS

2013/0005590 A1* 1/2013 Lou .................. C12N 15/635
506/8

FOREIGN PATENT DOCUMENTS

WO    WO 2012/170436 A1    12/2012

OTHER PUBLICATIONS

An et al., Synthesis of orthogonal transcription-translation networks. Proc Natl Acad Sci U S A. May 26, 2009;106(21):8477-82. doi: 10.1073/pnas.0900267106. Epub May 14, 2009.
Campbell et al., A conserved structural module regulates transcriptional responses to diverse stress signals in bacteria. Mol Cell. Sep. 7, 2007;27(5):793-805.
Chen et al., Sequestration-based bistability enables tuning of the switching boundaries and design of a latch. Mol Syst Biol. 2012;8:620. doi: 10.1038/msb.2012.52.
Grigorova et al., Fine-tuning of the *Escherichia coli* sigmaE envelope stress response relies on multiple mechanisms to inhibit signal-independent proteolysis of the transmembrane anti-sigma factor, RseA. Genes Dev. Nov. 1, 2004;18(21):2686-97.
Kumar et al., A hybrid sigma subunit directs RNA polymerase to a hybrid promoter in *Escherichia coli*. J Mol Biol. Mar. 10, 1995;246(5):563-71.
Liu et al., Identification and characterization of the cognate anti-sigma factor and specific promoter elements of a T. tengcongensis ECF sigma factor. PLoS One. 2012;7(7):e40885. doi: 10.1371/journal.pone.0040885. Epub Jul. 16, 2012.
Locke et al., Stochastic pulse regulation in bacterial stress response. Science. Oct. 21, 2011;334(6054):366-9. doi: 10.1126/science.1208144. Epub Oct. 6, 2011.
Rhodius et al., Conserved and variable functions of the sigmaE stress response in related genomes. PLoS Biol. Jan. 2006;4(1):e2.
Shin et al., An *E. coli* cell-free expression toolbox: application to synthetic gene circuits and artificial cells. ACS Synth Biol. Jan. 20, 2012;1(1):29-41. doi: 10.1021/sb200016s. Epub Jan. 6, 2012.
Shultzaberger et al., Anatomy of *Escherichia coli* sigma70 promoters. Nucleic Acids Res. 2007;35(3):771-88. Epub Dec. 22, 2006.
Staroń et al., The third pillar of bacterial signal transduction: classification of the extracytoplasmic function (ECF) sigma factor protein family. Mol Microbiol. Nov. 2009;74(3):557-81. doi: 10.1111/j.1365-2958.2009.06870.x. Epub Sep. 8, 2009.
Tamsir et al., Robust multicellular computing using genetically encoded NOR gates and chemical 'wires'. Nature. Jan. 13, 2011;469(7329):212-5. doi: 10.1038/nature09565. Epub Dec. 8, 2010.
Tiwari et al., Bistable responses in bacterial genetic networks: designs and dynamical consequences. Math Biosci. May 2011;231(1):76-89. doi: 10.1016/j.mbs.2011.03.004. Epub Mar. 6, 2011.
Weiss et al., Genetic circuit building blocks for cellular computation, communications, and signal processing. Natural Computing. 2003;2(1):47-84.
Dehaseth et al., Nonspecific interactions of *Escherichia coli* RNA polymerase with native and denatured DNA: differences in the binding behavior of core and holoenzyme. Biochemistry. May 2, 1978;17(9):1612-22.

(Continued)

*Primary Examiner* — James S Ketter
(74) *Attorney, Agent, or Firm* — Wolf, Greenfield & Sacks, P.C.

(57) ABSTRACT

The invention relates to anti-sigma factors ("anti-sigmas") that bind to sigma factors and block activation of transcription. Anti-sigmas and their cognate sigma factors provide a highly effective mechanism for regulating gene expression in genetic circuits.

16 Claims, 26 Drawing Sheets

(56) References Cited

OTHER PUBLICATIONS

Feklístov et al., Bacterial sigma factors: a historical, structural, and genomic perspective. Annu Rev Microbiol. 2014;68:357-76. doi: 10.1146/annurev-micro-092412-155737.

Grigorova et al., Insights into transcriptional regulation and sigma competition from an equilibrium model of RNA polymerase binding to DNA. Proc Natl Acad Sci U S A. Apr. 4, 2006;103(14):5332-7.

Gruber et al., Multiple sigma subunits and the partitioning of bacterial transcription space. Annu Rev Microbiol. 2003;57:441-66.

Purnick et al., The second wave of synthetic biology: from modules to systems. Nat Rev Mol Cell Biol. Jun. 2009;10(6):410-22. doi: 10.1038/nrm2698.

Rhodius et al., Design of orthogonal genetic switches based on a crosstalk map of σs, anti-σs, and promoters. Mol Syst Biol. Oct. 29, 2013;9:702. doi: 10.1038/msb.2013.58.

PCT/US2013/032145, dated Jun. 25, 2013, International Search Report and Written Opinion.

PCT/US2013/032145, dated Oct. 9, 2014, International Preliminary Report on Patentability.

* cited by examiner

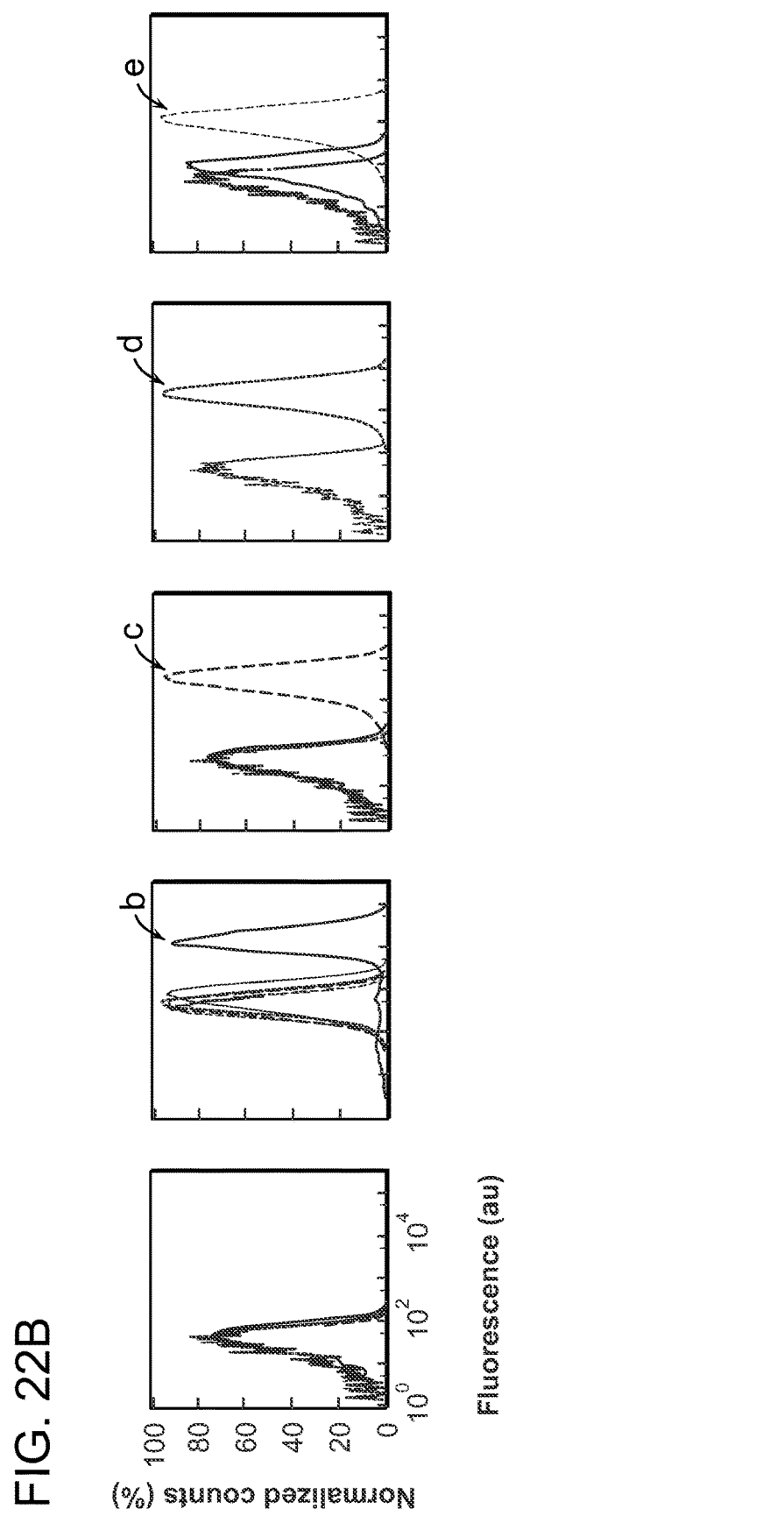

SEQUENCE LISTING

```
<160> NUMBER OF SEQ ID NOS: 67

<210> SEQ ID NO 1
<211> LENGTH: 216
<212> TYPE: PRT
<213> ORGANISM: Pseudoalteromonas atlantica T6c

<400> SEQUENCE: 1

Met Ser Asn Tyr Asp Asn Ala Glu Leu Leu Ala Leu Trp Leu Glu Gly
1               5                   10                  15
```

```
Lys Leu Thr Pro Lys Gln Arg Asp Glu Phe Glu Gln Arg Cys Ile Gln
            20                  25                  30

Asp Ser Gln Phe Ala Glu Gln Val Asp Ala Ala Ala Met Val Lys Ile
            35                  40                  45

Gly Ala Asp Asp Tyr Ser Ser Glu Val Pro Gln Trp Asn Lys Ala
 50                  55                  60

Ala Thr Phe Glu Pro Gln Gln Ala Asn Asn Ser Gly Ser Trp Leu Ser
 65                  70                  75                  80

Gly Val Ser Leu Val Thr Ser Ala Leu Ala Ile Val Leu Val Leu Thr
                    85                  90                  95

Gly Thr Gln Val Thr Thr Ser Glu Gly Glu Leu Arg Ile Arg Phe Gly
                   100                 105                 110

Ser Gly Gln Ser Glu Gln Ala Leu Val Lys Leu Val Asp Ser Lys Leu
                   115                 120                 125

Asp Ala Phe Lys Gln Asn Gln Gln Asp Ala Phe Thr Leu Tyr Ala Gln
            130                 135                 140

Thr Leu Gln Gln Gln Gln Ser Glu Ser Ala Ser Gln Leu Thr Asn Tyr
145                 150                 155                 160

Leu Leu Ser Ser Ser Arg Lys Glu Arg Glu Asp Phe Ala Glu Leu
                   165                 170                 175

Ile Lys Phe Val Asn Gln Gln Arg Ser Asp Asp Gln Leu Phe Tyr Ala
                   180                 185                 190

Arg Gln Leu Asn Gln Leu Gln Gln Asp Val Tyr His Asp Ala Thr Gly
            195                 200                 205

Val Ala Leu Glu Ser Ile Gln Gln
            210                 215

<210> SEQ ID NO 2
<211> LENGTH: 202
<212> TYPE: PRT
<213> ORGANISM: Shewanella frigidimarina NCIMB 400

<400> SEQUENCE: 2

Met Asn Gln Ser Pro Gln Asp Leu Asp Ser Leu Ile Lys Ser Leu Pro
 1               5                  10                  15

Leu Glu Met Gln Pro Thr Thr Asp Leu Trp Pro Glu Ile Thr Ala Gln
            20                  25                  30

Leu Ser Pro Gln Ser Gln Gln Lys Thr His Leu Thr Arg Pro Trp Leu
            35                  40                  45

Ile Ala Ala Ser Val Ala Val Leu Ser Leu Leu Ala Met Leu Leu Trp
 50                  55                  60

Gln Arg Pro Asp Gly Asn Ser Leu Leu Pro Gln Thr Ala Thr Ile Thr
65                  70                  75                  80

Thr Thr Val Pro Gly Ala Thr Leu Asn Thr Glu Ala Thr Leu Ala Glu
                    85                  90                  95

Ser Thr Leu Val Glu Leu Val Asp Gln Ile Ala Leu Thr His Gln Thr
                   100                 105                 110

Gln Leu Asp Val Phe Asn Gln Asn Gln Tyr Thr Val Ser Trp Gln Leu
            115                 120                 125

Ser Ser Thr Asp Ala Pro Gln Gln Ile Gln Ser Asp Ile Ser Gln Ala
            130                 135                 140

Leu Ala Glu Leu Asp Thr Ala Ser Lys Gln Val Gln Ala Ala Leu Lys
145                 150                 155                 160

Gln Gln Pro Thr Asn Gln Gln Met Trp Gln Leu Trp Arg Trp Ile Met
```

```
                165                 170                 175
Gln Arg Gln Ile Thr Leu Leu Gln Gln Gly Gln Lys Leu Pro Phe Thr
            180                 185                 190

Ser Lys Arg Thr Ser Gln Gly Asn Thr Ile
        195                 200

<210> SEQ ID NO 3
<211> LENGTH: 198
<212> TYPE: PRT
<213> ORGANISM: Shewanella amazonensis SB2B

<400> SEQUENCE: 3

Met Glu Lys Thr Gly Gln Glu Trp Val Ser Ala Ser Val Asp Gly Glu
1               5                   10                  15

Thr Asp Arg Gln Thr Leu Ala Glu Leu Ala Ala Asp Thr Asp Ser His
            20                  25                  30

Ala Lys Trp Gln Arg Tyr His Leu Met Gly Asp Ala Met Arg Asp Glu
        35                  40                  45

Leu Pro Gln Ala Met Pro Leu Asp Leu Ser Ala Arg Ile Ala Ala Ala
    50                  55                  60

Leu Glu Asp Glu Pro Thr Ile Leu Ala Pro Lys Val Glu Arg Glu Ala
65                  70                  75                  80

Thr Gln Ala Pro Ser Arg Ala Val Val Pro Phe Met Arg Gln Leu
                85                  90                  95

Gly Gln Tyr Gly Ile Ala Ala Val Ala Leu Met Ala Val Val Gly
            100                 105                 110

Val Gln Asn Tyr Gln Ser Thr Gln Asp Asp Ala Pro Leu Pro Val Leu
        115                 120                 125

Asn Thr Arg Pro Leu Val Gly Thr Ala Thr Pro Val Ser Leu Gln Thr
    130                 135                 140

Gly Pro Val Ala Asn Gln Asn Gln Gly Asn Ala Asn Asp Gln Leu Leu
145                 150                 155                 160

Glu Gln Arg Arg Arg Ile Asn Ala Tyr Leu Gln Asp His Met Leu Gln
                165                 170                 175

Gln Arg Leu Asn Thr Gly Ala Val Val Asp Asp Asn Ser Glu Val Thr
            180                 185                 190

Pro Ile Pro Val Asn Arg
        195

<210> SEQ ID NO 4
<211> LENGTH: 216
<212> TYPE: PRT
<213> ORGANISM: Escherichia coli K12

<400> SEQUENCE: 4

Met Gln Lys Glu Gln Leu Ser Ala Leu Met Asp Gly Glu Thr Leu Asp
1               5                   10                  15

Ser Glu Leu Leu Asn Glu Leu Ala His Asn Pro Glu Met Gln Lys Thr
            20                  25                  30

Trp Glu Ser Tyr His Leu Ile Arg Asp Ser Met Arg Gly Asp Thr Pro
        35                  40                  45

Glu Val Leu His Phe Asp Ile Ser Arg Val Met Ala Ala Ile Glu
    50                  55                  60

Glu Glu Pro Val Arg Gln Pro Ala Thr Leu Ile Pro Glu Ala Gln Pro
65                  70                  75                  80

Ala Pro His Gln Trp Gln Lys Met Pro Phe Trp Gln Lys Val Arg Pro
```

```
                        85                  90                  95
Trp Ala Ala Gln Leu Thr Gln Met Gly Val Ala Ala Cys Val Ser Leu
                100                 105                 110

Ala Val Ile Val Gly Val Gln His Tyr Asn Gly Gln Ser Glu Thr Ser
            115                 120                 125

Gln Gln Pro Glu Thr Pro Val Phe Asn Thr Leu Pro Met Met Gly Lys
        130                 135                 140

Ala Ser Pro Val Ser Leu Gly Val Pro Ser Glu Ala Thr Ala Asn Asn
145                 150                 155                 160

Gly Gln Gln Gln Gln Val Gln Glu Gln Arg Arg Arg Ile Asn Ala Met
                165                 170                 175

Leu Gln Asp Tyr Glu Leu Gln Arg Arg Leu His Ser Glu Gln Leu Gln
            180                 185                 190

Phe Glu Gln Ala Gln Thr Gln Gln Ala Ala Val Gln Val Pro Gly Ile
        195                 200                 205

Gln Thr Leu Gly Thr Gln Ser Gln
    210                 215

<210> SEQ ID NO 5
<211> LENGTH: 119
<212> TYPE: PRT
<213> ORGANISM: Bacteroides thetaiotaomicron VPI-5482

<400> SEQUENCE: 5

Met Asp Lys Asp Phe Asp Phe Asp Asn Ile Gly Lys Arg Thr Pro Tyr
1               5                   10                  15

Arg Thr Pro Asp Asn Phe Phe Glu Glu Thr Gln Arg Lys Ile Leu Glu
            20                  25                  30

Arg Thr Val Asp Glu Gln Arg Lys Arg Arg Leu Lys Arg Ile Ile
        35                  40                  45

Pro Thr Val Ile Ala Val Ala Ala Val Leu Ala Gly Ile Leu Phe Thr
    50                  55                  60

Pro Ser Leu Arg Tyr Met Asn Thr Asp Thr Pro Ser Ala Ser Asn Ile
65                  70                  75                  80

Leu Ala Val Asp Lys Asn Asn Val Thr Thr Asp Pro Val Asp Lys Trp
                85                  90                  95

Ile Lys Glu Leu Ser Asp Glu Glu Leu Glu Glu Leu Val Ser Phe Ser
                100                 105                 110

Glu Asn Asp Ile Phe Leu Asn
            115

<210> SEQ ID NO 6
<211> LENGTH: 136
<212> TYPE: PRT
<213> ORGANISM: Porphyromonas gingivalis W83

<400> SEQUENCE: 6

Met Lys Gln Phe Asp Pro Asp Val Asn Ile Arg Pro Lys Glu Asp Ser
1               5                   10                  15

Ile Arg His Tyr Ser Val Pro Asp Asp Tyr Phe Ala Ser Phe Thr Asp
            20                  25                  30

Lys Leu Met Ala Gln Ile Pro Ala Val Lys Glu Glu Asn Thr Val Val
        35                  40                  45

Val Pro Ser Val Ala Leu Trp Pro Lys Leu Arg Pro Leu Leu Tyr Leu
    50                  55                  60

Ala Ala Ser Phe Leu Leu Met Ile Gly Met Phe Lys Ala Phe Ser Leu
```

```
                65                  70                  75                  80
Phe Gly Val Gly Ser Asp Thr Gly Arg Thr Thr Ser Thr Ser Ala Gly
                85                  90                  95

Leu Val Ala Leu Asp His Gly Asp Thr Arg Trp Ser Glu Asp Thr Asp
            100                 105                 110

Tyr Arg Asp Phe Leu His Asp Asn Cys Ala Glu Thr Val Ser Asp Glu
            115                 120                 125

Trp Val Leu Thr Asp Phe Ser Glu
            130                 135

<210> SEQ ID NO 7
<211> LENGTH: 117
<212> TYPE: PRT
<213> ORGANISM: Chlorobium tepidum TLS

<400> SEQUENCE: 7

Met Asn Arg Thr Thr Glu Gln Arg Asn Ala Glu Val Met Lys Thr Ile
1               5                   10                  15

Gly Leu Leu Asp Gln Met Pro Arg Val Glu Val Asp His Leu Phe Arg
            20                  25                  30

Val Arg Leu Met Gln Arg Ile Glu Ala Met Glu Val Lys Lys Thr Ser
        35                  40                  45

Trp Ser Ala Leu Pro Gly Gly Ala Phe Asn Pro Arg Leu Ala Phe Met
    50                  55                  60

Ala Leu Leu Leu Met Leu Asn Ile Ala Ser Ala Leu Met Leu Phe Met
65                  70                  75                  80

His Gly Thr Pro Gln Ala Thr Gly Ser Ser Gly Ala Ile Ala Glu Ser
                85                  90                  95

Leu Thr Glu Asp Tyr Gly Gly Pro Ala Leu Ser Tyr Tyr Asp Asp Gln
            100                 105                 110

Thr Thr Ile Asp Arg
        115

<210> SEQ ID NO 8
<211> LENGTH: 320
<212> TYPE: PRT
<213> ORGANISM: Pseudomonas syringae pv. tomato str. DC3000

<400> SEQUENCE: 8

Met Ser Asp Gln Arg Glu Pro Ser Glu Arg Met Ile Thr Glu Ala Ala
1               5                   10                  15

Ser Trp Leu Ala Leu Leu Gln Asp Glu Pro Val Ser Ala Ala Asp Arg
            20                  25                  30

His Ala Phe Glu Arg Trp Arg Lys Ala Asp Pro Gly His Gln Leu Ala
        35                  40                  45

Leu Ser Arg Met Gln Ser Leu Trp Gly Ser Phe Asp Glu Leu Ser Asp
    50                  55                  60

Thr Pro Ala Arg Ile Ala Leu Arg Gln Thr Phe Ala Pro Ala Gly Ser
65                  70                  75                  80

Lys Pro Thr Ser Arg Thr Val Gln Ala Leu Ala Leu Val Gly Val Leu
                85                  90                  95

Val Cys Gly Trp Met Ser Val Glu Arg Leu Pro Val Trp Met Ala Asp
            100                 105                 110

Arg His Thr Asp Val Gly Glu Arg Ser Glu Phe Ser Leu Ala Asp Gly
            115                 120                 125

Ser Gln Val Gln Leu Asn Ser Gly Ser Ala Leu Asp Val Lys Phe Asp
```

```
Gly Arg Gln Arg Val Ile Glu Leu Leu Gln Gly Glu Leu Trp Val Glu
145                 150                 155                 160

Val Ala Lys Asp Val Gln Arg Pro Phe Val Val Arg Thr Asp Gln Gly
                165                 170                 175

Thr Ile Thr Ala Leu Gly Thr Arg Phe Val Val Arg Arg Gly Glu Glu
            180                 185                 190

Gly Thr Thr Val Ser Val Leu Glu Ser Ala Ile Ala Ala Gln Ala Asn
            195                 200                 205

Thr Ala Asp Val Ile Asn Val Ala Thr Gly Gln Gln Ala Leu Leu Lys
            210                 215                 220

Asp Gly Arg Val Gln Thr Pro His Ala Leu Gly Ser Asp Asp Pro Ala
225                 230                 235                 240

Asp Trp Thr Arg Gly Val Leu Lys Val Asp Asp Gln Pro Leu Ser Glu
                245                 250                 255

Val Leu Gln Thr Leu Ala Thr Tyr Arg His Gly Leu Leu Arg Tyr Asp
                260                 265                 270

Thr Gln Ala Leu Ala Gly Leu Arg Val Ser Gly Val Phe Arg Leu Asp
            275                 280                 285

Asp Thr Asp Ala Ala Leu Ala Thr Leu Ala Asp Asn Leu Pro Ile Lys
290                 295                 300

Val Glu Arg Phe Thr Asp Leu Leu Val Ile Val Lys Pro Asp Ala Arg
305                 310                 315                 320

<210> SEQ ID NO 9
<211> LENGTH: 318
<212> TYPE: PRT
<213> ORGANISM: Pseudomonas putida KT2440

<400> SEQUENCE: 9

Met Ser Asn Leu Pro Val Ser Ser Arg Val Leu Glu Ala Ala Ile Ala
1               5                   10                  15

Trp Lys Leu Ser Leu Gly Glu Ser Ser Gly Thr Pro Asp Glu Arg Asn
                20                  25                  30

Glu Phe Met Arg Trp His Ala Ala Ser Glu Glu His Ala Arg Ala Trp
            35                  40                  45

Arg Gln Leu Gly Ala Met Asp Gln Arg Val Ser Ala Ala Ala Gly Pro
50                  55                  60

Ala Arg Gln Ala Leu Leu Gln Ser Arg Ala Ser Leu Arg Arg Arg Ile
65                  70                  75                  80

Gly Lys Val Gly Gly Gly Leu Ala Gly Thr Phe Leu Leu Gly Ala Leu
                85                  90                  95

Leu Ala Trp Val Gly Ala Pro Ser Leu Ala Pro Ser Tyr Trp Leu Ala
                100                 105                 110

Asp Gln Arg Thr Ala Thr Gly Glu Leu Arg Thr Leu Arg Leu Glu Asp
            115                 120                 125

Gly Thr Leu Leu Ser Leu Asn Thr His Thr Ala Val Asp Ile Glu Tyr
130                 135                 140

Ala Gly Ala Gln Arg Val Ile Val Leu His Gln Gly Glu Ile Ser Val
145                 150                 155                 160

Glu Thr Gly His Gln Asp Pro Arg Pro Leu Leu Val Arg Thr Glu Asp
                165                 170                 175

Gly Arg Leu Arg Pro Leu Gly Thr Arg Phe Leu Val Arg Arg Glu Ala
            180                 185                 190
```

Gly Gly Thr Arg Leu Glu Val Leu Gln Ala Ser Val Ala Met Pro
            195                 200                 205

His Asp Ser Gly Asp Glu Gln Val Leu Arg Glu Gly Gln Gln Val Leu
210                 215                 220

Met Asn Ala Asn Gly Leu Gly Glu Val Gly Thr Val Pro Ala Gly Ala
225                 230                 235                 240

Asp Ala Trp Thr Arg Gly Met Leu Val Val Asp Asn Val Arg Leu Gly
                245                 250                 255

Asp Leu Leu Ala Thr Leu Gly Gln Tyr Arg Ser Gly Tyr Leu Gly Val
                260                 265                 270

Asp Ala Lys Val Ala Asp Leu Arg Val Thr Gly Ser Phe Pro Leu Thr
            275                 280                 285

Asn Thr Asp Leu Ala Leu Ala Ser Leu Val Pro Ala Leu Pro Val Lys
            290                 295                 300

Ile Glu Arg His Thr Gln Trp Trp Val Asn Val Thr Ser Lys
305                 310                 315

<210> SEQ ID NO 10
<211> LENGTH: 323
<212> TYPE: PRT
<213> ORGANISM: Pseudomonas aeruginosa PAO1

<400> SEQUENCE: 10

Met Ser Ala Asp Asp Arg His Ser Pro Val Arg Ala Arg Val Leu Asp
1               5                   10                  15

Glu Ala Ile Ala Trp Gln Leu Leu Asp Ser Gly Glu Ala His Pro
                20                  25                  30

Asp Asp His Arg Ala Phe His Arg Trp Tyr Ala Ala His Pro Glu His
            35                  40                  45

Glu Arg Ala Trp Glu Gln Leu Gly Gly Leu Asp Arg His Leu Ala Arg
    50                  55                  60

Ala Ala Asn Gly Pro Ala Arg Asn Ala Leu Leu Ser Gly Asn Ala Arg
65              70                  75                  80

Phe Lys Arg Arg Leu Arg Arg Leu Gly Gly Ser Ala Leu Gly Leu Val
                85                  90                  95

Leu Ala Leu Gly Val Gly Leu Gly Val Ala Asn Arg Tyr Val Pro Val
            100                 105                 110

Arg Tyr Leu Leu Ala Asp Ala Tyr Ser Ala Thr Gly Glu Gln Arg Glu
        115                 120                 125

Leu Thr Leu Pro Asp Ala Thr His Val Arg Leu Asn Ser Arg Ser Ala
    130                 135                 140

Ile Asp Val Arg Phe Asp Gly Glu Arg Arg Gln Val Val Leu Leu Ala
145                 150                 155                 160

Gly Glu Ile Leu Val Glu Thr Ala His Gly Asp Pro Arg Pro Phe Val
                165                 170                 175

Val Ser Ser Ala Asp Gly Asp Met Arg Ala Leu Gly Thr Arg Phe Leu
            180                 185                 190

Val Arg Arg Glu Glu Pro Gly Thr Arg Leu Thr Val Leu Gln Ser Ala
        195                 200                 205

Val Ala Ala Arg Ala Glu Thr Leu Ser Glu Glu Arg Val Ile Lys Glu
    210                 215                 220

Gly Gln Gln Val Leu Ile Leu Pro Gln Gly Leu Gln Ala Ser Glu Ala
225                 230                 235                 240

Ala Pro Ala Leu Ala Gly Ala Trp Ala Gln Gly Met Leu Val Val Glu
                245                 250                 255

-continued

```
Asn Ala Arg Leu Ala Asp Leu Val Ala Glu Leu Gly Arg Tyr Ser Pro
                260                 265                 270

Ala Leu Leu Gln Val Asp Pro Ser Ile Ala Asp Leu Arg Val Thr Gly
            275                 280                 285

Ser Phe Pro Leu Lys Asp Thr Arg Leu Ala Leu Gln Ala Leu Glu Pro
290                 295                 300

Ser Leu Pro Val Arg Ser Val Arg His Asn Ala Trp Trp Phe Glu Val
305                 310                 315                 320

Val Pro Arg

<210> SEQ ID NO 11
<211> LENGTH: 328
<212> TYPE: PRT
<213> ORGANISM: Pseudomonas aeruginosa PAO1

<400> SEQUENCE: 11

Met Asn Ser Pro Gln Glu Gln Gln Ile Arg Gln Gln Ala Ala Glu
1               5                   10                  15

Trp Ala Ile Arg Leu Asp Gly Gly Asp Leu Asp Arg Ser Arg Arg Glu
                20                  25                  30

Ala Leu Asp Gly Trp Leu Ala Ala Asp Pro Arg His Arg Ala Ala Leu
            35                  40                  45

Ala Leu Ala Gln Arg Thr Trp Lys Gln Leu Gly Ser Leu Ala Glu Pro
        50                  55                  60

Arg Thr Met Val Gln Thr Pro Val Ala Ser Pro Arg Arg Ala Gly
65                  70                  75                  80

Gly Arg Arg Lys Gly Trp Arg Gly Trp Ala Ala Ala Ala Val Leu
                85                  90                  95

Leu Ala Leu Gly Ser Ala Trp Asn Glu Arg Asp Ala Gly Val Ser Trp
            100                 105                 110

Leu Ala Asp His Ser Thr Gly Lys Gly Glu Val Arg Ile Leu Arg Leu
        115                 120                 125

Val Asp Gly Ser Glu Val Glu Leu Asp Ala Gln Ser Ala Ile Asp Val
    130                 135                 140

Ala Tyr Asp Ser Arg Glu Arg Val Arg Leu Leu Glu Gly Ser Ala
145                 150                 155                 160

Ile Phe Arg Ala Ala Pro Arg Ala Gly Arg Glu Thr Arg Pro Phe Val
                165                 170                 175

Val Glu Ser Ala Gly Gly Ser Thr Arg Ala Leu Gly Thr Arg Phe Leu
            180                 185                 190

Val Ser Arg Asn Asp Asp Gly Ser Val Gln Val Gly Val Leu Glu His
        195                 200                 205

Arg Val Ala Val Ala Leu Ala His Pro Arg Thr Gly Thr Val Gly Arg
    210                 215                 220

Arg Glu Leu Gly Glu Gly Glu Ser Leu Arg Tyr Ser Ala Glu Gly Gly
225                 230                 235                 240

Val Glu Ala Pro Leu Gly Gly Arg Leu Asp Asp Leu Thr Ser Trp Arg
                245                 250                 255

Arg Gly Leu Leu Val Phe Asp Glu Gln Pro Leu Gly Glu Val Val Ala
            260                 265                 270

Arg Leu Asn Arg Tyr Arg Pro Gly His Leu Leu Val Ala Pro Gly Ala
        275                 280                 285

Leu Ala Gln Arg Arg Val Ser Gly Val Phe Arg Val Ala Asp Leu Glu
    290                 295                 300
```

Ala Ser Leu Gln Ser Ile Ser Asp Glu Leu Gly Val Arg Ser Leu Gly
305                 310                 315                 320

Leu Ala Gly Val Thr Leu Leu Tyr
                325

<210> SEQ ID NO 12
<211> LENGTH: 319
<212> TYPE: PRT
<213> ORGANISM: Pseudomonas aeruginosa PAO1

<400> SEQUENCE: 12

Met Thr Ala Ser Asp Ser Ala Ala Asp Glu Thr Gly Asp Leu Arg His
1               5                   10                  15

Glu Ala His Ala Trp Val Ile Ser Leu Thr Ser Gly Arg Val Thr Gln
                20                  25                  30

Gly Asp Ala Arg Ala Phe Arg Gln Trp Cys Ala Arg Ser Pro Gln His
            35                  40                  45

Leu Arg Ala Phe Val Glu Ala Arg Asp Leu Trp Gln Ala Leu Gly Ser
    50                  55                  60

Ala Ala Ala Leu Pro Leu Glu Pro Pro Ala Val Ala Gln Ile Ala Pro
65                  70                  75                  80

Arg Arg Phe Gly Arg Arg Trp Phe Val Gly Gly Ala Leu Ala Ala Ser
                85                  90                  95

Val Ala Leu Phe Val Leu Arg Pro Ser Leu Leu Asp His Gly Leu Gly
                100                 105                 110

Gly Ala Asp Tyr Val Thr Ala Val Gly Glu Gln Arg Gln Val Gln Val
            115                 120                 125

Ser Gly Glu Thr Arg Ile Glu Met Asn Thr Arg Thr Arg Leu Asn Val
    130                 135                 140

Arg Arg Asn Gln Glu Gln Gln Glu Thr Ile Glu Leu Leu Gly Gly Glu
145                 150                 155                 160

Ala Glu Ile Ile Ala Ser His Pro Pro Gln Ser Ser Leu Arg Val Met
                165                 170                 175

Ala Gly Ser Ala Trp Leu Ser Ala Ser Arg Ala Arg Phe Asn Val Arg
                180                 185                 190

Ser Ser Gly Asp Val Cys Val Val Thr Cys Leu Glu Gly Ser Val Arg
            195                 200                 205

Leu Glu His Leu Gly Gln Arg Leu Asp Leu Gln Ala Gly Gln Gln Leu
    210                 215                 220

Thr Phe Asp Glu Arg Arg Asn Gly Pro Pro Val Pro Phe Asp Val Ala
225                 230                 235                 240

Glu Val Met Ala Trp Arg Glu Arg Met Leu Val Phe Asn Asp Val Pro
                245                 250                 255

Leu Ala Thr Val Ile Asp Glu Ile Asn Arg Tyr Arg Pro Gly Met Leu
                260                 265                 270

Leu Leu Leu Asp Lys Ala Leu Gly Arg Arg Val Gln Ala Arg Phe
            275                 280                 285

Ser Leu Asp Gln Leu Ala Asp Val Ala Thr Leu Ile Arg Asp Ala Tyr
    290                 295                 300

Gly Ile Glu Val Thr Arg Leu Pro Gly Gly Val Val Leu Leu Gly
305                 310                 315

<210> SEQ ID NO 13
<211> LENGTH: 316
<212> TYPE: PRT

<213> ORGANISM: Pseudomonas fluorescens Pf-5

<400> SEQUENCE: 13

Met Asn Ile Phe Ser Ile Ser Thr Pro Gln Ala Ser Ala Asp Gln Gln
1               5                   10                  15

Leu Leu Asn Glu Ala Arg Asp Trp Leu Val Leu Thr Ser Gly Gln
            20                  25                  30

Ala Thr Ala Ala Asp Ala Arg Ala Leu Arg Gln Trp Cys Gly Gln Ser
        35                  40                  45

Pro Gln His Ala Ala Ala Phe Glu Gln Thr Lys Ala Leu Trp His Cys
    50                  55                  60

Leu Gln Pro Ala Ala Ala Leu Leu Glu Gln Gln Ala Arg Pro Arg His
65                  70                  75                  80

Phe Gly Arg Arg Ala Phe Leu Gly Gly Ala Leu Ala Ala Ser Ala Ala
                85                  90                  95

Leu Phe Met Val Arg Leu Thr Val Pro Gly Gly Phe Ala Gly Leu Thr
            100                 105                 110

Ala Asp Phe Ala Thr Glu Val Gly Glu Gln Arg Arg Val Asp Leu Ala
        115                 120                 125

Glu Gly Val Ser Leu Glu Leu Asn Thr Gln Thr Arg Ile Ser Arg Arg
    130                 135                 140

Asp Leu Gly Ala Gly Glu Gln Gly Ile Glu Leu Leu Glu Gly Glu Val
145                 150                 155                 160

Glu Val Phe Ser Gln Arg Leu Gln Pro Leu Lys Val Gln Ala Gly Glu
                165                 170                 175

Gly Trp Leu Ser Ala Arg Gln Ala Arg Phe Asn Leu Arg Asn Thr Asp
            180                 185                 190

His Gln Val Cys Val Thr Cys Ile Glu Gly Ser Leu Gln Val Asp Val
        195                 200                 205

Ala Gly Arg Ser Ile Gly Leu Asp Ser Gly Arg Gln Leu Thr Tyr Asp
    210                 215                 220

Pro Arg Ser Ile Gly Glu Pro Gln Val Val Asp Ile His Ser Val Ile
225                 230                 235                 240

Ala Trp Arg Glu Gln Val Leu Val Phe Asp Asn Ala Ser Leu Asn Thr
                245                 250                 255

Val Ile Ser Glu Ile Asn Arg Tyr Arg Pro Gly Met Leu Val Leu Leu
            260                 265                 270

Asn Ala Glu Leu Gly Lys Arg Lys Val Gln Ala Arg Phe Asn Leu Asn
        275                 280                 285

Gln Leu Ala Gly Val Ala Leu Leu Ile Arg Asp Ala Tyr Gly Ala Lys
    290                 295                 300

Cys Thr Glu Leu Pro Gly Gly Val Val Leu Leu Ser
305                 310                 315

<210> SEQ ID NO 14
<211> LENGTH: 314
<212> TYPE: PRT
<213> ORGANISM: Pseudomonas fluorescens Pf-5

<400> SEQUENCE: 14

Met Trp Gln Ala Ala Met Asp Trp Leu Leu Gln Cys His Ser Ala Pro
1               5                   10                  15

Asp Asp Ala Leu Leu Gln Gln Ala His Ala Arg Trp Leu Ala Ala Asp
            20                  25                  30

Glu Arg His Ala Val Ala Trp Arg Lys Ala Glu Lys Val Trp Leu Leu

```
            35                  40                  45
Ser Gly Gly Leu Ala Pro Leu Glu Pro Val Pro Gln Pro Leu Pro
 50                  55                  60

Thr Pro Leu Arg Ala Arg Arg Asn Arg Pro Arg Arg Ala Leu Lys Ala
 65                  70                  75                  80

Leu Ala Leu Ala Ala Cys Leu Leu Leu Leu Ala Gly Pro Thr Pro Pro
                 85                  90                  95

Thr Ala His Thr Ser Pro Ala Gly Glu His Arg Gln Val Leu Leu Ser
                100                 105                 110

Asp Gly Ser Arg Ile Glu Leu Gly Ser Asp Ser Ala Ile Arg Val Asp
            115                 120                 125

Phe Glu Pro Gly Thr Arg Ala Val Thr Leu Leu Arg Gly Gln Ala Phe
130                 135                 140

Phe Glu Val Ser His Asp Ala Ser Arg Pro Phe Thr Val Gln Ala Ala
145                 150                 155                 160

Asp Val Lys Val Arg Val Ile Gly Thr Ala Phe Asp Val Asp Leu Ser
                165                 170                 175

Arg Thr Ala Val Val Ala Val Gln Ser Gly Ala Val Gln Val Arg
            180                 185                 190

Asp Gly Arg Gly Glu Leu Ala Val Pro Ala Leu Gly Pro Gly Asp Ser
            195                 200                 205

Leu Arg Leu Gly Leu Asp Gln Gly Pro Pro Gln Arg Gly Arg Leu Leu
210                 215                 220

Pro Gly Gln Val Ala Pro Trp Arg Gln Trp Gln Leu Leu Val Asn Asp
225                 230                 235                 240

Arg Pro Leu Ser Glu Val Val Glu Ala Leu Gln Asp Tyr Tyr Pro Gly
                245                 250                 255

Val Leu Leu Leu Thr Asp Pro Ala Leu Gly Glu Arg Arg Ile Thr Ala
                260                 265                 270

Ser Leu Asn Leu Arg Ser Pro Val Ser Ala Leu Gln Leu Ala Ile Ala
            275                 280                 285

Pro Leu Gly Gly His Leu Arg Gln Trp Gly Pro Tyr Leu Thr Leu Ile
290                 295                 300

Arg Lys Glu Pro Gln Val Pro Ala Lys Gln
305                 310

<210> SEQ ID NO 15
<211> LENGTH: 358
<212> TYPE: PRT
<213> ORGANISM: Pseudoalteromonas haloplanktis TAC125

<400> SEQUENCE: 15

Met Ser Asn Ile His Gln Phe Thr Pro Lys Asp Leu Ile Leu Glu Thr
 1               5                  10                  15

Ala Ala Asn Trp Ile Ser Ala Ile Asp Arg Gly Leu Asn Lys Val Glu
                20                  25                  30

Lys Glu Gln Phe Lys Leu Trp Met Leu Gln Ser Asn Ala His Gln Asp
            35                  40                  45

Ala Val Tyr Glu Leu Ala Lys Leu Trp Asp Glu Leu Ser Val Leu Asn
 50                  55                  60

Glu Leu Ser Thr Leu Phe Pro His Lys Asn Asn Thr Glu Glu Lys Ser
 65                  70                  75                  80

Lys Trp Val Phe Ser Tyr Gly Ile Ala Ala Ser Leu Phe Ala Ala Leu
                85                  90                  95
```

Met Ile Cys Ser Tyr Leu Leu Val Asn Leu Glu Thr Gly Tyr Asn Gln
                100                 105                 110

Ala Leu Ala Lys Val Asn Tyr Thr Lys Ile Tyr Lys Thr Lys Val Gly
            115                 120                 125

Glu Gln Ala Thr Tyr Val Leu Pro Asp Gly Thr Ile Val Gln Leu Asn
        130                 135                 140

Thr Asn Ser Leu Leu Glu Val Ala Tyr Ser Lys Gly Arg Arg Gln Leu
145                 150                 155                 160

Leu Leu Ser Arg Gly Glu Gly Arg Phe Asn Val Ala Lys Asp Ala Thr
                165                 170                 175

Arg Pro Phe Ser Val Met Ala Gly Asp Lys Ser Phe Thr Ala Leu Gly
            180                 185                 190

Thr Val Phe Asn Val Gln Arg Asn Thr Ser Ser His Leu Glu Leu Val
        195                 200                 205

Val Thr Glu Gly Lys Val Met Ile Thr Asp Pro Ser Val Ala Val Asp
210                 215                 220

Ala Asn Asp Phe Lys Ala Tyr Gln Leu Ala Asp Asn Ser Thr Gln Lys
225                 230                 235                 240

Ile Arg Lys Ile Asn Ala Asn Ile Val Leu Ser Gly Glu Lys Ala Ile
                245                 250                 255

Ile Glu Lys Ser Val Thr Ala Pro Ile Lys Arg Leu Ser Ala Asp Asp
            260                 265                 270

Val Gln Arg Asp Leu Ala Trp Gln Asn Gly Met Leu Ile Phe Asn Gly
        275                 280                 285

Glu Gln Leu Ser Asp Ala Leu Asn Glu Val Ser Arg Tyr Thr Ala Thr
290                 295                 300

Arg Phe Glu Leu Ser Ser Ala Glu Leu Ala Asn Ile Lys Val Ala Gly
305                 310                 315                 320

Val Phe Lys Ala Gly Asp Val Ala Gly Leu Leu Glu Ser Leu Lys Thr
                325                 330                 335

Asn Phe Ser Ile Asp His Glu Arg Leu Gly Glu His Val Val Ser Leu
            340                 345                 350

Lys Arg Gln Thr Lys Ser
        355

<210> SEQ ID NO 16
<211> LENGTH: 219
<212> TYPE: PRT
<213> ORGANISM: Vibrio parahaemolyticus RIMD 2210633

<400> SEQUENCE: 16

Met Asn Lys His Pro Asp Asn Asn Leu Leu Glu Ala Tyr Ala Ser Gly
1               5                   10                  15

Ser Ile Asp Ala Val Ser Gly Leu Val Val Ala Thr His Leu Glu Thr
            20                  25                  30

Cys Ser Lys Cys Arg Ala Tyr Val Asn Gln Val Glu Ala Ser Gln Ala
        35                  40                  45

Asn Thr Val Ser Glu Ser Pro Ser Glu Tyr Ser Pro Glu Phe Asp Asp
    50                  55                  60

Met Leu Asn Asp Ile Ile Asn Ala Glu Pro Val Asn Asp Asn Val Val
65                  70                  75                  80

Ile Gln Asp Thr Ala Phe Val Asn Val Ala Gly Lys Ser Phe Glu Leu
                85                  90                  95

Pro Lys Thr Leu Val Arg Phe Ser Asp Leu Val Gly Ser Trp Arg Ser
            100                 105                 110

```
Tyr Gly Gly Lys Val Phe Ser Ala Gln Ile Asp Leu Gly Glu Asp Ala
            115                 120                 125

Arg Val Ser Leu Met Tyr Ile Gly Glu Asn Val Gln Ile Pro Gln His
        130                 135                 140

Thr His Arg Gly Leu Glu Ser Thr Leu Val Leu His Gly Gly Phe Ser
145                 150                 155                 160

Asp Glu Asp Gly Gln Tyr Glu Glu Gly Asp Leu Met Val Arg Asp Ala
                165                 170                 175

Ser Val Lys His Ser Pro Phe Thr Gln Glu Gly Glu Asp Cys Leu Cys
                180                 185                 190

Leu Thr Val Leu Thr Glu Pro Met Ile Phe Thr Gln Gly Val Ala Arg
            195                 200                 205

Ile Phe Asn Leu Phe Gly Lys Gly Leu Tyr Pro
            210                 215

<210> SEQ ID NO 17
<211> LENGTH: 220
<212> TYPE: PRT
<213> ORGANISM: Pseudomonas syringae pv. tomato str. DC3000

<400> SEQUENCE: 17

Met Gly Pro Leu His His Pro Asp Asp Ala Thr Leu Ile Ser Tyr Ala
1               5                   10                  15

Ala Gly Ala Leu Ser Gln Val Ile Ala Val Val Thr Ala Ala His Leu
            20                  25                  30

Glu Arg Cys Ala Glu Cys Arg Ala Arg Leu Arg Gln Ala Glu Gln Ile
        35                  40                  45

Gly Gly Val Leu Met Gln Gln Ser Ile Ser Arg Val Val Pro Leu Lys
    50                  55                  60

Ser Arg Met Ala Met Leu Ala Arg Leu Asp Glu Gln Glu Thr Ser Val
65                  70                  75                  80

Asp Ser Val Met His Ala Met Pro Ala Ala Asn His Asp Pro Asp Leu
                85                  90                  95

Leu Pro His Cys Met His Ala His Phe Gly Arg His Leu Ser Thr Leu
            100                 105                 110

Lys Trp Lys Thr Leu Ile Pro Gly Val Gln Arg Val Ser Ala Gln Gly
        115                 120                 125

Ile Glu Gln Gly Asn Leu Met Leu Leu Lys Ile Ala Pro Gly Val Ser
    130                 135                 140

Met Pro Val His Ser His Glu Ser Gly Glu Met Thr Met Val Leu Lys
145                 150                 155                 160

Gly Ala Tyr His Asp Val Gln Gly Glu Phe Gly Leu Asn Asp Val Ala
                165                 170                 175

Asp Leu Asp Ser His Ile Gln His Gln Pro Ile Ala Tyr Pro Asp Arg
                180                 185                 190

Glu Cys Ile Cys Val Leu Ala Ala Glu Ser Lys Leu Arg Phe His Gly
            195                 200                 205

Trp Met Ala Arg Met Met Gln Pro Phe Phe Gly Ile
            210                 215                 220

<210> SEQ ID NO 18
<211> LENGTH: 271
<212> TYPE: PRT
<213> ORGANISM: Anaeromyxobacter dehalogenans 2CP-C

<400> SEQUENCE: 18
```

Met Arg Thr Asp Ser Thr Leu Thr Ala Ala Met Asp Cys Arg Glu Leu
1               5                   10                  15

Glu Arg Ser Ile Asp Ala Tyr Leu Asp Gly Phe Asp Glu Arg Glu
            20                  25                  30

Arg Ala Glu Ala Glu Ala His Leu Ala Thr Cys Thr Pro Cys Arg Ala
        35                  40                  45

Met Ala Asp Arg Gln Gly Ala Leu Arg Leu Ala Leu Arg Ala Lys Leu
50                  55                  60

Arg Glu Ala Met Ala Ser Pro Ala Ala Gly Cys Ala Pro Pro His
65              70                  75                  80

Leu Arg Ala Arg Val Arg Thr Ser Leu Ala His Glu Arg Pro Leu
                85                  90                  95

Trp Arg Arg Val Leu Gln Pro Val Pro Val Ala Val Ala Ala Cys
                100                 105                 110

Ala Met Gly Val Leu Val Leu Ala Gly His Arg Gly Asp Thr Ala
            115                 120                 125

Leu Val Asp Asp Ala Ile Arg Val His His Arg Ala Leu Pro Leu Glu
130                 135                 140

Val Asp Ala Ala Ala Met Pro Gly Trp Phe Ala Gly Lys Leu Asp Phe
145                 150                 155                 160

His Pro Ala Leu Pro His Phe Ala Gly Ala Val Ala Arg Leu Glu Gly
                165                 170                 175

Ala Arg Leu Ser Asn Leu Arg Glu Trp Pro Ala Ala Tyr Val Arg Tyr
                180                 185                 190

Gln Leu Pro Arg Gly Gln Ala Gly Leu Phe Ile Val Asp Asp Pro Asp
                195                 200                 205

Arg Arg Phe Asp Thr Pro Gly Arg Glu Val Lys Val Gly Pro Gln Val
210                 215                 220

Val Arg Val Val Asn Ala Arg Gly Tyr Asn Val Ala Val Trp Arg Gln
225                 230                 235                 240

Asp Glu Ile Val Tyr Ser Leu Val Ser Asp Leu Asp Glu Asp Ala Leu
                245                 250                 255

Phe Lys Leu Val Gln Ala Ala Gln Ala Glu Ala Ala Gly Arg
                260                 265                 270

```
<210> SEQ ID NO 19
<211> LENGTH: 302
<212> TYPE: PRT
<213> ORGANISM: Myxococcus xanthus DK 1622

<400> SEQUENCE: 19
```

Met Asn Cys Gln Asp Leu Glu Arg Leu Leu Tyr Pro Tyr Leu Asp Gly
1               5                   10                  15

Glu Phe Gln Pro Glu Glu Arg Val Asp Leu Glu Thr His Leu Ser Gly
            20                  25                  30

Cys Ala Asp Cys Arg Arg Ala Glu Glu Lys Gln Met Gln Gln
        35                  40                  45

Ala Leu Arg Arg Ala Ala Arg His Ser Val Ser Gly Met Arg Ala Pro
50                  55                  60

Ala Ser Leu Arg Ala Gly Ile Gln Val Gly Leu Lys Gln Glu Gln Arg
65                  70                  75                  80

Arg Val Gln Phe Gly Val Trp Leu Arg Ala Gly Ala Met Ala Leu Val
                85                  90                  95

Val Val Thr Val Gly Gly Gly Trp Ala Ala Phe His Ala Glu Gln Arg

```
                100                 105                 110
Leu Ser Ala Ala Arg Thr Glu Ala Val Gln Arg His Ser Lys Ser Lys
            115                 120                 125

Ala Leu Pro Phe Glu Ile Ala Ser Asn Thr Pro Glu Gln Val Glu Glu
        130                 135                 140

Trp Phe Lys Asp Lys Val Asp Pro Arg Ile Thr Val Pro Gln Ile Pro
145                 150                 155                 160

Lys Ala Lys Pro Leu Gly Gly Arg Ile Ser Ile Leu Asn Gly Arg Glu
                165                 170                 175

Val Ala Tyr Ile Ser Tyr Glu Thr Leu Pro Asp Asn Glu Gly Glu Pro
            180                 185                 190

Ser Arg Arg Leu Gly Val Phe Val Leu Pro Gly Asp Asn Glu Val Val
        195                 200                 205

Ile Pro Lys Phe Gln Ala Leu Gln Ala Val Glu Val Asp Ser Ala Gln
            210                 215                 220

Gly Phe Asn Val Val Thr Trp Arg Asp Asp Glu Ile Val Tyr Glu Met
225                 230                 235                 240

Val Thr Asp Met Asp Glu Ser Asp Ile Arg Arg Met Leu Ala Glu Arg
                245                 250                 255

Asp Ser Gly Glu Lys Leu Ala Arg Lys Ser Ala Pro Glu Ala Asp Glu
            260                 265                 270

Pro Leu Tyr Ser Leu Pro Pro Ala Pro Arg Thr Pro His Ser Trp Pro
        275                 280                 285

Pro Ile Ser Val Glu Pro Val Thr Tyr Pro Thr Tyr Pro Gln
            290                 295                 300

<210> SEQ ID NO 20
<211> LENGTH: 66
<212> TYPE: PRT
<213> ORGANISM: Photorhabdus luminescens subsp. laumondii TTO1

<400> SEQUENCE: 20

Met Leu Ser Cys Tyr Gln Ala Thr Arg Leu Met Ser Gln Ala Leu Asp
1               5                   10                  15

Glu Lys Ile Val Leu Ser Gln His Val Gln Leu Met Leu His Leu Lys
            20                  25                  30

Ile Cys Asp Gly Cys Arg Asn Phe Arg Gln Gln Leu Ala Asp Leu Arg
        35                  40                  45

Thr Met Thr Ser Ala Phe Ala Arg Gly Glu Asn Glu Asn Gln Asn Lys
    50                  55                  60

Val Thr
65

<210> SEQ ID NO 21
<211> LENGTH: 64
<212> TYPE: PRT
<213> ORGANISM: Haemophilus ducreyi 35000HP

<400> SEQUENCE: 21

Met Asn Cys Glu His Ala Ser Glu Leu Ile Ser Leu Asn Cys Glu Gln
1               5                   10                  15

Lys Leu Lys Val Lys Asp Ser Leu Gln Leu Gln Ile His Leu Trp Leu
            20                  25                  30

Cys Pro Lys Cys Arg His Phe Lys Lys Asn Asn Glu Met Arg Lys
        35                  40                  45

Leu Leu Gln Asn Tyr Cys Asp Pro Lys Ser Asn Cys Glu Lys Glu Thr
```

<210> SEQ ID NO 22
<211> LENGTH: 329
<212> TYPE: PRT
<213> ORGANISM: Streptomyces coelicolor A3(2)

<400> SEQUENCE: 22

Met Ser Gly Ser Arg Pro Glu Pro Glu Gly His Leu Ala Glu Gln His
1               5                   10                  15

Leu Gly Asp Arg Leu Ser Ala Leu Val Asp Gly Glu Leu Gly His Asp
            20                  25                  30

Ala Arg Glu Arg Val Leu Ala His Val Ala Thr Cys Pro Lys Cys Lys
        35                  40                  45

Ala Glu Val Asp Ala Gln Arg Arg Leu Lys Asn Val Phe Ala Glu Ala
    50                  55                  60

Ala Pro Pro Ala Pro Ser Glu Ser Phe Leu Ala Arg Leu Gln Gly Leu
65                  70                  75                  80

Pro Gly Gly Gly Asp Ser Asp Gly Gly Ser Pro Phe Ser Gly Leu
                85                  90                  95

Pro Gly Gly Phe Gly Ala Ser Ala Ala Ser Gly Val Phe Gly Pro Arg
            100                 105                 110

Arg Asp Glu Arg Phe Glu Phe Asp Tyr Val Pro Ala Gly Ser His Thr
        115                 120                 125

Pro Val Leu Pro Ser Ala Thr Ser Gly Arg Gly Phe Arg Ile His Glu
    130                 135                 140

Val Gly Arg His Glu Ser Asp Arg Ser Ala Ser Arg Gly Leu Arg Phe
145                 150                 155                 160

Ala Phe Ala Ala Gly Ala Val Ser Leu Ala Ala Ile Ala Leu Gly
                165                 170                 175

Gly Val Thr Leu Gly Thr Pro Asp Thr Thr Thr Glu Ala Arg Gly Ser
            180                 185                 190

Gly Ser Gly Ser Asn Val Thr Pro Leu Arg Thr Pro Gly Ser Ala Ala
        195                 200                 205

Ala Thr Gly Ser Glu Ser Gln Arg Arg Thr Ala Gly Pro Leu Leu
    210                 215                 220

Gly Gln Gly Gln Arg Ala Leu Gly Asp Leu Pro Val Ala Ser Thr Thr
225                 230                 235                 240

Ala Ser Ala Pro Leu Leu Pro Gly Met Pro Ala Pro Ala Gly Gly Asp
                245                 250                 255

Ala Arg Gln Gln Ala Val Arg Ala Leu Thr Thr Pro Val Thr Ala Gly
            260                 265                 270

Ala Ala Ala Met Ser Pro Leu Ile Arg Pro Leu Glu Ala Val Pro Pro
        275                 280                 285

Leu Ser Leu Ser Ser Trp Ser Ala Ala Pro Glu Val Arg Pro Pro Gly
    290                 295                 300

Leu Leu Ala Ala Pro Asp Pro Ala Pro Ser Pro Tyr Pro Ala Ala Ser
305                 310                 315                 320

Pro Ala Ala Ser Ser Ser Pro Leu Arg
                325

<210> SEQ ID NO 23
<211> LENGTH: 154
<212> TYPE: PRT
<213> ORGANISM: Mycobacterium tuberculosis H37Rv

<400> SEQUENCE: 23

Met Ala Asp Pro Gly Ser Val Gly His Val Phe Arg Arg Ala Phe Ser
1               5                   10                  15

Trp Leu Pro Ala Gln Phe Ala Ser Gln Ser Asp Ala Pro Val Gly Ala
            20                  25                  30

Pro Arg Gln Phe Arg Ser Thr Glu His Leu Ser Ile Glu Ala Ile Ala
        35                  40                  45

Ala Phe Val Asp Gly Glu Leu Arg Met Asn Ala His Leu Arg Ala Ala
    50                  55                  60

His His Leu Ser Leu Cys Ala Gln Cys Ala Ala Glu Val Asp Asp Gln
65                  70                  75                  80

Ser Arg Ala Arg Ala Ala Leu Arg Asp Ser His Pro Ile Arg Ile Pro
                85                  90                  95

Ser Thr Leu Leu Gly Leu Leu Ser Glu Ile Pro Arg Cys Pro Pro Glu
            100                 105                 110

Gly Pro Ser Lys Gly Ser Ser Gly Ser Ser Gln Gly Pro Pro Asp
        115                 120                 125

Gly Ala Ala Ala Gly Phe Gly Asp Arg Phe Ala Asp Gly Asp Gly Gly
    130                 135                 140

Asn Arg Gly Arg Gln Ser Arg Val Arg Arg
145                 150

<210> SEQ ID NO 24
<211> LENGTH: 68
<212> TYPE: PRT
<213> ORGANISM: Rhodobacter sphaeroides 2.4.1

<400> SEQUENCE: 24

Met Ala Gln Ser Thr Glu Pro Lys Ala Ser Pro Gln Glu Ala Thr Ala
1               5                   10                  15

Lys Gly Gly Asp Asn Thr Lys Gly Lys Ser Arg Lys Glu Leu Gln Gln
            20                  25                  30

Gln Ile Asp Glu Asn Leu Arg Arg Val Tyr Glu Glu Ala Leu Val Gln
        35                  40                  45

Glu Val Pro Asp Arg Phe Ala Met Leu Leu Asp Gln Leu Arg Gln Lys
    50                  55                  60

Gly Thr Gly Lys
65

<210> SEQ ID NO 25
<211> LENGTH: 68
<212> TYPE: PRT
<213> ORGANISM: Caulobacter crescentus CB15

<400> SEQUENCE: 25

Met Asn Phe Gly Val Glu Asp Met Ile Glu His Val Pro Met Glu Asp
1               5                   10                  15

Lys Arg Lys Gly Ala Ala Ala Leu Asp Glu Ala Arg Leu Arg Gln Gln
            20                  25                  30

Ala Ile Gly Val Lys Leu Arg Gln Met Phe Asp Glu Val Val Asn Glu
        35                  40                  45

Pro Val Pro Asp Glu Phe Leu Ala Ile Leu Arg Lys Ala Glu Arg Pro
    50                  55                  60

Ala Gly Gly Glu
65

```
<210> SEQ ID NO 26
<211> LENGTH: 213
<212> TYPE: PRT
<213> ORGANISM: Pseudomonas putida KT2440

<400> SEQUENCE: 26

Met Lys Thr Asp Asp Leu Ile Ala Leu Leu Ala Ala Gly Glu Gly Pro
1               5                   10                  15

Val Pro Arg His Ala Val Gly Arg Met Ala Val Ala Ala Leu Gly
            20                  25                  30

Gly Leu Thr Ala Ala Leu Leu Leu Thr Ile Thr Leu Tyr Gly Val Arg
                35                  40                  45

Ser Asp Ile Thr Glu Val Ala Gln Thr Pro Leu Phe Trp Gly Lys Val
        50                  55                  60

Ala Phe Pro Thr Ser Leu Ala Leu Ile Gly Leu Trp Leu Thr Ser Arg
65                  70                  75                  80

Leu Ala Arg Pro Gly Gly Lys Gly Ala Ala Gly Trp Lys Met Leu Gly
                85                  90                  95

Leu Pro Leu Leu Leu Val Trp Cys Gly Ala Ala Val Ser Ile Ala Gly
                100                 105                 110

Ala Pro Val Asp Ala Arg Ala Asp Leu Leu Phe Gly Thr Trp Arg
                115                 120                 125

Thr Cys Ala Leu Asn Ile Ala Leu Leu Ser Val Pro Ala Phe Val Thr
130                 135                 140

Val Phe Trp Ala Leu Lys Gly Leu Ala Pro Thr Arg Leu Arg Leu Ala
145                 150                 155                 160

Gly Ala Ala Gly Gly Leu Leu Ala Gly Ser Ser Ala Thr Val Ala Tyr
                165                 170                 175

Cys Leu His Cys Pro Glu Met Gly Val Pro Phe Trp Gly Val Trp Tyr
                180                 185                 190

Val Leu Gly Met Leu Val Pro Thr Val Leu Gly Ala Trp Trp Gly Pro
                195                 200                 205

Arg Met Leu Arg Trp
        210

<210> SEQ ID NO 27
<211> LENGTH: 214
<212> TYPE: PRT
<213> ORGANISM: Pseudomonas entomophila L48

<400> SEQUENCE: 27

Met Met Lys Thr Asp Glu Leu Ile Ser Leu Leu Ala Thr Ala Glu Gly
1               5                   10                  15

Pro Val Asp Arg His Ala Leu Ala Arg Arg Leu Gly Leu Ala Leu Leu
            20                  25                  30

Ala Gly Leu Leu Gly Ala Leu Leu Thr Val Ala Leu Tyr Gly Val
                35                  40                  45

Arg Ser Asp Leu Ala Glu Val Ala Arg Thr Pro Leu Phe Trp Ala Lys
        50                  55                  60

Val Ala Leu Pro Thr Ser Leu Ala Leu Leu Gly Leu Trp Leu Thr Gln
65                  70                  75                  80

Arg Leu Ala Arg Pro Gly Val Arg Gly Gly Ala Leu Trp Gly Leu Leu
                85                  90                  95

Gly Val Pro Leu Leu Leu Val Trp Leu Gly Ala Ala Ile Ser Leu Phe
                100                 105                 110

Gly Ala Pro Pro Glu Ala Arg Ala Asp Leu Ile Phe Gly Arg Thr Trp
```

```
            115                 120                 125
Arg Thr Cys Ala Leu Asn Ile Thr Leu Leu Ser Thr Pro Val Phe Ile
    130                 135                 140

Ala Val Phe Trp Ala Leu Arg Gly Leu Ala Pro Thr Arg Leu Arg Gln
145                 150                 155                 160

Ala Gly Ala Ala Gly Leu Leu Ala Gly Ser Thr Ala Thr Leu Val
                165                 170                 175

Tyr Cys Leu His Cys Pro Glu Met Gly Val Pro Phe Trp Gly Leu Trp
                180                 185                 190

Tyr Leu Leu Gly Met Leu Val Pro Thr Leu Leu Gly Ala Val Leu Gly
                195                 200                 205

Pro Arg Leu Leu Arg Trp
    210

<210> SEQ ID NO 28
<211> LENGTH: 262
<212> TYPE: PRT
<213> ORGANISM: Streptomyces coelicolor A3(2)

<400> SEQUENCE: 28

Met Gln Gly Thr Pro Ala Pro Asn Glu His Glu Thr Val Gly Ala Tyr
1               5                   10                  15

Ala Leu Gly Ile Leu Asp Asp Ala Glu Ala Thr Ala Phe Glu Ala His
                20                  25                  30

Leu Ala Thr Cys Glu Trp Cys Ala Gln Gln Leu Asp Glu Leu Ala Gly
            35                  40                  45

Met Glu Pro Met Met Ala Ala Leu Ala Asp Leu Pro Gly Thr Gly Thr
    50                  55                  60

Pro Ala Val Ala Glu Ser Leu Thr Val Lys Pro Ser Ala Arg Leu Ser
65                  70                  75                  80

Glu Lys Leu Val Asp Glu Val Ala Glu Arg Ala Ser Lys Arg Arg
                85                  90                  95

Arg Asn Phe Tyr Leu Val Gly Thr Ala Ala Ala Leu Ile Ile Gly Gly
                100                 105                 110

Pro Phe Ala Ala Val Ala Thr Thr Gly Gly Gly Gly Gly Gly Asp
            115                 120                 125

Asp Gly Gly Gly Arg Arg Ala Glu Ala Thr Gln Gln Ala Ala Ser Pro
    130                 135                 140

Ala Glu Ser Ala Phe Ala Ala Met Pro Asp Arg Val Thr Ala Thr Asp
145                 150                 155                 160

Pro Gly Thr Gln Val Ser Ala Thr Val Ala Leu Glu Lys Lys Ala Trp
                165                 170                 175

Gly Thr Glu Thr Val Leu Glu Leu Lys Asn Leu Lys Gly Pro Gln Lys
                180                 185                 190

Cys Ser Leu Ile Ala Val Gly Lys Asn Gly Glu Arg Glu Thr Leu Thr
                195                 200                 205

Ser Trp Ser Val Pro Asp Trp Gly Tyr Gly Ile Pro Gly Ala Thr Thr
    210                 215                 220

Glu Lys Ala Lys Lys Pro Leu Tyr Val His Gly Gly Ala Ala Phe Glu
225                 230                 235                 240

Pro Asn Gln Ile Ser His Phe Glu Val Met Thr Phe Asp Gly Lys Arg
                245                 250                 255

Leu Val Glu Val Asp Ala
            260
```

-continued

<210> SEQ ID NO 29
<211> LENGTH: 250
<212> TYPE: PRT
<213> ORGANISM: Mycobacterium tuberculosis H37Rv

<400> SEQUENCE: 29

Met Thr Met Pro Leu Arg Gly Leu Gly Pro Asp Asp Thr Gly Val
1               5                   10                  15

Arg Glu Val Ser Thr Gly Asp Asp His His Tyr Ala Met Trp Asp Ala
            20                  25                  30

Ala Tyr Val Leu Gly Ala Leu Ser Ala Ala Asp Arg Arg Glu Phe Glu
        35                  40                  45

Ala His Leu Ala Gly Cys Pro Glu Cys Arg Gly Ala Val Thr Glu Leu
    50                  55                  60

Cys Gly Val Pro Ala Leu Leu Ser Gln Leu Asp Arg Asp Glu Val Ala
65                  70                  75                  80

Ala Ile Ser Glu Ser Ala Pro Thr Val Val Ala Ser Gly Leu Ser Pro
                85                  90                  95

Glu Leu Leu Pro Ser Leu Leu Ala Ala Val His Arg Arg Arg Arg Arg
            100                 105                 110

Thr Arg Leu Ile Thr Trp Val Ala Ser Ser Ala Ala Ala Ala Val Leu
        115                 120                 125

Ala Ile Gly Val Leu Val Gly Val Gln Gly His Ser Ala Ala Pro Gln
    130                 135                 140

Arg Ala Ala Val Ser Ala Leu Pro Met Ala Gln Val Gly Thr Gln Leu
145                 150                 155                 160

Leu Ala Ser Thr Val Ser Ile Ser Gly Glu Pro Trp Gly Thr Phe Ile
                165                 170                 175

Asn Leu Arg Cys Val Cys Leu Ala Pro Pro Tyr Ala Ser His Asp Thr
            180                 185                 190

Leu Ala Met Val Val Val Gly Arg Asp Gly Ser Gln Thr Arg Leu Ala
        195                 200                 205

Thr Trp Leu Ala Glu Pro Gly His Thr Ala Thr Pro Ala Gly Ser Ile
    210                 215                 220

Ser Thr Pro Val Asp Gln Ile Ala Ala Val Gln Val Ala Ala Asp
225                 230                 235                 240

Thr Gly Gln Val Leu Leu Gln Arg Ser Leu
                245                 250

<210> SEQ ID NO 30
<211> LENGTH: 281
<212> TYPE: PRT
<213> ORGANISM: Xanthomonas axonopodis pv. citri str. 306

<400> SEQUENCE: 30

Met Ser Gly Thr Met Ser Thr Pro Phe Pro Ile Asp Gln Glu Pro Pro
1               5                   10                  15

Arg Asp Val Leu Ala Gly Glu Tyr Val Leu Gly Leu Leu Ser Ala Glu
            20                  25                  30

Glu Arg Leu Ala Ala Glu Gln Arg Ile Ala Thr Asp Gly Gln Phe Ala
        35                  40                  45

Gln Ala Val Leu Gln Trp Gln Glu Leu Leu Ala Pro Leu Leu Glu Glu
    50                  55                  60

Ile Val Ala Gln Thr Pro Pro Asp Gln Val Trp Val Arg Val Arg Gln
65                  70                  75                  80

```
Ala Leu Gly Phe Asp Thr Pro Leu Arg Ala Val Pro Ser Ala Ala Pro
                85                  90                  95

Val Ser Thr Thr Ala Pro Ala Ala Pro Leu Trp Asn Ser Val Arg Phe
            100                 105                 110

Trp Arg Trp Ala Ser Val Gly Gly Leu Ala Thr Ala Ala Val Cys Val
        115                 120                 125

Leu Ala Leu Leu Asn Leu Arg Thr Pro Pro Ala Pro Val Gln Pro Pro
    130                 135                 140

His Thr Gly Glu Val Val Gln Thr Pro Val Thr Pro Pro Ala Thr Asn
145                 150                 155                 160

Pro Pro Ala Ala Thr Gly Ile Ala Met Thr Ser Thr Leu Ala Thr Glu
                165                 170                 175

Asp Gly Arg Pro Gly Tyr Val Ala Leu Met Asp Ala Asp Lys His Thr
            180                 185                 190

Ile Thr Val Thr Pro Leu Asp Arg Thr Ala Thr Ala Asp Lys Val Pro
        195                 200                 205

Glu Leu Trp Leu Ile Thr Pro Asp Gly Lys Ala His Ser Met Gly Thr
    210                 215                 220

Phe Asp Asp Gln Arg Ala Arg Arg Ala Gln Ile Pro Asp Gln Leu Met
225                 230                 235                 240

Pro Met Leu Ser Asn Glu Ala Ile Leu Ala Val Thr Leu Glu Pro Pro
                245                 250                 255

Gly Gly Ala Pro Gly Gly Val Ala Thr Gly Thr Val Val Ala Lys Gly
            260                 265                 270

Gly Ile Ser Thr Leu Ala Met Ala Pro
        275                 280

<210> SEQ ID NO 31
<211> LENGTH: 279
<212> TYPE: PRT
<213> ORGANISM: Xanthomonas campestris pv. campestris str. ATCC 33913

<400> SEQUENCE: 31

Met Ser Gly Thr Met Ser Thr Pro Phe Pro Ile Asp Gln Glu Pro Pro
1               5                   10                  15

Arg Asp Val Leu Ala Gly Glu Tyr Val Leu Gly Leu Leu Ser Ala Asp
            20                  25                  30

Asp Arg Leu Ala Val Glu Gln Arg Ile Ala Thr Asp Ala Gln Phe Ala
        35                  40                  45

Gln Ala Val Ala Gln Trp Gln Glu His Leu Ala Pro Leu Leu Glu Glu
    50                  55                  60

Ile Ala Ala Val Thr Pro Ala Asp Gln Val Trp Thr Arg Val Arg Gln
65                  70                  75                  80

Ala Leu Gly Phe Asp Thr Pro Leu His Ala Val Pro Ala Ser Gly Val
                85                  90                  95

Gln Ser Pro Ala Pro Pro Ala Ala Val Pro Leu Trp Asn Ser Val Arg
            100                 105                 110

Phe Trp Arg Trp Ala Ser Ala Gly Gly Leu Ala Thr Ala Ala Val Cys
        115                 120                 125

Val Leu Ala Leu Leu Ser Val Arg Ala Pro Pro Thr Ala Pro Pro Ser
    130                 135                 140

Gly Pro Val Gln Asn Thr Pro Ile Val Gln Thr Pro Pro Ala Lys Pro
145                 150                 155                 160

Pro Ala Thr Gly Ile Ala Met Thr Ser Thr Leu Ala Thr Ala Asp Gly
                165                 170                 175
```

```
Arg Pro Gly Tyr Val Ala Leu Met Asp Ala Asp Lys Gln Val Ile Thr
                180                 185                 190

Val Thr Pro Leu Asp Arg Thr Ala Thr Ala Gly Lys Val Pro Glu Leu
            195                 200                 205

Trp Leu Ile Thr Pro Asp Gly Lys Ala His Ser Met Gly Val Phe Asp
    210                 215                 220

Asp Gln Arg Ala Arg Ala Ser Ile Pro Ala Pro Leu Met Pro Met
225                 230                 235                 240

Leu Ser Asn Glu Ala Ile Leu Ala Val Thr Leu Glu Pro Pro Gly Gly
                245                 250                 255

Ala Pro Gly Gly Val Ala Thr Gly Thr Val Val Ala Lys Gly Gly Ile
            260                 265                 270

Ser Thr Leu Ala Met Ala Pro
            275
```

<210> SEQ ID NO 32
<211> LENGTH: 250
<212> TYPE: PRT
<213> ORGANISM: Streptomyces coelicolor A3(2)

<400> SEQUENCE: 32

```
Met Arg Thr Glu Asp Leu His Ser Leu Thr Gly Ala Tyr Ala Leu His
1               5                   10                  15

Ala Leu Pro Asp Asp Glu Arg Glu Ala Phe Glu Arg His Leu Ala Gly
                20                  25                  30

Cys Ala Thr Cys Glu Gln Glu Ala Arg Glu Phe Ala Ala Ala Thr Ala
            35                  40                  45

Arg Leu Gly Leu Ala Ala Thr Val Pro Ala Pro Ala Leu Arg Asp
    50                  55                  60

Arg Val Leu His Arg Val Thr Thr Val Arg Gln Val Pro Pro Gly Gly
65                  70                  75                  80

Gly Thr Ala Glu Lys Ala Arg Arg Val Val Pro Arg Gly Arg Gly Leu
                85                  90                  95

Ala Arg Trp Ala Leu Ala Ala Cys Val Ala Ala Ala Gly Leu Gly
            100                 105                 110

Gly Thr Ala Val Trp Gln Tyr Glu Arg Ala Gln Asp Ala Gly Gln Arg
        115                 120                 125

Ala Ala Gln Ala Glu Arg Arg Ala Glu Thr Leu Ala Gly Val Leu Ala
    130                 135                 140

Ala Pro Asp Ala Glu Ser Arg Thr Ala Arg Leu Ala Asp Gly Ala Ser
145                 150                 155                 160

Gly Thr Leu Val Val Ser Glu Arg Gln Asp Arg Ala Val Phe Leu Ala
                165                 170                 175

Ser Gly Met Ala Glu Pro Pro Arg Gly Lys Val Tyr Gln Leu Trp Phe
            180                 185                 190

Asp Asp His Gly Thr Met Arg Ser Ala Gly Leu Met Asp Pro Gly Ser
        195                 200                 205

Thr Ser Gln Ala Val Leu Met Asp Gly Ala Val Asp Gly Ala Ala Gly
    210                 215                 220

Val Gly Ile Thr Val Glu Pro Ala Gly Gly Ser Lys Gln Pro Thr Ser
225                 230                 235                 240

Asp Pro Ile Ala Leu Leu Ser Met Pro Ala
                245                 250
```

-continued

<210> SEQ ID NO 33
<211> LENGTH: 232
<212> TYPE: PRT
<213> ORGANISM: Mycobacterium tuberculosis H37Rv

<400> SEQUENCE: 33

```
Met Thr Glu His Thr Asp Phe Glu Leu Leu Glu Leu Ala Thr Pro Tyr
1               5                   10                  15

Ala Leu Asn Ala Val Ser Asp Asp Glu Arg Ala Asp Ile Asp Arg Arg
            20                  25                  30

Val Ala Ala Ala Pro Ser Pro Val Ala Ala Phe Asn Asp Glu Val
        35                  40                  45

Arg Ala Val Arg Glu Thr Met Ala Val Val Ser Ala Thr Thr Ala
50                  55                  60

Glu Pro Pro Ala His Leu Arg Thr Ala Ile Leu Asp Ala Thr Lys Pro
65                  70                  75                  80

Glu Val Arg Arg Gln Ser Arg Trp Arg Thr Ala Ala Phe Ala Ser Ala
                85                  90                  95

Ala Ala Ile Ala Val Gly Leu Gly Ala Phe Gly Leu Gly Val Leu Thr
            100                 105                 110

Arg Pro Ser Pro Pro Thr Val Ala Glu Gln Val Leu Thr Ala Pro
        115                 120                 125

Asp Val Arg Thr Val Ser Arg Pro Leu Gly Ala Gly Thr Ala Thr Val
130                 135                 140

Val Phe Ser Arg Asp Arg Asn Thr Gly Leu Leu Val Met Asn Asn Val
145                 150                 155                 160

Ala Pro Pro Ser Arg Gly Thr Val Tyr Gln Met Trp Leu Leu Gly Gly
                165                 170                 175

Ala Lys Gly Pro Arg Ser Ala Gly Thr Met Gly Thr Ala Ala Val Thr
            180                 185                 190

Pro Ser Thr Thr Ala Thr Leu Thr Asp Leu Gly Ala Ser Thr Ala Leu
        195                 200                 205

Ala Phe Thr Val Glu Pro Gly Thr Gly Ser Pro Gln Pro Thr Gly Thr
210                 215                 220

Ile Leu Ala Glu Leu Pro Leu Gly
225                 230
```

<210> SEQ ID NO 34
<211> LENGTH: 143
<212> TYPE: PRT
<213> ORGANISM: Pseudomonas fluorescens Pf-5

<400> SEQUENCE: 34

```
Met Thr Pro Glu Arg Phe Val His Leu Ala Asp Ala Tyr Gly Ala Asp
1               5                   10                  15

Leu Gln Arg Trp Pro Ser Ala Glu Arg Ala Ala Gln Ala Leu Leu
            20                  25                  30

Asp Cys Gly Asp Ala Gln Ala Val Ala Ala Leu Arg Gln Ala His Trp
35                  40                  45

Leu Asp Ser Gln Leu Asp Arg Tyr Gln Val Pro Ala Pro Ser Pro Ala
50                  55                  60

Leu Ala Gln Arg Ile Ile Ala Ala Gln Pro Gly Ala Pro Phe
65                  70                  75                  80

Trp Ser Arg Tyr Ala Gly Trp Leu Ala Ser Leu Gly Trp Val Gly Val
                85                  90                  95

Gly Leu Thr Gly Val Ala Ala Gly Met Leu Ala Val Ala Leu Ser Leu
```

```
                        100                 105                 110
Pro Leu Ser Thr Ser Ala Glu Ala Leu Pro Ser Val Phe Asp Gln Ser
                115                 120                 125

Asp Ala Glu Phe Val Leu Ser Ile Asn Ala Glu Glu Ala Glu Gln
        130                 135                 140

<210> SEQ ID NO 35
<211> LENGTH: 418
<212> TYPE: PRT
<213> ORGANISM: Bacteroides thetaiotaomicron VPI-5482

<400> SEQUENCE: 35

Met Glu Glu Lys Glu Leu Trp Met Asn Lys Leu Lys Glu Lys Leu Gly
1               5                   10                  15

Asp Tyr Ser Glu Pro Leu Pro Ala Ser Gly Trp Glu Gln Leu Glu Lys
            20                  25                  30

Glu Leu Met Pro Pro Val Glu Arg Lys Ile Tyr Pro Tyr Arg Lys Trp
        35                  40                  45

Thr Val Ala Ala Ala Val Ile Leu Leu Ala Leu Gly Ser Ser Val
    50                  55                  60

Ser Leu Tyr Phe Leu Gly Thr Pro Ala Ala Asp Glu Ile Arg His Ala
65                  70                  75                  80

Lys Thr Pro Ala Leu Ala Ser Val Pro Asp Val Leu Pro Asp Ala Gln
                85                  90                  95

Gln Pro Asp Met Thr Gly Thr Thr Ile Glu Pro Val Val Arg Pro Val
            100                 105                 110

Val Lys Asn Arg Ile Ala Lys Ala Glu Arg Asn Ile Pro Gln Pro Thr
        115                 120                 125

Ala Asn Ile Asp Glu Pro Val Lys Lys Glu Gln Pro Ser Glu Leu
    130                 135                 140

Asn Ala Gln Thr Gly Asp Arg Lys Glu Lys Glu Val Glu Pro Val
145                 150                 155                 160

Glu Glu Thr Lys Ala Ile Arg His Lys Pro Ala Asp Thr Glu Gln Pro
                165                 170                 175

Arg Asn Lys Pro Arg Arg Pro Ser Ser Arg Asp Lys Leu His Ile Pro
            180                 185                 190

Ala Glu Lys Ala Ser Ser Gln Lys Gly Thr Trp Ser Met Gly Leu Ser
        195                 200                 205

Val Gly Asn Ser Gly Gly Ala Ser Thr Glu Leu Gly Ser Gly Ile Pro
    210                 215                 220

Ser Tyr Met Ser Arg Val Ser Met Val Ser Val Ser Asn Gly Leu Leu
225                 230                 235                 240

Ser Ile Pro Asn Asp Gln Gln Leu Val Phe Glu Asp Gly Val Pro Tyr
                245                 250                 255

Leu Arg Gln Ala Asn Gln Val Val Asp Met Glu His His Gln Pro Ile
            260                 265                 270

Ser Phe Gly Leu Ser Val Arg Lys Ser Leu Ala Lys Gly Phe Ser Val
        275                 280                 285

Glu Thr Gly Leu Thr Tyr Thr Leu Leu Ser Ser Asp Ala Lys Phe Ala
    290                 295                 300

Asp Ser Asp Gln Lys Thr Glu Gln Lys Leu His Tyr Leu Gly Ile Pro
305                 310                 315                 320

Leu Lys Ala Asn Trp Asn Phe Leu Asp Lys Lys Leu Phe Thr Leu Tyr
                325                 330                 335
```

Val Ser Gly Gly Gly Met Ile Glu Lys Cys Val Tyr Gly Lys Leu Gly
            340                 345                 350

Thr Glu Lys Glu Thr Val Lys Pro Leu Gln Phe Ser Val Ser Gly Ala
        355                 360                 365

Val Gly Ala Gln Phe Asn Ala Thr Lys Arg Val Gly Ile Tyr Val Glu
    370                 375                 380

Pro Gly Val Ala Tyr Phe Phe Asp Asp Gly Ser Asp Val Gln Thr Ile
385                 390                 395                 400

Arg Lys Glu Asn Pro Phe Asn Phe Asn Ile Gln Ala Gly Ile Arg Leu
                405                 410                 415

Thr Tyr

<210> SEQ ID NO 36
<211> LENGTH: 215
<212> TYPE: PRT
<213> ORGANISM: Xanthomonas axonopodis pv. citri str. 306

<400> SEQUENCE: 36

Met Glu Leu Asp Asp Ile Ala Val Ala Trp Arg Ser Leu Glu Gln Arg
1               5                   10                  15

Leu Asp Gln His Ala Ala Leu Ala Gly Gln Val Leu Gly Asp Leu Arg
            20                  25                  30

Ser His Ala Ala Arg Ala His Leu Arg Pro Leu Trp Leu Ser Gln Ser
        35                  40                  45

Ala Gln Leu Leu Cys Ala Ile Ala Leu Ser Gly Leu Val Ala His Ser
    50                  55                  60

Trp Leu Ala Phe Pro Glu Gln Ala Ala Ile Val Gly Gly Val Leu
65                  70                  75                  80

Leu Gln Ile Trp Cys Val Ala Leu Ala Ala Ser Ala Ala Arg Gln Leu
                85                  90                  95

Trp Leu Leu Ser Gln Leu Asp Phe Ala Arg Pro Leu Leu Gln Thr Gln
            100                 105                 110

Arg Ala Leu Ala Gln Leu Arg Arg Trp Arg Thr Arg Val Ala Pro Trp
        115                 120                 125

Leu Gly Val Ala Phe Trp Val Leu Trp Val Ala Val Ala Asp Ala Ala
    130                 135                 140

Trp Arg Ala Leu Thr Gly Arg Ser Leu Pro Tyr Ala Trp Leu Leu Cys
145                 150                 155                 160

Asn Leu Leu Val Gly Val Leu Gly Ile Gly Thr Trp Leu Gly Tyr
                165                 170                 175

Arg Arg Leu Gln Arg Ser Gly His Pro Trp Leu Glu Arg Leu Asp Thr
            180                 185                 190

Val His Ala Gly Arg Ser Val Ala Arg Thr Glu Thr Leu Leu Glu Gln
        195                 200                 205

Ile Ala Arg Phe Gln Arg Glu
    210                 215

<210> SEQ ID NO 37
<211> LENGTH: 215
<212> TYPE: PRT
<213> ORGANISM: Xanthomonas campestris pv. campestris str. ATCC 33913

<400> SEQUENCE: 37

Met Glu Leu Asp Asp Met Lys His Ala Trp Gln Thr Leu Glu Gln Arg
1               5                   10                  15

Leu Asp Gln Gln Ala Ala Gln Thr Gly Gln Leu Leu Gly Val Val His

```
            20                  25                  30
Glu Glu Thr Val Arg Ser Ser Leu Arg Pro Leu Trp Val Ala Gln Thr
         35                  40                  45

Ala Gln Leu Leu Cys Ala Leu Ala Leu Ala Ile Val Ser Ala Arg Ser
     50                  55                  60

Trp Ile Pro His Thr Asp Gln Pro Val Ala Val Ile Gly Gly Val Leu
 65                  70                  75                  80

Leu Gln Ala Trp Cys Met Ala Leu Ala Ile Ser Ala Met Val Gln Leu
                 85                  90                  95

Gln Leu Leu Thr Gln Phe Asn Val Ala Gly Pro Leu Leu Arg Thr Gln
             100                 105                 110

His Ala Leu Ala Arg Leu Arg Arg Trp Arg Thr Arg Val Ala Pro Trp
         115                 120                 125

Leu Gly Val Ala Phe Trp Val Leu Trp Ile Ala Val Ala Asp Ala Leu
     130                 135                 140

Trp Arg Ala Leu Thr Gly Gln Thr Leu Pro Thr Asp Trp Leu Val Leu
145                 150                 155                 160

Asn Leu Leu Val Gly Val Ala Gly Gly Ile Gly Thr Trp Leu Gly Phe
                 165                 170                 175

Arg Arg Leu Gln Arg Ala Gln His Pro Trp Leu Glu Arg Ile Asp Arg
             180                 185                 190

Ala His Ala Gly Thr Gly Val Ile Arg Ala Glu Arg Met Leu Glu Glu
         195                 200                 205

Ile Ala Arg Phe Gln Arg Asp
     210                 215

<210> SEQ ID NO 38
<211> LENGTH: 222
<212> TYPE: PRT
<213> ORGANISM: Clostridium acetobutylicum ATCC 824

<400> SEQUENCE: 38

Met Asp Asp Lys Asn Leu Phe Arg Asn Tyr Asn Asp Ile Val Val Ser
 1               5                  10                  15

Glu Glu Glu Ile Glu Lys Tyr Glu Thr Lys Lys Val Asp Asp Asp Val
                 20                  25                  30

Leu Ser Lys Met Lys Asn Lys Val Lys Lys Leu Tyr Met Lys Val Asn
             35                  40                  45

Met Glu Glu Ala Phe Glu Lys Val Lys Gln Phe Glu Asp Asp Glu
         50                  55                  60

Lys Val Glu Tyr Met Phe Trp Ala Glu Thr Tyr Gly Val Arg Lys Tyr
 65                  70                  75                  80

Gln Met Val Cys Gly Gly Tyr Tyr Ser Leu Glu Gly Ala Ile Ser Asn
                 85                  90                  95

Asp Trp Gly Thr Lys Thr Gly Ile Val Leu Thr Asn Lys Gly Ile Phe
             100                 105                 110

Gly Ile Glu Thr Asn Asp Ala Tyr Gly Val Leu Lys Ile Lys Asn Phe
         115                 120                 125

Arg Phe Lys Asp Val Glu Tyr Ile Glu Ser Lys Lys Ile Lys Asn Asn
     130                 135                 140

Phe Thr Val Phe Ala Ile Lys Ser Thr Ser Gly Ile Glu Ile Lys Val
145                 150                 155                 160

Glu Ile Tyr Asn Gly Asp Arg His Ile Lys Phe Leu Asn Tyr Ile Arg
                 165                 170                 175
```

```
Asn Asn Asn Ile Lys Val Asn Ile Arg Met Ile Gln Asp Arg Lys Ile
            180                 185                 190

Gln Ile Ala Tyr Val Ser Ile Ile Ile Ile Met Ile Phe Ile Ile
            195                 200                 205

Phe Val Ile Ser Ser Ser Ile Met Arg Ser Gly Ile Thr Lys
            210                 215                 220

<210> SEQ ID NO 39
<211> LENGTH: 366
<212> TYPE: PRT
<213> ORGANISM: Bacillus anthracis str. Ames

<400> SEQUENCE: 39

Met Lys Asp Ile Tyr Glu Leu Leu Asn Asp Ile Asp Ile Asp Glu Lys
1               5                   10                  15

Glu Leu Glu Glu Ile Glu Ala Ser Glu Ile Lys Glu Lys Val Lys
            20                  25                  30

Arg Asn Val Lys Gln Ser Ile Arg Thr Lys Lys Met Lys Ser Trp
            35                  40                  45

Lys Lys Gly Val Ala Ala Ser Ile Leu Val Gly Leu Ser Val Thr
50                  55                  60

Thr Leu Gly Ile Gly Phe Pro Thr Tyr Ala Gly Leu Pro Ile Val
65              70                  75                  80

Gly Asp Ile Phe Arg Phe Leu Asp Asn Gly Arg Thr Gly Leu Tyr Glu
                85                  90                  95

Asn Tyr Lys Glu Phe Ser Thr Glu Leu Asn Met Thr Arg Glu Ser Asn
            100                 105                 110

Gly Val Lys Val Thr Ile Asn Asp Val Ile Ser Asp Gly Arg Thr Leu
            115                 120                 125

Ser Ile Thr Tyr Ser Leu Glu Ser Glu Gln Asp Leu Gly Asp Asp Pro
            130                 135                 140

Ile Ile Leu Gly Gly Leu Asp Ile Met Asp Ala His Gly Ser Ser Gly
145                 150                 155                 160

Ser Gly Lys Met Thr Lys Val Thr Glu Lys Lys Tyr Val Gly Met Val
                165                 170                 175

Thr Thr Thr His His Asp Ser Asn Lys Lys Asp Lys Val Asn Phe Arg
            180                 185                 190

Trp Asn Ile Glu Gly Ile Glu Ile Pro Asp Arg Lys Lys Ser Ile Gln
            195                 200                 205

Gly His Trp Asn Phe Ala Leu Thr Val Lys Ser Met Asp Ser Lys Glu
        210                 215                 220

Arg Thr Ile Gly Gly Ser Ser Glu Lys Glu Gly Ile Lys Ala Asn Met
225                 230                 235                 240

Glu Lys Val Ala Met Ser Pro Val Ser Phe Ile Leu Tyr Tyr Asn Gln
                245                 250                 255

Glu Val Ser Lys Gly Ala Arg Lys Glu Trp Asp Ser Val Asp Val Glu
            260                 265                 270

Leu Thr Val Lys Asp Asp Leu Gly Asn Asp Tyr Ser Gly Glu Gly Asn
        275                 280                 285

Gly Gly Ser Gly Asn Asp Pro Tyr Asn Ile Arg Trp Ser Ala Thr Phe
        290                 295                 300

Gln Lys Leu Asn Glu Asn Ala Thr Lys Leu Ile Val Thr Pro Arg Val
305                 310                 315                 320

His Leu Arg Val His Thr Pro Glu Asn His Gly Gly Val Glu Tyr Val
                325                 330                 335
```

```
Asn Gly Lys Glu Lys Ile Glu Val Pro Asn Lys Glu Ala Lys Lys
            340                 345                 350

Lys Asp Ile Val Leu Asp Asp Ile Val Ile Asp Leu Lys Lys
        355                 360                 365

<210> SEQ ID NO 40
<211> LENGTH: 201
<212> TYPE: PRT
<213> ORGANISM: Nostoc sp. PCC 7120

<400> SEQUENCE: 40

Met Thr Thr Asp Ser Asn Phe Asn Asp Pro Cys Arg Arg Gln Phe Ser
1               5                   10                  15

Arg Asp Leu Pro Gln Lys Met Ala Arg His Thr Asn Glu Ala Thr Gly
            20                  25                  30

Ala Met Asp Met Val Lys Arg Asp Arg Phe Glu Leu Leu Ser Ala Tyr
        35                  40                  45

Leu Gly Gly Glu Val Thr Ala Ala Glu Arg Arg Gln Val Glu Asp Trp
    50                  55                  60

Pro Ala Asn Asp Val Ala Val Gln Arg Leu Tyr Ser Arg Leu Leu Lys
65                  70                  75                  80

Leu Arg Gln Gly Ile Arg Thr Met Pro Ile Pro Thr Ala Gln Gln Ser
                85                  90                  95

Pro Glu Thr Thr Ala Glu Gln Val Phe Ala Lys Val Asn Arg Arg Ser
            100                 105                 110

Arg Leu Ala Trp Lys Leu Gly Gly Ala Ala Val Ala Ala Cys Val Ile
        115                 120                 125

Gly Ala Val Thr Asn Trp Leu Pro Gly Arg Gln Thr Gly Ile Pro Gln
    130                 135                 140

Leu Ala Gln Gln Pro Gln Glu Gln Pro Thr Gln Ala Val Thr Thr Pro
145                 150                 155                 160

Asp Ala Leu Pro Met Ile Ala Leu Asn Asn Pro Val Ile Glu Ile Pro
                165                 170                 175

Lys Ala Ala Val Ala Ser Pro Thr Lys Phe Ile Gln Pro Gln Pro Gln
            180                 185                 190

Leu Gly Glu Ile Pro Pro Asp Ile Asn
        195                 200

<210> SEQ ID NO 41
<211> LENGTH: 201
<212> TYPE: PRT
<213> ORGANISM: Nostoc sp. PCC 7120

<400> SEQUENCE: 41

Met Thr Thr Asp Ser Asn Phe Asn Asp Pro Cys Arg Arg Gln Phe Ser
1               5                   10                  15

Arg Asp Leu Pro Gln Lys Met Ala Arg His Thr Asn Glu Ala Thr Gly
            20                  25                  30

Ala Met Asp Met Val Lys Arg Asp Arg Ser Glu Leu Leu Ser Ala Tyr
        35                  40                  45

Leu Asp Gly Glu Val Thr Ala Ala Glu Arg Arg Gln Val Glu Asp Trp
    50                  55                  60

Leu Ala Asn Asp Val Ala Val Gln Arg Leu Tyr Ser Arg Leu Leu Lys
65                  70                  75                  80

Leu Arg Gln Gly Ile Arg Thr Met Pro Ile Pro Thr Ala Gln Gln Ser
                85                  90                  95
```

```
Pro Glu Thr Thr Ala Glu Gln Val Phe Ala Lys Val Asn Arg Arg Ser
            100                 105                 110

Arg Leu Ala Trp Lys Leu Gly Gly Ala Ala Val Ala Ala Cys Val Ile
        115                 120                 125

Gly Ala Val Thr Asn Trp Leu Pro Gly Arg Gln Thr Gly Ile Pro Gln
130                 135                 140

Leu Ala Gln Gln Pro Gln Glu Gln Pro Thr Gln Ala Val Thr Thr Pro
145                 150                 155                 160

Asp Ala Leu Pro Met Ile Ala Leu Asn Asn Pro Val Ile Glu Ile Pro
                165                 170                 175

Lys Ala Ala Val Ala Ser Pro Thr Lys Phe Ile Gln Pro Gln Pro Gln
            180                 185                 190

Leu Gly Glu Ile Pro Pro Asp Ile Asn
        195                 200

<210> SEQ ID NO 42
<211> LENGTH: 191
<212> TYPE: PRT
<213> ORGANISM: Synechococcus sp. PCC 7002

<400> SEQUENCE: 42

Met Asn Glu Ser Phe Ser Gln Arg Gln Thr Asp Gly Asp Arg Arg
1               5                   10                  15

Gly Gly Asp Leu Glu Met Lys Lys Asn His Thr Ser His Gln His
            20                  25                  30

Thr Asp Ser Glu Thr Pro Met Gly His Asn Phe Glu Gln Phe Gln Arg
        35                  40                  45

Leu Ser Ala Tyr Phe Asp Gly Glu Ala Thr Pro Ala Glu Arg Lys Glu
50                  55                  60

Ile Gln His Leu Leu Asp Thr Asp Pro Gln Val Lys Gln Tyr Gln
65                  70                  75                  80

Gln Leu Arg Gln Leu Lys Gln Ala Leu Gln Leu Pro Ile Pro Thr
                85                  90                  95

Ser Ile Ser Ala Gln Tyr Leu Gly Gln Arg Val Leu Ala Arg Leu Arg
            100                 105                 110

Arg Ser Gln Leu Arg Thr Leu Ser Leu Trp Gly Ser Gly Ala Ile Ala
        115                 120                 125

Ala Leu Phe Val Ala Gly Val Met Gly Gln Met Pro Arg Leu Asn Phe
130                 135                 140

Asp Arg Phe Ala Lys Asn Asp Pro Asp Gln Gln Pro Thr Ala Ala Leu
145                 150                 155                 160

Val Glu Thr Ser Pro Gln Gly Glu Ala Leu Val Val Ala Leu Asn
                165                 170                 175

Arg Pro Val Leu Gln Ile Pro Lys Leu Ala Thr Thr Glu Ser Pro
            180                 185                 190

<210> SEQ ID NO 43
<211> LENGTH: 252
<212> TYPE: PRT
<213> ORGANISM: Pseudomonas fluorescens Pf0-1

<400> SEQUENCE: 43

Met Asn Ala Pro Ser Asp Glu Gln Leu Val Ala Tyr Leu Asp Asp Glu
1               5                   10                  15

Leu Asp Arg Glu Gln Arg Ser Gln Leu Asp Asn Leu Ile Ala Asp Asp
            20                  25                  30
```

```
Pro Leu Leu Ser Leu Arg Val Gln Trp Leu Ser Arg Ser Ser Leu Pro
        35                  40                  45

Phe Lys Ala Ala Tyr Asp Glu Leu Ala Gln Gln Ala Pro Leu Asp Arg
    50                  55                  60

Leu Gln Ala Arg Leu Asp Ala Ala Pro Ser Pro Gln Lys Pro Val Phe
65                  70                  75                  80

Ser Arg Arg Trp Phe Ile Gly Ala Ala Ala Ala Gly Val Ala Leu Ala
                85                  90                  95

Ala Val Ala Ala Asp Arg Leu Phe Leu Ala Trp Gln Ala Gln Gln Ser
            100                 105                 110

His Asn Trp Arg Glu Leu Val Gly Asp Tyr Met Ala Leu Tyr Val Pro
        115                 120                 125

Gln Thr Leu Glu His Leu Pro Thr Asp Glu Ala Ser Gln Leu Ala Gln
    130                 135                 140

Leu Arg Thr Val Asp Ala Arg Leu Gly Val Ser Leu Ser Pro Ala Lys
145                 150                 155                 160

Leu Lys Leu Pro Gly Ala Gln Phe Lys Arg Ala Gln Leu Leu Glu Tyr
                165                 170                 175

Gly Gly Val Pro Ile Ala Gln Met Thr Trp Leu Asp Ala Lys Tyr Gly
            180                 185                 190

Pro Leu Ala Leu Cys Val Thr Arg Thr Asn Ser Gly Ser Gln Pro Leu
        195                 200                 205

Ala His Glu Arg Arg His Gly Met Asn Val Val Tyr Trp Thr Glu Arg
    210                 215                 220

Glu His Ala Trp Met Leu Ile Gly His His Pro Ala Ser Glu Leu Glu
225                 230                 235                 240

Asp Met Ala Lys Met Phe Lys Thr Arg Leu Asn Val
                245                 250

<210> SEQ ID NO 44
<211> LENGTH: 247
<212> TYPE: PRT
<213> ORGANISM: Xanthomonas oryzae pv. oryzae KACC10331

<400> SEQUENCE: 44

Met Lys Asp Ile Asp Glu Ser Thr Leu Leu Ala Tyr Ala Asp Gly Ala
1               5                   10                  15

Leu Thr Pro Asp Gln Ala Gly Arg Val Glu Ala Val Leu Ala Ala Asp
            20                  25                  30

Pro Gln Arg Ala Ala Asp Val Arg Gln Leu Gln Gln Val Lys Ala Arg
        35                  40                  45

Leu Arg Asn Gly Tyr Ala Ser Val Leu Glu Glu Pro Ile Pro Ala His
    50                  55                  60

Leu Leu Asp Ala Ala Arg Gln Arg Pro Pro Pro Ser Pro Gln Thr Ser
65                  70                  75                  80

Val Val Thr Ala Thr Ala Pro Ile Gln Ala Pro Ala Thr Arg Gln His
                85                  90                  95

Ala Thr Arg Arg Trp Ala Val Pro Thr Ser Ile Ala Ala Ala Leu Leu
            100                 105                 110

Ile Gly Leu Trp Leu Trp Gln Arg Gln Pro Ala Gln Pro Ala Pro Ser
        115                 120                 125

Ala Leu Leu Ala Glu Gln Gly His Asp Ala Ser Gly Thr Leu Ala Leu
    130                 135                 140

Ala Leu Asp Arg Gln Leu Ser Gly Glu Gln Gln Gly Lys Ile Arg Met
```

```
145                 150                 155                 160
Gly Leu Ser Phe Arg Ala His Asp Gly Arg Tyr Cys Arg Ser Phe Ser
                165                 170                 175
Leu Gln Ser Ser His Ala Gly Leu Ala Cys Arg Gln Gly Glu Arg Trp
                180                 185                 190
Arg Ile Glu Ala Val Ser Pro Leu Gln Pro Gln Arg Asn Asp Ser Glu
                195                 200                 205
Leu Arg Met Ala Ser Ser Thr Leu Pro Ala Ala Leu Leu Asp Ala Ile
        210                 215                 220
Asp Ala Arg Ile Asp Gly Gln Ala Leu Asp Ala Glu Gly Glu Arg Ser
225                 230                 235                 240
Ala Arg Ala Arg His Trp Arg
                245

<210> SEQ ID NO 45
<211> LENGTH: 254
<212> TYPE: PRT
<213> ORGANISM: Mycobacterium bovis AF2122/97

<400> SEQUENCE: 45

Met Ser Ala Ala Asp Lys Asp Pro Asp Lys His Ser Ala Asp Ala Asp
1               5                   10                  15
Pro Pro Leu Thr Val Glu Leu Leu Ala Asp Leu Gln Ala Gly Leu Leu
                20                  25                  30
Asp Asp Ala Thr Ala Ala Arg Ile Arg Ser Arg Val Arg Ser Asp Pro
            35                  40                  45
Gln Ala Gln Gln Ile Leu Arg Ala Leu Asn Arg Val Arg Arg Asp Val
        50                  55                  60
Ala Ala Met Gly Ala Asp Pro Ala Trp Gly Pro Ala Ala Arg Pro Ala
65                  70                  75                  80
Val Val Asp Ser Ile Ser Ala Ala Leu Arg Ser Ala Arg Pro Asn Ser
                85                  90                  95
Ser Pro Gly Ala Ala His Ala Ala Arg Pro His Val His Pro Val Arg
                100                 105                 110
Met Ile Ala Gly Ala Ala Gly Leu Cys Ala Val Ala Thr Ala Ile Gly
            115                 120                 125
Val Gly Ala Val Val Asp Ala Pro Pro Ala Pro Ser Ala Pro Thr
        130                 135                 140
Thr Ala Gln His Ile Thr Val Ser Lys Pro Ala Pro Val Ile Pro Leu
145                 150                 155                 160
Ser Arg Pro Gln Val Leu Asp Leu Leu His His Thr Pro Asp Tyr Gly
                165                 170                 175
Pro Pro Gly Gly Pro Leu Gly Asp Pro Ser Arg Arg Thr Ser Cys Leu
                180                 185                 190
Ser Gly Leu Gly Tyr Pro Ala Ser Thr Pro Val Leu Gly Ala Gln Pro
            195                 200                 205
Ile Asp Ile Asp Ala Arg Pro Ala Val Leu Leu Val Ile Pro Ala Asp
        210                 215                 220
Thr Pro Asp Lys Leu Ala Val Phe Ala Val Ala Pro His Cys Ser Ala
225                 230                 235                 240
Ala Asp Thr Gly Leu Leu Ala Ser Thr Val Val Pro Arg Ala
                245                 250

<210> SEQ ID NO 46
<211> LENGTH: 282
```

<212> TYPE: PRT
<213> ORGANISM: Streptomyces coelicolor A3(2)

<400> SEQUENCE: 46

```
Met Thr Gly His Pro Asp Val Ala Glu Ile Ala Asp Leu Ala Glu Gly
1               5                   10                  15

Leu Leu Pro Thr Thr Arg Thr Glu Val Arg Gln His Leu Glu Ser
            20                  25                  30

Cys Glu Leu Cys Ala Asp Val Tyr Ala Ser Leu Thr Glu Ile Gln Gly
            35                  40                  45

Leu Leu Gly Thr Leu Pro Ala Pro Ala Pro Met Pro Asp Asp Val Ala
        50                  55                  60

Ala Arg Ile Asp Ala Ala Leu Ala Ala Glu Pro Pro Leu Gly Ile Ala
65                  70                  75                  80

Asp Gly Thr Arg Val Ser Arg Glu Thr Ser Thr Pro Ala Asp Arg Pro
                85                  90                  95

Ala Gly His Ala Arg Pro Ser Ser Thr Gly Pro Gly Arg Lys Asp Arg
            100                 105                 110

Arg Arg Gly Gly Arg Arg Ile Ala Val Leu Gly Ala Val Ala Ala
        115                 120                 125

Ala Ala Ala Ile Gly Ile Gly Ser Val Val Ser Ser Leu Thr Glu
        130                 135                 140

Asp Ser Ser Ser Gly Asn Thr Ala Arg Glu Gln Gln Thr Ala Ile Ala
145                 150                 155                 160

Asp Thr Phe Ser Glu Gly Arg Leu Lys Asp Arg Val Thr Asn Leu Val
                165                 170                 175

Ala Asp Gly Ser Ala Glu Asn Gly Ser Arg Thr Pro Arg Ser Phe Gly
            180                 185                 190

Met Glu Ser Glu Asn Gly Gly Thr Ala Glu Asn His Val Phe Lys
        195                 200                 205

Gln Pro Thr Val Pro Glu Cys Ile Arg Lys Gly Ile Gly Arg Asp Asp
        210                 215                 220

Ala Val Ile Ala Thr Glu Pro Gly Val Tyr Lys Gly Arg Glu Ala Leu
225                 230                 235                 240

Leu Val Val Leu Pro Asp Ala Thr Asn Asp Thr Gln Val Thr Ala Tyr
                245                 250                 255

Ile Val Glu Thr Ala Cys Val Asp Gln Pro Ala Val Gly Lys Ala Lys
                260                 265                 270

Ile Leu Leu Glu His Ser Tyr Ala Arg Ser
            275                 280
```

<210> SEQ ID NO 47
<211> LENGTH: 253
<212> TYPE: PRT
<213> ORGANISM: Vibrio cholerae O1 biovar eltor str. N16961

<400> SEQUENCE: 47

```
Met Val Gln Asn Thr Thr Arg Ser Ser Lys Met Asp Glu Leu Glu Phe
1               5                   10                  15

Arg Arg Lys Val Met Ser Asp Pro Lys Gln Arg Asp Asn Asp Thr Leu
            20                  25                  30

Asp Met Met Thr Ser Ser Glu Ala Asn Ala Lys Phe Val Asp Asp Val
            35                  40                  45

Leu Gln Leu Asp Lys Gln Ile Ala Gln Ala Phe Lys Val Asp Val Pro
        50                  55                  60
```

```
Asp Asp Leu Ala Asp Lys Ile Leu Phe Lys Gln Thr Thr Leu Val Glu
 65                  70                  75                  80

Asp Glu Lys Val Ile Arg Pro Gln Phe Val Arg Lys Ala Met Ala Ile
                 85                  90                  95

Ala Ala Ser Val Ala Phe Thr Ala Gly Leu Leu Val Gly Gln Ile Gln
            100                 105                 110

Trp Gly Asn Leu Leu Ile Ser Pro Ala Gln Ala Ser Leu Ser Asp Met
        115                 120                 125

Ala Val Gln His Val Ile His Glu Gly Phe Val Asn Arg Leu Asp
    130                 135                 140

Glu Gln Ala Asp Met Gln Gln Ile Asn Ala Lys Met Arg Pro Phe Ala
145                 150                 155                 160

Tyr Lys Met Glu Gly Asp Phe Pro Tyr His Val Tyr Leu Asn His
                165                 170                 175

Cys Gly Phe Gly Lys Asp Asn Ala Val His Met Val Phe Gln Gly Glu
            180                 185                 190

Lys Gly Lys Val Thr Leu Phe Phe Thr Pro Ile His Ser Ala Gln Ser
        195                 200                 205

Ser Leu Phe Lys Gln Glu Gly Met Ala Gly Ile Glu Pro Val Gly
    210                 215                 220

Asn Ala Ser Leu Ile Leu Val Gly Glu Lys Asp Glu Asn Leu Thr Asn
225                 230                 235                 240

Ile Ala Asn Lys Leu Met Pro Met Ile Gln Ser Ser Ile
                245                 250

<210> SEQ ID NO 48
<211> LENGTH: 235
<212> TYPE: PRT
<213> ORGANISM: Shewanella frigidimarina NCIMB 400

<400> SEQUENCE: 48

Met Asp Asp Leu Gln Phe Arg Arg His Ala Tyr Gly Asp Pro Asn Asn
 1               5                  10                  15

Gln Ala Asp Asp Phe Leu Ala His Leu Ala Glu Asn Glu Asp Asp Ala
                20                  25                  30

Lys Phe Val Lys Asp Leu Gln Ala Phe Asp His Lys Leu Thr Gln Ala
             35                  40                  45

Leu Asn Ile Ser Val Pro Asp Gly Leu Ala Asp Lys Leu Ile Leu Arg
         50                  55                  60

Gln Gln Leu Ser Gln His Gln Lys Ser Lys Lys Gln Thr Arg Tyr Leu
 65                  70                  75                  80

Met Ala Met Ala Ala Ser Val Ala Phe Ile Val Gly Val Ser Phe Ser
                 85                  90                  95

Leu Leu Arg Phe Thr Pro Val Asn Leu Gly Glu Asn Ser Leu Ala His
            100                 105                 110

Val His His Glu Thr Lys Ala Leu Val Met Glu Gln Asp Ile Gly Phe
        115                 120                 125

Asn Asp Val Asn Phe Lys Leu Ala Ser Leu Glu Gly Leu Ser Asp Ser
    130                 135                 140

Lys Phe Ile Gln Gln Pro Gly Arg Val Phe Tyr Thr Ser Tyr Cys Asp
145                 150                 155                 160

Phe Gln Gly Val Lys Ser Leu His Leu Val Met Ala Asp Glu Asn Gly
                165                 170                 175

Asn Lys Val Thr Leu Phe Ile Val Pro Val Glu Ser Arg Ile Val Leu
            180                 185                 190
```

```
Glu Glu Ala Phe Ala Asp Asn Gln Tyr Lys Gly Gln Ser Phe Gln Thr
        195                 200                 205

Ala Asp Ala Tyr Met Val Leu Val Gly Glu Pro Ala Ser Asp Leu Glu
210                 215                 220

Phe Val Lys Lys Glu Val Glu Asn Thr Phe Ile
225                 230                 235

<210> SEQ ID NO 49
<211> LENGTH: 285
<212> TYPE: PRT
<213> ORGANISM: Bacillus subtilis subsp. subtilis str. 168

<400> SEQUENCE: 49

Met Asp Lys Arg Leu Gln Gln Leu Arg Glu Glu Tyr Lys Asn Val Gln
1               5                   10                  15

Ile Pro Lys Glu Leu Asp Ile Ile Val Glu Lys Ala Leu Gln Gln Glu
            20                  25                  30

Pro Lys Lys Lys Arg Ile Val Met Trp Pro Thr Ser Ala Ala Ile Ala
        35                  40                  45

Ala Ala Ile Leu Phe Thr Ala Leu Val Asn Ile Asn Pro Asp Ala Ala
    50                  55                  60

Gln Ala Met Ser Lys Ile Pro Val Ile Gly Lys Ile Val Lys Ala Ile
65                  70                  75                  80

Thr Phe Ile Glu Ile Lys Glu Glu Lys Asp Gln Ser Ser Ile Asp Val
                85                  90                  95

Lys Thr Pro Ala Leu Ser Gly Leu Ser Asn Lys Glu Leu Glu Asn Ser
            100                 105                 110

Ile Asn Glu Lys Tyr Leu Lys Glu Ser Gln Gln Leu Tyr Lys Glu Phe
        115                 120                 125

Ile Gln Ser Thr Ser Lys Asn Lys Lys Gly His Leu Ser Ile Tyr Ser
    130                 135                 140

Asp Tyr Glu Thr Val Thr Asp Thr Pro Asp Leu Leu Ser Ile Arg Arg
145                 150                 155                 160

Asn Ile Glu Thr Thr Gln Ala Ser Ser Tyr Thr Gln Ser Arg Tyr Ile
                165                 170                 175

Thr Ile Asp Lys Lys Asn Asp Ile Leu Leu Thr Leu Lys Ser Leu Phe
            180                 185                 190

Lys Asp Glu Arg Tyr Ile Lys Val Ile Ser Gln Asn Ile Lys Glu Gln
        195                 200                 205

Met Lys Gln Gln Met Lys Glu Asp Pro Asn Lys Ile Tyr Trp Leu Thr
    210                 215                 220

Asp Glu Asp Ala Glu Pro Phe Lys Thr Ile Leu Pro Asp Gln Thr Phe
225                 230                 235                 240

Tyr Ile Thr Glu Asp His Lys Leu Val Ile Ser Phe Asp Glu Tyr Glu
                245                 250                 255

Val Ala Pro Gly Tyr Met Gly Val Thr Glu Phe Thr Ile Pro Thr Gly
            260                 265                 270

Val Ile Ser Asn Leu Leu Val Gly Glu Arg Tyr Ile Arg
        275                 280                 285

<210> SEQ ID NO 50
<211> LENGTH: 414
<212> TYPE: PRT
<213> ORGANISM: Clostridium perfringens str. 13

<400> SEQUENCE: 50
```

-continued

```
Met Ile Asp Asp Phe Asp Arg Lys Leu Phe Glu Met Ala Arg Glu Ser
1               5                   10                  15

Lys Val Lys Glu Pro Asn Ala Leu Lys Tyr Lys Val Asp Tyr Thr Phe
            20                  25                  30

Lys Lys Leu Lys Lys Asn Lys Phe Asn Phe Arg His Leu Gly Ser Ile
            35                  40                  45

Ala Ala Ile Leu Ile Phe Cys Ile Leu Ser Val Gly Ile Tyr Phe Pro
        50                  55                  60

Thr Tyr Ala Met Asn Ile Pro Ile Leu Gly Asp Val Val Glu Ile Leu
65                  70                  75                  80

Ser Asn Lys Phe Asn Leu Ser Gly Tyr Glu Ile Asn Ala Gln Asn Leu
                85                  90                  95

Asn Tyr Gln Val Ser Asn Glu Asp Tyr Thr Leu Thr Ile Glu Ser Ala
                100                 105                 110

Tyr Tyr Asn Gly Leu Glu Thr Thr Phe Phe Phe Lys Ile Lys Gly Asn
            115                 120                 125

Ala Lys Leu Asn Lys Ser Gly Gln Tyr Phe Phe Glu Ala Asn Phe Lys
        130                 135                 140

Tyr Asn Glu Asp Ile Ser Tyr Glu Gly Gly Leu Glu Lys Gly Glu Phe
145                 150                 155                 160

Ile Asp Asp Tyr Thr Phe Ala Gly Met Met Thr Phe Tyr Ile Asn Pro
                165                 170                 175

Tyr Ser Glu Ser Lys Leu Pro Glu Lys Phe Asn Ile Lys Phe Ser Ile
                180                 185                 190

Pro Asn Ile Ile Ala Asp Ser Glu Ile Leu Ala Val Asn Ser Asp Thr
            195                 200                 205

Leu Asn Leu Ser Phe Asp Ile Thr Asp Leu Asn Val Lys Glu Thr Lys
        210                 215                 220

Ile Asn Lys Glu Ile Gln Ala Asn Glu Asn Ser Ile Leu Ile Ser Ser
225                 230                 235                 240

Ile Lys Lys Tyr Pro Thr Ser Ile Val Ile Asp Tyr Asp Glu Lys Phe
                245                 250                 255

Asn Asn Pro Glu Asn Lys Leu Ser Phe Ile Leu Trp His Glu Thr Leu
                260                 265                 270

Gly Gln Ile Asn Tyr Leu Leu Pro Ser Thr Pro Gly Lys Leu Phe Ile
            275                 280                 285

Val Pro Lys Thr Arg Ser Lys Leu Asn Val Asp Asn Leu Ile Lys Glu
        290                 295                 300

Ser Met Pro Leu Ser Ile Gly Glu Thr Lys Thr Phe Gly Lys Val Gly
305                 310                 315                 320

Lys Val Ser Ile Glu Asn Ile Glu Thr Lys Asp Gly Lys Thr Tyr Ile
                325                 330                 335

Ser Ile Arg Lys Thr Gly Asp Ile Asn Ser Tyr Asp Phe Asn Ile Ile
            340                 345                 350

Lys Lys Glu Asn Ile Asn Ser Lys Leu Asn Met Tyr Glu Tyr Glu Thr
        355                 360                 365

Lys Val Ile Gly Ile Leu Asp Thr Leu Thr Thr Tyr Val Ile Pro Asp
        370                 375                 380

Phe Thr Ser Asp Ile Asp Tyr Leu Leu Glu Tyr Glu Tyr Ile Ser Asn
385                 390                 395                 400

Asp Asp Ile Glu Ile Leu Tyr Asp Gln Ile Ile Glu Ile Asn
            405                 410
```

<210> SEQ ID NO 51
<211> LENGTH: 106
<212> TYPE: PRT
<213> ORGANISM: Bacillus subtilis subsp. subtilis str. 168

<400> SEQUENCE: 51

Met Asn Lys Glu Lys Leu Ser Asp His Leu Lys Ser Glu Trp Lys Lys
1               5                   10                  15

Ile Asp Gln Thr Ala Asn Pro Ser Ile Pro Asn Gln Lys Glu Leu Leu
            20                  25                  30

His Gln Leu Ser Gln Met Lys Ala Glu Tyr Arg Lys Lys Leu Leu Gln
        35                  40                  45

Glu Ile Ile Leu Phe Val Phe Cys Ala Leu Met Val Val Ser Ala Ala
    50                  55                  60

Ile Leu Ala Phe Thr Gln Ala Pro Ala Val Phe Ile Val Leu Gln Val
65                  70                  75                  80

Cys Val Leu Ala Val Leu Pro Ile Leu Ile Ala Ala Glu Lys Lys Arg
                85                  90                  95

His Leu Gly Glu Cys Glu Val Lys Arg Gly
            100                 105

<210> SEQ ID NO 52
<211> LENGTH: 231
<212> TYPE: PRT
<213> ORGANISM: Bradyrhizobium japonicum USDA 110

<400> SEQUENCE: 52

Met Met Ala Leu Ser Lys Lys Met Leu Glu Gln Glu Pro Ser Glu Ile
1               5                   10                  15

Glu Leu Leu Leu Pro Trp His Ala Ala Gly Thr Leu Asn Ala Arg Asp
            20                  25                  30

Ala Arg Arg Val Glu Asp Ala Leu Ala Arg Asp Pro Glu Leu Ala Lys
        35                  40                  45

Gln Tyr Ala Ala Ile Arg Gly Glu Tyr Glu Glu Thr Ile His Leu Asn
    50                  55                  60

Glu Ser Leu Gly Ala Pro Ser Arg Ala Met Gln Lys Leu Phe Gly
65                  70                  75                  80

Ala Ile Asp Ala Glu Pro Ala Arg Glu Thr Gly Ser Leu Pro Leu Ser
                85                  90                  95

Ala Arg Ile Ala Thr Phe Phe Ala Ser Leu Ser Pro Arg Thr Leu Ala
            100                 105                 110

Trp Ser Ala Ser Leu Gly Ala Val Ala Leu Val Leu Gln Ala Gly Ile
        115                 120                 125

Ile Gly Ala Val Leu Met Lys Thr Gln Pro Thr Thr Phe Gln Thr Ala
    130                 135                 140

Ser Leu Ser Thr Ser Ala Pro Ile Thr Arg Glu Leu Gly Ala Ala Val
145                 150                 155                 160

Ala Pro Ala Arg Ala Leu Val Arg Phe Thr Pro Glu Ala Arg Val Ala
                165                 170                 175

Asp Ile Thr Ala Leu Leu Asp Ser Tyr Gln Ala Ser Ile Ile Gly Asp
            180                 185                 190

Ala Lys Gly Gly Met Phe Arg Leu Gln Phe Asp Lys Ala Met Ser Gln
        195                 200                 205

Asp Glu Leu Ala Ser Leu Leu Gly Arg Met Gln Arg Glu Lys Phe Val
    210                 215                 220

Asn Leu Ala Val Ala Ala Pro
225                 230

<210> SEQ ID NO 53
<211> LENGTH: 277
<212> TYPE: PRT
<213> ORGANISM: Rhodopseudomonas palustris CGA009

<400> SEQUENCE: 53

Met Met Ala Met Ser Asn Thr Met Pro Asp Pro Arg Glu Pro Gly Asp
1               5                   10                  15

Val Glu Ala Leu Leu Pro Trp Tyr Ala Ala Gly Thr Leu Asn Ala Arg
            20                  25                  30

Asp Ala Arg Arg Val Ala Asp Ala Leu Asp Arg Asp Pro Ala Leu Ala
        35                  40                  45

Arg Gln Tyr Ala Val Ile Leu Glu Glu Tyr Ala Ser Thr Ile Glu Leu
    50                  55                  60

Asn Glu Ser Leu Gly Ala Pro Ser Ser Arg Ala Met Gln Lys Leu Phe
65                  70                  75                  80

Ala Ala Ile Asp Ala Glu Pro Ala Arg Ala Pro Gly Ala Gly Gln Gly
                85                  90                  95

Leu Gly Ala Arg Phe Ala Gly Phe Phe Ala Gly Leu Ser Pro Lys Ala
            100                 105                 110

Leu Ala Trp Ser Ala Ser Val Ala Gly Leu Ala Leu Leu Gln Ala
        115                 120                 125

Gly Leu Ile Gly Ala Leu Leu Thr Trp Pro His Ala Ala Pro Val Gln
    130                 135                 140

Thr Ala Ala Tyr Gln Pro Gln Arg Glu Val Ala Arg Ala Pro Ala Ser
145                 150                 155                 160

Ser Pro Ala Pro Ala Thr Val Ser Pro Ala Ala Met Ala Asp
                165                 170                 175

Arg Ala Ala Asp Ala Gly Lys Ser Thr Pro Pro Met Val Met Ala Glu
            180                 185                 190

Arg Ser Gly Gly Pro Val Val Arg Ser Leu Ala Pro Gln Ser Gly Pro
        195                 200                 205

Arg Val Leu Val Lys Phe Ala Pro Glu Ala Arg Ala Ser Glu Ile Ala
    210                 215                 220

Ala Leu Leu Asp Gln Tyr Asn Ala Val Val Asp Ser Ser Arg Gly
225                 230                 235                 240

Gly Leu Phe Arg Leu Gln Phe Gly Thr Gln Ser Leu Ser Lys Gln Asp
                245                 250                 255

Gln Glu Thr Leu Ile Gly Arg Leu Gln Lys Glu Pro Val Val Ser Val
            260                 265                 270

Val Leu Ser Ala Pro
        275

<210> SEQ ID NO 54
<211> LENGTH: 134
<212> TYPE: PRT
<213> ORGANISM: Streptomyces coelicolor A3(2)

<400> SEQUENCE: 54

Met Gly His Val His Pro Ser His Leu Val Glu Leu Ala Leu Gly His
1               5                   10                  15

Ala Ser Gly Glu Ala Asp Val Gly Ala Leu Arg His Ala Ala Ser Cys
            20                  25                  30

```
Pro Arg Cys Arg Glu Glu Leu Leu Arg Leu Thr Arg Val Thr Ala
            35                  40                  45

Ala Arg Gly Ala Glu Ala Ser Asp Leu Pro Val Pro Pro Glu Arg
        50                  55                  60

Val Trp Gln Arg Ile Ala Leu Glu Val Leu Pro Glu Thr Asp Arg Val
 65                  70                  75                  80

Pro Arg Leu Arg Glu Ser Ser Ala His Gly Ser Ala Asp Glu Arg Val
                85                  90                  95

Arg Gly Ser Gln Arg Arg Trp Thr Asp His Ala Gly Glu Gly Leu Leu
            100                 105                 110

Gly Leu Ala Leu Ala Ile Ala Val Leu Leu Leu Arg Arg Trp Arg Ile
            115                 120                 125

Arg Ala Gly Ser Gly Asn
    130
```

<210> SEQ ID NO 55
<211> LENGTH: 210
<212> TYPE: PRT
<213> ORGANISM: Nitrosococcus oceani ATCC 19707

<400> SEQUENCE: 55

```
Met Lys Arg Lys Glu Asn Lys Ala Trp Ile Asp Leu Ala Leu Glu Asn
 1               5                  10                  15

Leu Ser Glu Lys Glu Leu Lys Glu Leu Arg Gln Asn Leu Ala Ser Asp
                20                  25                  30

Pro Gln Phe Gln Glu Glu Leu Val Ser Val Lys Glu Leu Leu Ala Ala
            35                  40                  45

Ile Ala Leu Asn Leu Glu Pro Glu Pro Ala Pro Glu Leu Lys Ala
        50                  55                  60

Arg Leu Leu Asp Gly Ile Cys Gly Lys Asn Arg Phe Leu Pro Phe Leu
 65                  70                  75                  80

Ser Arg Leu Thr Glu Leu Phe Asp Leu Ser Pro Arg Glu Ala Gln Ala
                85                  90                  95

Tyr Leu Glu Arg Leu Asp Asp Pro Thr Ala Trp Lys Thr Val Leu Pro
            100                 105                 110

Gly Val Gln Thr Ile Lys Ile Gln Ala Gly Pro Ala Thr Ala Gly Ala
            115                 120                 125

Lys Ser Asn Phe Leu Arg Val Leu Pro Gly Ala Ser Phe Pro Tyr His
        130                 135                 140

Thr His Arg Gly Leu Glu Ser Ser Leu Leu Gln Gly Cys Cys Arg
145                 150                 155                 160

Ser Glu Asp Gly Val Ile Asn Arg Ala Gly Asp Leu Leu Tyr Gln Glu
                165                 170                 175

Thr Gly Thr Ala His Ser Phe Gln Val Ile Ser Glu Gln Ala Val Ile
            180                 185                 190

Ala Ala Val Val Cys Phe Gly Ile Asp Phe Ile Asn Pro Pro Asp Arg
        195                 200                 205

Lys Arg
    210
```

<210> SEQ ID NO 56
<211> LENGTH: 249
<212> TYPE: PRT
<213> ORGANISM: Shewanella oneidensis MR-1

<400> SEQUENCE: 56

```
Met Ser Asn Ser Thr Leu Ser Ser Glu Glu Gln Ala Leu His Gln Glu
1               5                   10                  15

Val Ser Ala Trp Tyr Phe Arg Gln Ala Leu Glu Met Pro Pro Glu Arg
            20                  25                  30

Leu Asp Gln Asp Ile Leu Arg Leu Ala Gln Thr Gln Leu Ser Glu Arg
            35                  40                  45

Asn Val Ser Gln Leu Thr Pro Ser Ala Met Pro Ile Trp Arg Arg Phe
50                  55                  60

Pro Trp Val Leu Ser Ser Ala Ala Ser Leu Val Ile Val Val Gly Leu
65                  70                  75                  80

Val Met Leu Asn Arg Gly Gln Phe Glu Glu Asp Met Gly Ala Pro Ala
                85                  90                  95

Ala Leu Thr Met Ser Ala Pro Met Pro Ala Ala His Val Ala Ser Asp
            100                 105                 110

Val Ala Asp Ala Lys Val Gln Glu Ala Glu Met Ala Ser Gln Ala Arg
            115                 120                 125

Leu Val Glu Asp Thr Ala Lys Gln Asn Ala Pro Lys Glu Met Met Met
130                 135                 140

Ala Gln Ala Asn Met Ala Ala Glu Glu Asn Ile Gln Ala Lys Ser Arg
145                 150                 155                 160

Ser Leu Pro Gln Val Ala Arg Ala His Pro Glu Gly Asp Val Gln Ala
            165                 170                 175

Thr Ala Asn Thr Asp Thr Ala Ala Leu Met Leu Ser Leu Ala Arg Leu
            180                 185                 190

Gln Glu Leu Ile Glu Ser Lys Gln Ile Gln Glu Ala Leu Ala Leu Glu
            195                 200                 205

Gln Thr Leu Val Lys Gln Tyr Pro Glu Leu Ser His Ile Ser Ser Ala
210                 215                 220

Lys Val Ala Ala Asp Ala Lys Ala Ile Ala Lys Phe Lys Ala Leu
225                 230                 235                 240

Gln Gln Gln Leu His Pro Leu Arg Asn
                245

<210> SEQ ID NO 57
<211> LENGTH: 254
<212> TYPE: PRT
<213> ORGANISM: Pseudomonas aeruginosa PAO1

<400> SEQUENCE: 57

Met Asn Pro Gln Lys His Ser Ala Ser Val Ala Glu Glu Gln Met Leu
1               5                   10                  15

Ala His Phe Arg Ala His Ala Pro Gln Gln Pro Ala Pro Ala Leu Asp
            20                  25                  30

Gln Ala Ile Leu Ala Ala Ala Arg Arg Gln Ala Ala His Val Glu Pro
            35                  40                  45

Ala Arg Ser Trp Trp Arg Arg Trp Leu Glu Ala Ser Arg Arg Pro Arg
50                  55                  60

Trp Gln Ala Ala Phe Ala Ser Leu Leu Gly Val Ala Leu Val Leu Gly
65                  70                  75                  80

Leu Val Ser His Asn Val Leu Asp Asp Ala Glu Arg Gln Ala Arg Pro
                85                  90                  95

Glu Val Ala Phe Ser Asp Val Pro Leu Arg Asp Gly Val Ala Gly Ala
            100                 105                 110

Ala Ala Ala Lys Arg Ala Met Arg Ala Pro Ala Ala Pro Ala Pro Leu
            115                 120                 125
```

```
Ser Gly Glu Met Ser Glu Pro Pro Ala Leu Leu Ala Ser Tyr Ala Ser
    130                 135                 140

Ser Gly Glu Ala Pro Gln Leu Met Ala Glu Ala Ala Pro Pro Ala Pro
145                 150                 155                 160

Ala Ala Leu Ala Asp Arg Pro Pro Ala Gln Ala Ala Gln Gln Ala Lys
                165                 170                 175

Val Gln Ala Ala Leu Ala Gly Asp Phe Val Ala Gln Ala Arg Gly Lys
            180                 185                 190

Ala Val Ala Val Lys Pro Glu Val Leu Asp Glu Ala Leu Gly Ala Val
        195                 200                 205

Leu Ala Leu Arg Glu Gln Gly Lys Thr Glu Gln Ala Ala Thr Gln Leu
    210                 215                 220

Ala Glu Leu Gln Lys Arg Phe Pro Gly Glu Asn Leu Val Glu Arg Leu
225                 230                 235                 240

Glu Arg Leu Ala Thr Ile Ala Ala Ser Ala Arg Lys Arg Pro
                245                 250

<210> SEQ ID NO 58
<211> LENGTH: 140
<212> TYPE: PRT
<213> ORGANISM: Burkholderia thailandensis E264

<400> SEQUENCE: 58

Met Ser Ser Ala Pro Ala Thr Lys Glu Glu Val Asp Phe Ala Leu Lys
1               5                   10                  15

Val Arg Arg Ala Leu Asp Glu Arg Ala Ala Ser Leu Pro Asp Ala Thr
            20                  25                  30

Thr Asp Arg Leu Ala Ala Ala Arg Arg Ala Ala Leu Ala Arg Lys Lys
        35                  40                  45

Pro Asp Ala Ala Ile Val Leu Val Pro Ala Leu Ala Gly Ser Ala Gly
    50                  55                  60

Thr Leu Glu Leu Arg Pro Pro Gly Glu Pro Arg Lys Ser Leu Ala Arg
65                  70                  75                  80

Arg Leu Ala Arg Ala Trp Pro Leu Ala Leu Leu Leu Ala Gly Leu Ile
                85                  90                  95

Gly Ile Ala Tyr Trp Glu Asp Met Gln Arg Thr Ala Glu Leu Ala Asp
            100                 105                 110

Ile Asp Ala Ala Met Leu Ser Asp Asn Leu Pro Leu Thr Ala Tyr Leu
        115                 120                 125

Asp His Gly Phe Asn Ala Tyr Leu Ser His Thr His
    130                 135                 140

<210> SEQ ID NO 59
<211> LENGTH: 454
<212> TYPE: PRT
<213> ORGANISM: Streptomyces coelicolor A3(2)

<400> SEQUENCE: 59

Met Ser Asp Gly Asn Asp Ala Arg Pro Asp Ala Arg Asp Gly His Asp
1               5                   10                  15

Pro Gly Ser Asp Ala Arg Asp Gly His Asp Pro Gly Ser His Ala Arg
            20                  25                  30

Asp Gly His Asp Pro Gly Ala Gly Pro Phe Asp Gly His Gly Pro Gly
        35                  40                  45

Ser Asp Ala Gly Asp Gly Asp Asp Ala Gly Pro Asp Ala Arg Asp Gly
    50                  55                  60
```

His Gly Ala Pro Ala Gly Pro Ala Gly Arg Glu Gln Arg Lys His Pro
65                  70                  75                  80

His Asp Thr His Asp Met His Asp Thr His Asp Thr His Ala Gly Lys
            85                  90                  95

Gly Thr Val Asn His Gly Pro Ala Ala Gln Gly Pro Asp Ala Pro Gly
        100                 105                 110

Ala Asp Gly Pro Ala Thr Asp Glu Ala Ala Leu Arg Ala Met Met Gln
    115                 120                 125

Arg Ala Val Arg Glu Met Glu Pro Ser Asp Gly Thr Leu Glu His Leu
130                 135                 140

Arg Arg Ala Val Pro Ala Arg Arg Ala Arg Lys Arg Gln Ala Leu Val
145                 150                 155                 160

Gly Ala Ala Ala Ala Leu Phe Leu Gly Thr Ala Val Pro Ala Leu
                165                 170                 175

Val His Val Ser Asn Ala Thr Gly Ala Gly Ala Asp Pro Ser Val Ala
        180                 185                 190

Gly Asn Ala Ser Gln Ala Gln Gly Ala Ser Gln Gly Lys Asp Pro
    195                 200                 205

Ala Gly Gly Gln Ser Gly Val Ala Gly Thr Gly Asp Thr Pro Glu Asp
210                 215                 220

Arg Asp Lys Ala Asp Pro Lys Glu Thr Pro Gly Gly Lys Glu Pro Gly
225                 230                 235                 240

Ala Ala Thr Gly Ala Pro Pro Ser Gly Val Pro Ser Ala Ser Ser Pro
            245                 250                 255

Ala Asp Val Pro Ala Cys Ala Pro Gly Ser Leu Gly Pro Ala Val Ala
        260                 265                 270

Ser Ser Ala Glu Pro Asp Ser Thr Gly Val Val Tyr Gly Ser Phe Arg
    275                 280                 285

Val Thr Asn Val Ser Ser Asp Gly Cys Thr Val Thr Gly Pro Gly Thr
290                 295                 300

Val Val Thr Ala Ser Leu Gly Ala Ala Glu Ala Thr Arg Ile Gly Thr
305                 310                 315                 320

Ala Arg His Ala Ala Gly Asp Ala Ala Ala Gly Leu Pro Asp Pro Ser
            325                 330                 335

Leu Glu Thr Ala Ser Leu Ala Leu Ala Pro Gly Ala Ala Tyr Glu Val
        340                 345                 350

Gln Phe Ala Trp Val Pro Ser Glu Thr Cys Pro Thr Thr Gly Gly Thr
    355                 360                 365

Thr Gly Gly Ser Gly Gly Pro Ser Pro Asp Pro Ser Pro Thr Ala
            370                 375                 380

Asp Thr Thr Ala Ala Gly Gly Thr Ser Ala Gly Gly Glu Ala Gly
385                 390                 395                 400

Pro Thr Thr Gln Leu Ile Thr Glu Asp Gly Pro Ala Glu Gly Ser Val
            405                 410                 415

Ser Val Thr Tyr Thr Pro Glu Gly Gly Ser Gly Ser Ala Thr Ala Thr
        420                 425                 430

Val Ser Asn Ala Cys Ala Gly Thr Val Tyr Trp Thr Gly Leu Leu Ala
    435                 440                 445

Asp Ser Gly Ser Gly Ala
    450

<210> SEQ ID NO 60
<211> LENGTH: 387

<212> TYPE: PRT
<213> ORGANISM: Kineococcus radiotolerans SRS30216

<400> SEQUENCE: 60

```
Met Ser Asp Arg Thr Pro Leu Gly Pro Leu Pro Asp Pro Asp Gly Asp
1               5                   10                  15

Gly Glu Leu Ser Pro Thr Ala Arg Arg Leu Arg Glu Ala Leu Ala Ala
            20                  25                  30

Arg Ala Ala Gly Val His Pro Thr Asp Arg Leu Glu Glu Ile His Val
        35                  40                  45

Thr Ser Arg Ala Asp Arg Arg Ser Arg Thr Arg Ala Val Val Ala
    50                  55                  60

Ala Ala Gly Val Ala Ala Val Val Val Gly Gly Gly Tyr Ala
65                  70                  75                  80

Leu Ala Gln Arg Asp Gly Gly Ser Val Arg Thr Val Ala Gly Ser Pro
                85                  90                  95

Ala Ala Ala Pro Ala Ser Ser Thr Thr Thr Ala Ala Gly Ala Gly
            100                 105                 110

Thr Pro Gly Ala Thr Ala Pro Ala Ala Ala Pro Ala Pro Ala Thr Ala
            115                 120                 125

Ser Gly Ser Thr Gly Pro Ala Thr Ala Ala Thr Ser Ala Pro Ala Thr
            130                 135                 140

Ser Thr Pro Thr Gly Ala Ala Ala Pro Ala Leu Pro Thr Gly Ala Ala
145                 150                 155                 160

Arg Val Pro Val Tyr Trp Thr Gly Gly Gly Lys Leu Phe Arg Glu Phe
                165                 170                 175

Thr Pro Val Pro Gly Gly Arg Asp Asp Ala Thr Asn Ala Leu Gln Val
            180                 185                 190

Leu Leu Gly Gly Thr Ala Ala Asp Ala Asp Tyr Arg Thr Ser Trp Gly
            195                 200                 205

Val Asp Pro Ala Ala Glu Val Thr Arg Asp Gly Ser Gly Ala Tyr Val
            210                 215                 220

Val Asp Val Ser Ala Ala Val Ser Thr Pro Leu Ser Ala Pro Glu
225                 230                 235                 240

Ala Glu Leu Ala Val Gln Gln Leu Val His Thr Val Thr Ala Gly
                245                 250                 255

Gly Gly Ser Ala Pro Val Arg Leu Leu Val Asp Gly Arg Glu Gly Ala
            260                 265                 270

Thr Val Phe Gly Ser His Arg Val Pro Ala Ala Val Glu Arg Ala Pro
            275                 280                 285

Gln Val Asp Val Gln Ala Pro Ala Trp Ile Thr Gln Val Thr Pro Gly
            290                 295                 300

Ala Gly Ser Val Thr Val Ala Gly Val Gly Thr Ala Phe Glu Gly Thr
305                 310                 315                 320

Leu Leu Cys Thr Leu Thr Asp Ala Ala Gly Val Glu Val Ala Arg Glu
                325                 330                 335

Pro Val Gln Ala Gly Ala Asn Gly Thr Phe Gly Glu Phe Ser Leu Ala
            340                 345                 350

Val Ala Ala Pro Ala Gly Thr Tyr Thr Val Ala Val Phe Ala Pro Asp
            355                 360                 365

Glu Ser Gly Gly Glu Gly Pro Val Ala Val Gly Asp Thr Lys Thr Val
            370                 375                 380

Thr Val Arg
385
```

```
<210> SEQ ID NO 61
<211> LENGTH: 420
<212> TYPE: PRT
<213> ORGANISM: Streptomyces coelicolor A3(2)

<400> SEQUENCE: 61

Met Leu Glu Asn Glu Arg Gln Asp Pro Phe Glu Asp Arg Leu Gly Thr
1               5                   10                  15

Ala Leu Arg Asp Ala Gly Asp Gly Phe Glu Ala Asp Arg Ala Ala Leu
            20                  25                  30

Val Thr Ala Gly Arg Ala Arg Gly Arg Ala Leu Leu Arg Arg Arg
        35                  40                  45

Ala Ala Val Val Gly Gly Val Ala Gly Val Ala Leu Ala Gly Val Gly
    50                  55                  60

Gly Val Leu Val Leu Pro Ala Asp His Pro Ala Gly Pro Asp Arg Ser
65                  70                  75                  80

Gly Thr Ala Ser Ala Pro Ser Ala Gly Asp Ala Thr Thr Ala Ala Ala
                85                  90                  95

Ser Phe Thr Gly Asp Asp Leu Leu His Glu Leu Lys Gly Leu Leu Pro
            100                 105                 110

Pro Gly Thr Tyr Gly Glu Glu Ser Ala Arg Gly Ser Asp His Gln Leu
        115                 120                 125

Gly Pro Thr Ala Gln Leu Val Tyr Asp Asp Gly Ala Gly Ala Ala Ala
    130                 135                 140

Ile Gly Met Gly Phe Ala Arg Val Glu Pro Gly Ser Ala Gln Val Arg
145                 150                 155                 160

Glu Leu Met Ala Cys Pro Asp His Asn Ile Thr Pro Tyr Asp Asp Cys
                165                 170                 175

Ser Ser Asp Arg Leu Pro Asp Gly Ser Leu Leu Lys Leu Tyr Gln Gly
            180                 185                 190

Tyr Glu Tyr Pro Asp Leu Arg Val Asp Thr Lys Arg Trp Thr Ala Asp
        195                 200                 205

Leu Val Thr Ala Glu Gly Gln His Val Ser Val Ser Glu Trp Asn Ser
    210                 215                 220

Pro Ala Glu Lys Gly Ala Pro Val Ser Arg Glu Pro Pro Leu Ser
225                 230                 235                 240

Thr Glu Arg Leu Arg Glu Leu Val Thr Ala Gly Val Trp Arg Glu Val
                245                 250                 255

Val Asp Ala Val Pro Lys Ser Arg Lys Pro Arg Ser Ala Ala Pro
            260                 265                 270

Arg Thr Glu Arg Pro Glu Val Ser Gly Lys Ser Val Gly Asp Thr Leu
        275                 280                 285

Ala Ala Leu Leu Pro Arg Lys Leu Asp Val Val Ser Arg Gly Gly Gln
    290                 295                 300

Glu Ser Glu Tyr Ala Tyr Val Val Val Asp Asp Gly Arg Gly Arg Ser
305                 310                 315                 320

Leu Val Gln Ile Asn Val Gln His Gly Met Ala Asp Val Ala Gly Gln
                325                 330                 335

Leu Tyr Ala Asp Gly Glu Thr Leu Pro Asp Gly Thr Arg Val Ala Thr
            340                 345                 350

Arg Gln Gly Pro Gly Glu Lys Ala Gly Ser Gly Val Val Met Trp Thr
        355                 360                 365

Val Asp Thr Leu Arg Pro Gly Pro Ala Gly Phe Arg Val Val Ile Ser
```

```
            370                 375                 380
Ala Phe Asn Thr Gly Asp Gln Asn Lys Asp Ala Thr Arg Asp Ala Pro
385                 390                 395                 400

Ala Leu Thr Met Glu Gln Leu Arg Lys Ile Ala Leu Ser Gly Glu Trp
                405                 410                 415

Asp Arg Leu Arg
            420

<210> SEQ ID NO 62
<211> LENGTH: 342
<212> TYPE: PRT
<213> ORGANISM: Corynebacterium glutamicum ATCC 13032

<400> SEQUENCE: 62

Met Thr Arg Arg Leu His Gly Gly Glu Gln Asp Gly Gln Glu His Val
1               5                   10                  15

Lys Gly Gln Leu Lys Gln Leu Phe Asp Asp Ala Phe Leu Thr Asp
            20                  25                  30

Leu Ser Arg Gly Val Asp Pro Ser Glu Gly Asp Asp Ala Leu Ala Gly
                35                  40                  45

Leu Leu Leu Asp Leu Thr Lys Glu Ala Gln Glu Pro Pro Ala Thr Met
50                  55                  60

Pro Asp Trp Ser Thr Leu Leu Pro Gly Ile Leu Asp Gln Asp Gln Asp
65                  70                  75                  80

Leu Pro Val Glu Ser Thr Ser Asp Thr Thr Val Met Gln Ala Ser Asn
                85                  90                  95

Pro Ala Thr Gln Glu Phe Ala Pro Val Ser Ile Ser Asp Thr Pro Asn
            100                 105                 110

Thr Ala Thr Asn Ser Ala Asp Ala Asp Glu Ser Ala Thr Val Val Pro
        115                 120                 125

Leu Ala Ala Arg Arg Glu Lys Arg Ala Lys Ser Gly Ser Ser Gly Val
130                 135                 140

His Ser Leu Asp Ala Ser Ala Thr Gln Arg Lys Ser His Pro Phe Leu
145                 150                 155                 160

Ser Gly Leu Val Gly Ala Ala Ala Thr Leu Val Ile Ala Gly Gly
                165                 170                 175

Gly Ala Ala Val Tyr Asn Ala Asp Glu Asn Ser Pro Leu Tyr Gly Met
            180                 185                 190

Asn Gln Gln Leu Phe Gly Asn Gln Asp Ser Pro Ser Val Val Glu Leu
        195                 200                 205

Ala Ser Thr Leu Glu Glu Val Asp Ser Arg Thr Ala Ser Gly Asp Val
    210                 215                 220

Glu Gly Ala Arg Ala Leu Leu Glu Gln Ala Arg Ala Met Leu Asp Gly
225                 230                 235                 240

Met Ala Pro Pro Arg Lys Ala Pro Ser Glu Ala Thr Arg Thr Val Glu
                245                 250                 255

Ser Glu Pro Gly Thr Gln Thr Leu Thr Ala Thr Val Thr Glu Ser Ala
            260                 265                 270

Ser Pro Glu Pro Pro Val Thr Glu Thr Gln Thr Val Thr Ser Thr Glu
        275                 280                 285

Val Gln Thr Val Thr Thr Thr Ala Val Ala Pro Val Trp Thr Pro
    290                 295                 300

Asn Pro Glu Pro Thr Thr Thr Ala Ala Pro Thr Ser Thr Pro Ser Thr
305                 310                 315                 320
```

-continued

Gly Gly Gly Glu Gly Thr Gly Asn Asp Gly Asp Ser Gly Leu Val Pro
                325                 330                 335

Pro Gln Thr Pro Gly Asn
            340

<210> SEQ ID NO 63
<211> LENGTH: 299
<212> TYPE: PRT
<213> ORGANISM: Mycobacterium tuberculosis H37Rv

<400> SEQUENCE: 63

Met Arg Glu Phe Gly Asn Pro Leu Gly Asp Arg Pro Pro Leu Asp Glu
1               5                   10                  15

Leu Ala Arg Thr Asp Leu Leu Leu Asp Ala Leu Ala Glu Arg Glu Glu
            20                  25                  30

Val Asp Phe Ala Asp Pro Arg Asp Asp Ala Leu Ala Ala Leu Leu Gly
        35                  40                  45

Gln Trp Arg Asp Asp Leu Arg Trp Pro Pro Ala Ser Ala Leu Val Ser
    50                  55                  60

Gln Asp Glu Ala Val Ala Ala Leu Arg Ala Gly Val Ala Gln Arg Arg
65                  70                  75                  80

Arg Ala Arg Arg Ser Leu Ala Ala Val Gly Ser Val Ala Ala Ala Leu
                85                  90                  95

Leu Val Leu Ser Gly Phe Gly Ala Val Val Ala Asp Ala Arg Pro Gly
            100                 105                 110

Asp Leu Leu Tyr Gly Leu His Ala Met Met Phe Asn Arg Ser Arg Val
        115                 120                 125

Ser Asp Asp Gln Ile Val Leu Ser Ala Lys Ala Asn Leu Ala Lys Val
130                 135                 140

Glu Gln Met Ile Ala Gln Gly Gln Trp Ala Glu Ala Gln Asp Glu Leu
145                 150                 155                 160

Ala Glu Val Ser Ser Thr Val Gln Ala Val Thr Asp Gly Ser Arg Arg
                165                 170                 175

Gln Asp Leu Ile Asn Glu Val Asn Leu Leu Asn Thr Lys Val Glu Thr
            180                 185                 190

Arg Asp Pro Asn Ala Thr Leu Arg Pro Gly Ser Pro Ser Asn Pro Ala
        195                 200                 205

Ala Pro Gly Ser Val Gly Asn Ser Trp Thr Pro Leu Ala Pro Val Val
    210                 215                 220

Glu Pro Pro Thr Pro Pro Thr Pro Ala Ser Ala Ala Glu Pro Ser Met
225                 230                 235                 240

Ser Ala Gly Val Ser Glu Ser Pro Met Pro Asn Ser Thr Ser Thr Val
                245                 250                 255

Ala Ala Ser Pro Ser Thr Pro Ser Ser Lys Pro Glu Pro Gly Ser Ile
            260                 265                 270

Asp Pro Ser Leu Glu Pro Ala Asp Glu Ala Thr Asn Pro Ala Gly Gln
        275                 280                 285

Pro Ala Pro Glu Thr Pro Val Ser Pro Thr His
    290                 295

<210> SEQ ID NO 64
<211> LENGTH: 25
<212> TYPE: DNA
<213> ORGANISM: Artificial Sequence
<220> FEATURE:
<223> OTHER INFORMATION: Synthetic Polynucleotide

```
<400> SEQUENCE: 64
catgacaaaa tttttttagat gcgtt                                            25

<210> SEQ ID NO 65
<211> LENGTH: 57
<212> TYPE: PRT
<213> ORGANISM: Artificial Sequence
<220> FEATURE:
<223> OTHER INFORMATION: Synthetic Polypeptide

<400> SEQUENCE: 65

Ile Ala Val Asn Thr Ala Lys Asn Tyr Leu Val Ala Gln Gly Arg Arg
1               5                   10                  15

Pro Pro Ser Ser Asp Val Asp Ala Ile Glu Ala Glu Asn Phe Glu Ser
            20                  25                  30

Gly Gly Ala Leu Lys Glu Ile Ser Asn Pro Glu Asn Leu Met Leu Ser
        35                  40                  45

Glu Glu Leu Arg Gln Ile Val Phe Arg
    50                  55

<210> SEQ ID NO 66
<211> LENGTH: 49
<212> TYPE: PRT
<213> ORGANISM: Artificial Sequence
<220> FEATURE:
<223> OTHER INFORMATION: Synthetic Polypeptide

<400> SEQUENCE: 66

Ile Ala Arg Asn Leu Tyr Ile Asp Ser Val Arg Lys Asp Arg Gly Trp
1               5                   10                  15

Val Gln Val Gln Asn Ser Leu Glu Gln Leu Glu Arg Leu Glu Ala Pro
            20                  25                  30

Val Asp Arg Thr Leu Asp Tyr Ser Gln Arg Gln Glu Gln Gln Leu Asn
        35                  40                  45

Ser

<210> SEQ ID NO 67
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 67
aattgtgagc gctcacaatt                                                   20
```

ANTI-SIGMAS FOR PROGRAMMABLE TRANSCRIPTIONAL REGULATION

RELATED APPLICATIONS

This application is a national stage filing under 35 U.S.C. § 371 of international application PCT/US2013/032145, filed Mar. 15, 2013, which was published under PCT Article 21(2) in English, and claims the benefit under 35 U.S.C. § 119(e) of U.S. Provisional Application Ser. No. 61/616,176, entitled ANTI-SIGMAS FOR PROGRAMMABLE TRANSCRIPTIONAL REGULATION, filed on Mar. 27, 2012, the entire disclosure of each of which is herein incorporated by reference.

GOVERNMENT INTEREST

This invention was made with Government support under Grant No. R01 GM057755 awarded by the National Institutes of Health and under Contract No. EEC0540879 awarded by the National Science Foundation. The Government has certain rights in this invention.

FIELD OF INVENTION

The invention relates to recombinant genetic circuits comprising anti-sigma factors.

BACKGROUND OF INVENTION

Synthetic biology is limited by the small number of available and well-characterized transcription factors from which to program large genetic circuits. Bacterial sigma factors (as), the promoter recognition subunits of RNA polymerase (RNAP), are modular proteins with domains that recognize DNA sequences in the −10 and −35 regions of their target promoters[1]. In addition to the housekeeping σs (e.g., σ70 in *E. coli*) that recognize the thousands of canonical promoters essential for growth, bacteria have a variable number of stress-activated alternative σs that direct RNAP to distinct promoter sequences. This enables cells to express multiple genes associated with a particular developmental state or stress response[2] and execute complex gene expression dynamics that implement temporal control and serve as developmental checkpoints[3]. For example, spore formation in *B. subtilis* requires a cascade of 5 σs (σH→σF→σE→σG→σK)[4]. σs can be embedded in complex webs of partner swapping networks, including anti-σs, which physically block σs from interacting with RNAP[5-7], and anti-anti-σs. Such feedback loops and protein-protein interactions generate more complex dynamics for integrating many environmental and cellular signals[8].

SUMMARY OF INVENTION

Described herein are anti-sigma factors ("anti-sigmas") that bind to sigma factors and block activation of transcription. Anti-sigmas and their cognate sigma factors provide a highly effective mechanism for regulating gene expression in genetic circuits.

Aspects of the invention relate to a recombinant genetic circuit including an extracytoplasmic function (ECF) sigma factor; an anti-sigma factor that binds to the ECF sigma factor; and a promoter that is recognized by the ECF sigma factor. In some embodiments, the ECF sigma factor, the anti-sigma factor and/or the promoter are genetically engineered. In some embodiments, the ECF sigma factor and/or the promoter are chimeric.

In some embodiments, the recombinant genetic circuit is expressed within a host cell, which can be a prokaryotic cell or a eukaryotic cell. In some embodiments, the ECF sigma factor and/or anti-sigma factor are codon-optimized for expression in the host cell. In certain embodiments, the ECF sigma factor is selected from the group consisting of ECF01-ECF43. In certain embodiments, the anti-sigma factor is selected from the group of anti-sigma factors contained within Table 1.

In some embodiments, the recombinant genetic circuit comprises a combination of logic gates. In some embodiments, the logic gates are selected from the group consisting of AND, NAND, NOR, OR, NOT, XOR, EQUALS, AND, IMPLIES, and ANDN gates. In certain embodiments, the AND gates comprises an ECF sigma factor and a promoter that is recognized by the ECF sigma factor. In some embodiments, the recombinant genetic circuit is a component of a synthetic genetic switch. In certain embodiments, the synthetic genetic switch is bistable. In certain embodiments, the recombinant genetic circuit is a component of a pulse generator.

Further aspects of the invention relate to a system comprising a plurality of recombinant genetic circuits. In some embodiments, the ECF sigma factors and the anti-sigma factors are orthogonal.

Further aspects of the invention relate to a host cell comprising a heterologous genetic circuit including an extracytoplasmic function (ECF) sigma factor; an anti-sigma factor that binds to the ECF sigma factor; and a promoter that is recognized by the ECF sigma factor. In some embodiments, the ECF sigma factor, the anti-sigma factor and/or the promoter are genetically engineered. In some embodiments, the ECF sigma factor and/or the promoter are chimeric. In some embodiments, the host cell is a prokaryotic host cell.

In some embodiments, the genetic circuit comprises one or more logic gates selected from the group consisting of AND, NAND, NOR, OR, NOT, XOR, EQUALS, AND, IMPLIES, and ANDN gates. In certain embodiments, the AND gates comprises a sigma factor and a sigma factor target DNA sequence. In certain embodiments, two or more logic gates are combined by having the output promoter of an upstream gate serve as the input promoter of a downstream gate.

Further aspects of the invention relate to a library comprising two or more anti-sigma factors, wherein each anti-sigma factor selectively binds to one or more ECF sigma factors. In some embodiments, the library further includes one or more ECF sigma factors. In some embodiments, the library further includes one or more promoters that are recognized by the one or more sigma factors.

In some embodiments, the anti-sigma factors, ECF sigma factor and/or promoter are genetically engineered. In certain embodiments, the ECF sigma factor and/or promoter is chimeric. In some embodiments, the ECF sigma factors and/or anti-sigma factors are codon-optimized for expression in a host cell.

In some embodiments, the ECF sigma factors and the anti-sigma factors are orthogonal. In some embodiments, the ECF sigma factors are under the control of an inducible promoter. In certain embodiments, the ECF sigma factor is selected from the group consisting of ECF01-ECF43. In certain embodiments, the anti-sigma factor is selected from the anti-sigma factors within Table 1.

Further aspects of the invention relate to a non-transitory computer readable storage medium encoded with instructions, executable by a processor, for designing a host cell.

Further aspects of the invention relate to a computer product comprising a computer readable medium encoded with a plurality of instructions for controlling a computing system to perform an operation for designing a host cell.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 1A shows how sigmas recruit core RNA polymerase (RNAP) to promoters; a function that is inhibited by the anti-σ. Sigmas have a two-domain structure that binds to the −10 and −35 regions of the target promoter. FIG. 1B shows the complete libraries of 86 synthesized σs (top row) and their 62 cognate anti-σs (bottom row) organized as a phylogenetic tree. Asterisks indicate active σs (>5-fold activation) or anti-σs (>2-fold repression). Carets indicate σs or anti-σs that appear in the final orthogonal sets. All σs in the library are named ECFXX_YYYY, where "XX" denotes the ECF subgroup, and "YYYY" denotes the unique σ ID given by Staron and co-workers[7]. The anti-σs were named ASXX_YYYY, where "XX" and "YYYY" denote the ECF subgroup and unique ID of the cognate σ. Consequently, cognate σ/anti-σ pairs have the same numbering (e.g., ECF11_987 and AS11_987). FIG. 1C shows that for each σ, target promoters are identified through a process of computational search, selection, and design. The first step involves the organization of the ECF operons according to the subgroups defined by Mascher and co-workers[7].

FIG. 3A depicts an embodiment wherein ECF σs were induced by IPTG via a T7 expression system, and σ-dependent promoter activity was measured by gfp expression and flow cytometry. Plasmid pN565 encodes the IPTG inducible T7* expression system[19]; plasmid series pVRa and pVRb encode the ECF σ library and test promoter library, respectively. The specific example shown (ECF11_987 and P11_3726) is highlighted in the following subfigures. FIG. 3B depicts activities of active ECF σ library members titrated against their cognate target promoters. The grey lines show levels of GFP expression for one active ECF σ:promoter pair in each subgroup induced with 0, 10, 20, 50, and 100 μM IPTG. Highlighted in black is the averaged activity of sigma ECF11_987 against its promoter P11_3726. Data are shown from three independent assays and error bars represent one standard deviation. Plots of the other σ:promoter pairs are shown in more detail in FIG. 12. FIG. 3C depicts the liquid culture growth curves ($OD_{600}$) for each σ shown in part c under high induction (100 μM IPTG). Highlighted in black is the growth curve of sigma ECF11_987 averaged from three independent growth assays and the error bars represent one standard deviation. The growth curves of two negative controls are shown in dark grey. FIG. 3D depicts the activity of one promoter (P11_3726) for the complete library of active σs expressed with 100 μM IPTG. Each bar represents the average promoter activity from two independent assays and error bars represent one standard deviation. The two σs from subgroup 11 that were expected to activate the promoter are bracketed. FIG. 3E shows all cross-reactions for the 20 most orthogonal σ:promoter pairs. Each σ was induced with 100 μM IPTG, and the fold-induction was measured as the fluorescence with σ induction divided by the basal activity of the promoter in the absence of any σ. Each square represents the average fold-induction from two independent assays of a unique σ:promoter combination. All promoters were named using the convention Pxx_YYYY, where "XX" and "YYYY" denotes the subgroup and unique ID of the downstream parent σ gene (e.g. P02_2817 is the promoter upstream of σ ECF02_2817). Promoters containing synthetic UP-elements were renamed to Pxx_UPYYYY (e.g., P15_UP436). The σ:promoter pairs were ordered by the absolute amount of off target activity caused by/affecting the pair, with the lowest off-target activity in the upper left and the highest in the lower right. FIG. 3F shows promoter scores, as calculated from PWMs, compared to the experimental measurements in part e. The promoter scores are calculated using the ECF promoter models (UP+PWM-35+PWM-10+spacer penalty) for the −60 to +20 promoter fragment including 30 nt flanking vector sequence. The ECF11_987:P11_3726 activity is highlighted with an arrow. FIG. 3G shows ECF02_2817 and ECF11_3276 recombined in their flexible linker region between domains 2 and 4 to create chimeric σs ECF02-11 and ECF11-02 (FIG. 20). The promoters activated by the two parental σs were similarly recombined between the −10 and −35 regions to create chimeric promoters. FIG. 3H shows the activity and orthogonality of the σs and chimeric σs against their cognate promoters. All of the σs were induced with 10 μM IPTG and the fold-induction was as defined previously. Each square represents the average fold-induction from three independent assays.

FIG. 4A shows that in addition to the expression and reporter systems shown in FIG. 3A, cells contain the plasmid series pVRc, which allows HSL-inducible independent expression of anti-σs to bind and sequester σs. FIG. 4B sows repression of ECF11_987 activity on promoter P11_3726 by different anti-σs. Each bar represents average fold-repression, as defined by normalizing the fluorescence of cells containing the promoter with both induced σ (induced with 10 μM IPTG) and induced anti-σ (induced with 50 nM HSL)

against the fluorescence of cells containing just the promoter and induced sigma factor. Bar heights represent the average from three independent assays and error bars represent one standard deviation. FIG. 4C shows the cross reactivity of 12 anti-sigma factors on the set of 12 orthogonal σs targeted by the anti-σs. The activity of each σ paired with its cognate promoter was measured in the absence and presence of different anti-σs. Sigmas were partially induced (10 µM IPTG) and anti-σs maximally induced (50 nM HSL). Fold activity repression by the anti-σ, defined as the activity of the promoter in the absence of the anti-σ divided by the activity in its presence is indicated. The anti-σ:σ pairs were arranged in the same order as the σs in FIG. 3E. FIG. 4D shows the influence of the expression of the anti-σ for a series of switches. The plots show the transfer function of each σ-dependent promoter for differing expression levels of anti-σ induced by the inducer HSL: (a), no anti sigma plasmid; (b), 10 nM HSL; (c), 50 nM HSL.

FIG. 10A shows a Heatmap of 29 ECF sigma promoter models used to score all 706 identified ECF sigma promoters. Each promoter model, comprised of −35 and −10 PWMs and spacer penalties (Equation S3) was used to score target promoter sequences from approximately −40 to +1 (a 40 nt window starting from 5 nt upstream of the identified −35 motif) and the highest score for each sequence recorded. A high score represents a similar sequence to the promoter model; a low score (e.g., <0) represents a divergent sequence to the promoter model. Target promoters represent all 706 promoters identified in ECF sigma regulatory regions and are grouped by their parent ECF sigma subgroup. FIG. 10B shows a Heatmap of the 29-35 subsite models used to score all 706 identified ECF sigma promoters. FIG. 10C shows a Heatmap of the 29-10 subsite models used to score all 706 identified ECF sigma promoters.

FIG. 20 depicts chimeric sigma factor and promoter engineering.

DETAILED DESCRIPTION

Figure 1:
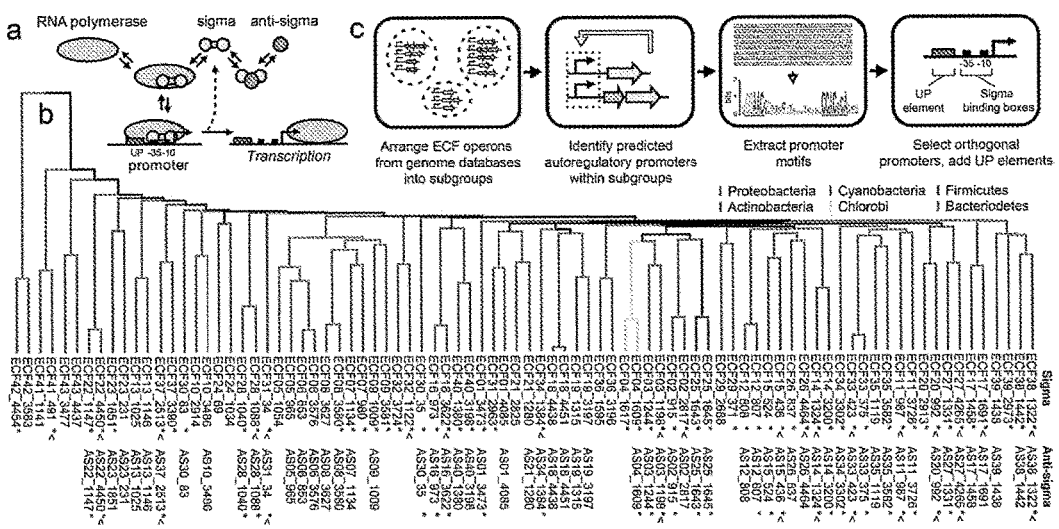
FIG. 1 depicts a strategy for the genomic mining of Extracytoplasmic Function (ECF) σs, anti-σs, and promoters.

The invention is based, at least in part, on the identification of multiple anti-sigmas from the genomes of diverse bacteria. Surprisingly, anti-sigmas were easily transferable between species and were found to function orthogonally with their cognate sigma factors even when derived from different organisms. Significantly, anti-sigmas serve as highly effective sequestering molecules in genetic circuits, dramatically expanding available tools for constructing and programming large genetic circuits.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Aspects of the invention relate to sigma factors. As used herein, a sigma (σ) factor refers to a sequence-specific DNA binding protein that recruits RNA polymerase (RNAP) to specific promoter sequences to initiate transcription. Bacterial cells contain several categories of sigma factors, including general or "housekeeping" sigma factors, which are involved in transcriptional activation of many genes. Other sigma factors serve more specialized functions, responding to certain cellular conditions and activating transcription of specific genes. The Extracytoplasmic Function (ECF) sigma factors represent the largest and most diverse group of sigma factors. Approximately 19,314 ECF sigma factors have been annotated (Ulrich et al. (2007) *Nucleic Acids Res.* 35, D386-390), and have been subdivided into 43 subgroups (Staron et. Al (2009) *Mol. Microbiol.* 74(3):557-81). A description of classification of sigma factors, including a listing of sigma factors ECF01-ECF43, from a variety of bacterial species, is incorporated by reference herein from WO 2012/170436, e.g., Table 1 on pages 28-30 of WO 2012/170436.

It should be appreciated that any sigma factor can be compatible with genetic circuits described herein and with methods for making and using such genetic circuits. In some embodiments, the sigma factor is an ECF sigma factor. For example, the ECF sigma factor can be ECF01, ECF02, ECF03, ECF04, ECF05, ECF06, ECF07, ECF08, ECF09, ECF10, ECF11, ECF12, ECF13, ECF14, ECF15, ECF16, ECF17, ECF18, ECF19, ECF20, ECF21, ECF22, ECF23, ECF24, ECF25, ECF26, ECF27, ECF28, ECF29, ECF30, ECF31, ECF32, ECF33, ECF34, ECF35, ECF36, ECF37, ECF38, ECF39, ECF40, ECF41, ECF42 or ECF43, as incorporated by reference from WO 2012/170436, or the ECF sigma factor can be a homolog of any of ECF01-ECF43 from other bacterial species, or can be any other ECF Sigma factor. The sigma factor can be naturally occurring or can be synthetic. As used herein, a naturally occurring sigma factor means that the sigma factor has the same sequence that it possesses in its natural environment, or a variant thereof, while a synthetic sigma factor refers to a sigma factor that has a different sequence than is possessed by a sigma factor in its natural environment. In some embodiments, genetic circuits can include multiple different sigma factors including different types of sigma factors.

ECF sigma factors bind to specific DNA sequences within their target promoters, referred to as "–10" and "–35" regions, based on measurement from the transcriptional start site. The –10 region is also referred to as a "Pribnow box", and is generally six nucleotides long. In some embodiments, the –10 region has the sequence TATAAT or a variant thereof. The sequence of the "–35 region" ranges from 8-12 nucleotides. In certain embodiments, the sequence of the –35 region is TGTTGACA or a variant thereof. It should be appreciated that any –10 or –35 regions of any sequence can be compatible with aspects of the invention. Sigma factors comprise a region referred to as "Region 2," which is a conserved domain that recognizes –10 regions of promoters, and a region referred to as "Region 4," which is a conserved domain that recognizes –35 regions of promoters.

Promoters recognized by ECF sigma factors can be naturally occurring or can be synthetic. As used herein, a naturally occurring promoter means that the promoter has the same sequence that it possesses in its natural environment, or a variant thereof, while synthetic refers to a promoter that has a different sequence than is possessed by a promoter in a natural environment. In some embodiments an ECF sigma factor recognizes the same promoter that it recognizes in its natural environment, while in other embodiments an ECF sigma factor recognizes a different promoter than the promoter that it recognizes in its natural environment.

ECF sigma factors can be chimeric. As used herein, a chimeric sigma factor refers to a sigma factor formed from portions of two or more sigma factors. For example, in some embodiments, a chimeric sigma factor comprises a "Region 2" from a first sigma factor and a "Region 4" from a second sigma factor, thereby generating a chimeric sigma factor with novel DNA binding activities. Chimeric sigma factors can include any combination of DNA binding domains from any sigma factor. A sigma factor, including a chimeric sigma factor can be a component of a library of DNA binding proteins, such as a library of sigma factors. Further aspects of the invention relate to the generation of a library of sigma factors including chimeric sigma factors. Example 1 describes a non-limiting example of a library containing 86 ECF sigmas including 2 from each of the 43 identified subgroups.

Promoters that are recognized by sigma factors can be chimeric. As used herein, a chimeric promoter refers to a promoter formed from portions of two or more promoters. For example, in some embodiments, a chimeric promoter includes a –10 region from a first promoter and a –35 region from a second promoter, thereby generating a novel promoter. Chimeric promoters can include any combination of regions that are recognized by sigma factors. A promoter, including a chimeric promoter, can be a component of a library. Further aspects of the invention relate to the generation of a library of promoters including chimeric promoters.

Aspects of the invention relate to a sigma factor and a cognate promoter. As used herein, a cognate promoter for a sigma factor refers to a promoter to which the sigma factor specifically binds. A sigma factor can have more than one cognate promoter.

Aspects of the invention encompass sigma factor-promoter interactions that are orthogonal. As used herein, an orthogonal sigma factor-promoter interaction refers to an interaction that does not exhibit "cross-talk," meaning that the sigma factor does not interfere with or regulate transcriptional regulatory elements in a system other than the transcriptional regulatory elements containing the cognate promoter of the sigma factor. In some embodiments ECF sigma factors autoregulate, meaning that an ECF sigma binds to a promoter of the gene encoding that ECF sigma, thereby regulating its own transcription.

Examples 1 and 2 describe a computational approach to identifying native promoters for subgroups of ECF sigma factors. Promoter modeling is described that predicts whether a promoter will be orthogonal with a given sigma factor or subgroup of sigma factors. In some embodiments, BioProspector is used, which allows the user to search for two sequence blocks (such as the −10 region and the −35 region) connected by a variable spacer (Liu et al. (2001) *Pac Symp Biocomput* 127-138). Example 1 demonstrates the identification of 706 promoters, including 29 promoter motifs in the 43 ECF sigma subgroups, and describing testing the orthogonality of such promoters. Examples 1 and 2 further demonstrate designing of orthogonal promoters for ECF sigma subgroups. As demonstrated in Examples 1 and 5 and FIGS. 3 and 20-22, engineered chimeric sigma factors and promoters were designed and demonstrated to function orthogonally.

Further aspects of the invention relate to the identification of anti-sigmas. As used herein, "anti-sigma factor," "anti-sigma" and "anti-σ" are used interchangeably to refer to a polypeptide that binds to a sigma factor and inhibits its ability to activate transcription. Examples 1 and 3 describes identification of 63 anti-sigmas from a variety of bacterial species and the demonstration that many of these anti-sigmas could inhibit their cognate sigma factor in *E. coli*, demonstrating that anti-sigmas exhibit a high level of transferability between species. As used herein a cognate sigma factor for an anti-sigma refers to a sigma factor to which the anti-sigma specifically binds. An anti-sigma can bind to more than one sigma factor.

Aspects of the invention encompass interactions between anti-sigmas and sigma factors that are orthogonal. As used herein, an orthogonal anti-sigma-sigma factor interaction refers to an interaction that does not exhibit "cross-talk," meaning that the anti-sigma does not interfere with or regulate elements in a system other than the elements containing the cognate sigma factor.

Figure 4:
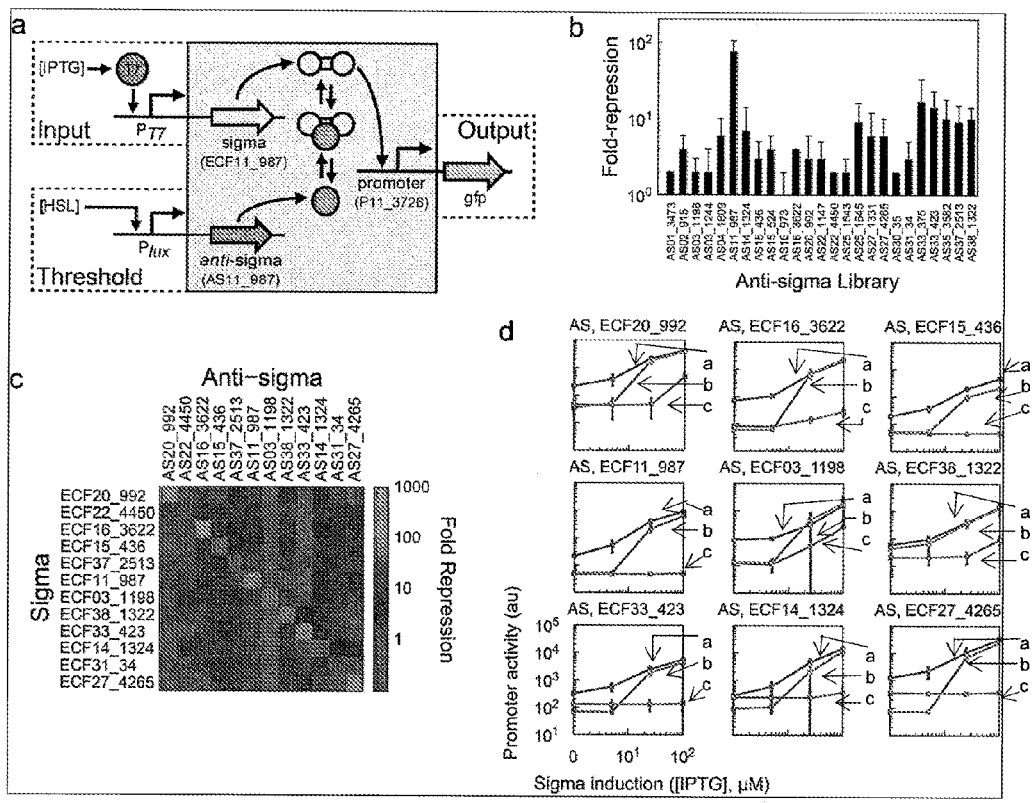
FIG. 4 demonstrates that anti-sigma factors can be used to create orthogonal threshold-gated switches.
Figure 5:
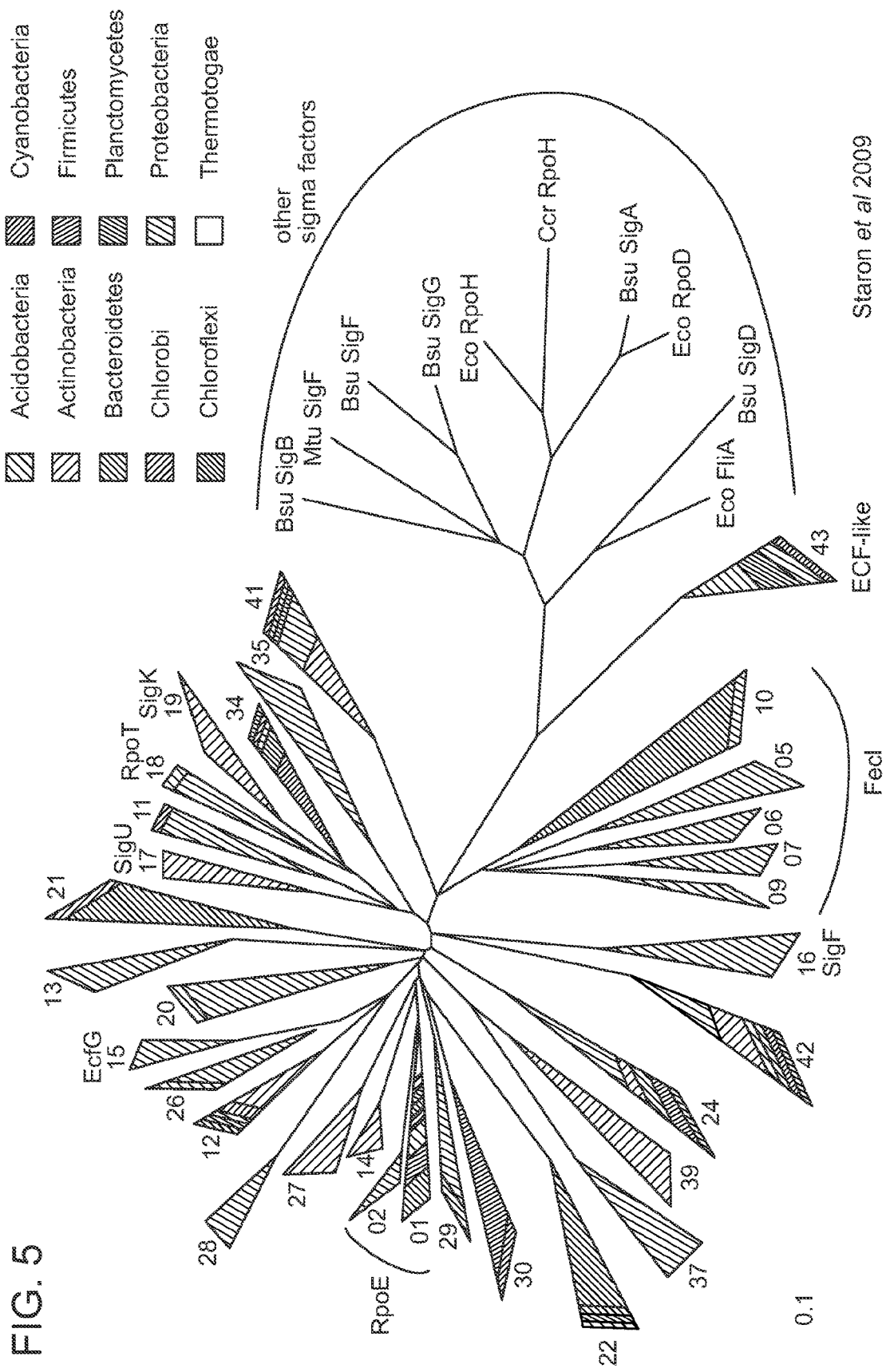
FIG. 5 depicts a phylogenetic tree of 1873 ECF sigmas across bacteria divided into 43 subgroups.
Figure 6:
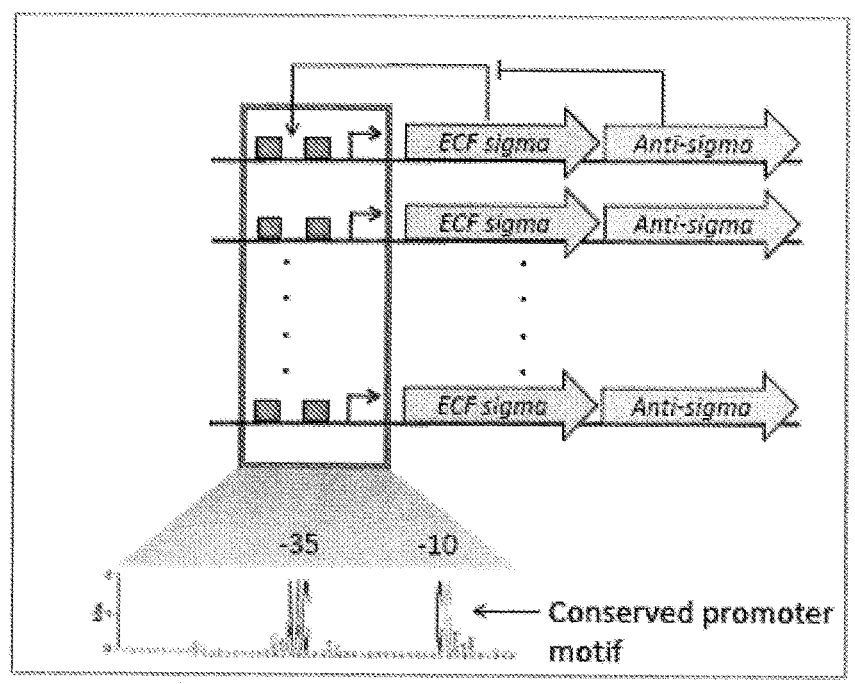
FIG. 6 depicts a method of identifying target promoters using bioinformatics. Each ECF sigma subgroup is predicted to recognize different promoter sequences. Previously, promoters were known for only 18 sigma subgroups (Staron et al. 2009). Many ECF sigmas autoregulate their expression; consequently, promoters can be found by searching for conserved motifs upstream of sigma genes in each subgroup. The upstream sequences of all sigmas within each subgroup were extracted. Conserved motifs were identified using a 2-block motif search algorithm (BioProspector). For each ECF sigma subgroup, upstream sequences of ECF sigma genes and ECF sigma operons were searched.
Figure 7:
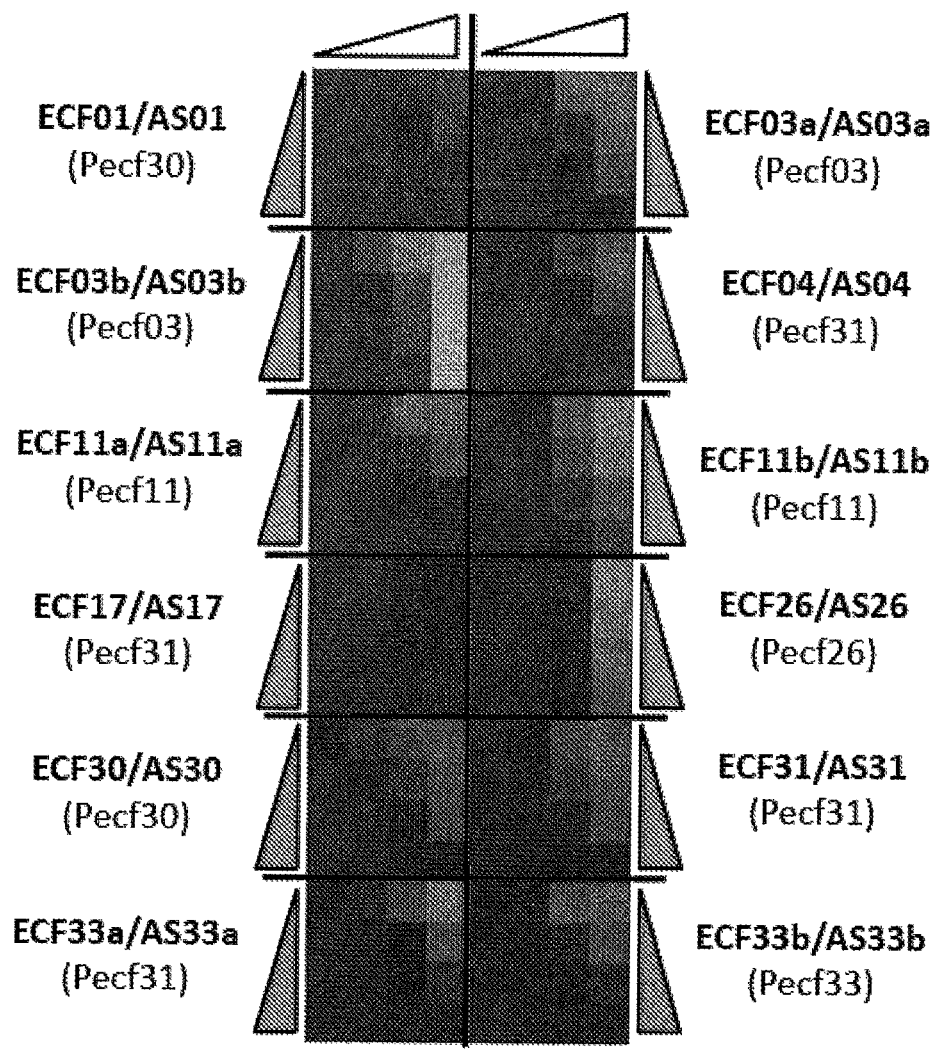
FIG. 7 depicts repression of ECF sigmas by their cognate anti-sigmas, tested in vivo at target promoters.
Figure 8:
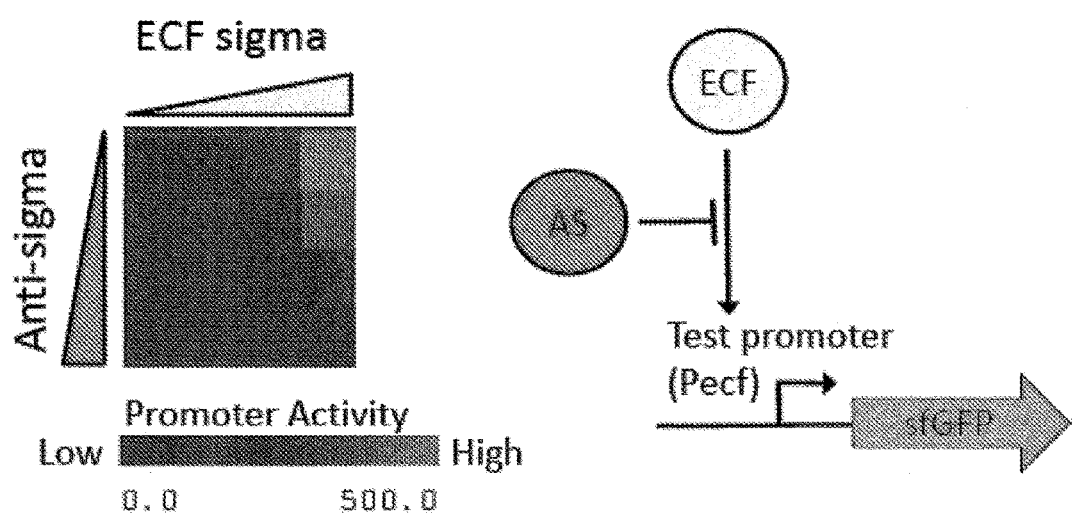
FIG. 8 depicts titration of sigma/anti-sigma pairs (ECF/AS) and measurement of promoter (Pecf) activity (fluorescence was measured by flow cytometry).
Figure 18:
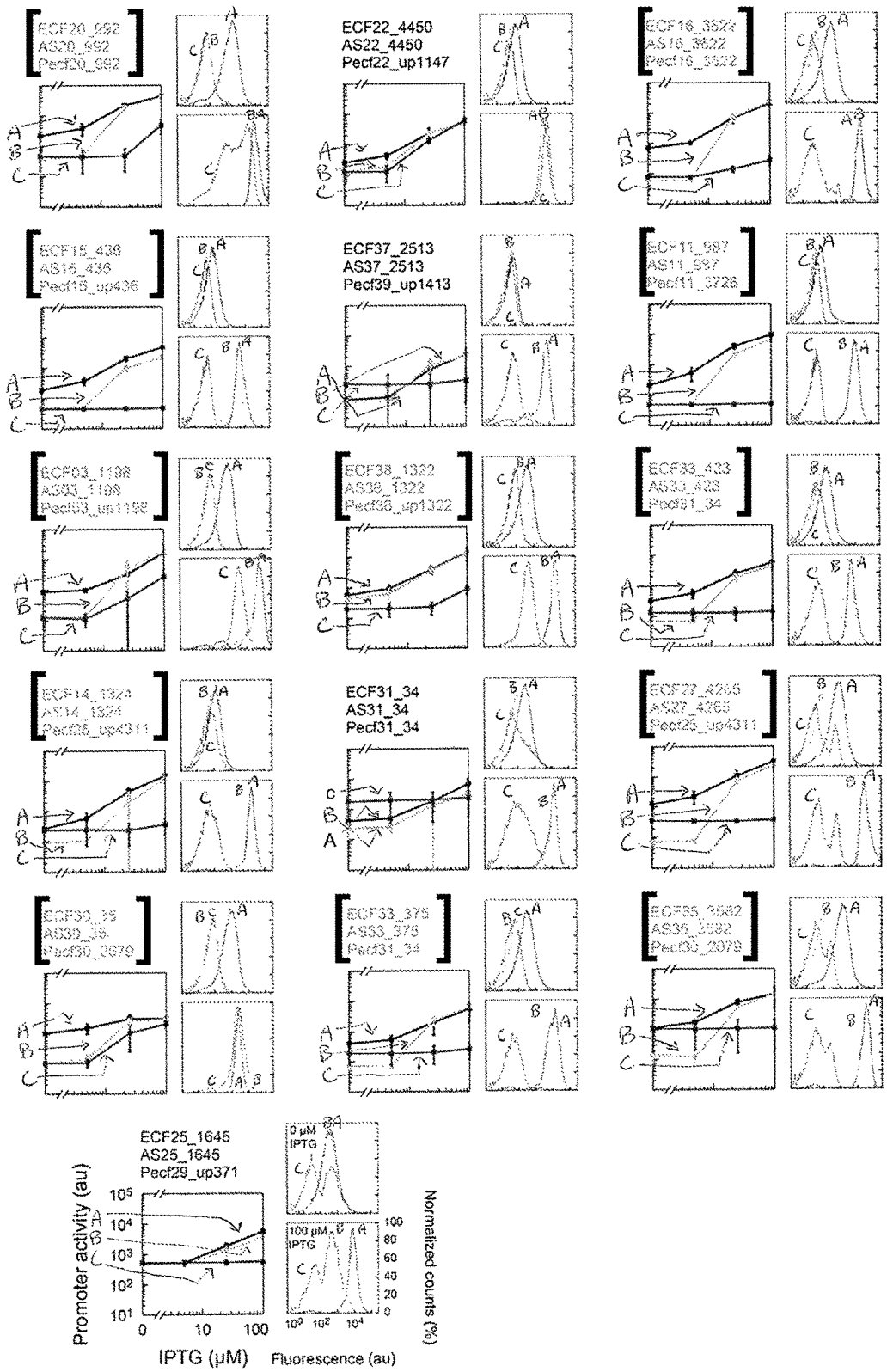
FIG. 18 depicts anti-sigma factor thresholding. Sixteen sets of anti-sigma, sigma factor, and promoter were assayed at varying inductions of both anti-sigma and sigma factor to characterize their ability to implement thresholding. The anti-sigmas were either not present (a), or induced at 0 nM HSL (b) or 50 nM HSL (c), while the sigma factors were induced at 0, 5, 25, and 100 µM IPTG. Plots represent the average promoter activity from three independent assays and error bars represent one standard deviation. Histograms show representative distributions from a 0 and 100 µM induction for each set. Bracketed titles indicate data shown in FIG. 4D.
Figure 19:
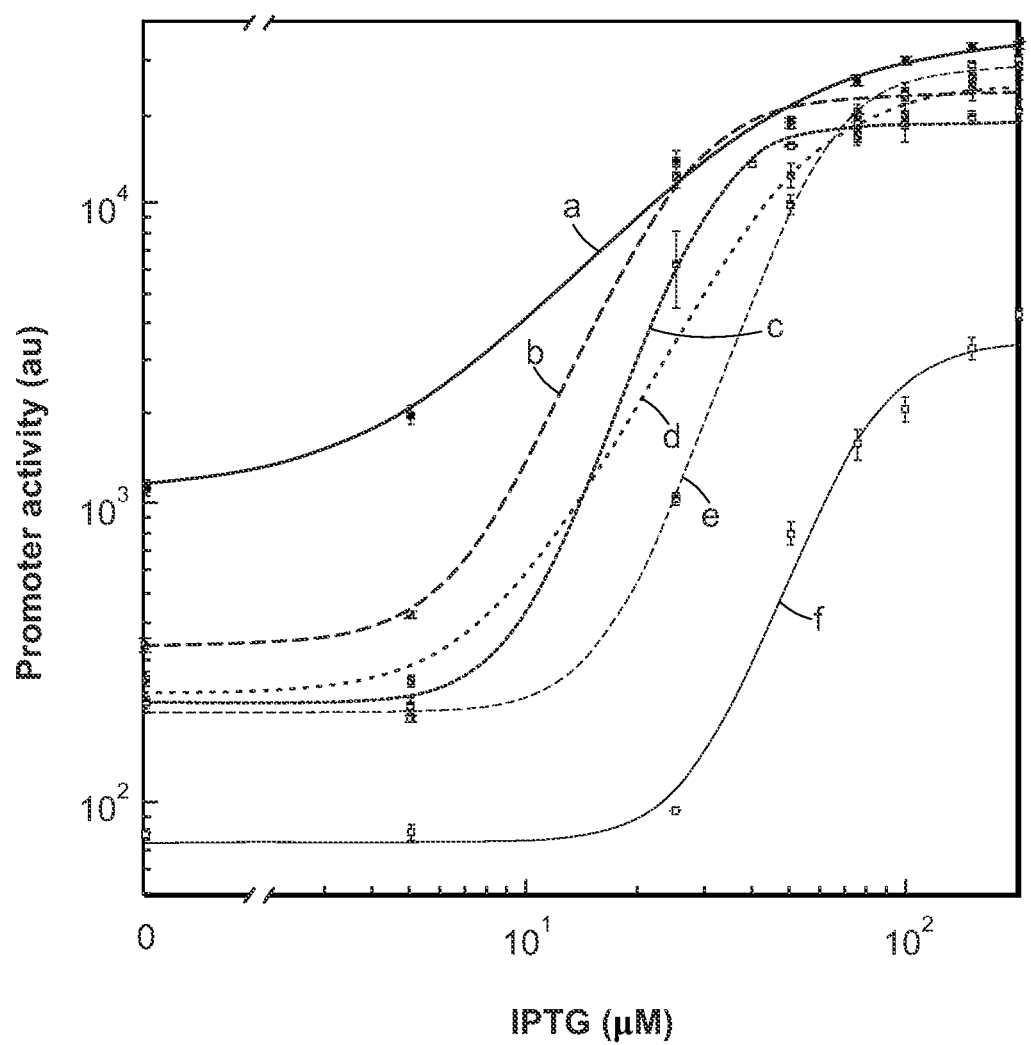
FIG. 19 depicts Hill fits to AS/ECF20_992 anti-sigma:sigma threshold switch. Threshold-gated switches were built using sigma factor ECF20_992 and its corresponding anti-sigma and promoter. ECF20_992 was induced with varying levels of IPTG (0, 5, 25, 50, 75, 100, 150, and 200 µM) in the presence of plasmids expressing AS20_992 from varying promoters: No anti-sigma (a), BBa_J23117 (b), BBa_J23105 (c), BBa_J23101 (d), BBa_J23100 (e), pLux induced with 50 nM HSL (f). Equation S5 was fit to the data using a relative least-squares algorithm and the fit is shown. The Hill coefficient n is higher when the anti-sigma is present: n=1.7 (No anti-sigma), n=3.3 (BBa_J23117), n=4.1 (BBa_J23105), n=2.6 (BBa_J23101), n=3.9 (BBa_J23100 and pLux). Plots represent the average promoter activity from three technical replicates (No anti-sigma) or three independent assays (all others) and error bars represent one standard deviation.
Figure 24:
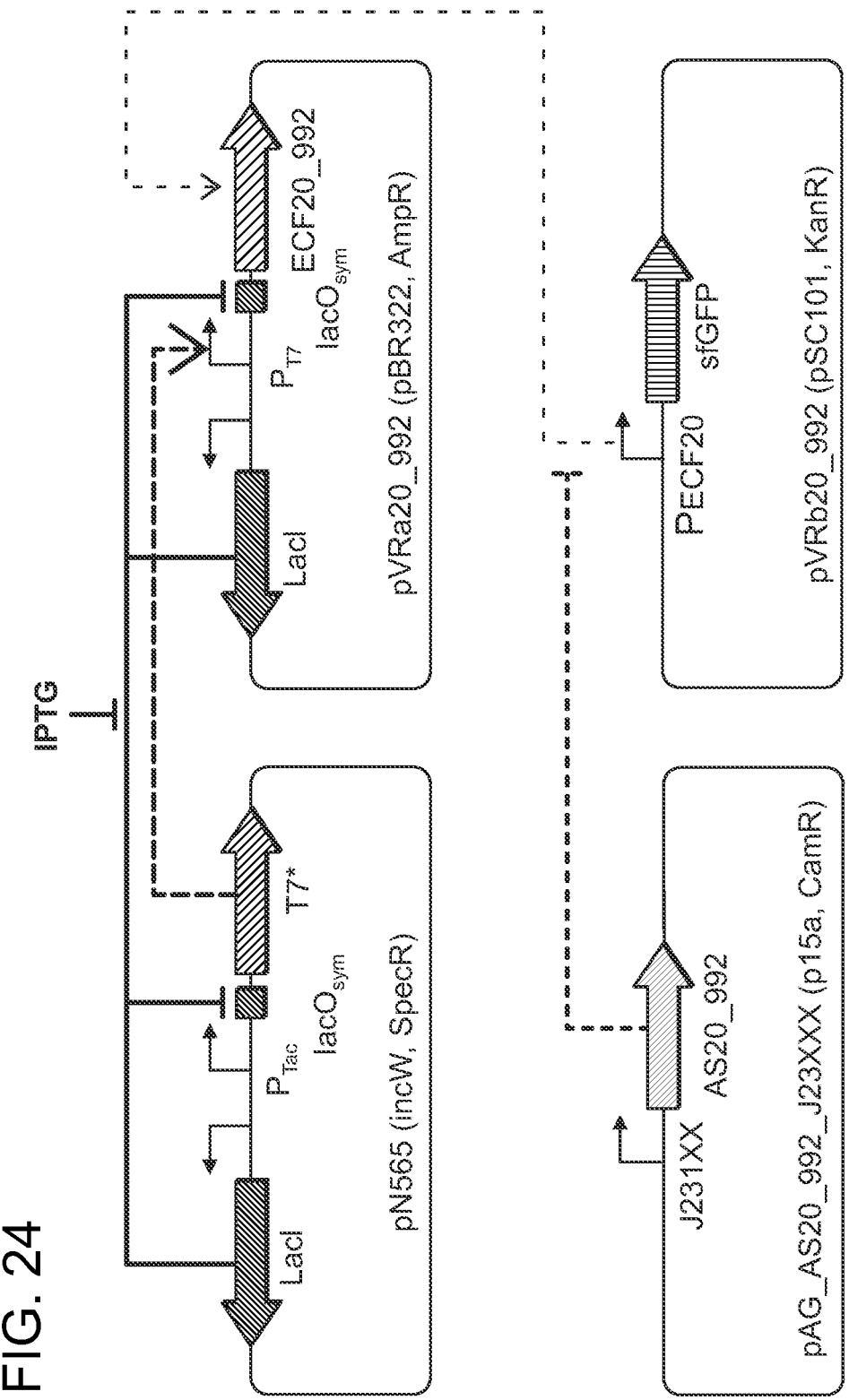
FIG. 24 depicts an alternate plasmid set used in anti-sigma threshold experiments. An alternate series of plasmids, pAG_AS20_992_123 XXX, replaces the pVRcXX_XXXX plasmid series used the anti-sigma library testing experiments (FIG. 23). This plasmid series expresses the anti-sigma factor AS20_992 from a range of constitutive promoters instead of from the Plux promoter.

Significantly, anti-sigmas were demonstrated herein to act as sequestering molecules in switches containing sigma factors. Sequestering molecules can lower background, increase cooperativity and allow the threshold to be tuned within switches (Buchler et al. (2009) *Molecular Systems Biology* 5). FIGS. 4, 19 and 24 reveal that the inclusion of anti-sigmas in switches comprising sigma factors results in decreased background and increased cooperativity. FIG. 18 reveals anti-sigma thresholding ability. Through sequestration, anti-sigmas serve to tune response characteristics within genetic circuits and facilitate the evolution of complex dynamics (Buchler et al. (2008) *J Mol Biol* 384:1106-1119).

Tables 1 and 2 describe anti-sigmas identified herein including providing sequence information for each anti-sigma.

TABLE 1

Sequences of Anti-sigma Factors

| Anti-sigma | Plasmid | Cognate ECF sigma | SEQ ID NO. | Sequence |
|---|---|---|---|---|
| AS01_3473 | pVRc01_3473 | ECF01_3473 | 1 | MSNYDNAELLALWLEGKLTPKQRDEFEQRCIQDSQ FAEQVDAAAMVKIGADDYSSSEVPQWNKAATFEP QQANNSGSWLSGVSLVTSALAIVLVLTGTQVTTSEG ELRIRFGSGQSEQALVKLVDSKLDAFKQNQQDAFTL YAQTLQQQQSESASQLTNYLLSSSRKERREDFAELI KFVNQQRSDDQLFYARQLNQLQQDVYHDATGVAL ESIQQ |
| AS01_4085 | pVRc01_4085 | ECF01_4085 | 2 | MNQSPQDLDSLIKSLPLEMQPTTDLWPEITAQLSPQS QQKTHLTRPWLIAASVAVLSLLAMLLWQRPDGNSL LPQTATITTTVPGATLNTEATLAESTLVELVDQIALT HQTQLDVFNQNQYTVSWQLSSTDAPQQIQSDISQAL AELDTASKQVQAALKQQPTNQQMWQLWRWIMQR QITLLQQGQKLPFTSKRTSQGNTI |
| AS02_915 | pVRc02_915 | ECF02_915 | 3 | MEKTGQEWVSASVDGETDRQTLAELAADTDSHAK WQRYHLMGDAMRDELPQAMPLDLSARIAAALEDE PTILAPKVEREATQAPSRAVVVPFMRQLGQYGIAAA VALMAVVGVQNYQSTQDDAPLPVLNTRPLVGTAT PVSLQTGPVANQNQGNANDQLLEQRRRINAYLQDH MLQQRLNTGAVVDDNSEVTPIPVNR |
| AS02_2817 | pVRc02_2817 | ECF02_2817 | 4 | MQKEQLSALMDGETLDSELLNELAHNPEMQKTWE SYHLIRDSMRGDTPEVLHFDISSRVMAAIEEEPVRQP ATLIPEAQPAPHQWQKMPFWQKVRPWAAQLTQMG VAACVSLAVIVGVQHYNGQSETSQQPETPVFNTLP MMGKASPVSLGVPSEATANNGQQQQVQEQRRRIN AMLQDYELQRRLHSEQLQFEQAQTQQAAVQVPGIQ TLGTQSQ |
| AS03_1198 | pVRc03_1198 | ECF03_1198 | 5 | MDKDFDFDNIGKRTPYRTPDNFFEETQRKILERTVD EQRKKRRLKRIIPTVIAVAAVLAGILFTPSLRYMNTD TPSASNILAVDKNNVTTDPVDKWIKELSDEELEELV SFSENDIFLN |
| AS03_1244 | pVRc03_1244 | ECF03_1244 | 6 | MKQFDPDVNIRPKEDSIRHYSVPDDYFASFTDKLMA QIPAVKEENTVVVPSVALWPKLRPLLYLAASFLLMI GMFKAFSLFGVGSDTGRTTSTSAGLVALDHGDTRW SEDTDYRDFLHDNCAETVSDEWVLTDFSE |

TABLE 1 -continued

Sequences of Anti-sigma Factors

| Anti-sigma | Plasmid | Cognate ECF sigma | SEQ ID NO. | Sequence |
|---|---|---|---|---|
| AS04_1609 | pVRc04_1609 | ECF04_1609 | 7 | MNRTTEQRNAEVMKTIGLLDQMPRVEVDHLFRVR LMQRIEAMEVKKTSWSALPGGAFNPRLAFMALLL MLNIASALMLFMHGTPQATGSSGAIAESLTEDYGGP ALSYYDDQTTIDR |
| AS05_965 | pVRc05_965 | ECF05_965 | 8 | MSDQREPSERMITEAASWLALLQDEPVSAADRHAF ERWRKADPGHQLALSRMQSLWGSFDELSDTPARIA LRQTFAPAGSKPTSRTVQALALVGVLVCGWMSVER LPVWMADRHTDVGERSEFSLADGSQVQLNSGSALD VKFDGRQRVIELLQGELWVEVAKDVQRPFVVRTDQ GTITALGTRFVVRRGEEGTTVSVLESAIAAQANTAD VINVATGQQALLKDGRVQTPHALGSDDPADWTRG VLKVDDQPLSEVLQTLATYRHGLLRYDTQALAGLR VSGVFRLDDTDAALATLADNLPIKVERFTDLLVIVK PDAR |
| AS06_853 | pVRc06_853 | ECF06_853 | 9 | MSNLPVSSRVLEAAIAWKLSLGESSGTPDERNEFMR WHAASEEHARAWRQLGAMDQRVSAAAGPARQAL LQSRASLRRRIGKVGGGLAGTFLLGALLAWVGAPS LAPSYWLADQRTATGELRTLRLEDGTLLSLNTHTA VDIEYAGAQRVIVLHQGEISVETGHQDPRPLLVRTE DGRLRPLGTRFLVRREAGGTRLEVLQASVAAMPHD SGDEQVLREGQQVLMNANGLGEVGTVPAGADAW TRGMLVVDNVRLGDLLATLGQYRSGYLGVDAKVA DLRVTGSFPLTNTDLALASLVPALPVKIERHTQWW VNVTSK |
| AS06_3576 | pVRc06_3576 | ECF06_3576 | 10 | MSADDRHSPVRARVLDEAIAWQLLLDSGEAHPDDH RAFHRWYAAHPEHERAWEQLGGLDRHLARAANGP ARNALLSGNARFKRRLRRLGGSALGLVLALGVGLG VANRYVPVRYLLADAYSATGEQRELTLPDATHVRL NSRSAIDVRFDGERRQVVLLAGEILVETAHGDPRPF VVSSADGDMRALGTRFLVRREEPGTRLTVLQSAVA ARAETLSEERVIKEGQQVLILPQGLQASEAAPALAG AWAQGMLVVENARLADLVAELGRYSPALLQVDPSI ADLRVTGSFPLKDTRLALQALEPSLPVRSVRHNAW WFEVVPR |
| AS07_1134 | pVRc07_1134 | ECF07_1134 | 11 | MNSPQEQQQIRQQAAEWAIRLDGGDLDRSRREALD GWLAADPRHRAALALAQRTWKQLGSLAEPRTMVQ TPVASAPRRAGGRRKGWRGWAAAAAVLLALGSA WNERDAGVSWLADHSTGKGEVRILRLVDGSEVEL DAQSAIDVAYDSRERRVRLLEGSAIFRAAPRAGRET RPFVVESAGGSTRALGTRFLVSRNDDGSVQVGVLE HRVAVALAHPRTGTVGRRELGEGESLRYSAEGGVE APLGGRLDDLTSWRRGLLVFDEQPLGEVVARLNRY RPGHLLVAPGALAQRRVSGVFRVADLEASLQSISDE LGVRSLGLAGVTLLY |
| AS08_3580 | pVRc08_3580 | ECF08_3580 | 12 | MTASDSAADETGDLRHEAHAWVISLTSGRVTQGDA RAFRQWCARSPQHLRAFVEARDLWQALGSAAALP LEPPAVAQIAPRRFGRRWFVGGALAASVALFVLRPS LLDHGLGGADYVTAVGEQRQVQVSGETRIEMNTRT RLNVRRNQEQQETIELLGGEAEIIASHPPQSSLRVMA GSAWLSASRARFNVRSSGDVCVVTCLEGSVRLEHL GQRLDLQAGQQLTFDERRNGPPVPFDVAEVMAWR ERMLVFNDVPLATVIDEINRYRPGMLLLLDKALGR RRVQARFSLDQLADVATLIRDAYGIEVTRLPGGVVL LG |
| AS08_3627 | pVRc08_3627 | ECF08_3627 | 13 | MNIFSISTPQASADQQLLNEARDWLVLLTSGQATAA DARALRQWCGQSPQHAAAFEQTKALWHCLQPAAA LLEQQARPRHFGRRAFLGGALAASAALFMVRLTVP GGFAGLTADFATEVGEQRRVDLAEGVSLELNTQTRI SRRDLGAGEQGIELLEGEVEVFSQRLQPLKVQAGEG WLSARQARFNLRNTDHQVCVTCIEGSLQVDVAGRS IGLDSGRQLTYDPRSIGEPQVVDIHSVIAWREQVLVF DNASLNTVISEINRYRPGMLVLLNAELGKRKVQARF NLNQLAGVALLIRDAYGAKCTELPGGVVLLS |
| AS09_1009 | pVRc09_1009 | ECF09_1009 | 14 | MWQAAMDWLLQCHSAPDDALLQQAHARWLAAD ERHAVAWRKAEKVWLLSGGLAPLEPPVPQPLPTPL RARRNRPRRALKALALAACLLLLAGPTPPTAHTSPA |

TABLE 1 -continued

Sequences of Anti-sigma Factors

| Anti-sigma | Plasmid | Cognate ECF sigma | SEQ ID NO. | Sequence |
|---|---|---|---|---|
| | | | | GEHRQVLLSDGSRIELGSDSAIRVDFEPGTRAVTLLR GQAFFEVSHDASRPFTVQAADVKVRVIGTAFDVDL SRTAVVVAVQSGAVQVRDGRGELAVPALGPGDSL RLGLDQGPPQRGRLLPGQVAPWRQWQLLVNDRPL SEVVEALQDYYPGVLLLTDPALGERRITASLNLRSP VSALQLAIAPLGGHLRQWGPYLTLIRKEPQVPAKQ |
| AS10_3486 | pVRc10_3486 | ECF10_3486 | 15 | MSNIHQFTPKDLILETAANWISAIDRGLNKVEKEQF KLWMLQSNAHQDAVYELAKLWDELSVLNELSTLF PHKNNTEEKSKWVFSYGIAASLFAALMICSYLLVNL ETGYNQALAKVNYTKIYKTKVGEQATYVLPDGTIV QLNTNSLLEVAYSKGRRQLLLSRGEGRFNVAKDAT RPFSVMAGDKSFTALGTVFNVQRNTSSHLELVVTE GKVMITDPSVAVDANDFKAYQLADNSTQKIRKINA NIVLSGEKAIIEKSVTAPIKRLSADDVQRDLAWQNG MLIFNGEQLSDALNEVSRYTATRFELSSAELANIKV AGVFKAGDVAGLLESLKTNFSIDHERLGEHVVSLK RQTKS |
| AS11_987 | pVRc11_987 | ECF11_987 | 16 | MNKHPDNNLLEAYASGSIDAVSGLVVATHLETCSK CRAYVNQVEASQANTVSESPSEYSPEFDDMLNDIIN AEPVNDNVVIQDTAFVNVAGKSFELPKTLVRFSDLV GSWRSYGGKVFSAQIDLGEDARVSLMYIGENVQIP QHTHRGLESTLVLHGGFSDEDGQYEEGDLMVRDAS VKHSPFTQEGEDCLCLTVLTEPMIFTQGVARIFNLFG KGLYP |
| AS11_3726 | pVRc11_3726 | ECF11_3726 | 17 | MGPLHHPDDATLISYAAGALSQVIAVVTAAHLERC AECRARLRQAEQIGGVLMQQSISRVVPLKSRMAML ARLDEQETSVDSVMHAMPAANHDPDLLPHCMHAH FGRHLSTLKWKTLIPGVQRVSAQGIEQGNLMLLKIA PGVSMPVHSHESGEMTMVLKGAYHDVQGEFGLND VADLDSHIQHQPIAYPDRECICVLAAESKLRFHGWM ARMMQPFFGI |
| AS12_807 | pVRc12_807 | ECF12_807 | 18 | MRTDSTLTAAMDCRELERSIDAYLDGEFDERERAE AEAHLATCTPCRAMADRQGALRLALRAKLREAMA SPAAAGCAPPHLRARVRTSLAHERRPLWRRVLQPV PVAAVAACAMGVLVVLAGHRGDTALVDDAIRVHH RALPLEVDAAAMPGWFAGKLDFHPALPHFAGAVA RLEGARLSNLREWPAAYVRYQLPRGQAGLFIVDDP DRRFDTPGREVKVGPQVVRVVNARGYNVAVWRQ DEIVYSLVSDLDEDALFKLVQAAQAEAAAGR |
| AS12_808 | pVRc12_808 | ECF12_808 | 19 | MNCQDLERLLYPYLDGEFQPEERVDLETHLSGCAD CRRRAEEEKQMQQALRRAARHSVSGMRAPASLRA GIQVGLKQEQRRVQFGVWLRAGAMALVVVTVGG GWAAFHAEQRLSAARTEAVQRHSKSKALPFEIASN TPEQVEEWFKDKVDPRITVPQIPKAKPLGGRISILNG REVAYISYETLPDNEGEPSRRLGVFVLPGDNEVVIPK FQALQAVEVDSAQGFNVVTWRDDEIVYEMVTDMD ESDIRRMLAERDSGEKLARKSAPEADEPLYSLPPAP RTPHSWPPISVEPVTYPTYPQ |
| AS13_1025 | pVRc13_1025 | ECF13_1025 | 20 | MLSCYQATRLMSQALDEKIVLSQHVQLMLHLKICD GCRNFRQQLADLRTMTSAFARGENENQNKVT |
| AS13_1146 | pVRc13_1146 | ECF13_1146 | 21 | MNCEHASELISLNCEQKLKVKDSLQLQIHLWLCPKC RHFKKNNNEMRKLLQNYCDPKSNCEKET |
| AS14_1324 | pVRc14_1324 | ECF14_1324 | 22 | MSGSRPEPEGHLAEQHLGDRLSALVDGELGHDARE RVLAHVATCPKCKAEVDAQRRLKNVFAEAAPPAPS ESFLARLQGLPGGGDSDGGGSPFSGLPGGFGASAAS GVFGPRRDERFEFDYVPAGSHTPVLPSATSGRGFRI HEVGRHESDRSASRGLRFAFAAAGAVSLAAIALGG VTLGTPDTTTEARGSGSGSNVTPLRTPGSAAATGSE SQRRRTAGPLLGQGQRALGDLPVASTTASAPLLPG MPAPAGGDARQQAVRALTTPVTAGAAAMSPLIRPL EAVPPLSLSSWSAAPEVRPPGLLAAPDPAPSPYPAAS PAASSSPLR |
| AS14_3200 | pVRc14_3200 | ECF14_3200 | 23 | MADPGSVGHVFRRAFSWLPAQFASQSDAPVGAPRQ FRSTEHLSIEAIAAFVDGELRMNAHLRAAHHLSLCA QCAAEVDDQSRARAALRDSHPIRIPSTLLGLLSEIPR |

TABLE 1 -continued

Sequences of Anti-sigma Factors

| Anti-sigma | Plasmid | Cognate ECF sigma | SEQ ID NO. | Sequence |
|---|---|---|---|---|
| | | | | CPPEGPSKGSSGGSSQGPPDGAAAGFGDRFADGDG GNRGRQSRVRR |
| AS15_436 | pVRc15_436 | ECF15_436 | 24 | MAQSTEPKASPQEATAKGGDNTKGKSRKELQQQID ENLRRVYEEALVQEVPDRFAMLLDQLRQKGTGK |
| AS15_524 | pVRc15_524 | ECF15_524 | 25 | MNFGVEDMIEHVPMEDKRKGAAALDEARLRQQAI GVKLRQMFDEVVNEPVPDEFLAILRKAERPAGGE |
| AS16_973 | pVRc16_973 | ECF16_973 | 26 | MKTDDLIALLAAGEGPVPRHAVGRRMAVAALGGL TAALLLTITLYGVRSDITEVAQTPLFWGKVAFPTSL ALIGLWLTSRLARPGGKGAAGWKMLGLPLLLVWC GAAVSIAGAPVDARADLLFGRTWRTCALNIALLSVP AFVTVFWALKGLAPTRLRLAGAAGGLLAGSSATVA YCLHCPEMGVPFWGVWYVLGMLVPTVLGAWWGP RMLRW |
| AS16_3622 | pVRc16_3622 | ECF16_3622 | 27 | MMKTDELISLLATAEGPVDRHALARRLGLALLAGL LGALLLTVALYGVRSDLAEVARTPLFWAKVALPTS LALLGLWLTQRLARPGVRGGALWGLLGVPLLLVW LGAAISLFGAPPEARADLIFGRTWRTCALNITLLSTP VFIAVFWALRGLAPTRLRQAGAAGGLLAGSTATLV YCLHCPEMGVPFWGLWYLLGMLVPTLLGAVLGPR LLRW |
| AS17_1458 | pVRc17_1458 | ECF17_1458 | 28 | MQGTPAPNEHETVGAYALGILDDAEATAFEAHLAT CEWCAQQLDELAGMEPMMAALADLPGTGTPAVAE SLTVKPSARLSEKLVDEVAERRASKRRRNFYLVGT AAALIIGGPFAAVATTGGGGGGGDDGGGRRAEATQ QAASPAESAFAAMPDRVTATDPGTQVSATVALEKK AWGTETVLELKNLKGPQKCSLIAVGKNGERETLTS WSVPDWGYGIPGATTEKAKKPLYVHGGAAFEPNQI SHFEVMTFDGKRLVEVDA |
| AS17_1691 | pVRc17_1691 | ECF17_1691 | 29 | MTMPLRGLGPPDDTGVREVSTGDDHHYAMWDAA YVLGALSAADRREFEAHLAGCPECRGAVTELCGVP ALLSQLDRDEVAAISESAPTVVASGLSPELLPSLLAA VHRRRRRTRLITWVASSAAAAVLAIGVLVGVQGHS AAPQRAAVSALPMAVGTQLLASTVSISGEPWGTFI NLRCVCLAPPYASHDTLAMVVVGRDGSQTRLATW LAEPGHTATPAGSISTPVDQIAAVQVVAADTGQVLL QRSL |
| AS18_4438 | pVRc18_4438 | ECF18_4438 | 30 | MSGTMSTPFPIDQEPPRDVLAGEYVLGLLSAEERLA AEQRIATDGQFAQAVLQWQELLAPLLEEIVAQTPPD QVWVRVRQALGFDTPLRAVPSAAPVSTTAPAAPLW NSVRFWRWASVGGLATAAVCVLALLNLRTPPAPV QPPHTGEVVQTPVTPPATNPPAATGIAMTSTLATED GRPGYVALMDADKHTITVTPLDRTATADKVPELWL ITPDGKAHSMGTFDDQRARRAQIPDQLMPMLSNEAI LAVTLEPPGGAPGGVATGTVVAKGGISTLAMAP |
| AS18_4451 | pVRc18_4451 | ECF18_4451 | 31 | MSGTMSTPFPIDQEPPRDVLAGEYVLGLLSADDRLA VEQRIATDAQFAQAVAQWQEHLAPLLEEIAAVTPA DQVWTRVRQALGFDTPLHAVPASGVQSPAPPAAVP LWNSVRFWRWASAGGLATAAVCVLALLSVRAPPT APPSGPVQNTPIVQTPPAKPPATGIAMTSTLATADGR PGYVALMDADKQVITVTPLDRTATAGKVPELWLIT PDGKAHSMGVFDDQRARRASIPAPLMPMLSNEAIL AVTLEPPGGAPGGVATGTVVAKGGISTLAMAP |
| AS19_1315 | pVRc19_1315 | ECF19_1315 | 32 | MRTEDLHSLTGAYALHALPDDEREAFERHLAGCAT CEQEAREFAAATARLGLAATVVPAPALRDRVLHRV TTVRQVPPGGGTAEKARRVVPRGRGLARWALAAC VAAAAGLGGTAVWQYERAQDAGQRAAQAERRAE TLAGVLAAPDAESRTARLADGASGTLVVSERQDRA VFLASGMAEPPRGKVYQLWFDDHGTMRSAGLMDP GSTSQAVLMDGAVDGAAGVGITVEPAGGSKQPTSD PIALLSMPA |
| AS19_3197 | pVRc19_3197 | ECF19_3197 | 33 | MTEHTDFELLELATPYALNAVSDDERADIDRRVAA APSPVAAAFNDEVRAVRETMAVVSAATTAEPPAHL RTAILDATKPEVRRQSRWRTAAFASAAAIAVGLGA FGLGVLTRPSPPPTVAEQVLTAPDVRTVSRPLGAGT |

TABLE 1 -continued

Sequences of Anti-sigma Factors

| Anti-sigma | Plasmid | Cognate ECF sigma | SEQ ID NO. | Sequence |
|---|---|---|---|---|
| | | | | ATVVFSRDRNTGLLVMNNVAPPSRGTVYQMWLLG GAKGPRSAGTMGTAAVTPSTTATLTDLGASTALAF TVEPGTGSPQPTGTILAELPLG |
| AS20_992 | pVRc20_992 | ECF20_992 | 34 | MTPERFVHLADAYGADLQRWPSAERAAAQALLDC GDAQAVAALRQAHWLDSQLDRYQVPAPSPALAQR IIAAAQQPGAPFWSRYAGWLASLGWVGVGLTGVA AGMLAVALSLPLSTSAEALPSVFDQSDAEFVLSINA EEAEQ |
| AS21_1280 | pVRc21_1280 | ECF21_1280 | 35 | MEEKELWMNKLKEKLGDYSEPLPASGWEQLEKEL MPPVERKIYPYRKWTVAAAAVILLALGSSVSLYFLG TPAADEIRHAKTPALASVPDVLPDAQQPDMTGTTIE PVVRPVVKNRIAKAERNIPQPTANIDEPVKKEEQPSE LNAQTGDRKEKEEVEPVEETKAIRHKPADTEQPRN KPRRPSSRDKLHIPAEKASSQKGTWSMGLSVGNSG GASTELGSGIPSYMSRVSMVSVSNGLLSIPNDQQLV FEDGVPYLRQANQVVDMEHHQPISFGLSVRKSLAK GFSVETGLTYTLLSSDAKFADSDQKTEQKLHYLGIP LKANWNFLDKKLFTLYVSGGGMIEKCVYGKLGTE KETVKPLQFSVSGAVGAQFNATKRVGIYVEPGVAY FFDDGSDVQTIRKENPFNFNIQAGIRLTY |
| AS22_1147 | pVRc22_1147 | ECF22_1147 | 36 | MELDDIAVAWRSLEQRLDQHAALAGQVLGDLRSH AARAHLRPLWLSQSAQLLCAIALSGLVAHSWLAFP EQAAAIVGGVLLQIWCVALAASAARQLWLLSQLDF ARPLLQTQRALAQLRRWRTRVAPWLGVAFWVLW VAVADAAWRALTGRSLPYAWLLCNLLVGVLGGIG TWLGYRRLQRSGHPWLERLDTVHAGRSVARTETLL EQIARFQRE |
| AS22_4450 | pVRc22_4450 | ECF22_4450 | 37 | MELDDMKHAWQTLEQRLDQQAAQTGQLLGVVHE ETVRSSLRPLWVAQTAQLLCALALAIVSARSWIPHT DQPVAVIGGVLLQAWCMALAISAMVQLQLLTQFN VAGPLLRTQHALARLRRWRTRVAPWLGVAFWVL WIAVADALWRALTGQTLPTDWLVLNLLVGVAGGI GTWLGFRRLQRAQHPWLERIDRAHAGTGVIRAERM LEEIARFQRD |
| AS23_231 | pVRc23_231 | ECF23_231 | 38 | MDDKNLFRNYNDIVVSEEEIEKYETKKVDDDVLSK MKNKVKKLYMKVNMEEAFEKVEKQFEDDEKVEY MFWAETYGVRKYQMVCGGYYSLEGAISNDWGTK TGIVLTNKGIFGIETNDAYGVLKIKNFRFKDVEYIES KKIKNNFTVFAIKSTSGIEIKVEIYNGDRHIKFLNYIR NNNIKVNIRMIQDRKIQIAYVSIIIIIMIFIIFVISSSIMR SGITK |
| AS23_1851 | pVRc23_1851 | ECF23_1851 | 39 | MKDIYELLNDIDIDEKELEEIEASEIEKEKVKRNVKQ SIRTKKKMKSWKKGVAAASILVGLSVTTLGIGFPTY AGGLPIVGDIFRFLDNGRTGLYENYKEFSTELNNITR ESNGVKVTINDVISDGRTLSITYSLESEQDLGDDPIIL GGLDIMDAHGSSGSGKMTKVTEKKYVGMVTTTHH DSNKKDKVNFRWNIEGIEIPDRKKSIQGHWNFALTV KSMDSKERTIGGSSEKEGIKANMEKVAMSPVSFILY YNQEVSKGARKEWDSVDVELTVKDDLGNDYSGEG NGGSGNDPYNIRWSATFQKLNENATKLIVTPRVHL RVHTPENHGGVEYVNGKEKKIEVPNKEAKKKDIVL DDIVIDLKK |
| AS25_1643_ clone433 | pVRc25_1643_ clone43 | ECF25_1643 | 40 | MTTDSNFNDPCRRQFSRDLPQKMARHTNEATGAM DMVKRDRFELLSAYLGGEVTAAERRQVEDWPAND VAVQRLYSRLLKLRQGIRTMPIPTAQQSPETTAEQV FAKVNRRSRLAWKLGGAAVAACVIGAVTNWLPGR QTGIPQLAQQPQEQPTQAVTTPDALPMIALNNPVIEI PKAAVASPTKFIQPQPQLGEIPPDIN |
| AS25_1643_ clone440 | pVRc25_1643_ clone44 | ECF25_1643 | 41 | MTTDSNFNDPCRRQFSRDLPQKMARHTNEATGAM DMVKRDRSELLSAYLDGEVTAAERRQVEDWLAND VAVQRLYSRLLKLRQGIRTMPIPTAQQSPETTAEQV FAKVNRRSRLAWKLGGAAVAACVIGAVTNWLPGR QTGIPQLAQQPQEQPTQAVTTPDALPMIALNNPVIEI PKAAVASPTKFIQPQPQLGEIPPDIN |

TABLE 1 -continued

Sequences of Anti-sigma Factors

| Anti-sigma | Plasmid | Cognate ECF sigma | SEQ ID NO. | Sequence |
|---|---|---|---|---|
| AS25_1645 | pVRc25_1645 | ECF25_1645 | 42 | MNESFSQRQTDGDRRRGGDLEMKKNHTSHQHHTD SETPMGHNFEQFQRLSAYFDGEATPAERKEIQHLLD TDPQVKQQYQQLRQLKQALQLLPIPTSISAQYLGQR VLARLRRSQLRTLSLWGSGAIAALFVAGVMGQMPR LNFDRFAKNDPDQQPTAALVETSPQGEEALVVALN RPVLQIPKLATTESP |
| AS26_837 | pVRc26_837 | ECF26_837 | 43 | MNAPSDEQLVAYLDDELDREQRSQLDNLIADDPLL SLRVQWLSRSSLPFKAAYDELAQQAPLDRLQARLD AAPSPQKPVFSRRWFIGAAAAGVALAAVAADRLFL AWQAQQSHNWRELVGDYMALYVPQTLEHLPTDEA SQLAQLRTVDARLGVSLSPAKLKLPGAQFKRAQLL EYGGVPIAQMTWLDAKYGPLALCVTRTNSGSQPLA HERRHGMNVVYWTEREHAWMLIGHHPASELEDM AKMFKTRLNV |
| AS26_4464 | pVRc26_4464 | ECF26_4464 | 44 | MKDIDESTLLAYADGALTPDQAGRVEAVLAADPQR AADVRQLQQVKARLRNGYASVLEEPIPAHLLDAAR QRPPPSPQTSVVTATAPIQAPATRQHATRRWAVPTSI AAALLIGLWLWQRQPAQPAPSALLAEQGHDASGTL ALALDRQLSGEQQGKIRMGLSFRAHDGRYCRSFSL QSSHAGLACRQGERWRIEAVSPLQPQRNDSELRMA SSTLPAALLDAIDARIDGQALDAEGERSARARHWR |
| AS27_1331 | pVRc27_1331 | ECF27_1331 | 45 | MSAADKDPDKHSADADPPLTVELLADLQAGLLDD ATAARIRSRVRSDPQAQQILRALNRVRRDVAAMGA DPAWGPAARPAVVDSISAALRSARPNSSPGAAHAA RPHVHPVRMIAGAAGLCAVATAIGVGAVVDAPPPA PSAPTTAQHITVSKPAPVIPLSRPQVLDLLHHTPDYG PPGGPLGDPSRRTSCLSGLGYPASTPVLGAQPIDIDA RPAVLLVIPADTPDKLAVFAVAPHCSAADTGLLAST VVPRA |
| AS27_4265 | pVRc27_4265 | ECF27_4265 | 46 | MTGHPDVAEIADLAEGLLPTTRTTEVRQHLESCELC ADVYASLTEIQGLLGTLPAPAPMPDDVAARIDAALA AEPPLGIADGTRVSRETSTPADRPAGHARPSSTGPGR KDRRGGRRRIAVLGAVAAAAAIGIGSVVVSSLTED SSSGNTAREQQTAIADTFSEGRLKDRVTNLVADGSA ENGSRTPRSFGMESENGGETAENHVFKQPTVPECIR KGIGRDDAVIATEPGVYKGREALLVVLPDATNDTQ VTAYIVETACVDQPAVGKAKILLEHSYARS |
| AS28_1040 | pVRc28_1040 | ECF28_1040 | 47 | MVQNTTRSSKMDELEFRRKVMSDPKQRDNDTLDM MTSSEANAKFVDDVLQLDKQIAQAFKVDVPDDLA DKILFKQTTLVEDEKVIRPQFVRKAMAIAASVAFTA GLLVGQIQWGNLLISPAQASLSDMAVQHVIHEEGFV NRLDEQADMQQINAKMRPFAYKMEGDFPYHVYYL NHCGFGKDNAVHMVFQGEKGKVTLFFTPIHSAQSS LFKQEGMAGIIEPVGNASLILVGEKDENLTNIANKL MPMIQSSI |
| AS28_1088 | pVRc28_1088 | ECF28_1088 | 48 | MDDLQFRRHAYGDPNNQADDFLAHLAENEDDAKF VKDLQAFDHKLTQALNISVPDGLADKLILRQQLSQH QKSKKQTRYLMAMAASVAFIVGVSFSLLRFTPVNL GENSLAHVHHETKALVMEQDIGFNDVNFKLASLEG LSDSKFIQQPGRVFYTSYCDFQGVKSLHLVMADEN GNKVTLFIVPVESRIVLEEAFADNQYKGQSFQTADA YMVLVGEPASDLEFVKKEVENTFI |
| AS30_35 | pVRc30_35 | ECF30_35 | 49 | MDKRLQQLREEYKNVQIPKELDIIVEKALQQEPKKK RIVMWPTSAAIAAAILFTALVNINPDAAQAMSKIPVI GKIVKAITFIEIKEEKDQSSIDVKTPALSGLSNKELEN SINEKYLKESQQLYKEFIQSTSKNKKGHLSIYSDYET VTDTPDLLSIRRNIETTQASSYTQSRYITIDKKNDILL TLKSLFKDERYIKVISQNIKEQMKQQMKEDPNKIYW LTDEDAEPFKTILPDQTFYITEDHKLVISFDEYEVAP GYMGVTEFTIPTGVISNLLVGERYIR |
| AS30_83 | pVRc30_83 | ECF30_83 | 50 | MIDDFDRKLFEMARESKVKEPNALKYKVDYTFKKL KKNKFNFRHLGSIAAILIFCILSVGIYFPTYAMNIPILG DVVEILSNKFNLSGYEINAQNLNYQVSNEDYTLTIES AYYNGLETTFFFKIKGNAKLNKSGQYFFEANFKYN EDISYEGGLEKGEFIDDYTFAGMMTFYINPYSESKLP |

TABLE 1 -continued

Sequences of Anti-sigma Factors

| Anti-sigma | Plasmid | Cognate ECF sigma | SEQ ID NO. | Sequence |
|---|---|---|---|---|
| | | | | EKFNIKFSIPNIIADSEILAVNSDTLNLSFDITDLNVKE TKINKEIQANENSILISSIKKYPTSIVIDYDEKFNNPEN KLSFILWHETLGQINYLLPSTPGKLFIVPKTRSKLNV DNLIKESMPLSIGETKTFGKVGKVSIENIETKDGKTY ISIRKTGDINSYDFNIIKKENINSKLNMYEYETKVIGI LDTLTTYVIPDFTSDIDYLLEYEYISNDDIEILYDQIIE IN |
| AS31_34 | pVRc31_34 | ECF31_34 | 51 | MNKEKLSDHLKSEWKKIDQTANPSIPNQKELLHQLS QMKAEYRKKLLQEIILFVFCALMVVSAAILAFTQAP AVFIVLQVCVLAVLPILIAAEKKRHLGECEVKRG |
| AS33_375 | pVRc33_375 | ECF33_375 | 52 | MMALSKKMLEQEPSEIELLLPWHAAGTLNARDARR VEDALARDPELAKYAAIRGEYEETIHLNESLGAPS ARAMQKLFGAIDAEPARETGSLPLSARIATFFASLSP RTLAWSASLGAVALVLQAGIIGAVLMKTQPTTFQT ASLSTSAPITRELGAAVAPARALVRFTPEARVADITA LLDSYQASIIGDAKGGMFRLQFDKAMSQDELASLL GRMQREKFVNLAVAAP |
| AS33_423 | pVRc33_423 | ECF33_423 | 53 | MMAMSNTMPDPREPGDVEALLPWYAAGTLNARD ARRVADALDRDPALARQYAVILEEYASTIELNESLG APSSRAMQKLFAAIDAEPARAPGAGQGLGARFAGF FAGLSPKALAWSASVAGLALLLQAGLIGALLTWPH AAPVQTAAYQPQREVARAPASSPAPATVSPPAAAM ADRAADAGKSTPPMVMAERSGGPVVRSLAPQSGPR VLVKFAPEARASEIAALLDQYNAVVVDSSRGGLFR LQFGTQSLSKQDQETLIGRLQKEPVVSVVLSAP |
| AS34_1384 | pVRc34_1384 | ECF34_1384 | 54 | MGHVHPSHLVELALGHASGEADVGALRHAASCPR CREELLRLTRVVTAARGAEASDLPVPPPERVWQRIA LEVLPETDRVPRLRESSAHGSADERVRGSQRRWTD HAGEGLLGLALAIAVLLLRRWRIRAGSGN |
| AS34_3302 | pVRc34_3302 | ECF34_3302 | 55 | MKRKENKAWIDLALENLSEKELKELRQNLASDPQF QEELVSVKELLAAIALNLEPEPPAPELKARLLDGICG KNRFLPFLSRLTELFDLSPREAQAYLERLDDPTAWK TVLPGVQTIKIQAGPATAGAKSNFLRVLPGASFPYH THRGLESSLLLQGCCRSEDGVINRAGDLLYQETGTA HSFQVISEQAVIAAVVCFGIDFINPPDRKR |
| AS35_1119 | pVRc35_1119 | ECF35_1119 | 56 | MSNSTLSSEEQALHQEVSAWYFRQALEMPPERLDQ DILRLAQTQLSERNVSQLTPSAMPIWRRFPWVLSSA ASLVIVVGLVMLNRGQFEEDMGAPAALTMSAPMP AAHVASDVADAKVQEAEMASQARLVEDTAKQNAP KEMMMAQANMAAEENIQAKSRSLPQVARAHPEGD VQATANTDTAALMLSLARLQELIESKQIQEALALEQ TLVKQYPELSHISSAKVAADDAKAIAKFKALQQQL HPLRN |
| AS35_3582 | pVRc35_3582 | ECF35_3582 | 57 | MNPQKHSASVAEEQMLAHFRAHAPQQPAPALDQAI LAAARRQAAHVEPARSWWRRWLEASRRPRWQAA FASLLGVALVLGLVSHNVLDDAERQARPEVAFSDV PLRDGVAGAAAAKRAMRAPAAPAPLSGEMSEPPAL LASYASSGEAPQLMAEAAPPAPAALADRPPAQAAQ QAKVQAALAGDFVAQARGKAVAVKPEVLDEALGA VLALREQGKTEQAATQLAELQKRFPGENLVERLER LATIAASARKRP |
| AS37_2513 | pVRc37_2513 | ECF37_2513 | 58 | MSSAPATKEEVDFALKVRRALDERAASLPDATTDR LAAARRAALARKKPDAAIVLVPALAGSAGTLELRP PGEPRKSLARRLARAWPLALLLAGLIGIAYWEDMQ RTAELADIDAAMLSDNLPLTAYLDHGFNAYLSHTH |
| AS38_1322 | pVRc38_1322 | ECF38_1322 | 59 | MSDGNDARPDARDGHDPGSDARDGHDPGSHARDG HDPGAGPFDGHGPGSDAGDGDDAGPDARDGHGAP AGPAGREQRKHPHDTHDMHDTHDTHAGKGTVNH GPAAQGPDAPGADGPATDEAALRAMMQRAVREM EPSDGTLEHLRRAVPARRARKRQALVGAAAAALFL GTAVPALVHVSNATGAGADPSVAGNASQAQGGAS QGKDPAGGQSVAGTGDTPEDRDKADPKETPGGK EPGAATGAPPSGVPSASSPADVPACAPGSLGPAVAS SAEPDSTGVVYGSFRVTNVSSDGCTVTGPGTVVTAS LGAAEATRIGTARHAAGDAAAGLPDPSLETASLAL |

TABLE 1 -continued

Sequences of Anti-sigma Factors

| Anti-sigma | Plasmid | Cognate ECF sigma | SEQ ID NO. | Sequence |
|---|---|---|---|---|
| | | | | APGAAYEVQFAWVPSETCPTTGGTTGGGSGGPSPD PSPTADTTAAGGTSAGGGEAGPTTQLITEDGPAEGS VSVTYTPEGGSGSATATVSNACAGTVYWTGLLADS GSGA |
| AS38_1442 | pVRc38_1442 | ECF38_1442 | 60 | MSDRTPLGPLPDPDGDGELSPTARRLREALAARAA GVHPTDRLEEIHVTSRADRRRSRTRAVVAAAGVAA VVVVGGGGYALAQRDGGSVRTVAGSPAAAPASST TTTAAGAGTPGATAPAAAPAPATASGSTGPATAAT SAPATSTPTGAAAPALPTGAARVPVYWTGGGKLFR EFTPVPGGRDDATNALQVLLGGTAADADYRTSWG VDPAAEVTRDGSGAYVVDVSAAAVSTPLSAPEAEL AVQQLVHTVTAAGGGSAPVRLLVDGREGATVFGS HRVPAAVERAPQVDVQAPAWITQVTPGAGSVTVA GVGTAFEGTLLCTLTDAAGVEVAREPVQAGANGTF GEFSLAVAAPAGTYTVAVFAPDESGGEGPVAVGDT KTVTVR |
| AS39_1438 | pVRc39_1438 | ECF39_1438 | 61 | MLENERQDPFEDRLGTALRDAGDGFEADRAALVTA GRARGRRALLRRRAAVVGGVAGVALAGVGGVLVL PADHPAGPDRSGTASAPSAGDATTAAASFTGDDLL HELKGLLPPGTYGEESARGSDHQLGPTAQLVYDDG AGAAAIGMGFARVEPGSAQVRELMACPDHNITPYD DCSSDRLPDGSLLKLYQGYEYPDLRVDTKRWTADL VTAEGQHVSVSEWNSPAEKGAPVSREEPPLSTERLR ELVTAGVWREVVDAVPKSRKPPRSAAPRTERPEVS GKSVGDTLAALLPRKLDVVSRGGQESEYAYVVVD DGRGRSLVQINVQHGMADVAGQLYADGETLPDGT RVATRQGPGEKAGSGVVMWTVDTLRPGPAGFRVV ISAFNTGDQNKDATRDAPALTMEQLRKIALSGEWD RLR |
| AS40_1380 | pVRc40_1380 | ECF40_1380 | 62 | MTRRLHGGEQDGQEHVKGQLKQLFDDDAFLTDLS RGVDPSEGDDALAGLLLDLTKEAQEPPATMPDWST LLPGILDQDQDLPVESTSDTTVMQASNPATQEFAPV SISDTPNTATNSADADESATVVPLAARREKRAKSGS SGVHSLDASATQRKSHPFLSGLVGAAAATLVIAGG GAAVYNADENSPLYGMNQQLFGNQDSPSVVELAST LEEVDSRTASGDVEGARALLEQARAMLDGMAPPR KAPSEATRTVESEPGTQTLTATVTESASPEPPVTETQ TVTSTEVQTVTTTAVAPPVWTPNPEPTTTAAPTSTPS TGGGEGTGNDGDSGLVPPQTPGN |
| AS40_3198 | pVRc40_3198 | ECF40_3198 | 63 | MREFGNPLGDRPPLDELARTDLLLDALAEREEVDF ADPRDDALAALLGQWRDDLRWPPASALVSQDEAV AALRAGVAQRRRARRSLAAVGSVAAALLVLSGFG AVVADARPGDLLYGLHAMMFNRSRVSDDQIVLSA KANLAKVEQMIAQGQWAEAQDELAEVSSTVQAVT DGSRRQDLINEVNLLNTKVETRDPNATLRPGSPSNP AAPGSVGNSWTPLAPVVEPPTPPTPASAAEPSMSAG VSESPMPNSTSTVAASPSTPSSKPEPGSIDPSLEPADE ATNPAGQPAPETPVSPTH |

TABLE 2

Classification information for anti-sigmas presented in Table 1

| Anti-sigma | SPECIES | CLASS | PHYLUM | GENOME |
|---|---|---|---|---|
| AS01_3473 | Pseudoalteromonas atlantica T6c | Gammaproteobacteria | Proteobacteria | Pseudoalteromonas_atlantica_ T6c_uid58283 |
| AS01_4085 | Shewanella frigidimarina NCIMB 400 | Gammaproteobacteria | Proteobacteria | Shewanella_frigidimarina_ NCIMB_400_uid58265 |
| AS02_915 | Shewanella amazonensis SB2B | Gammaproteobacteria | Proteobacteria | Shewanella_amazonensis_ SB2B_uid58257 |
| AS02_2817 | Escherichia coli K12 | Gammaproteobacteria | Proteobacteria | Escherichia_coli_K_12_ substr_MG1655_uid57779 |
| AS03_1198 | Bacteroides thetaiotaomicron VPI-5482 | | Bacteroidetes | Bacteroides_thetaiotaomicron_ VPI-5482 |

TABLE 2-continued

Classification information for anti-sigmas presented in Table 1

| Anti-sigma | SPECIES | CLASS | PHYLUM | GENOME |
|---|---|---|---|---|
| AS03_1244 | Porphyromonas gingivalis W83 | | Bacteroidetes | Porphyromonas_gingivalis_W83_uid57641 |
| AS04_1609 | Chlorobium tepidum TLS | Chlorobi | Chlorobi | Chlorobium_tepidum_TLS_uid57897 |
| AS05_965 | Pseudomonas syringae pv. tomato str. DC3000 | Gammaproteobacteria | Proteobacteria | Pseudomonas_syringae_tomato_DC3000_uid57967 |
| AS06_853 | Pseudomonas putida KT2440 | Gammaproteobacteria | Proteobacteria | Pseudomonas_putida_KT2440_uid57843 |
| AS06_3576 | Pseudomonas aeruginosa PAO1 | Gammaproteobacteria | Proteobacteria | Pseudomonas_aeruginosa_PAO1_uid57945 |
| AS07_1134 | Pseudomonas aeruginosa PAO1 | Gammaproteobacteria | Proteobacteria | Pseudomonas_aeruginosa_PAO1_uid57945 |
| AS08_3580 | Pseudomonas aeruginosa PAO1 | Gammaproteobacteria | Proteobacteria | Pseudomonas_aeruginosa_PAO1_uid57945 |
| AS08_3627 | Pseudomonas fluorescens Pf-5 | Gammaproteobacteria | Proteobacteria | Pseudomonas_fluorescens_Pf_5_uid57937 |
| AS09_1009 | Pseudomonas fluorescens Pf-5 | Gammaproteobacteria | Proteobacteria | Pseudomonas_fluorescens_Pf_5_uid57937 |
| AS10_3486 | Pseudoalteromonas haloplanktis TAC125 | Gammaproteobacteria | Proteobacteria | Pseudoalteromonas_haloplanktis_TAC125_uid58431 |
| AS11_987 | Vibrio parahaemolyticus RIMD 2210633 | Gammaproteobacteria | Proteobacteria | Vibrio_parahaemolyticus_RIMD_2210633_uid57969 |
| AS11_3726 | Pseudomonas syringae pv. tomato str. DC3000 | Gammaproteobacteria | Proteobacteria | Pseudomonas_syringae_tomato_DC3000_uid57967 |
| AS12_807 | Anaeromyxobacter dehalogenans 2CP-C | Deltaproteobacteria | Proteobacteria | Anaeromyxobacter_dehalogenans_2CP_C_uid58135 |
| AS12_808 | Myxococcus xanthus DK 1622 | Deltaproteobacteria | Proteobacteria | Myxococcus_xanthus_DK_1622_uid58003 |
| AS13_1025 | Photorhabdus luminescens subsp. laumondii TT01 | Gammaproteobacteria | Proteobacteria | Photorhabdus_luminescens |
| AS13_1146 | Haemophilus ducreyi 35000HP | Gammaproteobacteria | Proteobacteria | Haemophilus_ducreyi_35000HP_uid57625 |
| AS14_1324 | Streptomyces coelicolor A3(2) | | Actinobacteria | Streptomyces_coelicolor_A3_2_uid57801 |
| AS14_3200 | Mycobacterium tuberculosis H37Rv | | Actinobacteria | Mycobacterium_tuberculosis_H37Rv_uid57777 |
| AS15_436 | Rhodobacter sphaeroides 2.4.1 | Alphaproteobacteria | Proteobacteria | Rhodobacter_sphaeroides_2_4_1_uid57653 |
| AS15_524 | Caulobacter crescentus CB15 | Alphaproteobacteria | Proteobacteria | Caulobacter_crescentus_CB15_uid57891 |
| AS16_973 | Pseudomonas putida KT2440 | Gammaproteobacteria | Proteobacteria | Pseudomonas_putida_KT2440_uid57843 |
| AS16_3622 | Pseudomonas entomophila L48 | Gammaproteobacteria | Proteobacteria | Pseudomonas_entomophila_L48_uid58639 |
| AS17_1458 | Streptomyces coelicolor A3(2) | | Actinobacteria | Streptomyces_coelicolor_A3_2_uid57801 |
| AS17_1691 | Mycobacterium tuberculosis H37Rv | | Actinobacteria | Mycobacterium_tuberculosis_H37Rv_uid57777 |
| AS18_4438 | Xanthomonas axonopodis pv. citri str. 306 | Gammaproteobacteria | Proteobacteria | Xanthomonas_axonopodis_citri_306_uid57889 |
| AS18_4451 | Xanthomonas campestris pv. campestris str. ATCC 33913 | Gammaproteobacteria | Proteobacteria | Xanthomonas_campestris_ATCC_33913_uid57887 |
| AS19_1315 | Streptomyces coelicolor A3(2) | | Actinobacteria | Streptomyces_coelicolor_A3_2_uid57801 |
| AS19_3197 | Mycobacterium tuberculosis H37Rv | | Actinobacteria | Mycobacterium_tuberculosis_H37Rv_uid57777 |
| AS20_992 | Pseudomonas fluorescens Pf-5 | Gammaproteobacteria | Proteobacteria | Pseudomonas_fluorescens_Pf_5_uid57937 |
| AS21_1280 | Bacteroides thetaiotaomicron VPI-5482 | | Bacteroidetes | Bacteroides_thetaiotaomicron_VPI-5482 |
| AS22_1147 | Xanthomonas axonopodis pv. citri str. 306 | Gammaproteobacteria | Proteobacteria | Xanthomonas_axonopodis_citri_306_uid57889 |
| AS22_4450 | Xanthomonas campestris pv. campestris str. ATCC 33913 | Gammaproteobacteria | Proteobacteria | Xanthomonas_campestris_ATCC_33913_uid57887 |
| AS23_231 | Clostridium acetobutylicum ATCC 824 | Firmicutes | Firmicutes | Clostridium_acetobutylicum_ATCC_824_uid57677 |

TABLE 2-continued

Classification information for anti-sigmas presented in Table 1

| Anti-sigma | SPECIES | CLASS | PHYLUM | GENOME |
|---|---|---|---|---|
| AS23_1851 | Bacillus anthracis str. Ames | | Firmicutes | Bacillus_anthracis_Ames_uid57909 |
| AS25_1643_clone433 | Nostoc sp. PCC 7120 | | Cyanobacteria | Nostoc_PCC_7120_uid57803 |
| AS25_1643_clone440 | Nostoc sp. PCC 7120 | | Cyanobacteria | Nostoc_PCC_7120_uid57803 |
| AS25_1645 | Synechococcus sp. PCC 7002 | | Cyanobacteria | Synechococcus_PCC_7002_uid59137 |
| AS26_837 | Pseudomonas fluorescens PfO-1 | Gammaproteobacteria | Proteobacteria | Pseudomonas_fluorescens_Pf0_1_uid57591 |
| AS26_4464 | Xanthomonas oryzae pv. oryzae KACC10331 | Gammaproteobacteria | Proteobacteria | Xanthomonas_oryzae_KACC10331_uid58155 |
| AS27_1331 | Mycobacterium bovis AF2122/97 | | Actinobacteria | Mycobacterium_bovis_AF2122_97_uid57695 |
| AS27_4265 | Streptomyces coelicolor A3(2) | | Actinobacteria | Streptomyces_coelicolor_A3_2_uid57801 |
| AS28_1040 | Vibrio cholerae O1 biovar eltor str. N16961 | Gammaproteobacteria | Proteobacteria | Vibrio_cholerae_O1_biovar_El_Tor_N16961_uid57623 |
| AS28_1088 | Shewanella frigidimarina NCIMB 400 | Gammaproteobacteria | Proteobacteria | Shewanella_frigidimarina_NCIMB_400_uid58265 |
| AS30_35 | Bacillus subtilis subsp. subtilis str. 168 | | Firmicutes | Bacillus_subtilis_168_uid57675 |
| AS30_83 | Clostridium perfringens str. 13 | | Firmicutes | Clostridium_perfringens_13_uid57681 |
| AS31_34 | Bacillus subtilis subsp. subtilis str. 168 | | Firmicutes | Bacillus_subtilis_168_uid57675 |
| AS33_375 | Bradyrhizobium japonicum USDA 110 | Alphaproteobacteria | Proteobacteria | Bradyrhizobium_japonicum_USDA_110_uid57599 |
| AS33_423 | Rhodopseudomonas palustris CGA009 | Alphaproteobacteria | Proteobacteria | Rhodopseudomonas_palustris_CGA009 |
| AS34_1384 | Streptomyces coelicolor A3(2) | | Actinobacteria | Streptomyces_coelicolor_A32_uid57801 |
| AS34_3302 | Nitrosococcus oceani ATCC 19707 | Gammaproteobacteria | Proteobacteria | Nitrosococcus_oceani_ATCC_19707_uid58403 |
| AS35_1119 | Shewanella oneidensis MR-1 | Gammaproteobacteria | Proteobacteria | Shewanella_oneidensis_MR_1_uid57949 |
| AS35_3582 | Pseudomonas aeruginosa PAO1 | Gammaproteobacteria | Proteobacteria | Pseudomonas_aeruginosa_PAO1_uid57945 |
| AS37_2513 | Burkholderia thailandensis E264 | Betaproteobacteria | Proteobacteria | Burkholderia_thailandensis_E264_uid58081 |
| AS38_1322 | Streptomyces coelicolor A3(2) | | Actinobacteria | Streptomyces_coelicolor_A3_2_uid57801 |
| AS38_1442 | Kineococcus radiotolerans SRS30216 | | Actinobacteria | Kineococcus_radiotolerans_SRS30216_uid58067 |
| AS39_1438 | Streptomyces coelicolor A3(2) | | Actinobacteria | Streptomyces_coelicolor_A3_2_uid57801 |
| AS40_1380 | Corynebacterium glutamicum ATCC 13032 | | Actinobacteria | Corynebacterium_glutamicum_ATCC_13032_Bielefeld |
| AS40_3198 | Mycobacterium tuberculosis H37Rv | | Actinobacteria | Mycobacterium_tuberculosis_H37Rv_uid57777 |

Aspects of the invention relate to recombinant genetic circuits. As used herein "recombinant" and "heterologous" are used interchangeably to refer to a relationship between a cell and a polynucleotide wherein the polynucleotide originates from a foreign species, or, if from the same species, is modified from its original (native) form. As used herein, a genetic circuit refers to a collection of recombinant genetic components that responds to one or more inputs and performs a specific function, such as the regulation of the expression of one or more genetic components and/or regulation of an ultimate output of the circuit. In some embodiments, genetic circuit components can be used to implement a Boolean operation in living cells based on an input detected by the circuit.

Aspects of the invention relate to recombinant cells that comprise logic functions that influence how each cell responds to one more input signals. In some embodiments, a logic function can be a logic gate. As used herein, a "logic function," "logic gate" or "logic operation" refers to a fundamental building block of a circuit. Several non-limiting examples of logic gates compatible with aspects of the invention include AND, OR, NOT (also called INVERTER), NAND, NOR, IDENTITY, XOR, XNOR, EQUALS, IMPLIES, ANDN and N-IMPLIES gates. The use of Logic Gates is known to those of skill in the art (see, e.g. Horowitz and Hill (1990) The Art of Electronics, Cambridge University Press, Cambridge). Genetic circuits can comprise any number of logic gates. In some embodiments, NOR gates can comprise a transcriptional repressors and a transcriptional repressor target DNA sequence, while AND gates can comprise a transcriptional activator and a transcriptional activator target DNA sequence.

Genetic circuits can be comprised of one or more logic gates that process one or more input signals and generate an output according to a logic design. In some embodiments, genetic components respond to biological inputs and are regulated using combinations of repressors and activators. Non-limiting examples of logic gates using genetic components have been described (Tamsir et al. (2011) *Nature* 469(7329):212-215). In some embodiments, the genetic circuit functions as, for example, a switch, oscillator, pulse generator, latch, flip-flop, feedforward loop, or feedback loop.

Genetic circuits can comprise other components such as other transcriptional activators and transcriptional repressors. Non-limiting examples of transcriptional activators and transcriptional repressors are disclosed in and incorporated by reference from WO 2012/170436 (see, e.g., pages 27-40; Table 1 on pages 28-30; and Tables 2 and 3 on pages 36-38, of WO 2012/170436).

Aspects of the invention relate to recombinant host cells that express genetic circuits. It should be appreciated that the invention encompasses any type of recombinant cell, including prokaryotic and eukaryotic cells. As used herein, a "host cell" refers to a cell that is capable of replicating and/or transcribing and/or translating a recombinant gene. A host cell can be a prokaryotic cell or a eukaryotic cell and can be in vitro or in vivo. In some embodiments, a host cell is within a transgenic animal or plant.

In some embodiments the recombinant cell is a bacterial cell, such as *Escherichia* spp., *Streptomyces* spp., *Zymonas* spp., *Acetobacter* spp., *Citrobacter* spp., *Synechocystis* spp., *Rhizobium* spp., *Clostridium* spp., *Corynebacterium* spp., *Streptococcus* spp., *Xanthomonas* spp., *Lactobacillus* spp., *Lactococcus* spp., *Bacillus* spp., *Alcaligenes* spp., *Pseudomonas* spp., *Aeromonas* spp., *Azotobacter* spp., *Comamonas* spp., *Mycobacterium* spp., *Rhodococcus* spp., *Gluconobacter* spp., *Ralstonia* spp., *Acidithiobacillus* spp., *Microlunatus* spp., *Geobacter* spp., *Geobacillus* spp., *Arthrobacter* spp., *Flavobacterium* spp., *Serratia* spp., *Saccharopolyspora* spp., *Thermus* spp., *Stenotrophomonas* spp., *Chromobacterium* spp., *Sinorhizobium* spp., *Saccharopolyspora* spp., *Agrobacterium* spp. and *Pantoea* spp. The bacterial cell can be a Gram-negative cell such as an *Escherichia coli* (*E. coli*) cell, or a Gram-positive cell such as a species of *Bacillus*.

In other embodiments, the cell is an algal cell, a plant cell, an insect cell or a mammalian cell. In certain embodiments, the mammalian cell is a human cell.

In some embodiments, multicellular systems described herein contain cells that originate from more than one different type of organism.

Aspects of the invention relate to recombinant expression of one or more genes encoding components of genetic circuits. It should be appreciated that some cells compatible with the invention may express an endogenous copy of one or more of the genes associated with the invention as well as a recombinant copy. In some embodiments, if a cell has an endogenous copy of one or more of the genes associated with the invention, then the methods will not necessarily require adding a recombinant copy of the gene(s) that are endogenously expressed.

According to aspects of the invention, cell(s) that recombinantly express one or more components of genetic circuits are provided. It should be appreciated that the genes associated with the invention can be obtained from a variety of sources. As one of ordinary skill in the art would be aware, homologous genes for any of the genes described herein could be obtained from other species and could be identified by homology searches, for example through a protein BLAST search, available at the National Center for Biotechnology Information (NCBI) internet site (ncbi.nlm.nih.gov). Genes associated with the invention can be PCR amplified from DNA from any source of DNA which contains the given gene. In some embodiments, genes associated with the invention are synthetic. Any means of obtaining a gene associated with the invention are compatible with the instant invention. Aspects of the invention encompass any cell that recombinantly expresses one or more components of a genetic circuit as described herein.

One or more of the genes associated with the invention can be expressed in a recombinant expression vector. As used herein, a "vector" may be any of a number of nucleic acids into which a desired sequence or sequences may be inserted, such as by restriction and ligation, for transport between different genetic environments or for expression in a host cell. Vectors are typically composed of DNA, although RNA vectors are also available. Vectors include, but are not limited to: plasmids, fosmids, phagemids, virus genomes and artificial chromosomes.

A cloning vector is one which is able to replicate autonomously or integrated in the genome in a host cell, and which can be further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host cell such as a host bacterium or just a single time per host before the host reproduces by mitosis. In the case of phage, replication may occur actively during a lytic phase or passively during a lysogenic phase.

An expression vector is one into which a desired DNA sequence may be inserted, for example by restriction and ligation, such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase, luciferase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript can be translated into the desired protein or polypeptide.

When the nucleic acid molecule that encodes any of the genes associated with the claimed invention is expressed in a cell, a variety of transcription control sequences (e.g., promoter/enhancer sequences) can be used to direct its expression. The promoter can be a native promoter, i.e., the promoter of the gene in its endogenous context, which provides normal regulation of expression of the gene. In some embodiments the promoter can be constitutive, i.e., the promoter is unregulated allowing for continual transcription of its associated gene. A variety of conditional promoters also can be used, such as promoters controlled by the presence or absence of a molecule.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. In particular, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual*, Fourth Edition, Cold Spring Harbor Laboratory Press, 2012. Cells are genetically engineered by the introduction into the cells of heterologous DNA (RNA). That heterologous DNA (RNA) is placed under operable control of transcriptional elements to permit the expression of the heterologous DNA in the host cell. A nucleic acid molecule that comprises a gene associated with the invention can be introduced into a cell or cells using methods and techniques that are standard in the art.

In some embodiments, it may be advantageous to use a cell that has been optimized for expression of one or more polypeptides. As used herein, "optimizing expression" of a polypeptide refers to altering the nucleotide sequences of a coding sequence for a polypeptide to alter the expression of the polypeptide (e.g., by altering transcription of an RNA encoding the polypeptide) to achieve a desired result. In some embodiments, the desired result can be optimal expression, but in other embodiments the desired result can be simply obtaining sufficient expression in a heterologous host cell to test activity (e.g., DNA sequence binding) of the polypeptide.

In other embodiments, optimizing can also include altering the nucleotide sequence of the gene to alter or eliminate native transcriptional regulatory sequences in the gene, thereby eliminating possible regulation of expression of the gene in the heterologous host cell by the native transcriptional regulatory sequence(s). Optimization can include replacement of codons in the gene with other codons encoding the same amino acid. The replacement codons can be those that result in optimized codon usage for the host cell, or can be random codons encoding the same amino acid, but not necessarily selected for the most "preferred" codon in a particular host cell.

In some embodiments, it may be optimal to mutate the cell prior to or after introduction of recombinant gene products. In some embodiments, screening for mutations that lead to enhanced or reduced production of one or more genes may be conducted through a random mutagenesis screen, or through screening of known mutations. In some embodiments, shotgun cloning of genomic fragments can be used to identify genomic regions that lead to an increase or decrease in production of one or more genes, through screening cells or organisms that have these fragments for increased or decreased production of one or more genes. In some instances, one or more mutations may be combined in the same cell or organism. Recombinant gene expression can involve in some embodiments expressing a gene on a plasmid and/or integrating the gene into the chromosomal DNA of the cell. For example, nucleic acid molecules can be introduced by standard protocols such as transformation including chemical transformation and electroporation, transduction, particle bombardment, etc. Expressing the nucleic acid molecule can also be accomplished by integrating the nucleic acid molecule into the genome.

Optimization of protein expression may also require in some embodiments that a gene be modified before being introduced into a cell such as through codon optimization for expression in a bacterial cell. Codon usages for a variety of organisms can be accessed in the Codon Usage Database (http://www.kazusa.or.jp/codon/).

Protein engineering can also be used to optimize expression or activity of a protein. In certain embodiments a protein engineering approach could include determining the three dimensional (3D) structure of a protein or constructing a 3D homology model for the protein based on the structure of a related protein. Based on 3D models, mutations in a protein can be constructed and incorporated into a cell or organism, which could then be screened for increased or decreased production of a protein or for a given feature or phenotype.

A nucleic acid, polypeptide or fragment thereof described herein can be synthetic. As used herein, the term "synthetic" means artificially prepared. A synthetic nucleic acid or polypeptide is a nucleic acid or polypeptide that is synthesized and is not a naturally produced nucleic acid or polypeptide molecule (e.g., not produced in an animal or organism). It will be understood that the sequence of a natural nucleic acid or polypeptide (e.g., an endogenous nucleic acid or polypeptide) may be identical to the sequence of a synthetic nucleic acid or polypeptide, but the latter will have been prepared using at least one synthetic step.

Aspects of the invention thus involve recombinant expression of genes encoding sigma factors and anti-sigmas, functional modifications and variants of the foregoing, as well as uses relating thereto. Homologs and alleles of the nucleic acids associated with the invention can be identified by conventional techniques. Also encompassed by the invention are nucleic acids that hybridize under stringent conditions to the nucleic acids described herein. The term "stringent conditions" as used herein refers to parameters with which the art is familiar. Nucleic acid hybridization parameters may be found in references which compile such methods, e.g. *Molecular Cloning: A Laboratory Manual*, J. Sambrook, et al., eds., Fourth Edition, Cold Spring Harbor Laboratory Press, Cold Spring Harbor, N.Y., 2012, or *Current Protocols in Molecular Biology*, F. M. Ausubel, et al., eds., John Wiley & Sons, Inc., New York. More specifically, stringent conditions, as used herein, refers, for example, to hybridization at 65° C. in hybridization buffer (3.5×SSC, 0.02% Ficoll, 0.02% polyvinyl pyrrolidone, 0.02% Bovine Serum Albumin, 2.5 mM $NaH_2PO_4$ (pH7), 0.5% SDS, 2 mM EDTA). SSC is 0.15M sodium chloride/0.015M sodium citrate, pH 7; SDS is sodium dodecyl sulphate; and EDTA is ethylenediaminetetracetic acid. After hybridization, the membrane upon which the DNA is transferred is washed, for example, in 2×SSC at room temperature and then at 0.1-0.5×SSC/0.1×SDS at temperatures up to 68° C.

There are other conditions, reagents, and so forth which can be used, which result in a similar degree of stringency. The skilled artisan will be familiar with such conditions, and thus they are not given here. It will be understood, however, that the skilled artisan will be able to manipulate the conditions in a manner to permit the clear identification of homologs and alleles of nucleic acids of the invention (e.g., by using lower stringency conditions). The skilled artisan also is familiar with the methodology for screening cells and libraries for expression of such molecules which then are routinely isolated, followed by isolation of the pertinent nucleic acid molecule and sequencing.

In general, homologs and alleles typically will share at least 75% nucleotide identity and/or at least 90% amino acid identity to the sequences of nucleic acids and polypeptides, respectively, in some instances will share at least 90% nucleotide identity and/or at least 95% amino acid identity and in still other instances will share at least 95% nucleotide identity and/or at least 99% amino acid identity. In some embodiments, homologs and alleles share at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or more than 99% nucleotide identity and/or at least 90%, 91%, 92%, 93%, 94%, 95%, 96%, 97%, 98%, 99% or more than 99% amino acid identity. The homology can be calculated using various, publicly available software tools developed by NCBI (Bethesda, Md.) that can be obtained through the NCBI internet site. Exemplary tools include the BLAST software, also available at the NCBI internet site (www.ncbi.nlm.nih.gov). Pairwise and ClustalW alignments (BLOSUM30 matrix setting) as well as Kyte-Doolittle hydropathic analysis can be obtained using the MacVector sequence analysis software (Oxford Molecular Group). Watson-Crick complements of the foregoing nucleic acids also are embraced by the invention.

The invention also includes degenerate nucleic acids which include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into an elongating polypeptide. Similarly, nucleotide sequence triplets which encode other amino acid residues include, but are not limited to: CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code. The invention also embraces codon optimization to suit optimal codon usage of a host cell.

The invention also provides modified nucleic acid molecules which include additions, substitutions and deletions of one or more nucleotides. In preferred embodiments, these modified nucleic acid molecules and/or the polypeptides they encode retain at least one activity or function of the unmodified nucleic acid molecule and/or the polypeptides, such as enzymatic activity. In certain embodiments, the modified nucleic acid molecules encode modified polypeptides, preferably polypeptides having conservative amino acid substitutions as are described elsewhere herein. The modified nucleic acid molecules are structurally related to the unmodified nucleic acid molecules and in preferred embodiments are sufficiently structurally related to the unmodified nucleic acid molecules so that the modified and unmodified nucleic acid molecules hybridize under stringent conditions known to one of skill in the art.

For example, modified nucleic acid molecules which encode polypeptides having single amino acid changes can be prepared. Each of these nucleic acid molecules can have one, two or three nucleotide substitutions exclusive of nucleotide changes corresponding to the degeneracy of the genetic code as described herein. Likewise, modified nucleic acid molecules which encode polypeptides having two amino acid changes can be prepared which have, e.g., 2-6 nucleotide changes. Numerous modified nucleic acid molecules like these will be readily envisioned by one of skill in the art, including for example, substitutions of nucleotides in codons encoding amino acids 2 and 3, 2 and 4, 2 and 5, 2 and 6, and so on. In the foregoing example, each combination of two amino acids is included in the set of modified nucleic acid molecules, as well as all nucleotide substitutions which code for the amino acid substitutions. Additional nucleic acid molecules that encode polypeptides having additional substitutions (i.e., 3 or more), additions or deletions (e.g., by introduction of a stop codon or a splice site(s)) also can be prepared and are embraced by the invention as readily envisioned by one of ordinary skill in the art. Any of the foregoing nucleic acids or polypeptides can be tested by routine experimentation for retention of structural relation or activity to the nucleic acids and/or polypeptides disclosed herein.

The invention embraces variants of polypeptides. As used herein, a "variant" of a polypeptide is a polypeptide which contains one or more modifications to the primary amino acid sequence of the polypeptide. Modifications which create a variant can be made to a polypeptide 1) to reduce or eliminate an activity of a polypeptide; 2) to enhance a property of a polypeptide; 3) to provide a novel activity or property to a polypeptide, such as addition of an antigenic epitope or addition of a detectable moiety; or 4) to provide equivalent or better binding between molecules (e.g., an enzymatic substrate). Modifications to a polypeptide are typically made to the nucleic acid which encodes the polypeptide, and can include deletions, point mutations, truncations, amino acid substitutions and additions of amino acids or non-amino acid moieties. Alternatively, modifications can be made directly to the polypeptide, such as by cleavage, addition of a linker molecule, addition of a detectable moiety, such as biotin, addition of a fatty acid, and the like. Modifications also embrace fusion proteins comprising all or part of the amino acid sequence. One of skill in the art will be familiar with methods for predicting the effect on protein conformation of a change in protein sequence, and can thus "design" a variant of a polypeptide according to known methods. One example of such a method is described by Dahiyat and Mayo in *Science* 278:82-87, 1997, whereby proteins can be designed de novo. The method can be applied to a known protein to vary a only a portion of the polypeptide sequence. By applying the computational methods of Dahiyat and Mayo, specific variants of a polypeptide can be proposed and tested to determine whether the variant retains a desired conformation. In general, variants include polypeptides which are modified specifically to alter a feature of the polypeptide unrelated to its desired physiological activity. For example, cysteine residues can be substituted or deleted to prevent unwanted disulfide linkages. Similarly, certain amino acids can be changed to enhance expression of a polypeptide by eliminating proteolysis by proteases in an expression system (e.g., dibasic amino acid residues in yeast expression systems in which KEX2 protease activity is present).

Mutations of a nucleic acid which encode a polypeptide preferably preserve the amino acid reading frame of the coding sequence, and preferably do not create regions in the nucleic acid which are likely to hybridize to form secondary structures, such a hairpins or loops, which can be deleterious to expression of the variant polypeptide.

Mutations can be made by selecting an amino acid substitution, or by random mutagenesis of a selected site in a nucleic acid which encodes the polypeptide. Variant polypeptides are then expressed and tested for one or more activities to determine which mutation provides a variant polypeptide with the desired properties. Further mutations can be made to variants (or to non-variant polypeptides) which are silent as to the amino acid sequence of the polypeptide, but which provide preferred codons for translation in a particular host. The preferred codons for translation of a nucleic acid in, e.g., *E. coli*, are well known to those of ordinary skill in the art. Still other mutations can be made to the noncoding sequences of a gene or cDNA clone to enhance expression of the polypeptide. The activity of variant polypeptides can be tested by cloning the gene encoding the variant polypeptide into a bacterial or mammalian expression vector, introducing the vector into an appropriate host cell, expressing the variant polypeptide, and testing for a functional capability of the polypeptides as disclosed herein.

The skilled artisan will also realize that conservative amino acid substitutions may be made in polypeptides to provide functionally equivalent variants of the foregoing polypeptides, i.e., the variants retain the functional capabilities of the polypeptides. As used herein, a "conservative amino acid substitution" refers to an amino acid substitution which does not alter the relative charge or size characteristics of the protein in which the amino acid substitution is made. Variants can be prepared according to methods for altering polypeptide sequence known to one of ordinary skill in the art such as are found in references which compile such methods, e.g. *Molecular Cloning: A Laboratory Manual*, J. Sambrook, et al., eds., Fourth Edition, Cold Spring Harbor Laboratory Press, Cold Spring Harbor, N.Y., 2012, or *Current Protocols in Molecular Biology*, F. M. Ausubel, et al., eds., John Wiley & Sons, Inc., New York. Exemplary functionally equivalent variants of polypeptides include conservative amino acid substitutions in the amino acid sequences of proteins disclosed herein. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

In general, it is preferred that fewer than all of the amino acids are changed when preparing variant polypeptides. Where particular amino acid residues are known to confer function, such amino acids will not be replaced, or alternatively, will be replaced by conservative amino acid substitutions. Preferably, 1, 2, 3, 4, 5, 6, 7, 8, 9, 10, 11, 12, 13, 14, 15, 16, 17, 18, 19, 20 residues can be changed when preparing variant polypeptides. It is generally preferred that the fewest number of substitutions is made. Thus, one method for generating variant polypeptides is to substitute all other amino acids for a particular single amino acid, then assay activity of the variant, then repeat the process with one or more of the polypeptides having the best activity.

Conservative amino-acid substitutions in the amino acid sequence of a polypeptide to produce functionally equivalent variants of the polypeptide typically are made by alteration of a nucleic acid encoding the polypeptide. Such substitutions can be made by a variety of methods known to one of ordinary skill in the art. For example, amino acid substitutions may be made by PCR-directed mutation, site-directed mutagenesis according to the method of Kunkel (Kunkel, *Proc. Nat. Acad. Sci. U.S.A.* 82: 488-492, 1985), or by chemical synthesis of a gene encoding a polypeptide.

Genetic circuits described herein can contain elements other than sigma factors and anti-sigma factors. For example, genetic circuits can comprise transcriptional regulatory elements. As used herein, a "transcriptional regulatory elements" refer to any nucleotide sequence that influences transcription initiation and rate, or stability and/or mobility of a transcript product. Regulatory sequences include, but are not limited to, promoters, promoter control elements, protein binding sequences, 5' and 3' UTRs, transcriptional start sites, termination sequences, polyadenylation sequences, introns, etc. Such transcriptional regulatory sequences can be located either 5'-, 3'-, or within the coding region of the gene and can be either promote (positive regulatory element) or repress (negative regulatory element) gene transcription.

Aspects of the invention encompass a non-transitory computer readable storage medium encoded with instructions, executable by a processor, for designing a host cell and a computer product comprising a computer readable medium encoded with a plurality of instructions for controlling a computing system to perform an operation for designing a host cell. As used herein, "computer-readable medium" refers to any media that is involved in providing one or instructions to a processor for execution. Computer-readable media can be anything that a computer is able to read, such as, for example, disks, magnetic tape, CD-ROMs, any other optical medium, punch cards, paper tape, any other physical medium with patterns of holes, a RAM, PROM, and EPROM, a FLASH-EPROM, any other memory chip or cartridge or a carrier wave.

The present invention is further illustrated by the following Examples, which in no way should be construed as further limiting. The entire contents of all of the references (including literature references, issued patents, published patent applications, and co pending patent applications) cited throughout this application are hereby expressly incorporated by reference, including the entire contents of WO 2012/170436.

EXAMPLES

Example 1: ECF σ Factors, Anti-σs, and Promoters: A Complete Map of Crosstalk and Application to Synthetic Switches Cells react to their environment through gene regulatory networks, the integrity of which requires the minimization of undesired crosstalk between their component biomolecules. Here, a comprehensive map was established of the promoter specificities for ECF σs, which have a central role in prokaryotic gene expression, as well as their interaction with anti-σs. DNA synthesis was used to build 86 ECF σs (two from every subgroup), their promoters, and 63 anti-σs identified from the genomes of diverse bacteria. A subset of 20 σs and promoters were found to be highly orthogonal. The set was expanded by swapping the −35 and −10 promoter binding domains from different species to recognize new chimeric promoters. The orthogonal σs, anti-σs, and promoters were used to build synthetic genetic switches in *E. coli*. This demonstrated transferability of these regulators, which can be gleaned from diverse genomic contexts and made to function in a new host with minimal re-engineering.

ECF σs are the smallest and simplest alternative as, as well as the most abundant and phylogenetically diverse[7,9]. Possessing just the two domains that bind the promoter −10 and −35 regions[2] (FIG. 1A), they provide cells with a highly modular means to respond to their environment[7,10], often responding to a signal through the action of an anti-σ. ECF σs can autoregulate their own expression and that of their anti-σ[11,12]. This organization can lead to diverse dynamical phenomena, including ultrasensitive bistable switches and pulse generators[13-15]. Moreover, promoters of an ECF σ are highly conserved, facilitating identification, modeling, and rational design[7,16]. Promoter specificity also results in a large dynamic range of output, where the OFF state is very low in the absence of the σ and the ON state produces a high level of expression.

Their aggregate properties suggest that ECF σs may be ideal for implementing programs of gene expression for applications in biotechnology. Individual synthetic genetic circuits have been constructed using ECF σs to implement memory and timer functions[17,18]. Such circuits can be connected to form programs that implement control over metabolic pathways and cellular functions[19-21]. The size and sophistication of such programs has been growing, but have been limited by a lack of regulatory parts that are orthogonal; that is, can be simultaneously used without interference[22]. In the case of ECF σs, crosstalk can arise by binding to off-target promoters or anti-σs.

ECF σs may provide a large reservoir of orthogonal regulators with 19,314 currently annotated in the MiST database[23]. Bioinformatic analysis of the sequence relationships among ~2700 ECF σs by Mascher and colleagues[7] identified 43 phylogenetically distinct ECF a subgroups, thought to have similar promoter binding sequences within subgroups, but with significant variation between subgroups. It was hypothesized that if a significant fraction of these subgroups had σs with orthogonal promoter recognition, such that they target their cognate promoter with no detectable cross-reactivity to another σ, then there would be the potential to build large programs in single cells based on σs. This diversity can be physically accessed from the sequence databases by using high-throughput DNA synthesis and screening, in a process referred to as "part mining"[24]. Here, this approach was applied to construct a comprehensive library that encompasses the phylogenetic diversity of σs, anti-σs, and promoters from the 43 phylogenetically distinct ECF σ groups, generating a library of 86 ECF σs (2 from each subgroup) and their corresponding 63 anti-σs. Both sets of genes were optimized for expression in *E. coli*[25] and obtained via DNA synthesis (Example 6). The library was then functionally screened to identify an orthogonal subset (FIG. 1B).

Figure 2:
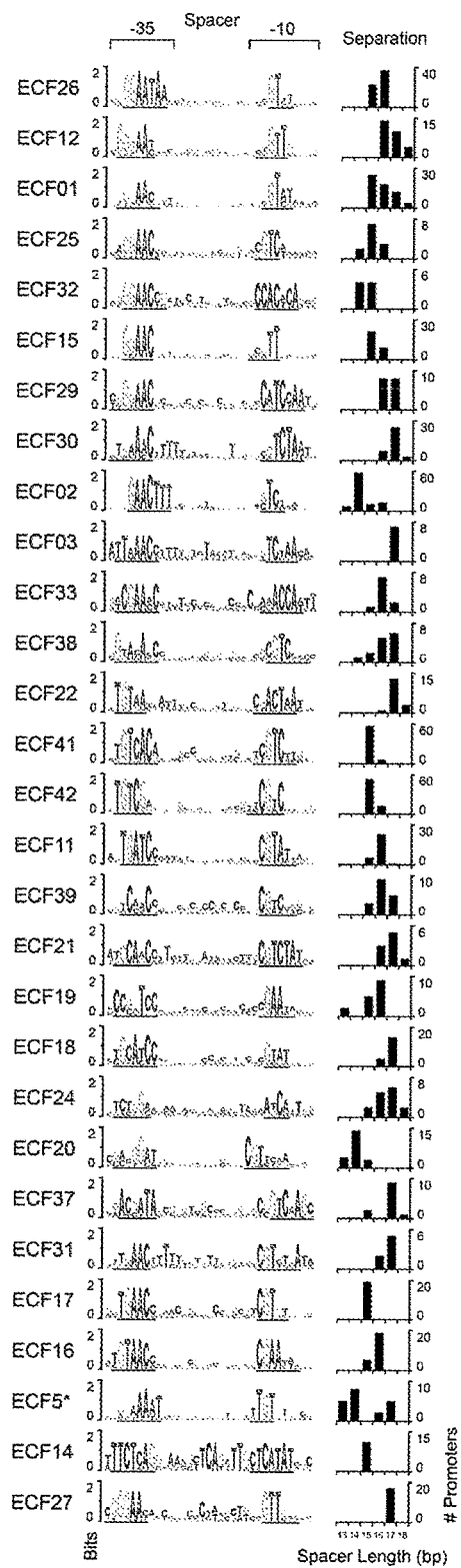
FIG. 2 reveals promoter models for 29 ECF sigma subgroups. The models contain a sequence logo illustrating the −35/−10 motifs and intervening spacer sequence. The exact −35 and −10 sequences identified by BioProspector[27] are underlined underneath each sequence logo. The bar chart histograms illustrate the number of promoters with different length distances between underlined −35 and −10 motifs. The promoters were organized vertically to cluster similar −35 and −10 motifs, as determined by eye. The bottom three promoter models (ECF5*, ECF14, ECF27) represent promoters that were not found to be active (>5-fold activation) in the specific embodiments tested. Promoter model ECF5* represents the model for subgroups 5-10.
Figure 3:
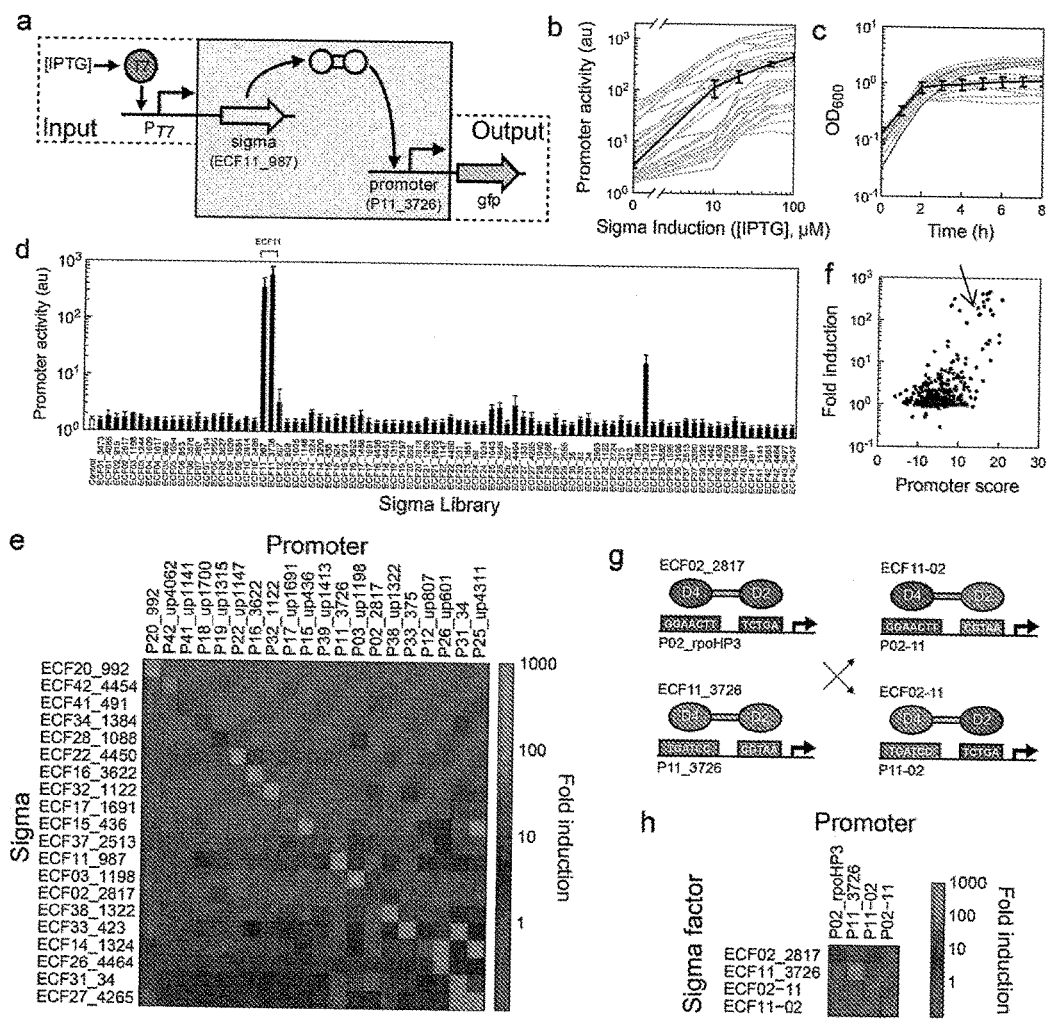
FIG. 3 depicts the activity and orthogonality of ECF σs.
Figure 9:
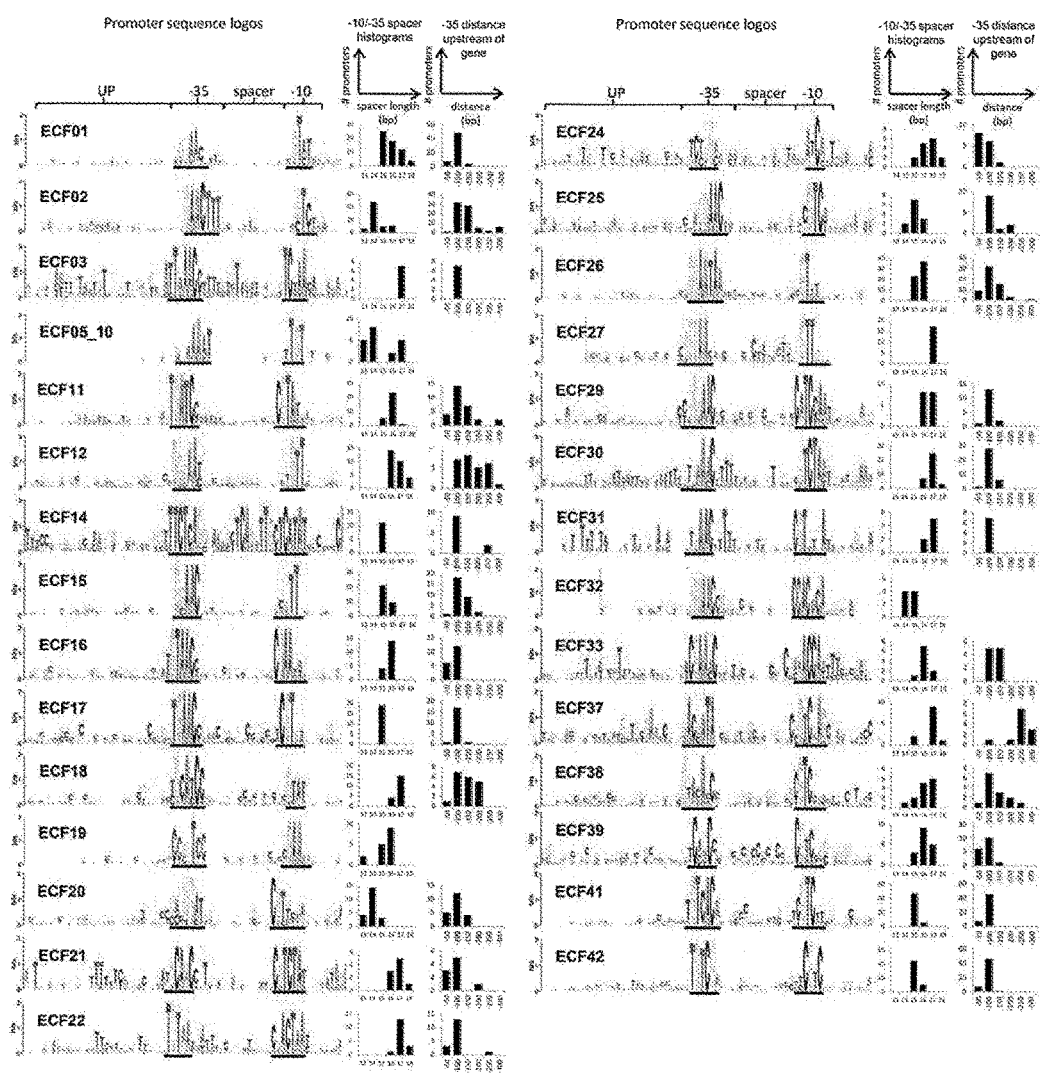
FIG. 9 depicts complete promoter models for each ECF subgroup. The models contain a sequence logo illustrating the upstream (UP) sequence, −35 sequence, spacer sequence, −10 sequence, and 10 bases following the −10. The histograms show, from all the analyzed promoters, the distance between the −35 and −10 motifs, and the distance between the −35 motif and the nearest downstream gene. The exact −35 and −10 sequences identified by the 2-block search algorithm, BioProspector, are underlined underneath each sequence logo, and were used to calculate the distances for the −10/−35 spacer histograms.

When mining regulators, a challenge is to determine the DNA sequence to which they bind in order to build a responsive promoter. To this end, a computational approach was developed that identifies native promoters for each subgroup and uses their sequences to build a promoter model. This model was used to select a promoter out of the genome and predict whether the promoter is specific to that subgroup (orthogonal). Native promoters were identified by exploiting that fact that most ECF σs autoregulate by targeting a promoter upstream of their own gene[7,9]. Consequently, promoter motifs can be found by searching for over-represented conserved motifs in the regulatory regions upstream of the σ genes in each subgroup. Using this information, Mascher identified motifs for 18/43 subgroups[8]. Using an automated procedure, all regulatory regions upstream of the σs and their putative operons were culled from their 329 cognate genomes. The 6 Fec-I like subgroups (ECF05-10) were excluded as they do not autoregulate[7,26]. Conserved promoter-like motifs were identified from the upstream sequences using BioProspector, which can search for two sequence blocks (i.e., the −10 and −35 regions) connected by a variable spacer[27]. This approach confirmed and improved the motifs identified by Mascher and co-workers[8]. These combined efforts identified 706 promoters and 29 promoter motifs in the 43 ECF σ subgroups. Promoter models were constructed for the promoter motifs based on position weight matrixes (PWMs)[28] for each ECF subgroup 16 and a spacer penalty for suboptimal motif spacing (FIGS. 2 and 9).

Using these promoter models, all 706 promoter sequences were scored for orthogonality, demonstrating that most promoters are highly orthogonal, with remarkably little crosstalk across subgroups (FIG. 10A). Surprisingly, the −10 and −35 sequences alone showed considerably less orthogonality than the entire promoter (FIG. 10B,C), indicating that high specificity is achieved by combining both promoter regions. It also implies that new promoter specificities can be achieved by swapping the protein domains that bind the −10 and −35 promoter regions. Candidate orthogonal promoters were designed for each of the 29 ECF σ subgroups, based on the predictions of the promoter models across all 706 promoters. The promoters selected were predicted to score highly against their cognate σ and poorly against other σs. Preference was given to promoters that occur immediately upstream from their σ. Promoters were also screened against having sequences similar to those recognized by *E. coli* σ70 and FecI. This was particularly relevant for promoters from AT-rich genomes that often contain σ70-like promoter sequences. The candidate promoters contained natural promoter sequences from −60 to +20, and were tested with their cognate σs (see below). Promoters from GC-rich genomes were often found to be non-functional and this was corrected by replacing the −35 to −60 region with a synthetic UP-element designed to enhance promoter recognition by the α-subunits of RNAP[29,30] (FIGS. 1C and 11). This process yielded a set of 18 promoters that were functional with σs from their cognate ECF subgroups. The promoters were retained from the remaining 11 subgroups in case they were activated by σs from different subgroups.

Figure 12:
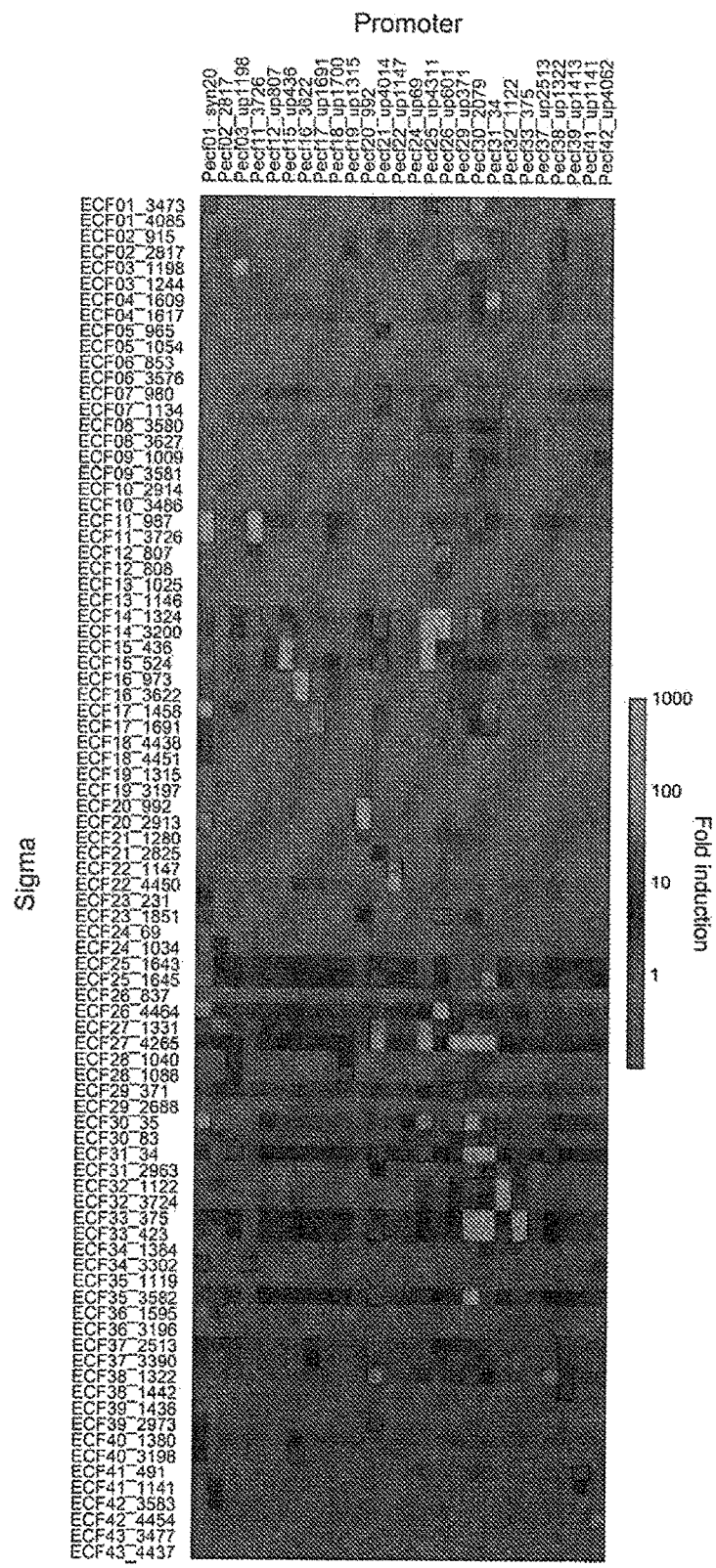
FIG. 12 depicts the activity of all ECF sigmas for all promoters constructed. A Heatmap of in vivo activities for the complete library of 86 ECF sigmas against 26 promoters is presented. Assays were performed by inducing ECF sigma expression with 100 µM IPTG for 6 hr during exponential growth and measuring promoter activity from GFP fluorescence using flow cytometry. Each square represents the average fold induction from at least two independent assays.
Figure 13:
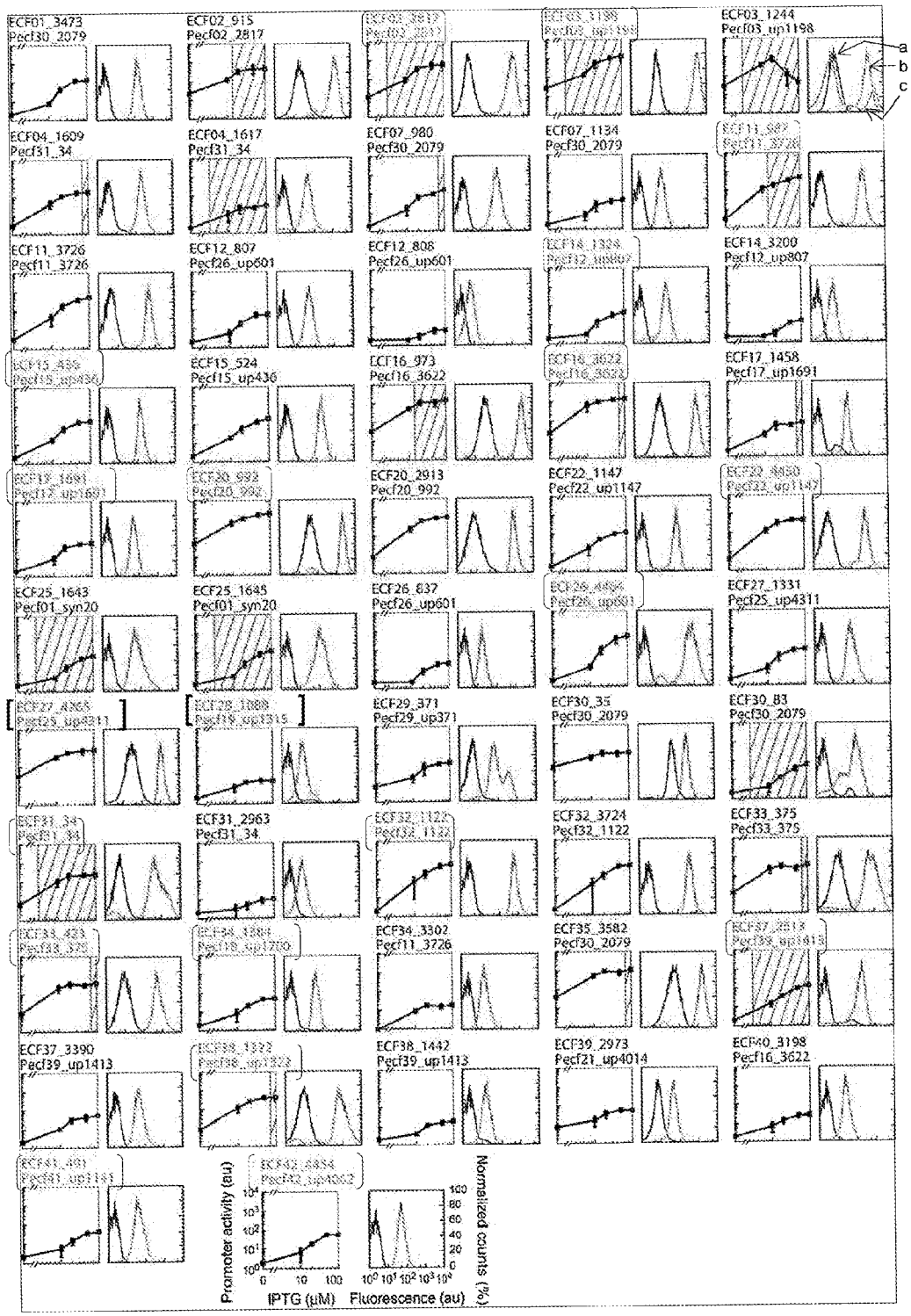
FIG. 13 depicts sigma titration assays. Each of the chosen 52 active ECF sigma factors was induced at 0, 10, 20, 50 and 100 µM IPTG with their most active cognate promoter in vivo. Assays were performed with 6 hr induction during exponential growth and promoter activity measured from GFP fluorescence using flow cytometry. Plots represent the average promoter activity from three independent assays and error bars represent one standard deviation. Hash marks indicate toxicity (as judged by a fall in the 8 hr $OD_{600}$ to 80% or lower of wild type; see Example 3 and FIG. 16; growth measurements were taken at 0, 10, 20, and 100 µM IPTG) occurring at different levels of IPTG induction. Cytometry distributions show typical log-scale histograms at 0 (black) and 100 µM IPTG (grey). One sigma:promoter pair, ECF03_1244:Pecf03_up1198, showed extreme toxicity at full induction, so three histograms are shown: (a)=0 µM, (b)=20 µM, (c)=100 µM. All cytometry histograms are shown with log scaling and normalized to the mode of the distribution. A portion of the cells falls on the Y-axis and is not visible when plotted in this way. Bracketed titles indicate that that sigma:promoter set was included in the orthogonal subset of the ECF sigma library (FIG. 3E).

A test system was devised to measure promoter activity and orthogonality. A phylogenetically diverse library of 86 σs comprised of 2 σs from each subgroup was built (FIG. 1B), and a multi-plasmid system was developed to control expression and enable transformation of different combinations of σs, anti-σs, and promoters to rapidly determine activity (FIG. 3A). The toxicity of each σ was measured. Under high induction, 80% exhibited near wild-type growth levels during exponential phase (>90% wild-type *E. coli* DH10b carrying an empty vector) (FIG. 3C). Each promoter was assayed against the complete set of σs, resulting in an exhaustive activity map based on measurements of 29 promoters×86 σs and identifying 26 active promoters (FIG. 12). Interestingly, 8 promoters that were non-functional with their cognate σs, were activated by σs from different ECF subgroups. This implies that these σs are regulated by other σs as part of a cascade rather than autoregulating themselves. Among the inactive σs, usually both examples from a subgroup were nonfunctional, suggesting that their promoter motifs were incorrect or a shared property of these σs prevents function in *E. coli*. In total, 58 of the 86 σs activated at least one promoter>5-fold. The transfer function was measured for each of the 52 most active σs against its most active promoter (FIGS. 3B and 13). This induction has a large dynamic range, from 9- to 270-fold. Many of the σ/promoter pairs are highly orthogonal and the 20 most orthogonal are shown in FIG. 3E. Some crosstalk was observed between different subgroups (e.g., ECF02, 07, 11, 14, 15, 17, 25, 27, 33) and these interactions can be predicted using the promoter models (FIG. 3F).

The σs in the library spanned 6 bacterial classes, but were biased towards organisms phylogenetically related to *E. coli* to increase their likelihood of binding *E. coli* core RNAP. Interestingly, functional or non-functional σs were found to exhibit no bias in their phylogenetic distance from *E. coli*. For example non-functional σs were observed from γ-proteobacteria, the same subclass as *E. coli*, and functional σs were observed from Firmicutes, the most distant class. This lack of bias underscores the surprising success rate of importing foreign σs from different genomes into *E. coli*. This also implies a high degree of conservation for the σ-RNAP binding interface required for function.

Figure 10:
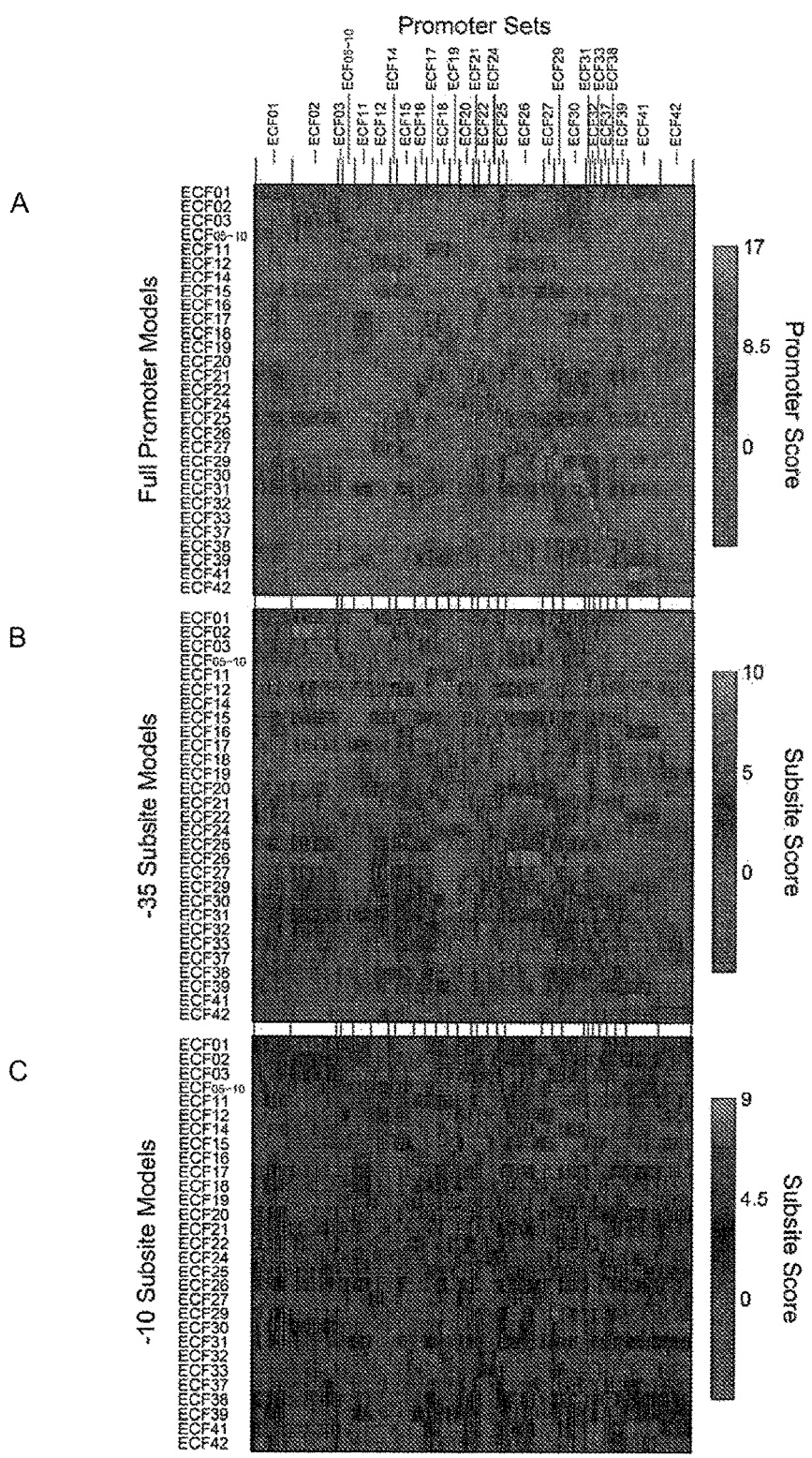
FIG. 10 depicts predicted orthogonality of ECF sigma promoter models and individual subsite models.
Figure 11:
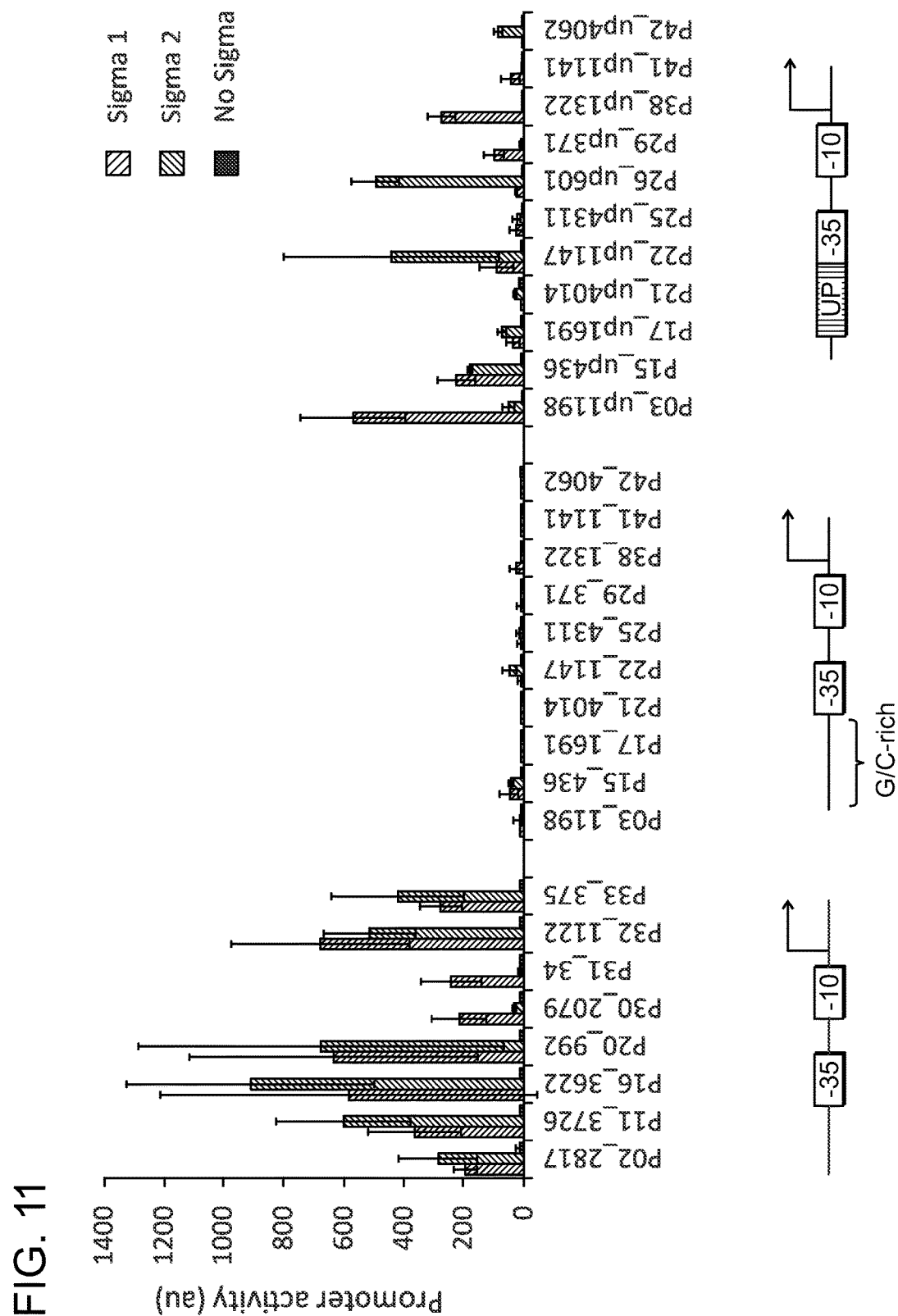
FIG. 11 depicts improvement of promoter activity by adding UP-elements. Promoter sequences were tested for activity against both cognate sigmas from their ECF sigma group. (Sigma 1 denotes the ECF with a lower number in the library, while sigma 2 denotes the higher one. For example, with P02_2817, sigma 1 is ECF02_915 and sigma 2 is ECF02_2817. In some embodiments, inactive promoters tended to contain G/C-rich upstream sequences. These sequences were replaced with synthetic UP-element (CATGACAAAATTTTTTAGATGCGTT; SEQ ID NO:64; −60 to −35), improving promoter activity. In vivo assays were performed by inducing ECF sigma expression with 100 µM IPTG for 6 hr during exponential growth and measuring promoter activity from GFP fluorescence using flow cytometry. Each bar represents the average promoter activity from at least two independent assays and error bars represent one standard deviation.
Figure 20A:
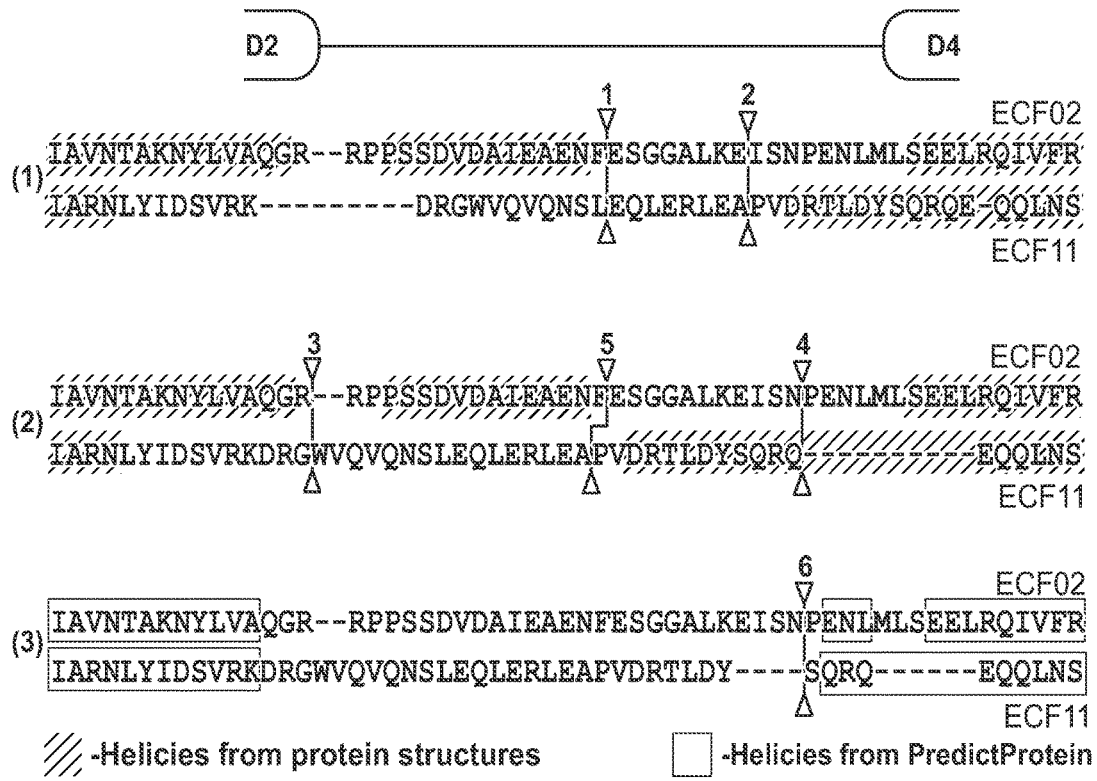
FIG. 20A presents three alignments (SEQ ID NOs: 65 & 66) of the flexible linker region connecting domains 2 and 4 of the parental sigma factors shown with the crossover seams derived from each alignment marked. Alignment 1 was generated through protein sequence alignment, hand-adjusted based on crystal structures. Alignment 2 was generated through protein sequence alignment alone. Alignment 3 was created with secondary structure prediction by PredictProtein. Each of the six marked seams was used to engineer one chimeric sigma factor of either orientation, for a total of 12 chimeric sigma factors.
Figure 20B:
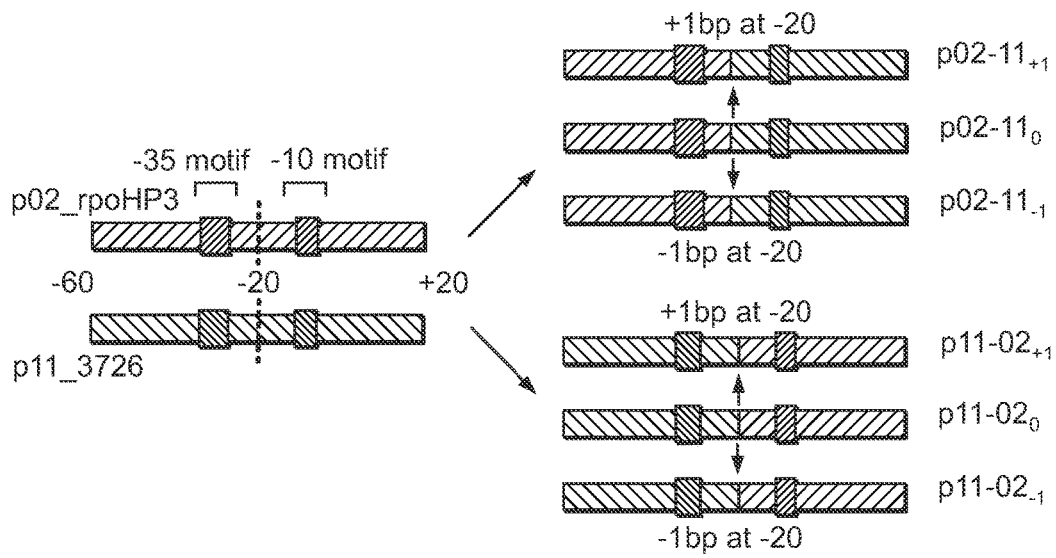
FIG. 20B presents three chimeric promoters of each orientation that were similarly engineered. pECF02_rpoHP3 and pECF11_3726 were recombined between −20 and −21 to make p02-110 and p11-020. To correct for any differences in optimal spacing between the chimeras and parental sigma factors, 1 bp was added or removed at the −20/−21 seam to make additional promoters with longer or shorter spacers.
Figure 21:
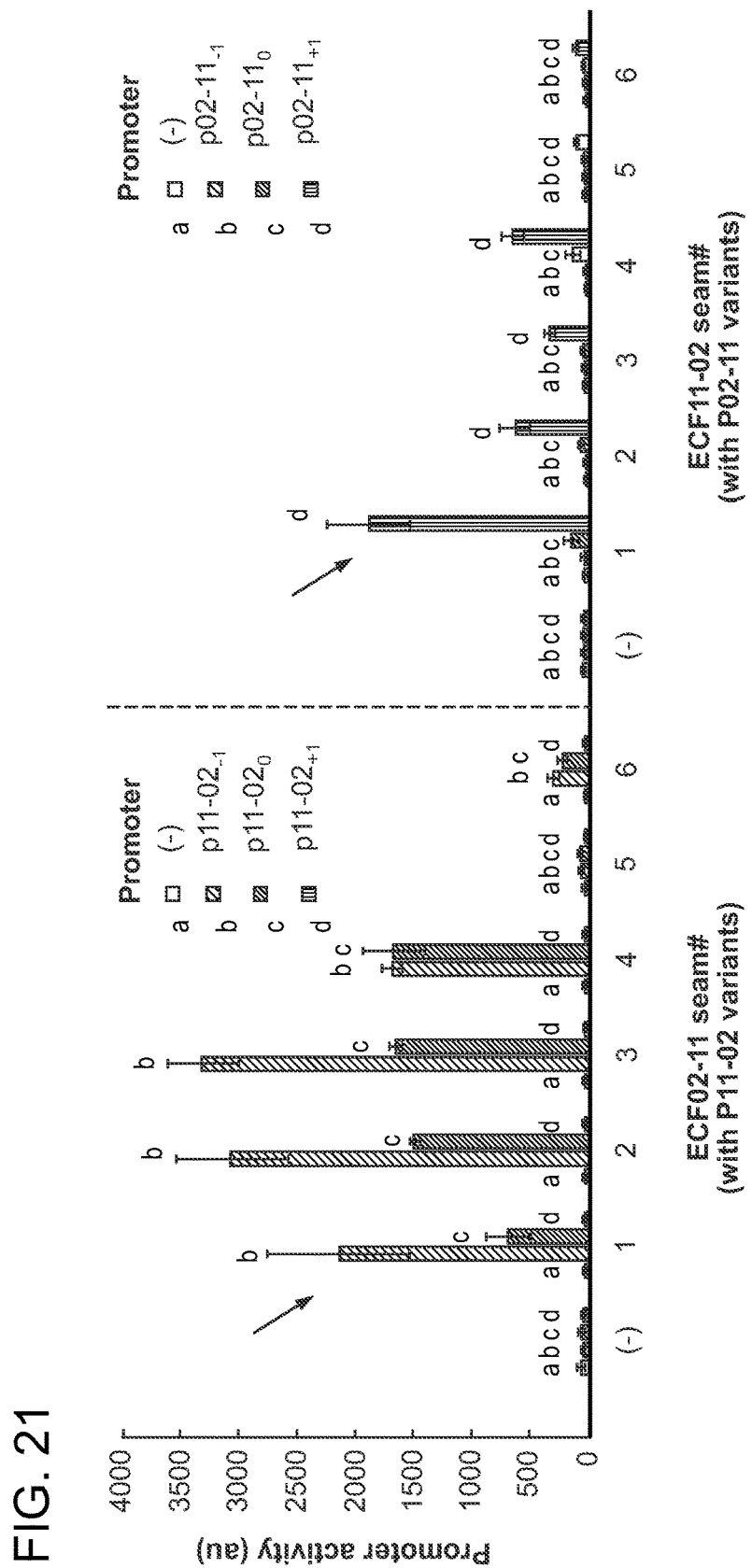
FIG. 21 depicts testing of chimeric sigma factor and chimeric promoter variants. Each of the engineered chimeric sigma factors was tested with each of the variants of its cognate chimeric promoter. Negative controls represent an empty plasmid lacking either a sigma factor coding region, or a sigma promoter:reporter cassette. Arrows point to the sigma chimera:chimera promoter pairs chosen for orthogonality testing. Assays were performed in vivo in CAG22216 cells at 30° C., induced for 6 hours with 10 µM IPTG, and promoter activity was measured by flow cytometry. Each bar represents the average promoter activity from three independent assays, each of which had three technical replicates, and error bars represent one standard deviation taken between the independent assays.
Figure 22A:
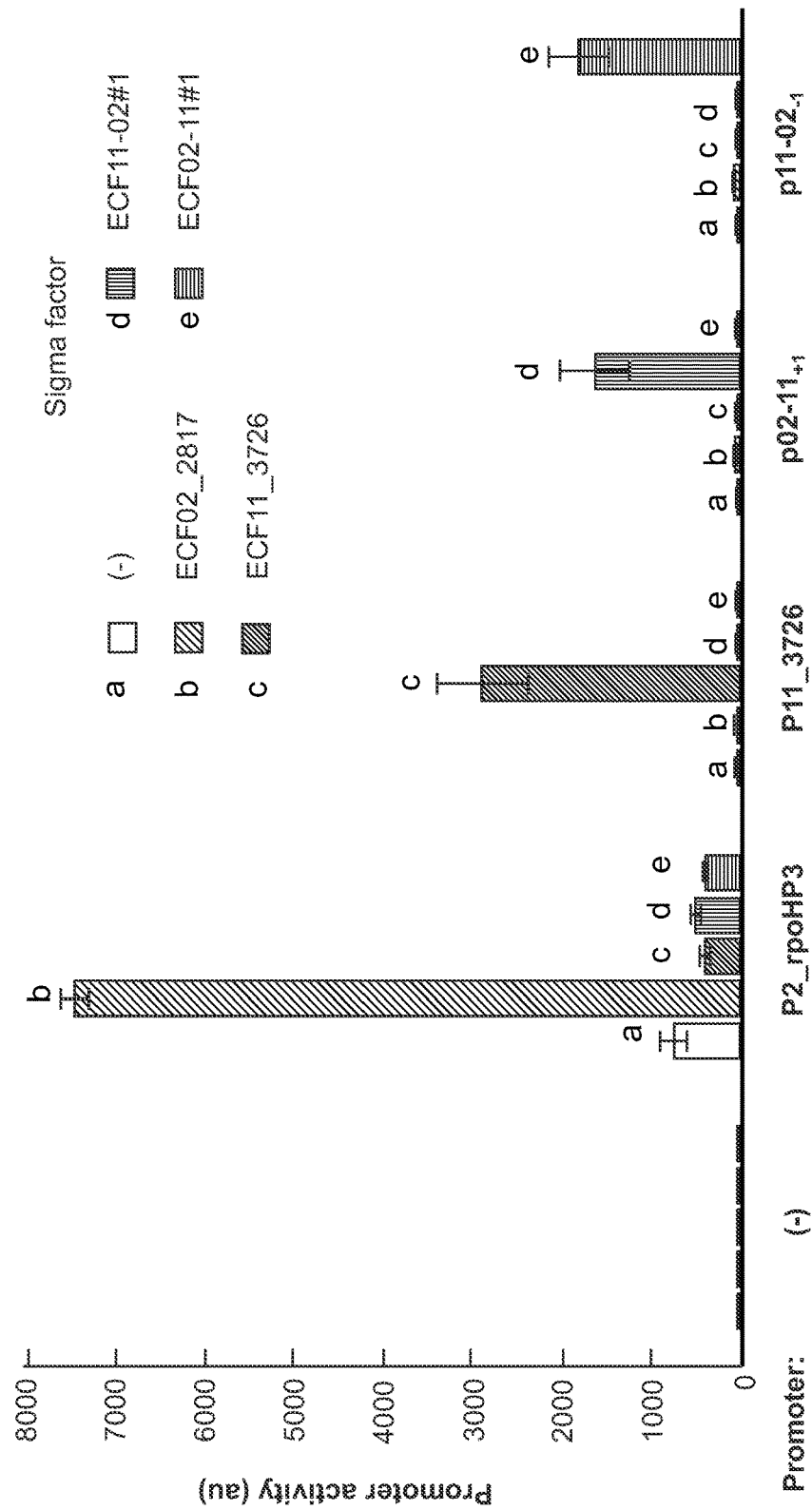
FIG. 22 depicts orthogonality testing of chimeric and parental sigma factors. The data corresponding to FIG. 3H are shown for the error bars (a) and cytometry data (b). Assays were performed in vivo in CAG22216 cells at 30° C., induced for 6 hours with 10 µM IPTG, and promoter activity was measured by flow cytometry. (−) controls represent cells carrying a plasmid identical to the chimeric sigma expression or reporter plasmids, but with the chimeric sigma gene, or promoter/reporter removed. Each bar represents the average promoter activity from three three independent assays, each of which had three technical replicates, and error bars represent one standard deviation taken between the independent assays. Histograms show representative flow cytometry distributions for each promoter in the presence of all of the sigma factors.

The ECF promoter models demonstrate that promoter specificity is generated through the combination of −10 and −35 motif recognition (FIG. 10). This implies that new promoters could be engineered by combining different −10 and −35 motifs. Indeed, a synthetic hybrid σ that combined the −10 DNA binding domain of σ70 with the −35 DNA binding domain of σ32 was able to recognize a cognate hybrid promoter containing a consensus σ32-35 motif and consensus −10 motif[31]. The ECF σs are simple, consisting two domains separated by a flexible linker. The N-terminal domain (Domain 2) binds the −10 motif and the C-terminal domain (Domain 4) binds the −35 motif 32-34. The question of whether these domains could be swapped between different ECF subgroups to create chimeric σs that activate chimeric promoters was investigated. Two σs were selected from different subgroups that recognize different −10 and −35 motifs: ECF02_2817 (*E. coli* σE) and ECF11_3726 (FIG. 3G). For each orientation, six chimeric σs were constructed by making crossovers in the disordered linker region and in helixes near the domain boundary (FIG. 20). Similarly, a library of three chimeric promoters was constructed based on the −35 and −10 motifs from P02_rpoHP3 and P11_3726 that represent a range of spacer lengths. From these small libraries, chimeric σs were identified that activate their chimeric promoters at a level equivalent to wild-type (FIGS. 3G, 21 and 22). Further, the chimeric σs are orthogonal, exhibiting negligible activity against the opposite promoter chimeras and the parental promoters. Interestingly, while *E. coli* σE, (ECF02_2817) is toxic at high concentrations[35], neither of the chimeras based on this σ exhibit toxicity. Extending this concept further, the promoter models roughly predict that there are 16 σ domains across subgroups that bind to different −35 sequences and 10 σ domains that bind to different −10 sequences. This estimates that, considering only DNA sequence specificity, there is an upper limit of ~160 potential ECF σs that could be orthogonal and potentially operate within one cell.

Figure 17:
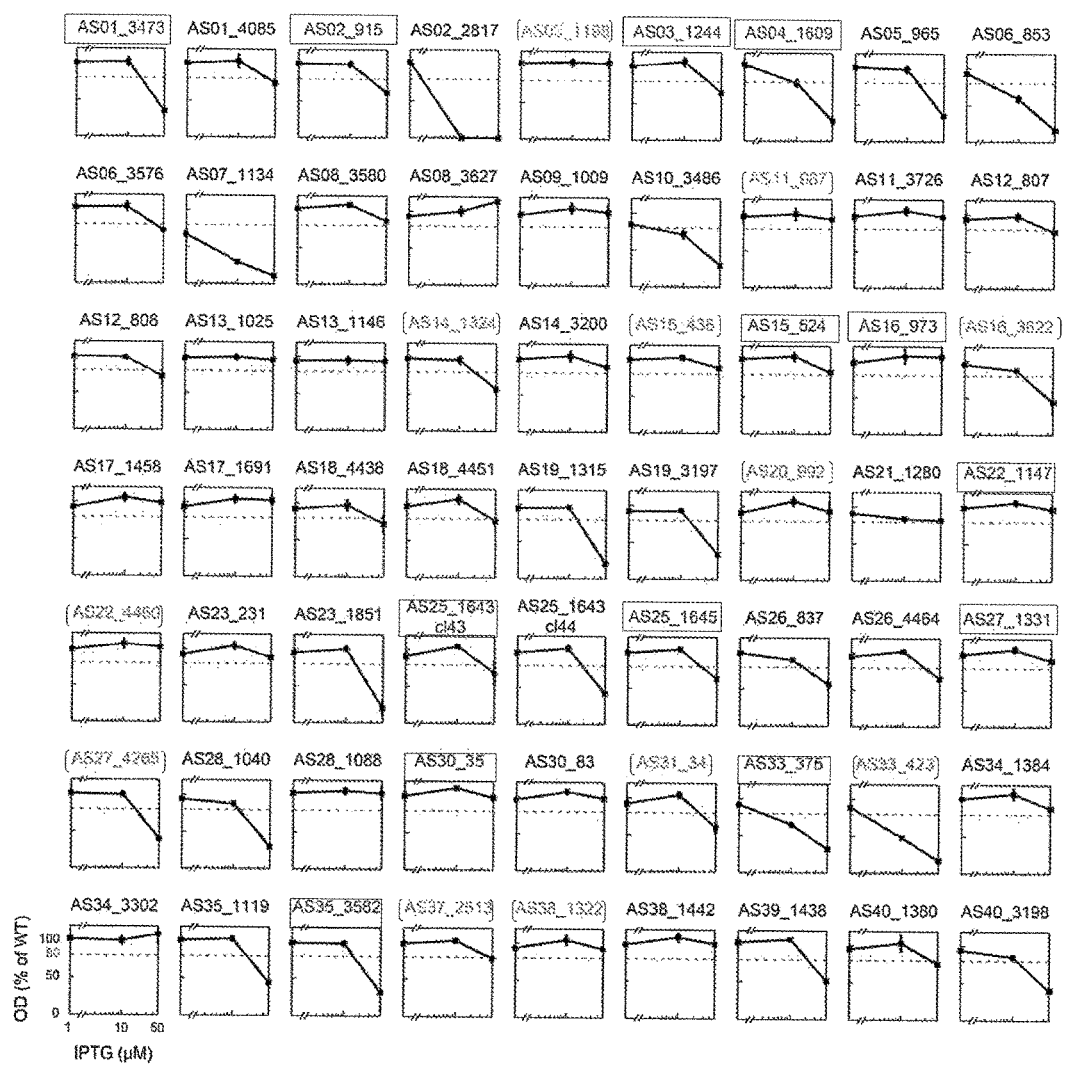
FIG. 17 depicts an anti-sigma transition phase growth assay. OD$_{600}$ measurements were taken after 8 hours of growth at different levels of expression of each of the anti-sigma factors in the library. Plots represents the average measurement from three independent assays normalized to cells not expressing an anti-sigma factor, and error bars represent one standard deviation. Boxed titles indicate the 25 anti-sigma factors tested for orthogonality (FIG. 15), and bracketed titles indicate anti-sigmas that repress ECF sigma factors in the final orthogonal set (FIG. 4C).

Anti-σs bind to σs and inhibit them by blocking their interaction with core RNAP. A library of the 63 cognate anti-σs under the control of a 3-O-C6-HSL inducible Plux promoter was constructed. Of these, 46 were associated with an active σ, and the most promising 35 were tested to determine whether they repressed activity of their cognate σ on its most active promoter. 32/35 anti-σs were able to repress the activity of their target σ more than 2-fold (FIG. 14), indicating that most anti-σs from different organisms were able to repress their target σ in *E. coli*. Compared to the σs, a larger fraction of the anti-σs exhibited toxicity when expressed in *E. coli*; this could occur by the interaction of the anti-σs with essential host σs such as ECF σE (FIG. 17).

Figure 15:
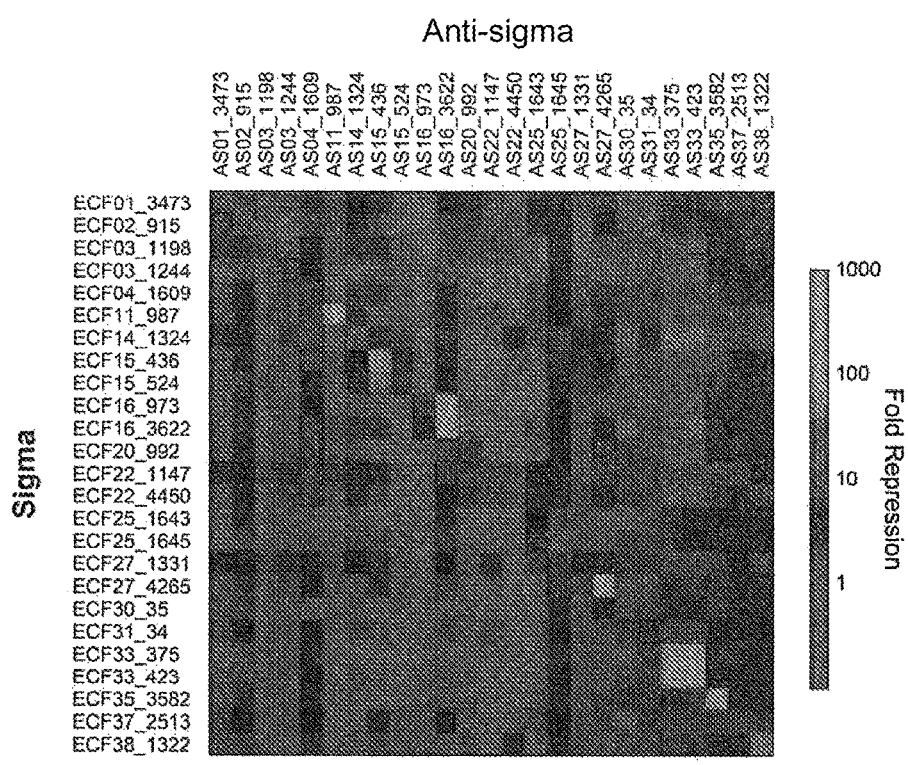
FIG. 15 demonstrates repression of ECF sigmas by all anti-sigmas. A heatmap of fold repression of sigma activity by different anti-sigmas is shown. Assays were performed by inducing ECF sigma expression with 10 µM IPTG and anti-sigma expression with 50 nM HSL for 6 hr during exponential growth and fold repression calculated from fluorescence measurements. Each square represents the average fold repression from three independent assays.

To determine the orthogonality of the anti-σ/σ interactions, the activity of each σ was measured in the presence of the 25 most active anti-σs. An example of this screen is shown in FIG. 4B where the anti-σ AS11_987 represses the activity of its cognate σ ECF11_987 by over 70-fold while the other anti-σs have a significantly smaller effect. Measurements of repression by all anti-σs against all σs reveal that most anti-σs specifically repress their cognate σ, but there is a higher background of cross-reactivity against non-cognate σs (FIG. 15). FIG. 4C shows a subset of this data for the 20 most orthogonal σs for which functional anti-σs were identified. When serving as switches, the majority of σs yield a graded induction of the output promoter (FIG. 3B). This induction occurs at a similar threshold of input activity. There is also a 100-fold range in the basal OFF state. All of these features pose a challenge for assembling the switches into larger programs: more complex dynamical behaviors require a cooperative response, connecting circuits requires matching their thresholds, and a high basal level can trigger the next circuit in series. Previously, it was demonstrated that the addition of a sequestering molecule into a switch lowers the background, increases cooperativity and allows the threshold to be tuned[36]. The question of whether the anti-σs serving as a sequestering molecule would improve these properties of the switches was tested. A series of switches was constructed based on controlling the expression level of anti-σ (FIGS. 4A and 24). In each case, as the expression level of the anti-σ increased, the basal level of expression decreased (up to 10-fold) and the cooperativity increased (FIG. 4D). For example, when the data for ECF20_992 is fit to a Hill function, the cooperativity goes from n=1.7 to 4.1 as a function of the expression of the anti-σ (FIG. 19). There was also an exquisite capacity for the threshold of the circuit to be tuned, in several cases, by over two orders of magnitude.

A surprising outcome of this work is the ease by which ECF σs, as well as their anti-σs and promoters, can be moved between diverse organisms and retain function. Many of these parts could be moved "as-is," but even those that could not only required modest engineering techniques to achieve functionality. This has implications for the horizontal transfer of these regulatory units between genomes. There is evidence for the horizontal transfer of ECF σs across species[37] and they also appear in mobile genomic islands and plasmids associated with resistance to environmental stress[38]. By providing a sequestration function, anti-σs can tune the response characteristics and facilitate the evolution of more complex dynamics[39]. Transferability and orthogonality are also essential features for applications in genetic engineering, which require the functional movement of such circuits into in a foreign host. Here, these properties of ECF σs across many species were characterized via part mining, where DNA synthesis is used to access large sets of genes identified from the growing sequence databases. This approach enables taking a comprehensive view towards the biochemical characterization of entire classes of genes, as well as providing a rich resource for the harnessing of these functions in biotechnology.

REFERENCES FOR EXAMPLE 1

1. Hook-Barnard, I. G. & Hinton, D. M. Transcription Initiation by Mix and Match Elements: Flexibility for Polymerase Binding to Bacterial Promoters. *Gene Regul Syst Bio* 1, 275-293 (2007).
2. Gruber, T. M. & Gross, C. A. Multiple Sigma Subunits and the Partitioning of Bacterial Transcription Space. *Annual Review of Microbiology* 57, 441-466 (2003).
3. Chater, K. F. Regulation of sporulation in *Streptomyces coelicolor* A3(2): a checkpoint multiplex? *Current Opinion in Microbiology* 4, 667-673 (2001).
4. Stragier, P. & Losick, R. MicroReview Cascades of sigma factors revisited. *Molecular Microbiology* 4, 1801-1806 (1990).
5. Helmann, J. D. Anti-sigma factors. *Current Opinion in Microbiology* 2, 135-141 (1999).
6. Campbell, E. A., Westblade, L. F. & Darst, S. A. Regulation of bacterial RNA polymerase σ factor activity: a structural perspective. *Curr Opin Microbiol* 11, 121-127 (2008).
7. Staroń, A. et al. The third pillar of bacterial signal transduction: classification of the extracytoplasmic function (ECF) σ factor protein family. *Molecular Microbiology* 74, 557-581 (2009).
8. Marles-Wright, J. & Lewis, R. J. Stress responses of bacteria. *Current Opinion in Structural Biology* 17, 755-760 (2007).
9. Helmann, J. D. in *Advances in Microbial Physiology* Volume 46, 47-110 (Academic Press, 2002).
10. Lonetto, M. A., Brown, K. L., Rudd, K. E. & Buttner, M. J. Analysis of the *Streptomyces coelicolor* sigE gene reveals the existence of a subfamily of eubacterial RNA polymerase sigma factors involved in the regulation of extracytoplasmic functions. *PNAS* 91, 7573-7577 (1994).
11. Rhodius, V. A., Suh, W. C., Nonaka, G., West, J. & Gross, C. A. Conserved and Variable Functions of the σE Stress Response in Related Genomes. *PLoS Biol* 4, e2 (2005).
12. Rouvière, P. E. et al. rpoE, the gene encoding the second heat-shock sigma factor, sigma E, in *Escherichia coli*. *EMBO J* 14, 1032-1042 (1995).
13. Voigt, C. A., Wolf, D. M. & Arkin, A. P. The *Bacillus subtilis* sin Operon An Evolvable Network Motif. *Genetics* 169, 1187-1202 (2005).
14. Tiwari, A., Ray, J. C. J., Narula, J. & Igoshin, 0. A. Bistable responses in bacterial genetic networks: Designs and dynamical consequences. *Mathematical Biosciences* 231, 76-89 (2011).
15. Locke, J. C. W., Young, J. W., Fontes, M., Jimenez, M. J. H. & Elowitz, M. B. Stochastic Pulse Regulation in Bacterial Stress Response. *Science* 334, 366-369 (2011).
16. Rhodius, V. A. & Mutalik, V. K. Predicting strength and function for promoters of the *Escherichia coli* alternative sigma factor, σE. *PNAS* 107, 2854-2859 (2010).
17. Shin, J. & Noireaux, V. An *E. coli* Cell-Free Expression Toolbox: Application to Synthetic Gene Circuits and Artificial Cells. *ACS Synth. Biol.* 1, 29-41 (2012).
18. Chen, D. & Arkin, A. P. Sequestration-based bistability enables tuning of the switching boundaries and design of a latch. *Molecular Systems Biology* 8, (2012).
19. Temme, K., Hill, R., Segall-Shapiro, T. H., Moser, F. & Voigt, C. A. Modular control of multiple pathways using engineered orthogonal T7 polymerases. *Nucl. Acids Res.* (2012).doi:10.1093/nar/gks597
20. Solomon, K. V., Sanders, T. M. & Prather, K. L. J. A dynamic metabolite valve for the control of central carbon metabolism. *Metab. Eng.* 14, 661-671 (2012).
21. Zhang, F., Carothers, J. M. & Keasling, J. D. Design of a dynamic sensor-regulator system for production of chemicals and fuels derived from fatty acids. *Nature Biotechnology* 30, 354-359 (2012).
22. Purnick, P. E. M. & Weiss, R. The second wave of synthetic biology: from modules to systems. *Nature Reviews Molecular Cell Biology* 10, 410-422 (2009).
23. Ulrich, L. E. & Zhulin, I. B. MiST: a microbial signal transduction database. *Nucleic Acids Res.* 35, D386-390 (2007).
24. Bayer, T. S. et al. Synthesis of Methyl Halides from Biomass Using Engineered Microbes. *J. Am. Chem. Soc.* 131, 6508-6515 (2009).
25. Raab, D., Graf, M., Notka, F., Schödl, T. & Wagner, R. The GeneOptimizer Algorithm: using a sliding window approach to cope with the vast sequence space in multiparameter DNA sequence optimization. *Syst Synth Biol* 4, 215-225 (2010).
26. Braun, V., Mahren, S. & Ogierman, M. Regulation of the FecI-type ECF sigma factor by transmembrane signalling. *Current Opinion in Microbiology* 6, 173-180 (2003).
27. Liu, X., Brutlag, D. L. & Liu, J. S. BioProspector: discovering conserved DNA motifs in upstream regulatory regions of co-expressed genes. *Pac Symp Biocomput* 127-138 (2001).
28. Staden, R. Computer methods to locate signals in nucleic acid sequences. *Nucleic Acids Res* 12, 505-519 (1984).
29. Gourse, R. L., Ross, W. & Gaal, T. UPs and downs in bacterial transcription initiation: the role of the alpha subunit of RNA polymerase in promoter recognition. *Molecular Microbiology* 37, 687-695 (2000).
30. Rhodius, V. A., Mutalik, V. K. & Gross, C. A. Predicting the strength of UP-elements and full-length *E. coli* aE promoters. *Nucl. Acids Res.* 40, 2907-2924 (2012).
31. Kumar, A. et al. A hybrid sigma subunit directs RNA polymerase to a hybrid promoter in *Escherichia coli*. *Journal of Molecular Biology* 246, 563-571 (1995).
32. Campbell, E. A. et al. Crystal Structure of *Escherichia coli* σE, with the Cytoplasmic Domain of Its Anti-σ RseA. *Molecular Cell* 11, 1067-1078 (2003).
33. Lane, W. J. & Darst, S. A. The Structural Basis for Promoter −35 Element Recognition by the Group IV σ Factors. *PLoS Biol* 4, e269 (2006).
34. Campbell, E. A. et al. A Conserved Structural Module Regulates Transcriptional Responses to Diverse Stress Signals in Bacteria. *Molecular Cell* 27, 793-805 (2007).
35. Nitta, T., Nagamitsu, H., Murata, M., Izu, H. & Yamada, M. Function of the ζE Regulon in Dead-Cell Lysis in Stationary-Phase *Escherichia coli*. *J. Bacteriol.* 182, 5231-5237 (2000).
36. Buchler, N. E. & Cross, F. R. Protein sequestration generates a flexible ultrasensitive response in a genetic network. *Molecular Systems Biology* 5, (2009).
37. Schmidt, T. R., Scott, E. J. & Dyer, D. W. Whole-genome phylogenies of the family Bacillaceae and expansion of the sigma factor gene family in the *Bacillus cereus* species-group. *BMC Genomics* 12, 430 (2011).
38. Van Houdt, R. et al. Variation in genomic islands contribute to genome plasticity in *Cupriavidus metallidurans*. *BMC Genomics* 13, 111 (2012).
39. Buchler, N. E. & Louis, M. Molecular Titration and Ultrasensitivity in Regulatory Networks. *Journal of Molecular Biology* 384, 1106-1119 (2008).

Example 2: Promoter Identification and Design

Identification of ECF Promoters Using Genomic Information

A three-step search strategy was used to maximize the identification of promoter sequences for each ECF sigma subgroup. First, based on the observations that many ECF sigma groups autoregulate their own gene expression[1] and that some sigmas may regulate their own anti-sigma[2], promoter motifs were searched for in sequences directly upstream of the sigma gene, sigma operon, and cognate anti-sigma gene. Second, upstream regulatory regions were extracted for all ECF sigmas within each subgroup to maximize the ability to find over-represented motifs. Third, BioProspector[3] was used to identify over-represented motifs in these upstream regulatory regions. BioProspector is a 2-block motif search algorithm that is ideally suited for bacterial promoters with variable length spacers between the −10 and −35 motifs. All ECF sigmas in subgroups 01-43 and their cognate anti-sigmas were identified from Staron and co-workers (incorporated by reference from Table S5 of Staron et al.)[1]. To enable efficient retrieval of their upstream regulatory sequences, all 1232 complete bacterial genome sequences and annotations were downloaded from the NCBI FTP site (Nov. 1, 2010). Both sigmas and anti-sigmas were identified from these genomes based on the annotation supplied by Staron et al: source genome, gene ID (GI) and their listed amino acid sequence (sigmas only). From the 1736 listed ECF sigmas and cognate 1203 anti-sigmas listed by Staron et al., 1329 sigmas and 880 anti-sigmas were successfully identified from the NCBI annotated genomes. The remaining sigmas and anti-sigmas were from genomes not listed in the NCBI database and therefore were not used in this analysis.

For each ECF sigma subgroup, three libraries of upstream regulatory sequences were extracted from: 1) directly upstream of the sigma gene; 2) directly upstream of the sigma gene operon (sigma operons were defined as all consecutive genes adjacent to the sigma gene, in the same orientation and separated by less than 50 nt from each other); 3) directly upstream of the cognate anti-sigma gene (if known). Most promoters occur near the start of genes but can be difficult to detect when searching long upstream regulatory sequences for over-represented motifs. To facilitate identification, different length upstream regulatory sequences were extracted for each library, from the start codon to 100, 150, 200 and 300 nt upstream. For each library, searches for over-represented motifs were performed using BioProspector with the short 100 nt upstream sequences first and then repeated with the successively longer sequences. Motif searches with BioProspector were performed only on the forward strand and the highest scoring motifs selected from 100 reinitializations. The search for 2-block motifs was typically of the form, W7 w5 G18 g15: where W and w denotes the length (nt) of the upstream and downstream blocks, respectively; and G and g denotes the maximum and minimum distances (nt) separating the two blocks, respectively. These parameters were varied iteratively to optimize the searches for different promoter motifs. From all the library, sequence and motif search combinations, the highest scoring 2-block motif was selected as the representative promoter motif for each ECF sigma. These were typically from the 100 or 200 nt sequences upstream of the ECF sigma gene or operon.

Promoters for ECF subgroups 05-10, 19, 27 and 32 listed in Staron et al. were not identified in our search. Subgroups 05-10 are not autoregulated[1] and the remaining subgroups only had a few sigmas with highly related upstream sequences, making it difficult to search for over-represented motifs. For all of these cases, the promoter sequences were obtained from Staron et al. and Bioprospector was used to redefine the −35 and −10 motifs. Promoter sequences and their −10/−35 motifs are incorporated by reference from WO 2012/170436 (see, for e.g., page 58 of WO 2012/170436).

ECF Sigma Promoter Modeling and Prediction

For each ECF sigma subgroup, the highest scoring 2-block motif identified by BioProspector was used to construct promoter models following the method described by Rhodius et. al.[4] The upstream and downstream motif sequences were used to compile Position Weight Matrices (PWMs)[5] for the −35 and −10 motifs, respectively. Specifically, for the regions identified by BioProspector, the weights ($W_{b,i}$) for each position (i) and base (b) were computed as $$W_{b,i}^{motif} = \ln\left[\frac{(n_{b,i} + 0.5)/(N + 2.0)}{P_b}\right] \quad (S1)$$

where $n_{b,i}$ is the number of times that the base b is found at position i in the promoter set, N is the number of promoters in the promoter set, and $P_b$ is the probability of finding a specific base at any given position (assumed to be 0.25). Bayesian pseudocounts of 50% were added to each base to represent the relative uncertainty in the promoter sequences. To evaluate a motif in a promoter, the appropriate weights can be summed for a given sequence of bases b at positions i to obtain a complete −35 or −10 score. Additionally, the variable distances between the −35 and −10 motifs were used to construct spacer length histograms and to calculate a penalty score S for suboptimal spacer lengths $$S = \ln\left[(f+0.0005F)/(F+0.0005F)\right] \quad (S2)$$

where F is the frequency of the most commonly observed (assumed to be optimal) spacer length in the promoter set, and f is the frequency of the spacer length in the promoter being evaluated. Bayesian pseudocounts of 0.5% of the frequency of the optimal spacer length were added to account for uncertainty.

The total promoter score was calculated as a sum of the −35 and −10 motifs evaluated with PWMs and the spacer length penalty $$\text{Score} = \sum_{i=1}^{L_{-35}} W_{b,i}^{-35} + \ln\left[\frac{(f+0.0005F)}{(F+0.0005F)}\right] + \sum_{i=1}^{L_{-10}} W_{b,i}^{-10} \quad (S3)$$

When visualizing motifs, the sequence logos of aligned promoter sequences were generated using WebLogo 3 (available at the WebLogo website; Composition set to 50% GC;[6]). For the Weblogos to compensate for the variable spacing between the −35 and −10 motifs for each promoter model, the distances between them was fixed to the most commonly observed spacer length. FIG. 2 focuses on the −35 and −10 regions. FIG. 9 contains the complete information for the promoter models, including more of the sequence flanking the −35 and −10 motifs, as well showing how far downstream of these promoters genes are found.

Predicted Orthogonality of the Promoters in the Library, as Well as of their Individual −35 and −10 Regions The 29 generated promoter models were used to analyze all 706 promoters in the promoter library (FIG. 10A). This analysis revealed a high level of predicted orthogonality between the ECF subgroups. A similar analysis was performed on just the −10 or −35 subsites, revealing far less predicted orthogonality (FIG. 10B,C). Equation S3 was used to evaluate the full promoters, and the first or third term of that equation was used for the −35 of −10 subsite analysis as appropriate.

Sigma 70 Promoter Modeling and Prediction

A sigma 70 promoter model was built to screen promoter constructs for potential overlapping sigma 70 promoter sequences. The sigma 70 promoter model was constructed from 674 known sigma 70 promoter sequences with experimentally determined transcription starts obtained from RegulonDB 7.0 (available at the website of CCG (Centro de Ciencias Genomicas). Since the −10 and −35 motifs of sigma 70 promoters are poorly conserved, work by Shultzaberger et al.[8] was used as a guide for identifying the motifs. A 2-step search using the 1 block function of BioProspector was used. First, the −10 motif was identified as a 6 mer between positions −16 to −5 (a large window was used to allow for inaccuracies mapping the start site). Next, the −35 motif was identified as a 6 mer 15-20 nt upstream of the identified −10 motif. Four PWMs were constructed using the method of Rhodius and Mutalik[4]. As discussed above, a PWM-35 was built for the −35 motif (aTTGaca) and a PWM-10 for the −10 motif (TAtaaT). In addition, a PWM-spacer was built for a 10-mer block aligned from −21 to −13 aligned with the −10. This incorporates the putative Zn finger contact (−21 to −18; 9), −17/−16 dyad and −15/−14 TG motif[10,11]. Finally, PWMstart was included to capture the transcription start site (−1/+1). All of these PWMs were built using Equation S1. Two spacer penalties were constructed with Equation S2 based on distance histograms between the −35, −10 and start motifs: a spacer penalty (−35 to −10) and a discriminator penalty (−10 to +1). Upstream sequences were scored using counts of overlapping A- and T-tracts between positions −57 to −37, assuming the 5' end of the −35 motif is at position −3612. From these terms, the total sigma 70 promoter score was calculated as:

$$\text{Score} = (\text{UP model}) + \text{PWM}_{-35} + \text{PWM}_{spacer} + \text{PWM}_{-10} + \text{PWM}_{start} + (\text{Spacer penalty}) + (\text{Discriminator penalty}) \quad (S4)$$

Inserting the terms described above in the subsection entitled "ECF sigma promoter modeling" yields, $$\text{Score} = (N_{AAA} + N_{TTT}) + \sum_{i=1}^{7} W_{b,i}^{-35} + \ln\left[\frac{(f_{spacer} + 0.0005 F_{spacer})}{(F_{spacer} + 0.0005 F_{spacer})}\right] + \sum_{i=1}^{6} W_{b,i}^{-10} + \ln\left[\frac{(f_{discrim} + 0.0005 F_{discrim})}{(F_{discrim} + 0.0005 F_{discrim})}\right] + \sum_{i=1}^{2} W_{b,i}^{start} \quad (S5)$$

where $N_{AAA}$ is the number of AAAs, and $N_{TTT}$ is the number of Ts proceeding the −35 site. Note that this promoter model is more complex than that used for the ECF sigma factors for several reasons. First, the additional $\text{PWM}_{spacer}$ term was based on a number of contacts between σ70 and the promoter region that are not known to occur with ECF sigma factors[9-11]. Second, the discriminator penalty and $\text{PWM}_{start}$ scores rely on the correct identification of the transcriptional start site for each promoter. This was experimentally established for the σ70 promoters, but is unknown for the ECF sigma promoters. Third, while the UP model could be applied to the ECF sigma promoters, it is not thought to vary between ECF sigma subfamilies and would therefore not affect the orthogonality of promoter recognition. As that was the main goal of modeling the ECF promoters, it was therefore left out of the computational analysis.

Improving Promoters with Synthetic UP Elements

Promoter sequences were initially tested for activity against both cognate sigmas from their own ECF sigma group. Many non-functional promoter constructs had poor upstream sequences with AAA and TTT-tract counts of ≤2. These were scored by counting the number of overlapping AAA- and TTT-tracts within the sequence window −35 to −57 (assuming that the 5' end of the −10 motif is at position −10). For these promoters, the sequence between −60 to −35 was replaced with a synthetic UP-element similar to that region in the Pecf02_2817 promoter; CATGACAAAATTTTTTAGATGCGTT (SEQ ID NO:64), which generates a score of 6. The A- and T-tracts were designed predominantly in the proximal a binding site (−47 to −57) to mimic the location of the observed A- and T-rich sequences of the active ECF sigma promoters. Adding the UP-element greatly increased the function of a number of the nonfunctional promoters (FIG. 12), and the UP-element was added to all promoters except for those that proved functional without it in this test (Pecf02_2817, Pecf11_3726, Pecf16_3622, Pecf20_992, Pecf30_2079, Pecf31_34, Pecf32_1122, Pecf33_375). UP-element modified promoters were used in all following experiments.

Example 3: Sigma and Anti-Sigma Library Characterization

Complete σ Screening Data, Including Multiple σs from Each Subgroup and Non-Orthogonal Data After promoter optimization, activity assays were performed combinatorially between all optimized promoters and all members of the ECF sigma library (FIG. 13). For each promoter, cells containing the promoter-gfp construct were transformed with the entire ECF sigma library in 96 well format, recovered, induced, and fluorescence measured with flow cytometry. Fluorescence measurements were compared to controls lacking sigma factors (but including the promoter-gfp construct) to calculate fold-induction (Example 6). This testing was used to identify the active sigma factors and promoters in the library, even in cases where the promoter models did not match their intended subgroup. Additionally, these results allowed the selection of a subset of orthogonal sigma factor:promoter pairs, which could be used in the same engineered system without crosstalk. The orthogonal subset of this data is shown in FIG. 3E.

Full Transfer Functions and Cytometry Data for Promoter Induction

Figure 14:
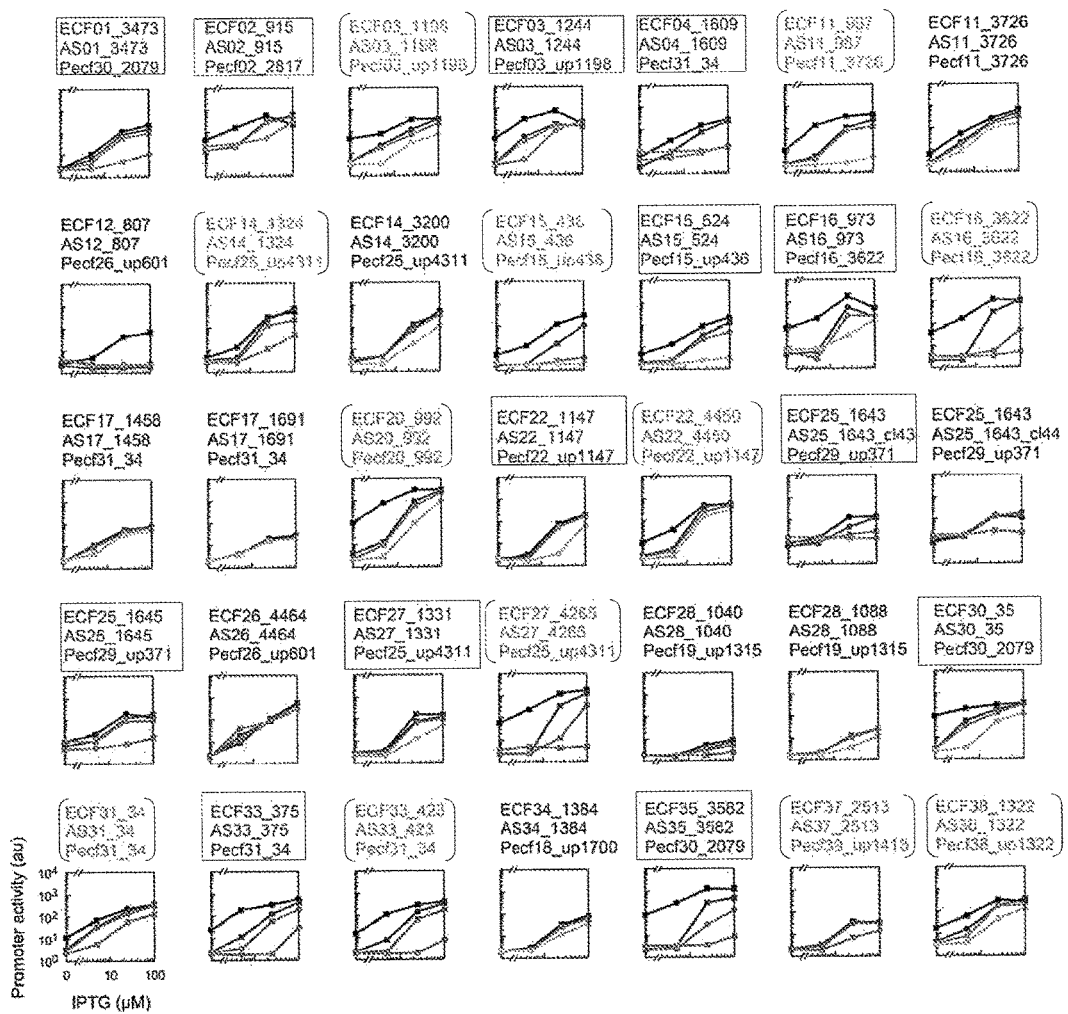
FIG. 14 depicts anti-sigma titration assays. Transfer functions are shown for 35 anti-sigma:ECF sigma:promoter sets. Promoter activity was measured across a range of anti-sigma and ECF sigma inductions. For each assay: from top to bottom inducing the anti-sigma, no anti-sigma control, anti-sigma with 0, 10 and 50 nM HSL; from left to right inducing ECF sigma, 0, 5, 20 and 100 µM IPTG. Assays were performed in vivo with a 6 hour induction and promoter activity determined by measuring the fluorescence of sfgfp with flow cytometry. Data is from a single replicate. Bracketed titles indicate that the anti-sigma ECF sigma:promoter set was active and targets one of the ECF sigmas in the orthogonal subset (included in FIG. 4C). Boxed titles indicate that the anti-sigma was one of the 25 tested in the combinatorial assay (FIG. 15).

Based on the combinatorial sigma:promoter matrix (FIG. 12), 58 members of the ECF sigma library were found to activate a promoter by at least 5-fold. Of these, 52 were chosen for further testing. Each of these 52 sigma factors was paired with its most active promoter from the combinatorial assay, and induced at multiple levels of IPTG to determine promoter activity at multiple levels of sigma factor (i.e., the induction curve) (FIG. 14). Measurements were performed in a similar manner to the combinatorial assay, at 0, 10, 20, and 50 μM IPTG in addition to 100 μM. These induction curves show a wide range of activities. A subset of this induction curve data consisting of one member from each active ECF sigma subgroup is shown in FIG. 3B.

Complete Anti-σ Screening Data

This section outlines the initial screen for anti-σ activity; more detailed titration curves for those deemed active are presented in Example 4. Of the 58 ECF sigma factors shown to activate a promoter by more than 5-fold (FIG. 13), 47 have cognate anti-sigma factors in the synthesized library. Based on the strength and orthogonality of the sigma:promoter interaction, the most promising 35 anti-sigma factors were chosen for further testing. To check for anti-sigma factor activity, titrations of the sigma and anti-sigma factors were performed with the promoter:reporter construct most activated by the sigma factor. These assays were performed using four levels of induction for the sigma factor (0, 5, 20, and 100 µM IPTG), and three for the anti-sigma factor (0, 50, and 100 nM HSL) in addition to a control lacking the anti-sigma expression plasmid. This test showed that 32 of the 35 tested anti-sigma factors were able to repress their cognate sigma factor by at least 2-fold (FIG. 14).

The 25 anti-sigmas with the best repression of their cognate sigma factor from the titration assay were chosen for combinatorial orthogonality testing (FIG. 15). In this test, the set of 25 anti-sigmas plus a no anti-sigma control was tested against the 25 sigma:promoter pairs targeted by the anti-sigmas. In order to better see any repression effects, the sigma factors were induced to an intermediate level (10 µM IPTG), while the anti-sigma factors were induced to a high level (50 nM HSL). This assay shows that a number of the anti-sigma:sigma interactions appear to be fairly orthogonal, while there are also a number that affect many sigma factors. In some cases, the broadly-active anti-sigma factors reduce growth (discussed below).

ECF Sigma Factor and Anti-Sigma Factor Library Growth Assays

Both the σ and anti-σ libraries were tested for toxic effects occurring with expression in *E. coli* DH10b. Toxicity can be due to aberrant gene expression or titration of host RNAP by the as, or by interaction of the anti-σs with essential host σs such as ECF $\sigma^E$. The effect of expressing the sigmas and anti-sigmas was measured using 3 types of growth assays across a range of inductions: 1) transition phase culture density in liquid LB media; 2) exponential growth rates in liquid LB media; 3) colony size on LB agar plates (FIGS. 3C; 21). For each condition, growth assays were performed from at least 3 separate transformations and across a range of inducer concentrations: 0, 10, 20 and 100 µM IPTG for the ECF sigma library; 0, 10 and 50 nM HSL for the anti-sigma library. The ECF sigma library assay strains were freshly transformed DH10b cells carrying pN565 with the pVRa plasmid library and plasmid pET21a (Novagen, Billerica, Mass.) as a no sigma control; the anti-sigma library assay strains were DH10b cells freshly transformed with the pVRc plasmid library and pACYC18413 as a no anti-sigma control.

Under low levels of induction (10 µM IPTG or 10 nM HSL for the σ and anti-σ libraries, respectively) 88% of the σ library and 75% of the anti-σ library exhibited near wild type growth levels by all metrics (>80% DH10b wild type growth). Under high induction levels (100 µM IPTG or 50 nM HSL for the σ and anti-σ libraries, respectively) most growth defects were observed during transition phase and by colony size. For the σ library, 98% exhibited near wild type growth levels (>80% DH10b wild type growth) during exponential growth, whilst 72% and 85% exhibited near wild type growth measured in transition phase or by colony size, respectively. A similar pattern was observed with the anti-σ library but with slightly larger defects: 78%, 43% and 43% exhibited near wild type growth levels during exponential growth, in transition phase and by colony size, respectively. In general, transition phase and colony size yielded a similar pattern of growth defects in both states across the σ and anti-σ libraries, (R=0.79 and 0.85, respectively), likely due to the transition/stationary phase growth properties of cells in the centre of colonies.

Both ECF σs from subgroup 02 exhibited the highest toxicity. *E. coli* ECF $\sigma^E$ is also from subgroup 02 and is represented by the candidate ECF02_2817 in the σ library. *E. coli* $\sigma^E$ is toxic when highly expressed[14]; consequently, the toxic effects of high expression of both ECF02 σ members in the library (ECF02_2817 and ECF02_915) suggest similar function. *E. coli* $\sigma^E$ is also essential[15,16]; accordingly, high expression of its cognate anti-σ AS02_2817 is lethal due to repression of host $\sigma^E$ activity. Interestingly, high expression of anti-σ AS02_915 from the same subgroup only gave reduced growth levels, suggesting that this anti-σ has reduced specificity for host $\sigma^E$. Both σ pairs from subgroups 03 and 25, and anti-σ pairs from subgroups 19, 33 and 35 were also highly toxic (<50% wild type growth), indicating similar activities of each member within the subgroup. There were also several instances of where just one subgroup member was toxic, indicating different functionality in an *E. coli* host (e.g. ability to bind *E. coli* RNAP). Importantly, the lack of toxicity of most library members suggests that they could have utility as orthogonal regulators in *E. coli*.

Example 4: Quantification of Anti-σ Threshold Control

Figure 16:
FIG. 16 depicts a sigma factor transition phase growth assay. OD$_{600}$ measurements were taken after 8 hours of growth at different levels of expression of each of the ECF sigma factors in the library. Plots represent the average measurement from three independent assays normalized to cells not expressing a sigma factor, and error bars represent one standard deviation. Boxed titles indicate 'active' ECF sigma factors with more than 5-fold induction of a promoter in the library, and bracketed titles indicate a ECF sigma factor in the final orthogonal set (FIG. 3E).

A subset of the anti-sigma:ECF sigma pairs were assayed in more detail to determine their capability to implement ultrasensitivity through sequestration[17] (FIG. 18). Sixteen of the sigma factor:anti-sigma factor:promoter sets previously tested were selected based on either: targeting one of the ECF sigma factors in the orthogonal subset, or having a promising induction curve in FIG. 16. These sets were induced at four levels (0, 5, 20, and 100 µM IPTG) of ECF sigma and three levels (no anti-sigma plasmid, 0 nM HSL induction, 50 nM HSL induction) of anti-sigma factor in triplicate (the assay method varied from that used in Example 3; see Example 6) and the promoter activities were measured. High expression of the anti-sigma factor often significantly reduced the promoter output at all levels of ECF sigma factor induction, in many cases also causing highly toxic effects. In contrast, the lower anti-sigma induction showed the desired threshold effect in many cases. At this level of anti-sigma, the higher levels of sigma factor induction showed promoter activity close to the no anti-sigma control, while the lower levels of sigma factor had much lower activity than the equivalent induction points with no anti-sigma. This differential repression is characteristic of a threshold system, and increases the utility of these proteins in applications where a more digital-like signal response is desired. The 9 anti-sigma:ECF sigma:promoter sets that have the best induction curves and correspond to an orthogonal ECF sigma factor are shown in FIG. 4D.

In addition, a threshold-gated switch was constructed using ECF20_992 and AS20_992 and characterized more thoroughly (FIG. 19). The inducible anti-sigma system was supplemented by a set of plasmids constituatively expressing the anti-sigma AS20_992 at a number of levels (FIG. 24). Changing the strength of a constitutive promoter allowed for finer control over the expression level of anti-sigma. This system was tested at 8 induction levels of the ECF sigma factor (0, 5, 25, 50, 75, 100, 150, 200 µM IPTG) in triplicate to characterize the transfer function. Finally, the Hill equation $$\frac{y - y_{min}}{y_{max} - y_{min}} = \frac{x^n}{x^n + K^n}$$

where x is the IPTG induction concentration, y is the output (promoter activity), $y_{max}$ is the maximum output, $y_{max}$ is the minimum output, K is the half-maximum, and n is the Hill coefficient, was used to fit the data using a nonlinear least-squares optimization function in MATLAB. The optimization was weighted inversely to the value at each point to minimize the relative least-squares error so that the model fit both the low and high ends of the data.

Example 5: Creating Chimeric Sigma Factors

Design of Chimeric Sigma Factors and Promoters

A combination of protein alignment, structural information, and secondary structure prediction algorithms were used to generate chimeric sigma factors from ECF02_2817 and ECF11_3726 (FIGS. 3G and 21A). These parental sigma factors were chosen since they have high activity in *E. coli* and there is protein structural information is available that could be used to guide the construction of the chimeras (ECF02_2817 (*E. coli* $\sigma^E$)[18] and *R. sphaeroides* $\sigma^E$, which belongs to the same subgroup as ECF11_372619). Chimeras of both orientations (N-terminal ECF02_2817/C-terminal ECF11_3726 and N-terminal ECF11_3726/C-terminal ECF02_2817) were created by recombining the parental proteins at six 'crossover seams' located in the flexible linker region between the conserved domains 2 and 4, which recognize the −10 and −35 promoter subsites, respectively. While domains 2 and 4 play the most important roles in promoter recognition, the linker region between these regions in Group I σs plays an important role in abortive initiation and promoter escape[20], and likely plays a similar role in the ECF σs. Consequently, the choice of crossover seams within the linkers of the ECF02_2817 and ECF11_3726 σ s may affect the functionality of the resultant chimeras. The structure and precise boundary of the linker region in the ECF σs is ambiguous for two reasons: 1) in both structures the ECF σs are bound to their cognate anti-σ, distorting the structure of the linker; 2) the amino acid sequence of the linker region is poorly conserved, making accurate alignments challenging.

In order to select a range of potentially functional crossover seams, the full library of 86 ECF sigma factors was initially aligned using ClustalW (available at the EMBL-EBI website)[21]. The alignment of ECF02_2817 and ECF11_3726 was then tweaked by hand based on the protein structures mentioned previously. Crossover seams 1 and 2 were located at either end of the flexible linker in this alignment. Due to some uncertainties in the structural analysis (specifically, that the linkers were too distorted by binding anti-σs for proper structural analysis) crossover seams 4, 5, and 6 were based off of the unaltered ClustalW alignment near the beginning, middle, and end of the linker. Finally, a secondary structure prediction algorithm, Predict-Protein[22], was used to analyze ECF02_2817 and ECF11_3726 for α-helices. Crossover seam 6 was placed one residue before the beginning of the first α-helix after the linker region in both proteins.

Chimeric promoters were similarly created by crossing over cognate promoters for ECF02_2817 and ECF11_3726 between the −10 and −35 boxes (FIG. 21B). The promoter rpoHP323 from *E. coli* was used as the parental pECF02 promoter, with a 1 bp mutation (T-34G) made from the WT sequence to differentiate it more from ECF11 promoters. (This promoter contains an overlapping σ70 promoter[23], which likely accounts for the high background induction level and low dynamic range of activation by ECF02.) The pECF11_3726 promoter from the ECF sigma library was chosen as the parental pECF11 promoter. In each case, to −60 to +20 region of the promoter was used, and these parental promoters were crossed over between −20 and −21 to make chimeric promoters. While the initially engineered chimeric promoters were functional, they were relatively weak when compared to the parental promoters. Without wishing to be bound by any theory, one explanation for reduced activity is that while the −10 and −35 recognition sites are identical to the parental plasmids, the spacing between them may not be optimal for the chimeric proteins. This is made even more likely because of uncertainties in identifying the −10 and −35 sites in the promoter, and because the ECF02 and 11 promoter models have different optimal spacings (FIGS. 2 and 9, ECF02 has optimal spacing 14, and ECF11 has optimal spacing 16). For these reasons, additional chimeric promoters were engineered with the −10 and −35 sites moved either 1 bp closer or 1 bp farther apart.

Chimeric Sigma Factor Characterization

The chimeric sigma factors and promoters were first assayed to determine which crossover seams and promoter variants were most successful (FIG. 22). Each of the six versions of each chimera was paired with each of the three versions of its cognate promoter, and the promoter activity determined in vivo. From this assay, it seems as though ECF sigma factors can tolerate chimeragenesis in many different areas and alignments within the linker. Despite the differing alignments used to design the chimeras, seams 1-4 produced very active chimeras for both ECF02-11 and ECF11-02, seams 5 and 6 were slightly active in ECF11-02, and seam 6 was slightly active in ECF02-11. Of these seams, seam 1 was chosen for further experimentation as it was the most active variant of ECF11-02, and one of the more active variants of ECF02-11. In contrast to the flexibility on protein crossover location, the chimeric promoter spacing had an extreme effect on sigma chimera activity. The initially built chimeric promoters had an intermediate level of activity, while pECF02-11-1 and pECF11-02+1 were greatly improved. In contrast, pECF11-02-1 and pECF02-11+1 were inactive, indicating that 1-2 bps of change in the distance between the −10 and −35 sites is enough to abrogate promoter activity. Based on these results, ECF11-02 #1, ECF02-11 #1, pECF02-11-1 and pECF11-02+1 were chosen as the chimeric sigma factors and promoters to be used for further chimera testing.

Figure 23:
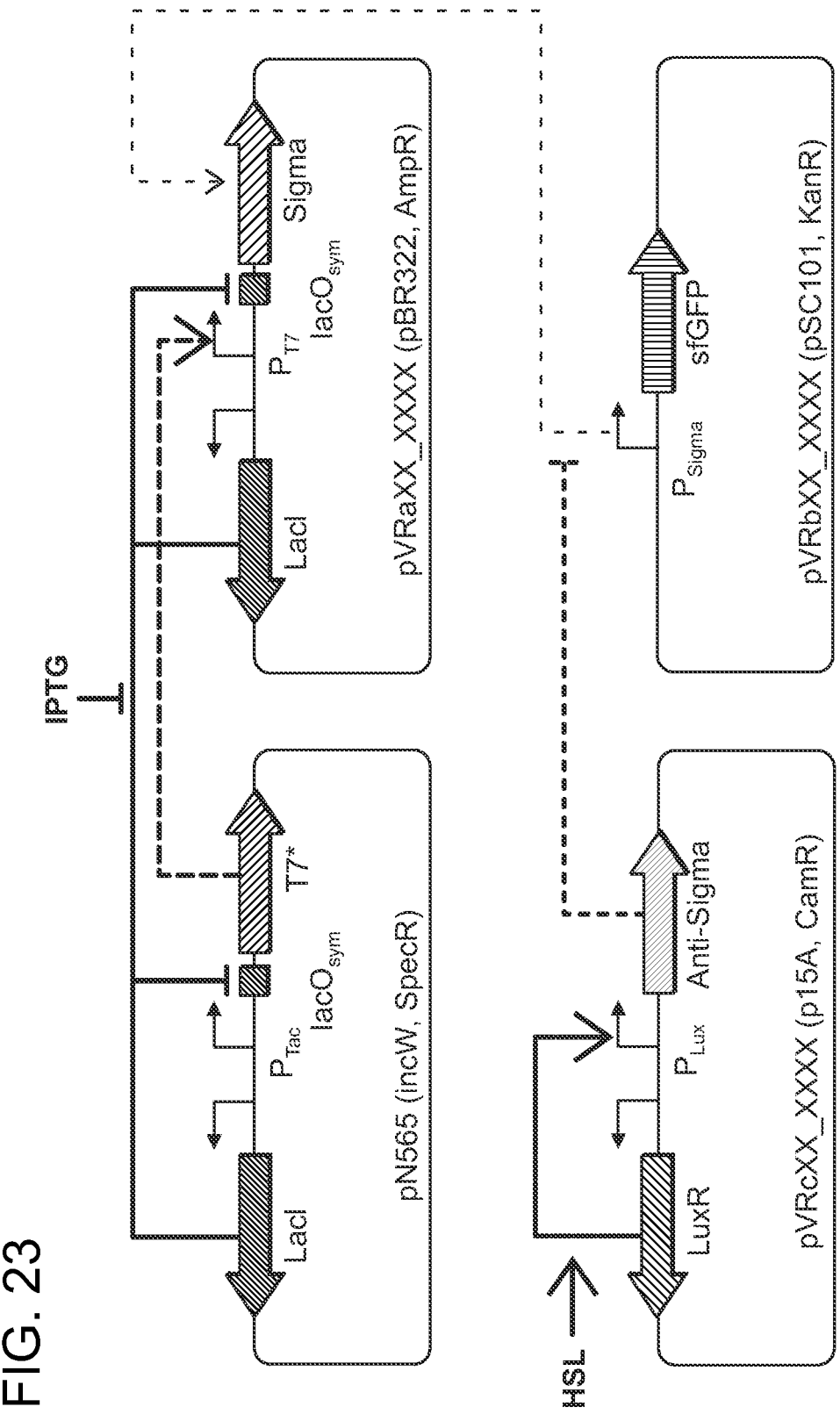
FIG. 23 depicts plasmids used for ECF sigma and anti-sigma characterization. Low processivity T7 RNA polymerase (T7*) was expressed from pN565 using an IPTG-inducible Ptac promoter with a symmetric lac operator (lacOsym). T7* was used to express the ECF sigma library via a T7 and IPTG induced promoter (consisting of the PT7 promoter sequence followed by a symmetric lac operator) from the pVRaXX_XXX plasmid series. Sigma-dependent promoters (PSigma) were carried on the pVRbXX_XXX plasmid series fused to superfolder gfp. The anti-sigma library carried on the pVRcXX_XXX plasmid series was under HSL control via the Plux promoter. XX_XXX in each of the library names represents which anti-sigma/ECF sigma/or sigma-dependent promoter the plasmid carries. For example, the set pVRa20_992, pVRb20_992, pVRc20_992 carries ECF20_992, AS20_992, and pECF20_992, respectively.

Next, using the optimized chimera constructs, the parental and chimeric sigma factors and promoters were tested with each other to check their orthogonality (FIGS. 23 and 3E). Each of the two parental sigma factors and chimeras from the most active seam was tested with each of the two parental promoters and best chimeric promoters. Promoter activity was measured in vivo, and fold-activation of each promoter was calculated using a negative control plasmid that does not express a sigma factor. This assay demonstrates that both the −10 and −35 site must be recognized to get ECF sigma factor promoter activation. The chimeric sigma factors activated their promoters by more than 50-fold more than the parental sigma factors, and the parental sigma promoters likewise only recognized the parental sigma factors. ECF02_2817:pECF02_rpoHP3 displayed the weakest activation at ~10-fold, however, this is due to extremely high background activation.

Example 6: Materials and Methods

Strains and Media

E. coli strain DH10b (MC1061 F-endA1 recA1 galE15 galK16 nupG rpsL ΔlacX74 Φ80lacZΔM15 araD139 Δ(ara, leu)7697 mcrA Δ(mrr-hsdRMS-mcrBC) λ-) (Durfee et al. 2008) was used for all manipulations and assays unless otherwise noted. E. coli DH10b strains were grown at 37° C. with aeration in LB Miller broth for expression assays, and in LB Miller broth, 2YT, SOB (2% Bacto-tryptone, 0.5% Bacto yeast extract, 10 mM NaCl, 2.5 mM KCl), SOB+Mg (SOB+10 mM MgCl$_2$, 10 mM MgSO$_4$), SOB+20 mM glucose, or SOC (SOB+Mg+20 mM glucose) for cloning and CaCl$_2$ high-throughput transformations. E. coli strain CAG22216 (MC1061λ (rpoH P3-lacZ) rpoE::Cam, CamR) 24 was used for expression and testing of chimeric sigma factors. E. coli CAG22216 strains were grown at 30° C. with aeration in the same media as E. coli DH10b. All cultures were supplemented with appropriate antibiotics. Expression of the ECF sigma library, chimeric sigma factors, and ECFs for threshold experiments, was induced with 0-100 µM IPTG (Isopropyl β-D-1-thiogalactopyranoside from Sigma Aldrich, #16758). The anti-sigma library was induced with 0-50 nM HSL (3-O-C6-HSL (N-(β-ketocaproyl)-L-Homoserine Lactone from Cayman Chemical, #10011207). Cultures were grown in either 14 mL Falcon tubes (BD, cat#352059), shaken at 250 rpm at 37° C. or 30° C., or 96-well format in sterile V96 tissue culture plates (NUNC, cat #249935) using an ELMI plate shaker-thermostat (DTS-4 from Elmi Ltd, Riga, Latvia) shaking at 1,000 rpm at 37° C. or 30° C. Plates were covered with gas-permeable membranes (AeraSeal from EK Scientific, cat #T896100-S).

Plasmids

A 4-plasmid system was used for expressing the ECF sigma, promoter and anti-sigma libraries (FIG. 23). Plasmid pN565 encodes an IPTG-inducible low processivity T7 RNA polymerase enzyme. This was used to weakly express the ECF sigma library under control of a T7-regulated promoter encoded on the pVRa plasmid series. The pVRb plasmid series carries the ECF sigma-dependent promoters fused to the fluorescent reporter, superfolder GFP (Pedelacq et al. 2006). The pVRc plasmid series encodes the anti-sigma library under control of HSL. Plasmid modifications were performed using Type II restriction enzyme cloning, PCR and one-step isothermal DNA assembly (Gibson et al. 2009). The ECF sigma and anti-sigma gene libraries were codon optimized for E. coli K12 MG1655, constructed by gene synthesis and assembled into their parent vectors by GeneArt, Life Technologies.

Plasmid pN565 (incW, SpecR) is a variant of the low processivity T7 RNA polymerase expression vector, pN24925 and is tightly regulated by IPTG. The plasmid encodes T7 RNAP with a GTG initiation codon for low translation, an N-terminal degradation tag and the active site mutation R632S. T7 RNAP is expressed from a weak RBS sequence tuned to 50 units using the RBS calculator26 and a modified Ptac promoter with a symmetrical LacO operator sequence (aattgtgagcgctcacaatt; SEQ ID NO:67), enabling near complete promoter repression in the absence of IPTG. The plasmid also encodes LacI.

Plasmid series pVRa (pBR322, AmpR) expresses the ECF sigma library from a T7-lacO promoter. The plasmids are derived from pET15b (Novagen) in which the thrombin cleavage site was replaced with a PreScission protease cleavage site. The series encodes codon optimized ECF sigma genes on NdeI-HindIII fragments in frame with an N-terminal His6 tag and intervening PreScission site. The ECF sigma library is described further in, and incorporated by reference from WO 2012/170436 (see, for e.g., pages 55-56 of WO 2012/170436).

Plasmid series pVRb (SC101, KanR) carries the ECF sigma-dependent promoter library fused to superfolder GFP (sfgfp)[27]. The plasmids are derived from the GFP expression vector, pUA6628, in which the reporter gene gfpmut2 was replaced with sfgfp on a BamHI-PstI fragment. Promoter sequences from −60 to +20 with respect to the transcription start site were inserted upstream of sfgfp into the BbsI-BamHI sites of pVRb (the 5' end of the −10 motif was assumed to be at position −10). For each promoter, DNA fragments were assembled from 4 overlapping 45-mer DNA oligos that corresponded to native promoter sequence, and 2 flanking vector specific oligos. The oligos were assembled by PCR to generate 120 bp fragments in which the 80 nt promoter sequence is flanked by 20 nt of vector sequence. The fragments were gel purified and assembled into purified pVRb BbsI-BamHI vector using one-step isothermal DNA assembly. The ECF promoter library is described further in, and incorporated by reference from, WO2012/170436 (see, for e.g., paragraph [0235] of WO2012/170436). Plasmid series pVRc (p15a, CmR) expresses the anti-sigma library from a HSL-regulated Plux promoter. The plasmids contain cat and LuxR under constitutive control, and replicate via a p15a origin. The plasmids and amino acid sequences of the anti-sigmas are listed in Table 1.

Anti-sigma threshold analysis was performed with a four-plasmid system very similar to that used to characterize the ECF sigma and anti-sigma libraries (FIG. 24). One additional plasmid series was used to supplement pVRc20_992 with a series of plasmids that constitutively express the anti-sigma. Plasmid series pAG_AS20_992_J23XXX (p15a, CmR) expresses AS20_992 from constitutive promoters of varying strengths. The plasmids are derived from pVRc20_992 in which LuxR and the Plux promoter were deleted and replaced by a constitutive promoter. Constitutive promoters BBa_J23100, BBa_J23101, BBa_J23105, and BBa_J23117 (in order of decreasing relative strength: 2547, 1791, 623, 162 au) were selected from the Registry of Standard Biological Parts (available on the iGEM Synthetic Biology website).

Figure 25:
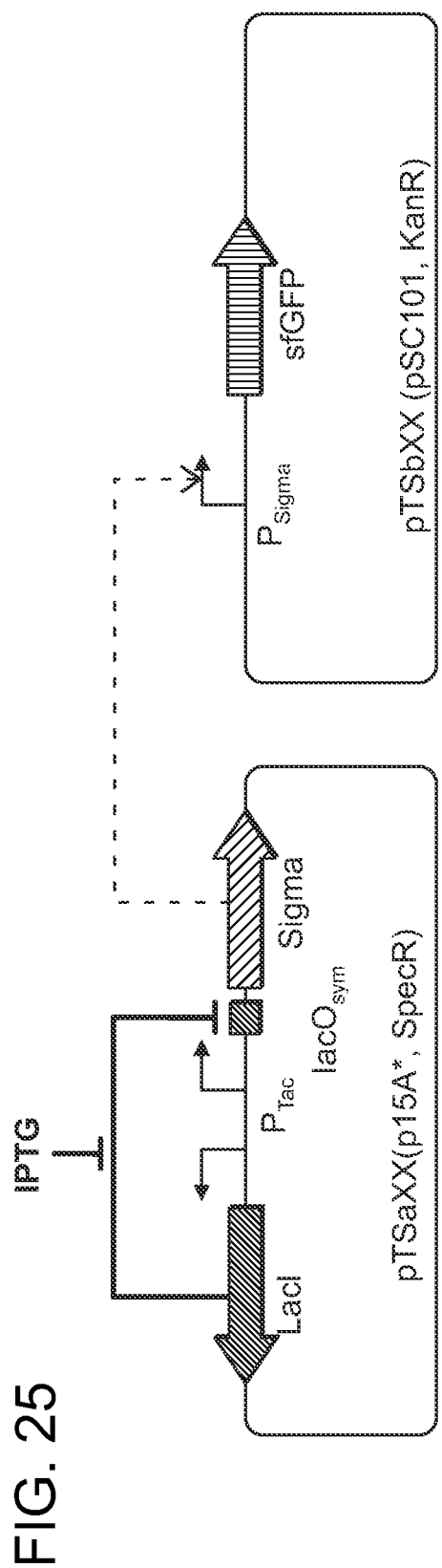
FIG. 25 depicts plasmids used for chimeric sigma characterization. A two plasmid system was used to characterize the chimeric sigma factors. Plasmid library pTSaXX expressed the parental or chimeric sigma factors under the control of an IPTG inducible PTac promoter with a symmetric lac operator (lacOsym). Plasmid library pTSbXX contained the parental and chimeric sigma factor-dependent promoters driving sfgfp.

A 2-plasmid system was used to test the chimeric sigma factors and their cognate promoters (FIG. 25). Plasmid series pTSaXX (p15a*, SpecR) expresses parental (ECF02_2817, ECF11_3726) and chimeric sigma factors under the control of a modified Ptac promoter with a symmetrical LacO operator sequence. These plasmids were derived from pSB3C529, and contain a mutation in the origin that causes them to be maintained at a higher copy number than wild-type p15a. Plasmid series pTSbXX (pSC101, KanR) contains parental and chimeric sigma-dependent promoters driving expression of sfgfp. These plasmids are very similar to plasmid series pVRb, with only the promoter region varying. All construction of these plasmid series was done with one-step isothermal DNA assembly or PCRs and blunt ligations.

High-Throughput Transformations of Sigma and Anti-Sigma Libraries

In vivo assays of strains carrying ECF sigma or anti-sigma libraries were performed from freshly transformed E. coli DH10b host cells. This was to reduce the occurrence of potential suppressor mutations from toxicity of some of the sigmas and anti-sigmas by long-term maintenance in a host. A CaCl$_2$-based high-throughput transformation protocol in 96-well format was employed that enabled convenient transformation of several hundred strains a day. CaCl$_2$ competent cells were prepared using the method of Hanahan et al.[30] for MC1061-based strains. Briefly, 50 ml cultures of cells were grown in SOB (-Mg) media, harvested at OD600=0.3, pelleted and supernatant discarded, cells resuspended and pelleted in 25 ml ice-cold $CaCl_2$ buffer (50 mM $CaCl_2$, 10 mM Tris.HCl pH 7.5) and then finally resuspended in 3.3 ml fresh ice-cold $CaCl_2$ buffer+15% glycerol. Plasmid DNA stocks of each library was prepared at 5 ng/1.11 in 96-well format. For transformation, 10 ng of each plasmid was placed into a sterile 96-well PCR-plate with 25 µl ice-cold $CaCl_2$ competent cells and incubated on ice for 60 min (for double plasmid transformations, 5 ng each plasmid+40 µl $CaCl_2$ competent cells was used). The entire PCR-plate was then heat-shocked at 42° C. in a dry-block for 2 min and then placed on ice for 5 min. Afterwards, cells were transferred to a fresh 96-well tissue culture plate containing 100 µl SOC, mixed, sealed with a breathable membrane and incubated at 37° C., 1000 rpm for 2 hr. 30 µl cells were then transferred to a fresh 96-well tissue culture plate containing 130 µl SOB+Mg+appropriate antibiotics for selection, covered with breathable membrane and incubated overnight (~16 hr) at 37° C., 1000 rpm. This liquid selection in the presence of antibiotics was sufficient to prevent growth of no plasmid controls. The fresh overnight transformants grown to saturation were used for all downstream assays by diluting 200-fold into fresh media with antibiotics and inducers, and growing fresh cultures as required.

ECF Sigma Activity Assays

The sigma-promoter gfp assays were performed in *E. coli* DH10b host cells using a 3 plasmid system: pN565 carrying IPTG-inducible T7 RNAP, pVRa plasmid series carrying the ECF-sigma library, and pVRb plasmid series carrying ECF promoters fused to sfgfp (FIG. 23). Titrations of a sigma against a specific promoter (FIGS. 3B and 13) were performed at 0, 5, 10, 20, 50, and 100 µM IPTG. Assays of all sigmas against all promoters (FIGS. 3E and 12) were also performed in 96-well format with each plate containing the entire ECF sigma library assayed against a specific promoter. Specifically, *E. coli* DH10b cells carrying pN565 and a specific pVRb promoter::sfgfp plasmid were transformed with the complete pVRa ECF sigma library and pET21a control in 96-well format. Overnight liquid transformants grown to saturation (~16 hr) were diluted 200-fold into fresh prewarmed LB+Spec, Amp, Kan and 100 µM IPTG in a 96-well cell culture plate and covered with a breathable membrane. Cultures were incubated in an Elmi plate shaker for 6 hr at 37° C., 1000 rpm. After 6 hr, 5 µl of culture was added to 200 µl PBS (137 mM NaCl, 2.7 mM KCl, 8 mM $Na_2HPO_4$, 2 mM $KH_2PO_4$) and 2 mg/ml Kanamycin. Samples were run on a BD Biosciences LSRII flow cytometer to quantify GFP accumulation.

Anti-Sigma Library Activity Assays

The anti-sigma activity assays were performed in *E. coli* DH10b host cells using a 4 plasmid system: pN565 carrying IPTG-inducible T7 RNAP, pVRa plasmid series carrying the ECF-sigma library, pVRb plasmid series carrying ECF promoters fused to sfgfp, and pVRc plasmid series carrying the anti-sigma library under HSL inducible control. Plasmid pACYC184 was used as a no anti-sigma control. Anti-sigma activity was determined by its ability to repress sigma activity. Accordingly, each sigma was paired with its most active promoter to determine fold repression in the presence and absence of anti-sigma. The anti-sigma activity assays were performed exactly as described for the sigma-promoter assays with the following differences: Anti-sigma-sigma titrations assays: In FIGS. 4B and 14, the transfer functions are shown for the sigma factor for different levels of anti-sigma expression. For each anti-sigma-sigma titration set, *E. coli* DH10b cells carrying pN565 and a specific pVRc anti-sigma were doubly transformed with pVRa ECF sigma/pVRb promoter plasmid pair. A single overnight transformation was then diluted 200-fold into 12 wells of a 96-well plate containing LB, Spec, Amp, Kan and Cm, and a 2-dimensional grid of inducer concentrations: 0, 5, 20 or 100 µM IPTG, and 0, 10 or 50 nM HSL. A no anti-sigma control was also included using DH10b pN565 pACYC184 cells doubly transformed with pVRa ECF sigma/pVRb promoter plasmid pair. The control was diluted 200-fold into 4 wells of a 96-well plate containing LB+Spec, Amp, Kan and Cm and 0, 10, 20 or 100 µM IPTG.

Anti-Sigma—Sigma Activity Assays

Each anti-sigma was assayed against all active sigmas paired with an active promoter in 96-well format (FIGS. 4C and 15). To maximize the ability of anti-sigmas to repress target sigmas, the sigmas were only partially induced with 10 µM IPTG and the anti-sigmas maximally induced with 50 nM HSL. DH10b cells carrying pN565 and a specific pVRc anti-sigma (or no anti-sigma control, pACYC184) were doubly transformed with a library of pVRa ECF sigma/pVRb promoter plasmid pairs. Overnight liquid transformants were diluted 200-fold into fresh prewarmed LB+Spec, Amp, Kan, 10 µM IPTG and 50 nM HSL.

Sigma and Anti-Sigma Exponential Phase Liquid Growth Rate Assays

These were performed by diluting freshly transformed overnight cultures 200-fold into prewarmed LB media with appropriate antibiotics and inducer. Cultures were in 96-well cell culture plates covered with a clear lid and were grown in a Varioskan plate reader/shaker (Thermo Fisher Scientific) at 37° C., shaking at 480 rpm, 6 mm orbital motion. Cell densities ($OD_{600}$) were recorded automatically by the Varioskan every 15 min for 2 hr during exponential growth. All $OD_{600}$ measurements on the Varioskan were converted to standard 1 cm pathlength ODs using a calibration curve generated from an exponentially growing 50 ml culture in a 250 ml shake-flask. Samples from the shake-flask were taken every hour throughout the growth curve and the $OD_{600}$ measured in a 1 cm pathlength cell with a standard spectrophotometer (with appropriate dilution so that $OD_{600}$ readings were always between 0.25-0.35) and from 160 samples measured in a 96-well cell culture plate by the Varioskan. The calibration curve generated from the plot of actual 1 cm pathlength $OD_{600}$ values versus 160 µl Varioskan $OD_{600}$ values was used to normalize all experimental culture ODs measured in the Varioskan. The normalized experimental OD readings were plotted as $\ln(OD_{600})$ versus time (h). Bacterial growth rate µ was calculated from the slope of the linear section of the plot, $$\mu = (\ln N_t - \ln N_0)/(t-t_0) \tag{S6}$$

where µ is the growth rate, N is the number of cells (approximated by OD), and t is time. The growth rates of all sigma and anti-sigma libraries were expressed as a percentage of WT (averaged from eight control cultures).

Transition Phase Liquid Cell Densities

These were performed exactly as the exponential phase growth rate assays with the following modifications. Assay cultures were induced and grown in the Varioskan for 8 hr and the growth curve monitored from $OD_{600}$ readings performed every hr. Wild-type cultures typically entered transition phase after 2-3 hr. Sick cultures often exhibited a decrease in culture $OD_{600}$ values during transition phase, likely due to cessation of growth and subsequent cell lysis. Transition phase cell densities were recorded from the final 8 hr $OD_{600}$ values, normalized to 1 cm pathlength ODs and presented as a percentage of WT $OD_{600}$ (from eight control cultures).

Colony Size Measurements

These were performed in 96-colony format from 96-well cultures. Fresh overnight transformants in 96-well format from each library were pinned onto separate LB-agar master plates containing appropriate antibiotics using a Singer Rotor robot and a 96-pin liquid to solid pinner head. Each plate was incubated overnight for 14 hr at 37° C. to grow colonies in 96-format. From each master plate, colonies were pinned onto inducer plates with the Singer robot using 96-pin solid to solid pinners. The inducer plates contained LB-agar plus appropriate antibiotics and IPTG or HSL inducer, and were incubated overnight for 14 hr at 37° C. to grow colonies in 96-format. Colony sizes were recorded using a 6 megapixel camera under controlled lighting[31], and colony diameter measured using automated image analysis software, HT Colony Grid Analyzer (available at the sourceforge.net website). The sizes of all sigma and anti-sigma expressing colonies were converted to a percentage of WT (from two control colonies).

Anti-Sigma Threshold Assays

The anti-sigma:sigma titrations were repeated in more detail (FIGS. 4D and 18). DH10b cells were transformed with pN565 and a set of pVRa, pVRb, and pVRc plasmids corresponding to one of 16 promising anti-sigma:sigma:promoter sets. A negative anti-sigma control for each set was also made that lacked the pVRc plasmid. Glycerol stocks were made of each strain and stored at −80° C. For each assay, the glycerol stocks were used to start overnights in LB+Amp, Spec, Kan, and Chl (or Amp, Spec, and Kan for the no-anti-sigma controls). After growing to saturation, these overnights were diluted 1:200 into LB+antibiotics in a 96-well cell culture plate. The four plasmid strains were added to a grid of inducer concentrations: 0, 5, 20 or 100 μM IPTG, and 0 or 50 nM HSL. The no-anti-sigma strains were added to inducing conditions of 0 nM HSL and 0, 5, 20 or 100 μM IPTG. Each 96-well plate was shaken at 37° C. for 6 hours at 37° C., 1000 rpm. 2 uL of each induction was added to 198 μL PBS+2 mg/mL Kanamycin and stored at 4° C. Samples were run on a BD Biosciences LSRFortessa flow cytometer to quantify GFP accumulation.

Anti-Sigma Threshold Switch Testing

For detailed characterization of a threshold switch (FIG. 19), the plasmid series pVRc was partially replaced with the plasmid series AG_AS20_992J23XXX, which expresses AS20_992 under the control of a series of constituative promoters (FIG. 24). This allowed for finer and more predictable control of intermediate anti-sigma expression levels in the switch. This switch was characterized in much the same way as the anti-sigma threshold assays. DH10b cells were transformed with pN565, pVRa20_992, pVRb20_992, and pVRc20_992 or one of AG_AS20_992_J23XXX, and glycerol stocks were made. A no-anti-sigma control was also made with only pN565, pVRa20_992, and pVRb20_992. Assays were run by diluting saturated overnights into 96 well cell culture plates with LB+antibiotics+0, 5, 20 or 100 μM IPTG. The strain with pVRc20_992 was run with 50 nM HSL for maximum induction, and the other strains had no HSL. 96-well plates were shaken for 6 hours at 37° C., 1000 rpm. 2 uL of each induction was added to 198 uL PBS+2 mg/mL Kanamycin and stored at 4 C. Samples were run on a BD Biosciences LSRFortessa flow cytometer to quantify GFP accumulation.

Chimeric Sigma Factor Assays

All assays (FIGS. 3H, 21, and 22) of chimeric sigma function were performed in strain CAG2221624 supplemented with antibiotics to maintain carried plasmids. A two plasmid assay system was used, consisting of the series pTSaXX, which contains the parental and chimeric sigma factors under IPTG inducible control, and pTSbXX, which contains the parental and chimeric sigma factor promoters driving sfgfp (FIG. 25).

Similar to the assays with ECF sigma or anti-sigma libraries, the chimeric sigma factors were transformed into cells directly before assaying. Z-competent (Zymo Research, cat# T3002) cell stocks of CAG22216 carrying plasmids from series pTSbXX were made per manufacturer's instructions. The day before the functional assay, 100 ng aliquots of plasmids from series pTSa were added to 50 uL Z-competent cells at 4° C. The cells were kept on ice for 30 seconds, incubated at room temperature for 120 seconds, 150 uL SOC was added and the cells were grown at 30° C., 1000 rpm for 2 hours. These growths were diluted 1:100 into 150 uL LB+Spec/Kan, and incubated 16 hrs at 30° C., 1000 rpm.

For both the assays, transformed overnights were diluted 1:200 into LB+Spec/Kan+10 uM IPTG and grown for 8 hours at 30° C., 1000 rpm. 5 uL of each induction was added to 195 uL PBS+2 mg/mL Kanamycin and stored at 4° C. Samples were run on a BD Biosciences LSRFortessa flow cytometer to quantify GFP accumulation.

Flow Cytometry Analysis

GFP fluorescence of the diluted samples was measured using either a BD Biosciences LSRII flow cytometer (UCSF) or a BD Biosciences LSRFortessa flow cytometer (MIT). Initial analysis of the ECF sigma and anti-sigma libraries was performed on the LSRII, while threshold analysis and chimera testing was done with the LSRFortessa. LSRII analysis: For each sample, 50,000 counts were recorded using a 0.5 μL/s flow rate. All data was exported in FCS2 format and processed using FlowJo (TreeStar Inc., Ashland, Oreg.). Data was gated by forward and side scatter and the geometric mean fluorescence calculated. LSRFortessa analysis: For each sample, at least 5,000 counts were recorded using a 0.5 μL/s flow rate. All data was exported in FCS3 format and processed using FlowJo (TreeStar Inc., Ashland, Oreg.). Data was gated by forward and side scatter then gated to remove any fluorescence values lower than 0. The geometric mean fluorescence was calculated from this gated population.

Fold Calculations

Promoter activity represents the mean fluorescence value obtained from flow cytometry analysis. Fold induction is calculated by dividing the promoter activity from a test population, containing both a sigma factor and a sigma-dependent reporter, by the promoter activity of a population of cells containing just the reporter. Inversely, fold repression is calculated by dividing the promoter activity of a population of cells containing a sigma factor and sigma reporter by the promoter activity of cells containing an anti-sigma factor, sigma factor, and sigma-reporter.

REFERENCES FOR EXAMPLES 2-6

1. Staroń, A. et al. The third pillar of bacterial signal transduction: classification of the extracytoplasmic function (ECF) σ factor protein family. *Molecular Microbiology* 74, 557-581 (2009).
2. Rhodius, V. A., Suh, W. C., Nonaka, G., West, J. & Gross, C. A. Conserved and Variable Functions of the σE Stress Response in Related Genomes. *PLoS Biol* 4, e2 (2005).

3. Liu, X., Brutlag, D. L. & Liu, J. S. BioProspector: discovering conserved DNA motifs in upstream regulatory regions of co-expressed genes. *Pac Symp Biocomput* 127-138 (2001).
4. Rhodius, V. A. & Mutalik, V. K. Predicting strength and function for promoters of the *Escherichia coli* alternative sigma factor, σE. *PNAS* 107, 2854-2859 (2010).
5. Staden, R. Computer methods to locate signals in nucleic acid sequences. *Nucleic Acids Res* 12, 505-519 (1984).
6. Crooks, G. E., Hon, G., Chandonia, J.-M. & Brenner, S. E. WebLogo: A Sequence Logo Generator. *Genome Res.* 14, 1188-1190 (2004).
7. Salgado, H. et al. RegulonDB v8.0: omics data sets, evolutionary conservation, regulatory phrases, cross-validated gold standards and more. *Nucleic Acids Res.* 41, D203-D213 (2013).
8. Shultzaberger, R. K., Chen, Z., Lewis, K. A. & Schneider, T. D. Anatomy of *Escherichia coli* σ70 promoters. *Nucl. Acids Res.* 35, 771-788 (2007).
9. Yuzenkova, Y., Tadigotla, V. R., Severinov, K. & Zenkin, N. A new basal promoter element recognized by RNA polymerase core enzyme. *The EMBO Journal* 30, 3766-3775 (2011).
10. Burr, T., Mitchell, J., Kolb, A., Minchin, S. & Busby, S. DNA sequence elements located immediately upstream of the −10 hexamer in *Escherichia coli* promoters: a systematic study. *Nucl. Acids Res.* 28, 1864-1870 (2000).
11. Mitchell, J. E., Zheng, D., Busby, S. J. W. & Minchin, S. D. Identification and analysis of 'extended −10' promoters in *Escherichia coli*. *Nucl. Acids Res.* 31, 4689-4695 (2003).
12. Rhodius, V. A., Mutalik, V. K. & Gross, C. A. Predicting the strength of UP-elements and full-length *E. coli* σE, promoters. *Nucl. Acids Res.* 40, 2907-2924 (2012).
13. Chang, A. C. & Cohen, S. N. Construction and characterization of amplifiable multicopy DNA cloning vehicles derived from the P15A cryptic miniplasmid. *J. Bacteriol.* 134, 1141-1156 (1978).
14. Nitta, T., Nagamitsu, H., Murata, M., Izu, H. & Yamada, M. Function of the ζE Regulon in Dead-Cell Lysis in Stationary-Phase *Escherichia coli*. *J. Bacteriol.* 182, 5231-5237 (2000).
15. Hiratsu, K., Amemura, M., Nashimoto, H., Shinagawa, H. & Makino, K. The rpoE gene of *Escherichia coli*, which encodes sigma E, is essential for bacterial growth at high temperature. *J. Bacteriol.* 177, 2918-2922 (1995).
16. Peñas, A. D. L., Connolly, L. & Gross, C. A. SigmaE is an essential sigma factor in *Escherichia coli*. *J. Bacteriol.* 179, 6862-6864 (1997).
17. Buchler, N. E. & Cross, F. R. Protein sequestration generates a flexible ultrasensitive response in a genetic network. *Molecular Systems Biology* 5, (2009).
18. Campbell, E. A. et al. Crystal Structure of *Escherichia coli* σE, with the Cytoplasmic Domain of Its Anti-σ RseA. *Molecular Cell* 11, 1067-1078 (2003).
19. Campbell, E. A. et al. A Conserved Structural Module Regulates Transcriptional Responses to Diverse Stress Signals in Bacteria. *Molecular Cell* 27, 793-805 (2007).
20. Murakami, K. S., Masuda, S. & Darst, S. A. Structural Basis of Transcription Initiation: RNA Polymerase Holoenzyme at 4 Å Resolution. *Science* 296, 1280-1284 (2002).
21. Larkin, M. A. et al. Clustal W and Clustal X version 2.0. *Bioinformatics* 23, 2947-2948 (2007).
22. Rost, B., Yachdav, G. & Liu, J. The PredictProtein server. *Nucleic Acids Research* 32, W321-W326 (2004).
23. Erickson, J. W., Vaughn, V., Walter, W. A., Neidhardt, F. C. & Gross, C. A. Regulation of the promoters and transcripts of rpoH, the *Escherichia coli* heat shock regulatory gene. *Genes Dev.* 1, 419-432 (1987).
24. Rouvière, P. E. et al. rpoE, the gene encoding the second heat-shock sigma factor, sigma E, in *Escherichia coli*. *EMBO J* 14, 1032-1042 (1995).
25. Temme, K., Hill, R., Segall-Shapiro, T. H., Moser, F. & Voigt, C. A. Modular control of multiple pathways using engineered orthogonal T7 polymerases. *Nucl. Acids Res.* (2012).doi:10.1093/nar/gks597
26. Salis, H. M., Mirsky, E. A. & Voigt, C. A. Automated design of synthetic ribosome binding sites to control protein expression. *Nature Biotechnology* 27, 946-950 (2009).
27. Pédelacq, J.-D., Cabantous, S., Tran, T., Terwilliger, T. C. & Waldo, G. S. Engineering and characterization of a superfolder green fluorescent protein. *Nature Biotechnology* 24, 79-88 (2005).
28. Zaslaver, A. et al. Just-in-time transcription program in metabolic pathways. *Nature Genetics* 36, 486-491 (2004).
29. Shetty, R., Endy, D. & Knight, T. Engineering BioBrick vectors from BioBrick parts. *Journal of Biological Engineering* 2, 5 (2008).
30. Hanahan, D., Jessee, J. & Bloom, F. R. Plasmid transformation of *Escherichia coli* and other bacteria. *Meth. Enzymol.* 204, 63-113 (1991).
31. Typas, A. et al. High-throughput, quantitative analyses of genetic interactions in *E. coli*. *Nature Methods* 5, 781-787 (2008).

EQUIVALENTS

Those skilled in the art will recognize, or be able to ascertain using no more than routine experimentation, many equivalents to the specific embodiments of the invention described herein. Such equivalents are intended to be encompassed by the following claims.

All references, including patent documents, disclosed herein are incorporated by reference in their entirety.

What is claimed is:

1. A recombinant synthetic genetic circuit comprising:
an extracytoplasmic function (ECF) sigma factor;
an anti-sigma factor that is the cognate of the ECF sigma factor; and
a promoter that is recognized by the ECF sigma factor, wherein the ECF sigma factor and anti-sigma factor are orthogonal, and
wherein the ECF sigma factor and/or the anti-sigma factor are genetically engineered.

2. The recombinant synthetic genetic circuit of claim 1, wherein the ECF sigma factor and/or the promoter are chimeric, and/or wherein the recombinant genetic circuit is expressed within a host cell and wherein the host cell is a prokaryotic cell or a eukaryotic cell, and/or wherein the ECF sigma factor and/or anti-sigma factor are codon-optimized for expression in the host cell, and/or wherein the ECF sigma factor is selected from the group consisting of ECF01-ECF43, and/or wherein the anti-sigma factor is selected from the group of anti-sigma factors contained within Table 1.

3. The recombinant synthetic genetic circuit of claim 1, wherein the recombinant synthetic genetic circuit comprises a combination of logic gates.

4. The recombinant synthetic genetic circuit of claim 3, wherein the logic gates are selected from the group consisting of AND, NAND, NOR, OR, NOT, XOR, EQUALS, AND, IMPLIES, and ANDN gates.

5. The recombinant synthetic genetic circuit of claim 4, wherein the AND gates comprises an ECF sigma factor and a promoter that is recognized by the ECF sigma factor.

6. The recombinant synthetic genetic circuit of claim 1, wherein the recombinant synthetic genetic circuit is a component of a synthetic genetic switch.

7. The recombinant synthetic genetic circuit of claim 6, wherein the synthetic genetic switch is bistable.

8. The recombinant synthetic genetic circuit of claim 1, wherein the recombinant synthetic genetic circuit is a component of a pulse generator.

9. A system comprising a plurality of recombinant synthetic genetic circuits of claim 1.

10. A host cell comprising a heterologous genetic circuit comprising
an extracytoplasmic function (ECF) sigma factor;
an anti-sigma factor that is the cognate of the ECF sigma factor; and
a promoter that is recognized by the ECF sigma factor, wherein the ECF sigma factor and anti-sigma factor are orthogonal.

11. The host cell of claim 10, wherein the ECF sigma factor, the anti-sigma factor and/or the promoter are genetically engineered, and/or wherein the ECF sigma factor and/or the promoter are chimeric, and/or wherein the host cell is a prokaryotic host cell, and/or wherein the genetic circuit comprises one or more logic gates selected from the group consisting of AND, NAND, NOR, OR, NOT, XOR, EQUALS, AND, IMPLIES, and ANDN gates.

12. The host cell of claim 11, wherein the AND gates comprises a sigma factor and a sigma factor target DNA sequence, and/or wherein two or more logic gates are combined by having the output promoter of an upstream gate serve as the input promoter of a downstream gate.

13. A library comprising two or more anti-sigma factors, wherein each anti-sigma factor selectively binds to one or more cognate ECF sigma factors, wherein the anti-sigma factor and the one or more cognate ECF sigma factors are orthogonal.

14. The library of claim 13, further comprising one or more cognate ECF sigma factors.

15. The library of claim 14, further comprising one or more promoters that are recognized by the one or more cognate ECF sigma factors.

16. The library of claim 15, wherein the anti-sigma factors, cognate ECF sigma factor and/or promoter are genetically engineered, and/or wherein the cognate ECF sigma factor and/or promoter is chimeric, and/or wherein the cognate ECF sigma factors and/or anti-sigma factors are codon-optimized for expression in a host cell, and/or wherein the cognate ECF sigma factors are under the control of an inducible promoter, and/or wherein the cognate ECF sigma factor is selected from the group consisting of ECF01-ECF43, and/or wherein the anti-sigma factor is selected from the anti-sigma factors within Table 1.

* * * * *